US012613191B2

(12) United States Patent
Zavaleta et al.

(10) Patent No.: US 12,613,191 B2
(45) Date of Patent: Apr. 28, 2026

(54) MULTIPLEXED RAMAN MOLECULAR IMAGING

(71) Applicant: UNIVERSITY OF SOUTHERN CALIFORNIA, Los Angeles, CA (US)

(72) Inventors: Cristina Zavaleta, Los Angeles, CA (US); Olga Eremina, Los Angeles, CA (US); Alexander Czaja, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 476 days.

(21) Appl. No.: 18/261,074

(22) PCT Filed: Jan. 21, 2022

(86) PCT No.: PCT/IB2022/050497

§ 371 (c)(1),
(2) Date: Jul. 11, 2023

(87) PCT Pub. No.: WO2022/157674

PCT Pub. Date: Jul. 28, 2022

(65) Prior Publication Data

US 2024/0085335 A1 Mar. 14, 2024

Related U.S. Application Data

(60) Provisional application No. 63/140,009, filed on Jan. 21, 2021.

(51) Int. Cl.
*G01N 21/65* (2006.01)
*G01N 33/543* (2006.01)
*G01N 33/58* (2006.01)

(52) U.S. Cl.
CPC ..... *G01N 21/658* (2013.01); *G01N 33/54346* (2013.01); *G01N 33/54373* (2013.01); *G01N 33/587* (2013.01)

(58) Field of Classification Search
CPC ................. G01N 21/658; G01N 21/65; G01N 33/54346; G01N 33/54373; G01N 33/587; G01J 3/44; A61B 5/00
See application file for complete search history.

(56) References Cited

U.S. PATENT DOCUMENTS 8,795,628 B2 * 8/2014 Gambhir ............. A61B 5/0075 424/9.1
2010/0279272 A1 11/2010 Burrell et al.
(Continued)

FOREIGN PATENT DOCUMENTS

WO WO-2009020680 A2 * 2/2009 ............ B82Y 30/00
WO WO-2022157674 A1 * 7/2022 ........... G01N 33/587

OTHER PUBLICATIONS

Patent Cooperation Treaty, International Search Report and Written Opinion issued in PCT/IB2022/050497, May 25, 2022, pp. 1-23.
(Continued)

*Primary Examiner* — Abdullahi Nur
(74) *Attorney, Agent, or Firm* — Pillsbury Winthrop Shaw Pittman, LLP

(57) ABSTRACT

This disclosure relates to a rapid molecular imaging strategy that utilizes Raman spectroscopy to interrogate the molecular expression of samples, for example, histology samples. This disclosure also relates to surface-enhanced Raman spectroscopy nanoparticles (SERS-NP) as contrast agents that exhibit unsurpassed multiplexing capabilities to offer exceptional specificity. This disclosure also relates to a SERS-NP comprising a Raman active metallic core, a Raman active layer, and a shell that may offer ultra-high diagnostic sensitivity (e.g., femtomolar level). This disclosure also relates to chemically modifying these new contrast agents to target a plurality of biomarkers within the sample. This disclosure also relates to rapid assessment of the
(Continued)

molecular expression profile of the entire sample, for example, a whole tissue section, in a single image.

45 Claims, 76 Drawing Sheets

(56) References Cited

U.S. PATENT DOCUMENTS

| | | | | |
|---|---|---|---|---|
| 2012/0179029 A1* | 7/2012 | Kircher | .................. | A61B 34/10 600/421 |
| 2014/0316255 A1* | 10/2014 | Garai | ..................... | A61B 34/20 600/478 |

OTHER PUBLICATIONS

Zavaleta et al., "Multiplexed imaging of surface enhanced Raman scattering nanotags in living mice using noninvasive Raman spectroscopy", Proceedings of the National Academy of Sciences, Aug. 11, 2009, pp. 13511-13516, vol. 106(32).

Zavaleta et al., "A Raman-based endoscopic strategy for multiplexed molecular imaging", Proceedings of the National Academy of Sciences, May 23, 2013, pp. E2288-E2297, vol. 110(25).

Leigh et al., "Method for Assessing the Reliability of Molecular Diagnostics Based on Multiplexed SERS-Coded Nanoparticles", PLoS One, Jan. 1, 2013, pp. 1-8, e62084, vol. 4.

Wang, Yu et al., "Surgical Guidance via Multiplexed Molecular Imaging of Fresh Tissues Labeled With SERS-Coded Nanoparticles", IEEE Journal of Selected Topics in Quantum Electronics, Jul. 1, 2016, pp. 1-11, vol. 22(4).

Kang et al., "Multiplexed Molecular Imaging of BiomarkerTargeted SERS Nanoparticles on Fresh Tissue Specimens with ChannelCompressed Spectrometry", PLOS One, Jan. 1, 2016, pp. 1-13, e0163473, vol. 11(9).

Guerrini et al., "Cancer characterization and diagnosis with SERS-encoded particles", Cancer Nanotechnology, Springer, Oct. 18, 2017, pp. 1-24, vol. 8(1).

Wang, Yunqing et al., "SERS Tags: Novel Optical Nanoprobes for Bioanalysis", Chemical Reviews, Dec. 28, 2012, pp. 1391-1428, vol. 113(3).

Wang, Zhuyuan et al., "SERS~Activated Platforms for Immunoassay: Probes, Encoding Methods, and Applications", Chemical Reviews, Jun. 28, 2017, pp. 7910-7963, vol. 117(12).

Eremina et al., "Selecting Surface-Enhanced Raman Spectroscopy Flavors for Multiplexed Imaging Applications: Beyond the Experiment", Journal of Physical Chemistry Letters, Jun. 17, 2021, pp. 5564-5570, vol. 12(23).

* cited by examiner

BPE 1,2-bis(4-pyridyl)ethylene

PODT 5-(4-pyridyl)-1,3,4-oxadiazole-2-thiol

PTT 5-(4-pyridyl)-1H-1,2,4-triazole-3-thiol

BMMBP 4,4′-bis(mercaptomethyl)biphenyl (a) (b) (c)

(A)

Plexities' Most Preferable log-determinant from 26-plex measured library (B)

Plexities' Least Preferable log-determinant from 26-plex measured library

MULTIPLEXED RAMAN MOLECULAR IMAGING

CROSS-REFERENCE TO RELATED APPLICATION

This patent application is the National Phase of International Application No. PCT/IB2022/050497 filed Jan. 21, 2022, which designated the U.S. and that International Application was published under PCT Article 21 (2) in English, which claims the benefit of priority to U.S. provisional patent application 63/140,009, entitled "Multiplexed Raman Molecular Pathology Imaging," filed Jan. 21, 2021. The entire contents of the foregoing applications are incorporated herein by reference, including all text, tables and drawings in its entirety.

BACKGROUND

Technical Field

This disclosure relates to a rapid molecular imaging strategy that utilizes Raman spectroscopy to interrogate the molecular expression of samples, for example, histology samples. This disclosure also relates to surface-enhanced Raman spectroscopy nanoparticles (SERS-NP) as contrast agents that exhibit unsurpassed multiplexing capabilities to offer exceptional specificity. This disclosure also relates to a SERS-NP comprising a Raman active metallic core, a Raman active layer, and a shell that may offer ultra-high diagnostic sensitivity (e.g., femtomolar level). This disclosure also relates to chemically modifying these new contrast agents to target a plurality of biomarkers within the sample. This disclosure also relates to rapid assessment of the molecular expression profile of the entire sample, for example, a whole tissue section, in a single image.

Description of Related Art

Improving how clinicians stratify patients for targeted therapies requires a comprehensive understanding, for example, of their tumor's molecular expression profile in the spatial context of the tissue's microenvironment. In this sense, staining for multiple biomarkers in one tissue section allows for more molecular information to be gleaned, aiding the clinical team in determining the most effective targeted therapy for the patient.

For example, molecular imaging modalities that visualize cellular and molecular processes central to cancer have already transformed cancer care. Some of these imaging modalities include positron emission tomography (PET), computed tomography (CT), and magnetic resonance imaging (MRI).

Optical molecular imaging techniques have recently translated into the clinical setting for diagnostic screening and surgical navigation, including fluorescence imaging Unlike the above imaging modalities, the optical molecular imaging techniques tend to be more cost-effective, utilize safer non-ionizing radiation agents, require less dedicated clinical space, and offer high-resolution imaging with high sensitivity and specificity.

However, existing optical histology imaging techniques have several limitations. For example, the gold-standard diagnosis of cancerous tumors currently utilizes immunohistochemical staining, often limited to interrogating a single biomarker within a given tissue section Immunostaining may need to be done across many subsequent tissue sections to probe multiple biomarkers, which is time-consuming and introduces the possibility that certain molecular expression relationships go unnoticed. As such, this current diagnosis technique offers limited molecular information on a single tissue section.

Therefore, several companies are developing new pathology imaging tools to interrogate multiple biomarkers within the same tissue section. However, many of these companies are using techniques that may be destructive, laborious, expensive, difficult to interpret, or time-consuming, thereby limiting their clinical use.

One imaging technique utilizes a destructive mass cytometry approach that ablates the tissue sample making it unusable for further pathological examination. The labor-intensive preparation process of this technique may also introduce artifacts that can distort the interpretation of the results. The mass cytometry instrument itself is expensive and bulky and requires a dedicated mass spectrometry specialist to operate. It also uses expensive metal tags that are slow to ablate, only yielding results after three days.

Another technique uses photo-cleavable oligonucleotide tags coupled to antibodies or RNA probes, then hybridized to tissue sections on slides, and then released via UV exposure. The released tags may be quantified and mapped back to the tissue location without providing cellular-level resolution. The process may be cumbersome, and the data may often be challenging to interpret. There are currently no established guidelines for normalizing and analyzing the data generated from the tissue sections leaving the pathologists with a lot of uncertainty.

Yet, another technique developed by General Electric (GE) utilizes a multiplexed fluorescence microscopy approach that offers a sub-cellular characterization of multiple analytes on formalin-fixed paraffin-embedded tissue sections. According to GE, this technique may reveal up to 60 biomarkers in one sample. One significant limitation of this technique that it may require repetitive fluorophore staining and bleaching. Each biomarker may only be interrogated separately by staining, imaging, and bleaching protocol to be then repeated for each biomarker of interest. That may mean taking up to 60 separate images on the same tissue sample that continuously needs to be stained and bleached. Such staining and bleaching may be time-consuming, may affect results, and may also destroy essential antigens on the tissue sample with the repetitive bleach-washing steps required.

RELATED ART REFERENCES

The following publications are related art for the background of this disclosure. One digit, two-digit, or three-digit numbers in the box brackets before each reference correspond to the numbers in the box brackets used in the other parts of this disclosure.

[1] Alabugin, A., Near-IR Photochemistry for Biology: Exploiting the Optical Window of Tissue. Photochem. Photobiol. 2019, 95 (3), 722-732.

[2] Albrecht, M. G.; Creighton, J. A., Anomalously Intense Raman Spectra of Pyridine at a Silver Electrode. J. Am. Chem. Soc. 1977, 99 (15), 5215-5217.

[3] Allam, M., Cai, S. & Coskun, A. F. Multiplex bioimaging of single-cell spatial profiles for precision cancer diagnostics and therapeutics. npj Precis. Oncol. 2020, 4, 11.

[4] Ansar, S. M.; Li, X.; Zou, S.; Zhang, D., Quantitative Comparison of Raman Activities, SERS Activities, and SERS Enhancement Factors of Organothiols: Implication to Chemical Enhancement. J. Phys. Chem. Lett. 2012, 3 (5), 560-565.
[5] Bensebaa, F. Chapter 7—Optoelectronics. Interface Sci. Technol., Vol. 19 (ed. Bensebaa, F.) 429-479 (Elsevier, 2013).
[6] Benz, F.; Chikkaraddy, R.; Salmon, A.; Ohadi, H.; de Nijs, B.; Mertens, J.; Carnegie, C.; Bowman, R. W.; Baumberg, J. J., SERS of Individual Nanoparticles on a Mirror: Size Does Matter, but so Does Shape. J. Phys. Chem. Lett. 2016, 7 (12), 2264-2269.
[7] Braso-Maristany, F. et al. Phenotypic changes of HER2-positive breast cancer during and after dual HER2 blockade. Nat. Commun. 2020, 11, 385.
[8] Brown, K. R.; Natan, M. J., Hydroxylamine Seeding of Colloidal Au Nanoparticles in Solution and on Surfaces. Langmuir 1998, 14 (4), 726-728.
[9] Butler, H. J. et al. Using Raman spectroscopy to characterize biological materials. Nat. Protoc. 2016, 11, 664-687.
[10] Campbell, J. L., et al. Multimodal assessment of SERS nanoparticle biodistribution post ingestion reveals new potential for clinical translation of Raman imaging. Biomaterials 2017, 135, 42-52.
[11] Cauberg, E. C., et al. A new generation of optical diagnostics for bladder cancer: technology, diagnostic accuracy, and future applications. Eur. Urol. 2019, 56, 287-296.
[12] Chen, R.; Jensen, L., Quantifying the Enhancement Mechanisms of Surface-Enhanced Raman Scattering Using a Raman Bond Model. J. Chem. Phys. 2020, 153 (22), 224704.
[13] Davis, R. M.; Campbell, J. L.; Burkitt, S.; Qiu, Z.; Kang, S.; Mehraein, M.; Miyasato, D.; Salinas, H.; Liu, J. T. C.; Zavaleta, C., A Raman Imaging Approach Using CD47 Antibody-Labeled SERS Nanoparticles for Identifying Breast Cancer and Its Potential to Guide Surgical Resection. Nanomaterials 2018, 8 (11), 953.
[14] Eheman, C., et al. Annual Report to the Nation on the status of cancer, 1975-2008, featuring cancers associated with excess weight and lack of sufficient physical activity. Cancer 2012, 118, 2338-2366.
[15] Eremina, O. E., Eremin, D. B., Czaja, A. & Zavaleta, C. Selecting Surface-Enhanced Raman Spectroscopy Flavors for Multiplexed Imaging Applications: Beyond the Experiment. J. Phys. Chem. Lett. 2021, 12, 5564-5570.
[16] Esenturk, E. N.; Walker, A. R. H., Surface-Enhanced Raman Scattering Spectroscopy via Gold Nanostars. J. Raman Spectrosc. 2009, 40 (1), 86-91.
[17] Fleischmann, M., Hendra, P. J. & McQuillan, A. J. Raman Spectra of Pyridine Adsorbed at a Silver Electrode. Chem. Phys. Lett. 1974, 26, 163-166.
[18] Freeman, R. G.; Doering, W. E.; Walton, I. D.; Penn, S. G.; Davis, G.; Wong, F.; Natan, M. J., Detection of Biomolecules Using Nanoparticle Surface Enhanced Raman Scattering Tags. Proc. SPIE 2005, 5705, 114-122.
[19] Frutiger, A. et al. Nonspecific binding-fundamental concepts and consequences for biosensing applications. Chem. Rev. 2021, 121, 8095-8160.
[20] Garai, E., et al. A real-time clinical endoscopic system for intraluminal, multiplexed imaging of surface-enhanced Raman scattering nanoparticles. PLoS One 2015, 10, e0123185.
[21] Garai, E., et al. High-sensitivity, real-time, ratiometric imaging of surface-enhanced Raman scattering nanoparticles with a clinically translatable Raman endoscope device. J. Biomed. Opt. 2013, 18, 096008.
[22] Gentles, A. J. et al. The prognostic landscape of genes and infiltrating immune cells across human cancers. Nat. Med. 2015, 21, 938-945.
[23] Gerdes, M. J. et al. Highly multiplexed single-cell analysis of formalin-fixed, paraffin-embedded cancer tissue. Proc. Natl. Acad. Sci. U. S. A. 2013, 110, 11982-11987.
[24] Giesen, C.; Wang, H. A. O.; Schapiro, D.; Zivanovic, N.; Jacobs, A.; Hattendorf, B.; Schiffler, P. J.; Grolimund, D.; Buhmann, J M.; Brandt, S.; Varga, Z.; Wild, P. J.; Gunther, D.; Bodenmiller, B., Highly Multiplexed Imaging of Tumor Tissues with Subcellular Resolution by Mass Cytometry. Nat. Methods 2014, 11 (4), 417-422.
[25] Haes, A. J., Chang, L., Klein, W. L. & Van Duyne, R. P. Detection of a biomarker for Alzheimer's disease from synthetic and clinical samples using a nanoscale optical biosensor. J. Am. Chem. Soc. 2005, 127, 2264-2271.
[26] Haka, A. S., et al. Diagnosing breast cancer by using Raman spectroscopy. Proc. Natl. Acad. Sci. U. S. A. 2005, 102, 12371-12376.
[27] Hanlon, E. B., et al. Prospects for in vivo Raman spectroscopy. Phys. Med. Biol. 2000, 45 (2), R1-59.
[28] Harvey, T. J., et al. Spectral discrimination of live prostate and bladder cancer cell lines using Raman optical tweezers. J. Biomed. Opt. 2008, 13, 064004.
[29] Head-Gordon, M., Quantum Chemistry and Molecular Processes. J. Phys. Chem. 1996, 100 (31), 13213-13225.
[30] Hu, F. et al. Supermultiplexed optical imaging and barcoding with engineered polyynes. Nat. Methods 2018, 15, 194-200.
[31] Hu, W.; Ye, S.; Zhang, Y.; Li, T.; Zhang, G.; Luo, Y.; Mukamel, S.; Jiang, J., Machine Learning Protocol for Surface-Enhanced Raman Spectroscopy. J. Phys. Chem. Lett. 2019, 10 (20), 6026-6031.
[32] Hu, W.; Tian, G.; Duan, S.; Lin, L.-L.; Ma, Y.; Luo, Y., Vibrational Identification for Conformations of Trans-1,2-bis (4-pyridyl) ethylene in Gold Molecular Junctions. Chem. Phys. 2015, 453-454, 20-25.
[33] Jeanmaire, D. L.; Van Duyne, R. P., Surface Raman Spectroelectrochemistry: Part I. Heterocyclic, Aromatic, and Aliphatic Amines Adsorbed on the Anodized Silver Electrode. J. Electroanal. Chem. Interfacial Electrochem. 1977, 84 (1), 1-20.
[34] Kanter, E. M., et al. Application of Raman spectroscopy for cervical dysplasia diagnosis. J Biophotonics 2, 81-90 (2009).
[35] Jokerst, J. V.; Miao, Z.; Zavaleta, C.; Cheng, Z.; Gambhir, S. S., Affibody-Functionalized Gold-Silica Nanoparticles for Raman Molecular Imaging of the Epidermal Growth Factor Receptor. Small 2011, 7 (5), 625-633.
[36] Kanter, E. M., Majumder, S., Kanter, G. J., Woeste, E. M. & Mahadevan-Jansen, A. Effect of hormonal variation on Raman spectra for cervical disease detection. Am. J. Obstet. Gynecol. 2009, 200 (5), 512 e511-515.
[37] Kapara, A.; Brunton, V. G.; Graham, D.; Faulds, K., Characterisation of Estrogen Receptor Alpha (ERα) Expression in Breast Cancer Cells and Effect of Drug Treatment Using Targeted Nanoparticles and SERS. Analyst 2020, 145 (22), 7225-7233.

[38] Kearns, H.; Shand, N. C.; Smith, W. E.; Faulds, K.; Graham, D., 1064 nm SERS of NIR Active Hollow Gold Nanotags. Phys. Chem. Chem. Phys. 2015, 17 (3), 1980-1986.

[39] Keren, S.; Zavaleta, C.; Cheng, Z.; de la Zerda, A.; Gheysens, O.; Gambhir, S. S., Noninvasive Molecular Imaging of Small Living Subjects Using Raman Spectroscopy. Proc. Natl. Acad. Sci. U. S. A. 2008, 105 (15), 5844-5849.

[40] Kircher, M. F., et al. A brain tumor molecular imaging strategy using a new triple-modality MRI-photoacoustic-Raman nanoparticle. Nat. Med. 2012, 18, 829-834.

[41] Kleinman, S. L. ; Sharma, B.; Blaber, M. G.; Henry, A.-I.; Valley, N.; Freeman, R. G.; Natan, M. J.; Schatz, G. C.; Van Duyne, R. P., Structure Enhancement Factor Relationships in Single Gold Nanoantennas by Surface-Enhanced Raman Excitation Spectroscopy. J. Am. Chem. Soc. 2013, 135 (1), 301-308.

[42] Kothapalli, S. R., et al. Deep tissue photoacoustic imaging using a miniaturized 2-D capacitive micromachined ultrasonic transducer array. IEEE Trans. Biomed. Eng. 2012, 59 (5), 1199-1204.

[43] Langer, J., et al. Present and Future of Surface-Enhanced Raman Scattering. ACS Nano 2020, 14 (1), 28-117.

[44] Leigh, S. Y., Som, M. & Liu, J. T. C. Method for Assessing the Reliability of Molecular Diagnostics Based on Multiplexed SERS-Coded Nanoparticles. PLoS ONE 2013, 8, e62084.

[45] Lenzi, E.; Jimenez de Aberasturi, D.; Liz-Marzán, L. M., Surface-Enhanced Raman Scattering Tags for Three-Dimensional Bioimaging and Biomarker Detection. ACS Sens. 2019, 4 (5), 1126-1137.

[46] Lewis, S. M. et al. Spatial omics and multiplexed imaging to explore cancer biology. Nat. Methods 2021, 18, 997-1012.

[47] Li, H.-C., Song, M. & Chang, C.-I. Simplex volume analysis for finding endmembers in hyperspectral imagery. Proc. SPIE 2015, 9501, 950107.

[48] Liz-Marzán, L. M.; Giersig, M.; Mulvaney, P., Synthesis of Nanosized Gold-Silica Core-Shell Particles. Langmuir 1996, 12 (18), 4329-4335.

[49] Lombardi, J. R.; Birke, R. L., The Theory of Surface-Enhanced Raman Scattering. J. Chem. Phys. 2012, 136 (14), 144704.

[50] Lopes, N. et al. Digital image analysis of multiplex fluorescence IHC in colorectal cancer recognizes the prognostic value of CDX2 and its negative correlation with SOX2. Lab Invest. 2020, 100, 120-134.

[51] Lutz, B. R., et al. Spectral analysis of multiplex Raman probe signatures. ACS Nano 2018, 2 (11), 2306-2314.

[52] Maheedhar, K., et al. diagnosis of ovarian cancer by Raman spectroscopy: a pilot study. Photomed. Laser Surg. 2008, 26, 83-90.

[53] Malini, R., et al. Discrimination of normal, inflammatory, premalignant, and malignant oral tissue: a Raman spectroscopy study. Biopolymers 2006, 81, 179-193.

[54] Medvedev, M. G.; Bushmarinov, I. S.; Sun, J.; Perdew, J. P.; Lyssenko, K. A., Density Functional Theory Is Straying from the Path toward the Exact Functional. Science 2017, 355 (6320), 49-52.

[55] Mohammed, A.; Hu, W.; Andersson, P. O.; Lundquist, M.; Landstrom, L.; Luo, Y.; Ågren, H., Cluster Approximations of Chemically Enhanced Molecule-Surface Raman Spectra: The Case of Trans-1,2-bis (4-pyridyl) ethylene (BPE) on Gold. Chem. Phys. Lett. 2013, 581, 70-73.

[56] Motz, J. T., et al. Real-time Raman system for in vivo disease diagnosis. J. Biomed. Opt. 2005, 10 (3), 031113.

[57] Motz, J. T., et al. Optical fiber probe for biomedical Raman spectroscopy. Appl. Opt. 2004, 43, 542-554.

[58] Muniz-Miranda, M.; Pagliai, M.; Cardini, G.; Schettino, V., Role of Surface Metal Clusters in SERS Spectra of Ligands Adsorbed on Ag Colloidal Nanoparticles. J. Phys. Chem. C 2008, 112 (3), 762-767.

[59] Mulvaney, S. P.; Musick, M. D.; Keating, C. D.; Natan, M. J., Glass-Coated, Analyte-Tagged Nanoparticles: A New Tagging System Based on Detection with Surface-Enhanced Raman Scattering. Langmuir 2003, 19 (11), 4784-4790.

[60] Olivares-Amaya, R.; Rappoport, D.; Munoz, P. A.; Peng, P.; Mazur, E.; Aspuru-Guzik, A., Can Mixed-Metal Surfaces Provide an Additional Enhancement to SERS? J. Phys. Chem. C 2012, 116 (29), 15568-15575.

[61] Parkhill, J. A.; Rappoport, D.; Aspuru-Guzik, A., Modeling Coherent Anti-Stokes Raman Scattering with Time-Dependent Density Functional Theory: Vacuum and Surface Enhancement. J. Phys. Chem. Lett. 2011, 2 (15), 1849-1854.

[62] Phan, H. T.; Heiderscheit, T. S.; Haes, A. J., Understanding Time-Dependent Surface-Enhanced Raman Scattering from Gold Nanosphere Aggregates Using Collision Theory. J. Phys. Chem. C 2020, 124 (26), 14287-14296.

[63] Ra, H., et al. Three-dimensional in vivo imaging by a handheld dual-axes confocal microscope. Opt. Express 2008, 16, 7224-7232.

[64] Raman, C. V. & Krishnan, K. S. A new type of secondary radiation. Nature 1928, 121, 501-502.

[65] Roca, M.; Haes, A. J., Silica-Void-Gold Nanoparticles: Temporally Stable Surface-Enhanced Raman Scattering Substrates. J. Am. Chem. Soc. 2008, 130 (43), 14273-14279.

[66] Salinas, H. R.; Miyasato, D. L.; Eremina, O. E.; Perez, R.; Gonzalez, K. L.; Czaja, A. T.; Burkitt, S.; Aron, A.; Fernando, A.; Ojeda, L. S.; Larson, K. N.; Mohamed, A. W.; Campbell, J. L.; Goins, B. A.; Zavaleta, C., A Colorful Approach towards Developing New Nano-based Imaging Contrast Agents for Improved Cancer Detection. Biomater. Sci. 2021, 9 (2), 482-495.

[67] Sánchez-Purrà, M.; Roig-Solvas, B.; Versiani, A.; Rodriguez-Quijada, C.; de Puig, H.; Bosch, I.; Gehrke, L.; Hamad-Schifferli, K., Design of SERS Nanotags for Multiplexed Lateral Flow Immunoassays. Mol. Syst. Des. Eng. 2017, 2 (4), 401-409.

[68] Sanchez-Purra, M.; Roig-Solvas, B.; Rodriguez-Quijada, C.; Leonardo, B. M.; Hamad-Schifferli, K., Reporter Selection for Nanotags in Multiplexed Surface Enhanced Raman Spectroscopy Assays. ACS Omega 2018, 3 (9), 10733-10742.

[69] Shanthil, M.; Thomas, R.; Swathi, R. S.; Thomas, K. G., Ag@$SiO_2$ Core-Shell Nanostructures: Distance-Dependent Plasmon Coupling and SERS Investigation. J. Phys. Chem. Lett. 2012, 3 (11), 1459-1464.

[70] Shao, Y., et al., Advances in Molecular Quantum Chemistry Contained in the Q-Chem 4 Program Package. Mol. Phys. 2015, 113 (2), 184-215.

[71] Sinha, L. et al., Quantification of the binding potential of cell-surface receptors in fresh excised specimens via dual-probe modeling of SERS nanoparticles. Sci. Rep. 2015, 5, 8582.
[72] Silva, W. R.; Keller, E. L.; Frontiera, R. R., Determination of Resonance Raman Cross-Sections for Use in Biological SERS Sensing with Femtosecond Stimulated Raman Spectroscopy. Anal. Chem. 2014, 86 (15), 7782-7787.
[73] Simmons, P. D., Jr.; Turley, H. K.; Silverstein, D. W.; Jensen, L.; Camden, J. P., Surface-Enhanced Spectroscopy for Higher-Order Light Scattering: A Combined Experimental and Theoretical Study of Second Hyper-Raman Scattering. J. Phys. Chem. Lett. 2015, 6 (24), 5067-5071.
[74] Smigal, C., et al., Trends in breast cancer by race and ethnicity: update 2006. CA Cancer J. Clin. 2006, 56 (3), 168-183.
[75] Stiles, P. L.; Dieringer, J. A.; Shah, N. C.; Van Duyne, R. P., Surface-Enhanced Raman Spectroscopy. Annu. Rev. Anal. Chem. 2008, 1, 601-626.
[76] Stepula, E.; Wang, X.-P.; Srivastav, S.; König, M.; Levermann, J.; Kasimir-Bauer, S.; Schlücker, S., 6-Color/1-Target Immuno-SERS Microscopy on the Same Single Cancer Cell. ACS Appl. Mater. Interfaces 2020, 12 (29), 32321-32327.
[77] Stöber, W.; Fink, A.; Bohn, E., Controlled Growth of Monodisperse Silica Spheres in the Micron Size Range. J. Colloid. Interface Sci. 1968, 26 (1), 62-69.
[78] et al. Human epidermal growth factor receptor cDNA sequence and aberrant expression of the amplified gene in A431 epidermoid carcinoma cells. Nature 1984, 309, 418-425.
[79] Van de Sompel, D., Garai, E., Zavaleta, C. & Gambhir, S. S. A hybrid least squares and principal component analysis algorithm for Raman spectroscopy. Conf. Proc. IEEE Eng. Med. Biol. Soc. 2011, 6971-6974.
[80] Wang, T. et al. Quantitative profiling of integrin alphavbeta3 on single cells with quantum dot labeling to reveal the phenotypic heterogeneity of glioblastoma. Nanoscale 2019, 11, 18224-18231.
[81] Wang, Y. W., et al. Raman-Encoded Molecular Imaging with Topically Applied SERS Nanoparticles for Intraoperative Guidance of Lumpectomy. Cancer Res. 2017, 77, 4506-4516.
[82] Wang, Y., Kang, S., Doerksen, J., Glaser, A. & Liu, J. Surgical Guidance via Multiplexed Molecular Imaging of Fresh Tissues Labeled with SERS-Coded Nanoparticles. IEEE J. Sel. Top. Quantum Electron. 2016, 22 (4), 6802911.
[83] Wang, Y. W., Kang, S., Khan, A., Bao, P. Q. & Liu, J. T. C. In vivo multiplexed molecular imaging of esophageal cancer via spectral endoscopy of topically applied SERS nanoparticles. Biomed. Opt. Express 2015, 6, 3714-3723.
[84] Wang, Y., et al. Quantitative molecular phenotyping with topically applied SERS nanoparticles for intraoperative guidance of breast cancer lumpectomy. Sci. Rep. 2016, 6, 21242.
[85] Wang, Y. W., et al. Multiplexed Molecular Imaging of Fresh Tissue Surfaces Enabled by Convection-Enhanced Topical Staining with SERS-Coded Nanoparticles. Small 2016, 12, 5612-5621.
[86] Wang, Y. W.; Yang, Q.; Kang, S.; Wall, M. A.; Liu, J. T. C., High-Speed Raman-Encoded Molecular Imaging of Freshly Excised Tissue Surfaces with Topically Applied SERRS Nanoparticles. J. Biomed. Opt. 2018, 23 (4), 046005.
[87] Wang, Y.; Yan, B.; Chen, L., SERS Tags: Novel Optical Nanoprobes for Bioanalysis. Chem. Rev. 2013, 113 (3), 1391-1428.
[88] Watkins, D. S. in Fundamentals of Matrix Computations, p. 261-288 (John Wiley & Sons, 2002).
[89] Wei, L.; Chen, Z.; Shi, L.; Long, R.; Anzalone, A. V.; Zhang, L.; Hu, F.; Yuste, R.; Cornish, V. W.; MM, W., Super-multiplex vibrational imaging. Nature 2017, 544 (7651), 465-470.
[90] Winter, M. N-FINDR: an algorithm for fast autonomous spectral end-member determination in hyperspectral data. Proc. SPIE 1999, 3753.
[91] Wojtynek, N. E. & Mohs, A. M. Image-guided tumor surgery: The emerging role of nanotechnology. Wiley Interdiscip. Rev.: Nanomed. Nanobiotechnol. 2020, 12, e1624.
[92] Xu, L. et al. Gambogenic acid inhibits fibroblast growth factor receptor signaling pathway in erlotinib-resistant non-small-cell lung cancer and suppresses patient-derived xenograft growth. Cell Death Dis. 2018, 9, 262.
[93] Yampolsky, S.; Fishman, D. A.; Dey, S.; Hulkko, E.; Banik, M.; Potma, E. O.; Apkarian, V. A., Seeing a Single Molecule Vibrate through Time-Resolved Coherent anti-Stokes Raman Scattering. Nat. Photonics 2014, 8, 650-656.
[94] Zavaleta, C., et al. Noninvasive Raman spectroscopy in living mice for evaluation of tumor targeting with carbon nanotubes. Nano Lett. 2008, 8, 2800-2805.
[95] Zavaleta, C. L.; Smith, B. R.; Walton, I.; Doering, W.; Davis, G.; Shojaei, B.; Natan, M. J.; Gambhir, S. S., Multiplexed Imaging of Surface Enhanced Raman Scattering Nanotags in Living Mice Using Noninvasive Raman Spectroscopy. Proc. Natl. Acad. Sci. U. S. A. 2009, 106 (32), 13511-13516.
[96] Zavaleta, C. L., Kircher, M. F. & Gambhir, S. S. Raman's "effect" on molecular imaging. J. Nucl. Med. 2011, 52, 1839-1844.
[97] Zavaleta, C. L.; Hartman, K. B.; Miao, Z.; James, M. L.; Kempen, P.; Thakor, A. S.; Nielsen, C. H.; Sinclair, R.; Cheng, Z.; Gambhir, S. S., Preclinical Evaluation of Raman Nanoparticle Biodistribution for Their Potential Use in Clinical Endoscopy Imaging. Small 2011, 7 (15), 2232-2240.
[98] Zavaleta, C. L.; Garai, E.; Liu, J. T. C.; Sensarn, S.; Mandella, M. J.; Van de Sompel, D.; Friedland, S.; Van Dam, J.; Contag, C. H.; Gambhir, S. S., A Raman-Based Endoscopic Strategy for Multiplexed Molecular Imaging. Proc. Natl. Acad. Sci. U. S. A. 2013, 110 (25), E2288-E2297.
[99] Zayak, A. T.; Choo, H.; Hu, Y. S.; Gargas, D. J.; Cabrini, S.; Bokor, J.; Schuck, P. J.; Neaton, J. B., Harnessing Chemical Raman Enhancement for Understanding Organic Adsorbate Binding on Metal Surfaces. J. Phys. Chem. Lett. 2012, 3 (10), 1357-1362.
[100] Zhang, F. et al. Quantification of epidermal growth factor receptor expression level and binding kinetics on cell surfaces by surface plasmon resonance imaging. Anal. Chem. 2015, 87, 9960-9965.
[101] Zhuang, Z.; Cheng, J.; Jia, H.; Zeng, J.; Han, X.; Zhao, B.; Zhang, H.; Zhang, G.; Zhao, W., Density Functional Theory Calculation of Vibrational Spectroscopy of Trans-1,2-bis(4-pyridyl)-ethylene. Vib. Spectrosc. 2007, 43 (2), 306-312.

[102] Zhuang, Z.; Shi, X.; Chen, Y.; Zuo, M., Surface-Enhanced Raman Scattering of Trans-1,2-bis(4-pyridyl)-ethylene on Silver by Theory Calculations. Spectrochim. Acta, Part A 2011, 79 (5), 1593-1599.

The entire content of each of the above publications is incorporated herein by reference.

SUMMARY

Examples described herein relate to a rapid molecular imaging strategy that utilizes Raman spectroscopy to interrogate the molecular expression of samples, for example, histology samples. The examples of this disclosure also relate to surface-enhanced Raman spectroscopy nanoparticles (SERS-NP) as contrast agents that exhibit unsurpassed multiplexing capabilities to offer exceptional specificity. The examples of this disclosure also relate to a SERS-NP comprising a Raman active metallic core, a Raman active layer, and a shell that may offer ultra-high diagnostic sensitivity (e.g., femtomolar level). The examples of this disclosure also relate to chemically modifying these new contrast agents to target a plurality of biomarkers within the sample. The examples of this disclosure also relate to rapid assessment of the molecular expression profile of the entire sample, for example, a whole tissue section, in a single image.

This disclosure relates to a surface enhanced Raman spectroscopy nanoparticle (SERS-NP). The SERS-NP may include a Raman active core and a Raman active layer; or a Raman active core, a Raman active layer, and a labeling agent; or a Raman active core, a Raman active layer, a labeling agent, and a shell. For example, this nanoparticle may include a Raman active core, and a Raman active layer. In another example, this nanoparticle may further include a labeling agent. In another example, this nanoparticle may further include a labeling agent and a shell. In these examples, the Raman active core may have an outer surface. In these examples, the Raman active layer may include a Raman reporter. In these examples, the Raman active core and the Raman reporter enhance Raman scattering and are thereby suitable for surface-enhanced Raman spectroscopy (SERS). In these examples, the Raman active layer may be formed on the outer surface of the Raman active core. In these examples, the labeling agent may be attached to the Raman active layer or the outer surface of the shell. In these examples, the Raman active layer may be positioned between the outer surface of the Raman active core and the inner surface of the shell.

In this disclosure, the Raman reporter may be any molecule that may cause, with a suitable core, a surface enhanced Raman scattering. For example, the Raman reporter may be a molecule selected by using a simulated Raman and/or SERS spectra calculated with density functional theory (DFT) and/or time dependent density functional theory (TDDFT). The Raman reporter may also be selected from Table 9, Raman reporter IDs 1-60, or a combination thereof. The Raman reporter may also be selected from Table 9, Raman reporter IDs 4-6, 8, 24, 29-31, 34, 39-42, and 46-49, or a combination thereof.

This disclosure also relates to a staining formulation, useful for staining a sample to identify at least one chemical moiety on at least one surface of the sample. The staining formulation may include at least one flavor ("SERS-flavor"). For example, the staining formulation may include at least two SERS-flavors, or at least three SERS-flavors, or at least four SERS-flavors, or at least five SERS-flavors, or at least six SERS-flavors, or at least seven SERS-flavors, or at least eight SERS-flavors, or at least nine SERS-flavors, or at least 10 SERS-flavors. For example, the staining formulation may include at least three SERS-flavors. For example, the staining formulation may include at least four SERS-flavors. For example, the staining formulation may include at least five SERS-flavors. Each SERS-flavor may include at least one surface enhanced Raman spectroscopy nanoparticle (SERS-NP). Each SERS-flavor's SERS-NP may include a Raman reporter and a Raman active core. Each SERS-flavor's SERS-NP may include a Raman reporter and/or Raman active core that is different than those of the other SERS-flavors in the staining formulation.

In this disclosure, each SERS-NP, SERS-flavor or staining formulation may have a Raman spectrum. This Raman spectrum may be determined at an excitation wave with any wavelength. For example, this spectrum may be determined at an excitation wave with about 785 nm wavelength. The determination of this Raman spectrum may be experimentally carried out by using a Raman spectrometer, or this Raman spectrum may be calculated by using a model resting on quantum mechanics.

Because each SERS-flavor may have a different spectrum than the other SERS-flavor that may be present in the staining formulation, when a Raman spectra of the staining formulation is acquired after the sample and/or the staining formulation is interrogated with an excitation wave, the peaks of the Raman spectrum of each SERS-flavor may overlap with each other, which may cause error in identification and/or quantification of the chemical moiety. This error may increase with increasing number of chemical moieties that need to be identified and/or quantified. This error may need to be minimized to increase the identification and/or quantification accuracy of the chemical moieties.

This error may be minimized by carefully choosing the SERS-flavors that may be included in the staining formulation. The SERS-flavors may be chosen by using a calculation method with which the peak overlap may be minimized Any such calculation method is within the scope of this disclosure. For example, a linear system sensitivity model (LSSM) or a spectral dissimilarity objective (SDO) may be used to choose the staining formulations' SERS-flavors such that an error caused by the SERS-flavors' Raman spectra's peak overlap is minimized For example, potential staining formulations may be ranked by using an LSSM or an SDO and a singular value decomposition (SVD) and calculating a metric. This metric may be any metric.

For example, this metric may be a condition number (such as $\kappa_2$), a determinant, a logarithm of this determinant, log(det), or a combination thereof. Using this metric, the staining formulations, which have potentials to minimize peak overlap errors, may be designed by ranking the potential formulations.

In this disclosure, a value of $\kappa_2$ may be in a range of a value greater than or equal to $\kappa_{2,most}$ to a value less than or equal to 95% of $\kappa_{2,least}$ to rank and choose the potential formulations. The value of $\kappa_2$ may also be in a range of: a value greater than or equal to $\kappa_{2,most}$ to a value less than or equal to 40% of $\kappa_{2,least}$; or a value greater than or equal to $\kappa_{2,most}$ to a value less than or equal to 45% of $\kappa_{2,least}$; or a value greater than or equal to $\kappa_{2,most}$ to a value less than or equal to 50% of $\kappa_{2,least}$; or a value greater than or equal to $\kappa_{2,most}$ to a value less than or equal to 55% of $\kappa_{2,least}$; or a value greater than or equal to $\kappa_{2,most}$ to a value less than or equal to 60% of $\kappa_{2,least}$; or a value greater than or equal to $\kappa_{2,most}$ to a value less than or equal to 65% of $\kappa_{2,least}$; or a value greater than or equal to $\kappa_{2,most}$ to a value less than or equal to 70% of $\kappa_{2,least}$; or a value greater than or equal to $\kappa_{2,most}$ to a value less than or equal to 75% of $\kappa_{2,least}$; or a value greater than or equal to $\kappa_{2,most}$ to a value less than or equal to 80% of $\kappa_{2,least}$; or a value greater than or equal to $\kappa_{2,most}$ to a value less than or equal to 85% of $\kappa_{2,least}$; or a value greater than or equal to $\kappa_{2,most}$ to a value less than or equal to 90% of $\kappa_{2,least}$. The potential staining formulations that may have $\kappa_2$ values within above $\kappa_2$ ranges are within the scope of this disclosure.

In this disclosure, $\kappa_{2,most}$ is the most preferable $\kappa_2$; and $\kappa_{2,least}$ is the least preferable $\kappa_2$. $\kappa_{2,most}$ and $\kappa_{2,least}$ may be calculated by using the following equations.

$$\kappa_{2,most}=0.0182X^2-0.0264X+1.$$

$$\kappa_{2,least}=-0.0172X^2+0.9048X+1.4992.$$

Where X is number of SERS-flavors.

In this disclosure, a value of log(det) may be in a range of a value less than or equal to $\log(\det)_{most}$ to a value greater than or equal to 95% of $\log(\det)_{least}$. The value of log(det) may also be in a range of: a value less than or equal to $\log(\det)_{most}$ to a value greater than or equal to 40% of $\log(\det)_{least}$; or a value less than or equal to $\log(\det)_{most}$ to a value greater than or equal to 45% of $\log(\det)_{least}$; or a value less than or equal to $\log(\det)_{most}$ to a value greater than or equal to 50% of $\log(\det)_{least}$; or a value less than or equal to $\log(\det)_{most}$ to a value greater than or equal to 55% of $\log(\det)_{least}$; or a value less than or equal to $\log(\det)_{most}$ to a value greater than or equal to 60% of $\log(\det)_{least}$; or a value less than or equal to $\log(\det)_{most}$ to a value greater than or equal to 65% of $\log(\det)_{least}$; or a value less than or equal to $\log(\det)_{most}$ to a value greater than or equal to 70% of $\log(\det)_{least}$; or a value less than or equal to $\log(\det)_{most}$ to a value greater than or equal to 75% of $\log(\det)_{least}$; or a value less than or equal to $\log(\det)_{most}$ to a value greater than or equal to 80% of $\log(\det)_{least}$; or a value less than or equal to $\log(\det)_{most}$ to a value greater than or equal to 85% of $\log(\det)_{least}$; or a value less than or equal to $\log(\det)_{most}$ to a value greater than or equal to 90% of $\log(\det)_{least}$. The potential staining formulations that may have log(det) values within above log(det) ranges are within the scope of this disclosure.

In this disclosure, $\log(\det)_{most}$ is most preferable log(det) and $\log(\det)_{least}$ is least preferable log(det). $\log(\det)_{most}$ and $\log(\det)_{least}$ may be calculated by using the following equations.

$$\log(\det)_{most}=-0.0105X^2-0.0861X-0.1917.$$

$$\log(\det)_{least}=-0.2032X^2+0.1229.$$

Where X is number of SERS-flavors.

In this disclosure, the Raman reporter may be any Raman reporter. For example, the Raman reporter may be a molecule selected by using a simulated Raman and/or SERS spectra calculated with density functional theory (DFT) and/or time dependent density functional theory (TDDFT). The Raman reporter may also be selected from Table 9, Raman reporter IDs 1-60, or a combination thereof. The Raman reporter may also be selected from Table 9, Raman reporter IDs 4-6, 8, 24, 29-31, 34, 39-42, and 46-49, or a combination thereof. The Raman reporters of Table 9 are as follows.

ID. No. 1: 1,2-Bis(4-pyridyl)ethylene
ID. No. 2: 5,5'-Dithiobis-(2-nitrobenzoic acid)
ID. No. 3: 5-(4-Pyridyl)-1,3,4-oxadiazole-2-thiol
ID. No. 4: 5-(4-Pyridyl)-1H-1,2,4-triazole-3-thiol
ID. No. 5: 4,4'-Bis(mercaptomethyl)biphenyl
ID. No. 6: 5-Amino-1,3,4-triazole-2-thiol
ID. No. 7: Thiophenol
ID. No. 8: 4-(Trifluoromethyl)thiophenol
ID. No. 9: 4,4'-Dipyridyl
ID. No. 10: d8-4,4'-Dipyridyl
ID. No. 11: 2,2'-Dipyridyl
ID. No. 12: 4,4'-Azopyridine
ID. No. 13: d8-4,4'-Azopyridine
ID. No. 14: Phthalazine
ID. No. 15: 2-Naphthalenethiol
ID. No. 16: 4-Mercaptobenzoic acid
ID. No. 17: 4-Mercaptopyridine
ID. No. 18: 2-Mercaptobenzothiazole
ID. No. 19: 4,4'-Thiobisbenzenethiol
ID. No. 20: 4-Aminothiophenol
ID. No. 21: 4-Nitrothiophenol
ID. No. 22: 2-Bromothiophenol
ID. No. 23: Benzyl mercaptan
ID. No. 24: 6-Amino-2-mercaptobenzothiazole
ID. No. 25: 1,2-bis(pyridin-4-yl)acetylene
ID. No. 26: (Z)-3-(3-fluoropyridin-4-yl)-2-(pyridin-4-yl)acrylonitrile
ID. No. 27: (E)-3-(2-(pyridin-4-yl)vinyl)benzenethiol
ID. No. 28: 2,5-bis(pyridin-4-yl)-1,3,4-thiadiazole
ID. No. 29: 4-Hydroxyl-2-mercapto-6-propylpyrimidine
ID. No. 30: 1-Phenyl-5-mercaptotetrazole
ID. No. 31: 4-Amino-5-(2-(pyridine-3-yl)ethyl)-4H-1,2,4-triazole-3-thiol
ID. No. 32: 2-Mercapto-4-phenylthiazole
ID. No. 33: 2-Mercaptobenzoxazole
ID. No. 34: 4-(1,2,3-Thiadiazol-4-yl)benzylamine
ID. No. 35: 2-Mercaptobenzimidazole
ID. No. 36: 4-Mercaptophenylboronic acid
ID. No. 37: 4-Phenylpyridine
ID. No. 38: 5-Chloro-2-mercaptobenzoxazole
ID. No. 39: 1-(3-Ethynyl-4-pyridyl)-2-(4-pyridyl)ethylene
ID. No. 40: 4,4'-dipyridyldisulfide
ID. No. 41: 1,2-bis(4-pyridyl)ethane
ID. No. 42: p-Terphenyl-4,4"-dithiol
ID. No. 43: Biphenyl-4,4'-dithiol
ID. No. 44: 4-(Mercaptomethyl)ethynylbenzene
ID. No. 45: 5-Phenyl-1H-1,2,4-triazole-3-thiol
ID. No. 46: (4-Pyrid-4-ylphenyl)methanol
ID. No. 47: 4-(4-Pyridyl)benzoic acid
ID. No. 48: 1,2-Bis(4-pyridyl)hydrazine
ID. No. 49: N-(Pyridin-4-methylene)pyridine-4-amine
ID. No. 50: 1,5-Dimercaptonaphthalene
ID. No. 51: 2-Thiazoline-2-thiol
ID. No. 52: 4-(1H-pyrazol-4-yl)pyridine
ID. No. 53: 2-Mercapto-5-nitroimidazole
ID. No. 54: 4-Mercaptobenzonitrile
ID. No. 55: 4-Chlorophenyl isothiocyanate
ID. No. 56: 4-(Trifluoromethyl)pyrimidine-2-thiol
ID. No. 57: 2-Quinolinethiol
ID. No. 58: 2-Mercaptopyrimidine
ID. No. 59: 5-(Trifluoromethyl)pyridine-2-thiol
ID. No. 60: 5-Fluorobenzoxazole-2-thiol In this disclosure, the staining formulation may further include at least one isotype control SERS-flavor. In another example, the isotype control Raman flavor may include at least one SERS-NP functionalized with a nonspecific IgG as a labeling agent to account for any untargeted binding to the sample.

In this disclosure, the sample may express at least one biomarker as a chemical moiety. Each SERS-flavor's SERS-NP may include a labeling agent that can bind to the at least one biomarker, or a chemical moiety that is not a biomarker. In one example, the sample may be a cell belonging to cancerous tissue. The sample may express a biomarker as a chemical moiety. The biomarker may include epidermal growth factor receptor (EGFR), cluster of differentiation-47 (CD47), integrin $\alpha_v\beta_3$, cMET, human epidermal growth factor receptor 2 (HER2), or a combination thereof.

This disclosure also relates to a SERS-flavor including a surface enhanced Raman spectroscopy nanoparticle (SERS-NP). In one example, the SERS-NP may include a Raman active core and a Raman active layer. In another example, the SERS-NP may include a Raman active core, a Raman active layer, and a labeling agent. In another example, the SERS-NP may include a Raman active core, a Raman active layer, a labeling agent, and a shell. The Raman active core may have an outer surface. The shell may have an inner surface and an outer surface. The Raman active layer may be positioned between the outer surface of the Raman active core and the inner surface of the shell. The labeling agent may be attached to the Raman active layer or the outer surface of the shell.

In this disclosure, the Raman active layer may include a Raman reporter. For example, the Raman reporter may be a molecule selected by using a simulated Raman and/or SERS spectra calculated with density functional theory (DFT) and/or time dependent density functional theory (TDDFT). The Raman reporter may also be selected from Table 9, Raman reporter IDs 1-60, or a combination thereof. The Raman reporter may also be selected from Table 9, Raman reporter IDs 4-6, 8, 24, 29-31, 34, 39-42, and 46-49, or a combination thereof.This disclosure also relates to a system useful for identifying and/or quantify at least one chemical moiety on at least one surface of a sample. The system may include a Raman spectroscopy system. The sample may be stained by using any staining formulation of this disclosure. The system may be configured to obtain and analyze Raman scattering of the sample. The system may further be configured to identify and quantify the chemical moiety. The system may further include a staining system configured to stain the sample.

In this disclosure, the Raman reporter may have an anchoring group to bind to the Raman active core. This anchoring group may include thiol, sulfide, disulfide, isothiocyanate, cyanate, nitrogen in aromatic ring, amine, or a combination thereof. In one example, the Raman reporter may bind to the Raman active core by hydrophobic or ionic interactions.

In this disclosure, the Raman active core may include a metal core, a metal oxide, an alloy thereof, or a composite thereof. In one example, the Raman active core may include a metal or a composite core. In another example, the Raman active core may include gold, silver, copper, platinum, palladium, titanium, carbon, aluminum, zinc, chromium, iron, an oxide thereof, an alloy thereof, or a composite thereof. In another example, the Raman active core may include gold, silver, copper, platinum, palladium, copper oxide, titanium oxide, iron oxide, zinc oxide, aluminum oxide, carbon, an alloy thereof, or a composite thereof. In another example, the Raman active core may include gold.

In this disclosure, the Raman active core may have any shape. For example, the Raman active core may include a core with empty inner core, a porous structure, a solid, a plate, a spherical particle, the like, or a combination thereof.

In this disclosure, the labeling agent may include a water soluble homobifunctional, heterobifunctional, or photoreactive crosslinker that may have a chemical group that can react with a functional group of an antibody or another biotargeting species. The labeling agent may further include another chemical group that can react with a functional group on the outer surface of the SERS-NP's shell. In one example, the labeling agent may include PEG. The labeling agent may further include an antibody, peptide, aptamer, or any other targeting ligand.

In this disclosure, the shell may include an oxide. Examples of an oxide may include silica, alumina, titania, zirconia, chitosan, modified cellulose, polyvinyl pyrrolidone, or a mixture thereof. In one example, the shell may include silica.

In this disclosure, the sample may include a solid sample, a liquid sample, or any combination thereof. In one example, the sample may include a tissue. In another example, the tissue may include human tissue, animal tissue, plant tissue, a virus, a bacterium, a cell, the like, or a combination thereof.

Any combination of above examples/embodiments/features/configurations is within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Figure 1:
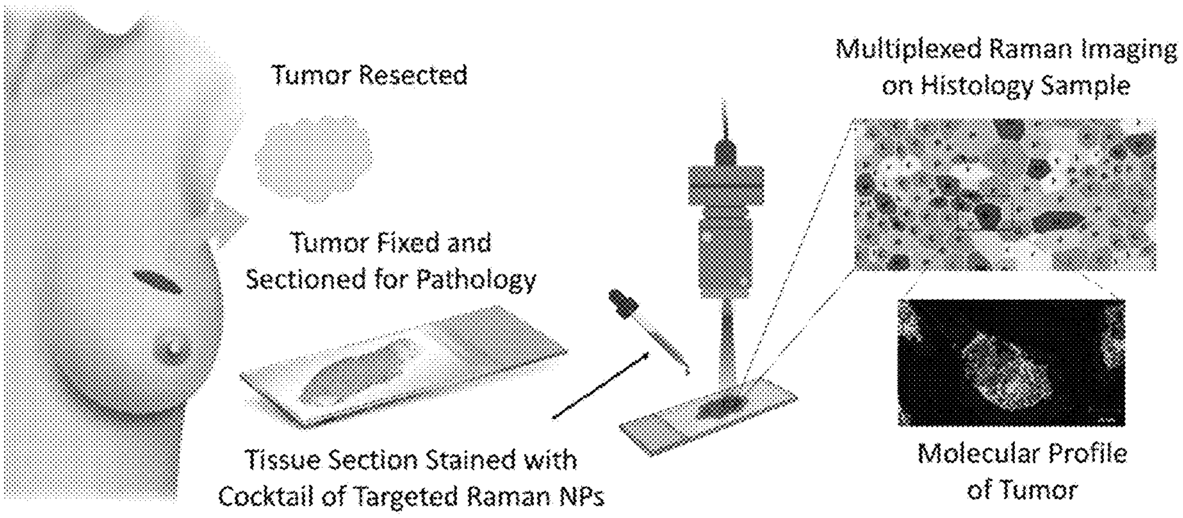
FIG. 1. An exemplary clinical strategy.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The following acronyms are used in this disclosure:

22DP: 2,2'-dipyridyl
2MBT: 2-mercaptobenzothiazole
2NT: 2-naphthalenethiol
44AP: 4,4'-azopyridine
44DP: 4,4'-dipyridyl
4MBA: 4-mercaptobenzoic acid
4MBN: 4-mercaptobenzonitrile
4MPY: 4-mercaptopyridine
4PP: 4-phenylpyridine
AMBT: 6-amino-2-mercaptobenzothiazole
APETT: 4-amino-5-(2-(pyridine-3-yl)ethyl)-4H-1,2,4-triazole-3-thiol
APTMS: (3-aminopropyl)trimethoxysilane
ATDT: 5-amino-1,3,4-triazole-2-thiol
ATP: 4-aminothiophenol
Au-NP: gold nanoparticle
BDT: biphenyl-4,4'-dithiol
BMMBP: 4,4'-bis(mercaptomethyl)biphenyl
BMP: benzyl mercaptan
BPA: 1,2-bis(pyridin-4-yl)acetylene
BPAN: 1,2-bis(4-pyridyl)ethane
BPE: trans-1,2-bis(4-pyridyl)ethylene
BPH: 1,2-bis(4-pyridyl)hydrazine
BPT: 2,5-bis(pyridin-4-yl)-1,3,4-thiadiazole
BTP: 2-bromothiophenol
CBOT: 5-chloro-2-mercaptobenzoxazole
CPITC: 4-chlorophenyl isothiocyanate
CT: computed tomography
$d_8$-44AP: $d_8$-4,4'-azopyridine
$d_8$-44DP:$d_8$-4,4'-Dipyridyl
DAB: 3,3' -diaminobenzidine
DCIS: ductal carcinoma in situ
DCLS: direct classical least squares
DFT: density functional theory
DMN:1,5-dimercaptonaphthalene
DL650: DyLight650
DLS: dynamic light scattering
DPDS: 4,4'-dipyridyldisulfide
DTNB: 5,5'-dithiobis-(2-nitrobenzoic acid)
ER enhancement factor
EGFR: epidermal growth factor receptor
EPPE: 1-(3-ethynyl-4-pyridyl)-2-(4-pyridyl)ethylene ER: estrogen receptor
FBT: 5 -fluorobenzoxazole-2-thiol
FFPE: formalin-fixed paraffin-embedded
fM: femtomolar
FPA: (Z)-3-(3-fluoropyridin-4-yl)-2-(pyridin-4-yl)acrylonitrile
HER2: human epidermal growth factor receptor 2
HLP: hybrid least-squares principal component analysis
HMPP: 4-hydroxyl-2-mercapto-6-propylpyrimidine
HPP: 4-(1H-pyrazol-4-yepyridine
IHC immunohistochemistry
$\kappa_2$: condition number of inversion based on the matrix-induced 2-norm
LOD: limit of detection
LSPR: localized surface plasmon resonance
LSSM: linear system sensitivity model
MBI: 2-mercaptobenzimidazole
MBO: 2-mercaptobenzoxazole
MMB: 4-(mercaptomethyl)ethynylbenzene
MNBI: 2-mercapto-5-nitroimidazole
MPBA: 4-mercaptophenylboronic acid
MPI: 2-mercaptopyrimidine
MPT: 2-mercapto-4-phenylthiazole
MRI: magnetic resonance imaging
NIR: near infrared
NNLS: non-negative least squares
NP: nanoparticle
NTA: nanoparticle tracking analysis
NTP: 4-nitrothiophenol
PBA: 4-(4-pyridyl)benzoic acid
PCA: principal component analysis
PEG: polyethylene glycol
PET: positron emission tomography
PhSH: thiophenol
PHTH: phthalazine
PHTT: 5-phenyl-1H-1,2,4-triazole-3-thiol
PMPA: N-(pyridin-4-methylene)pyridine-4-amine
PMT: 1-phenyl-5-mercaptotetrazole
PODT: 5-(4-pyridyl)-1,3,4-oxadiazole-2-thiol
PPM: (4-pyrid-4-ylphenyl)methanol
PR: progesterone receptor
PTT: 5-(4-pyridyl)-1H-1,2,4-triazole-3-thiol
PVB: (E)-3-(2-(pyridin-4-yl)vinyl)benzenethiol
QT: 2-quinolinethiol
SERRS: surface-enhanced resonance Raman spectroscopy
SERS: surface-enhanced Raman spectroscopy
SERS-NP: surface-enhanced Raman spectroscopy nanoparticle
SDO: spectral dissimilarity objective
SNR: signal to noise ratio
SVD: singular value decomposition
TAT: 2-thiazoline-2-thiol
TBA: 4-(1,2,3-thiadiazol-4-yl)benzylamine
TBBT: 4,4'-thiobisbenzenethiol
TDDFT: time dependent density functional theory
TDT: p-terphenyl-4,4"-dithiol
TFMPIT: 4-(trifluoromethyl)pyrimidine-2-thiol
TFMPT: 5 -(trifluoromethyl)pyridine-2-thiol
TFMTP: 4-(trifluoromethyl)thiophenol Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Examples described herein relate to a rapid molecular imaging strategy that utilizes Raman spectroscopy to interrogate the molecular expression of samples, for example, histology samples. The examples of this disclosure also relate to surface-enhanced Raman spectroscopy nanoparticles (SERS-NP) as contrast agents that exhibit unsurpassed multiplexing capabilities to offer exceptional specificity. The examples of this disclosure also relate to a SERS-NP comprising a Raman active metallic core, a Raman active layer, and a shell that may offer ultra-high diagnostic sensitivity (e.g., femtomolar level). The examples of this disclosure also relate to chemically modifying these new contrast agents to target a plurality of biomarkers within the sample. The examples of this disclosure also relate to rapid assessment of the molecular expression profile of the entire sample, for example, a whole tissue section, in a single image.

Raman spectroscopy in conjunction with surface-enhanced Raman spectroscopy nanoparticles (SERS-NPs) is an optical imaging technique that offers unsurpassed sensitivity (on the order of fM and down to single SERS-NPs) and multiplexing capabilities to the field of histology imaging with the potential to provide rich molecular details on the microscopic level. Incorporating it into the pathology workflow could enable physicians to better understand the patient's tumor type and stratify patients to receive the most effective therapeutic regimen possible. This unique imaging strategy also has the potential to identify new molecular trends in patients' tissue samples that could be used to predict how aggressive their tumor is or how well the patient is likely to respond to given therapies.

This innovative ex-vivo diagnostic strategy of this disclosure has a high likelihood for clinical translation, offering rapid whole tissue section imaging for multiple biomarkers simultaneously.

The unique imaging approach disclosed here, which potentially includes unprecedented optical multiplexing capabilities of Raman spectroscopy, may overcome all the limitations of prior techniques discussed above.

Raman spectroscopy of SERS-NPs is an optical imaging technique that offers unsurpassed sensitivity and multiplexing capabilities, making molecular mapping facile and a useful clinical tool for pathologists and oncologists. Multiplexed SERS-NPs may be conjugated with tumor-biomarker targeting ligands allowing for preferential binding of more than 20 biomarkers simultaneously within the tumor, thereby forming a molecular map of the excised specimens in a single imaging acquisition. Clinicians may utilize the imaging strategy of this disclosure on the same tissue sections prepared for histology. The diagnostic technology of this disclosure may enable physicians to customize a patient's therapy, resulting in improved patient response and overall outcome.

Our unique multiplexed pathology imaging approach may be simple, fast, and/or cost-effective. As such, this imaging approach may have multiplicity of applications where identification and/or quantification of a sample or a chemical moiety present in the sample is an objective. For example, this imaging approach may have applications including in neurosciences, immuno-profiling, agriculture food sciences, document identification, etc. In one example, this imaging approach may offer important predictive information to guide therapeutic decisions, for example, for breast cancer patients. Our imaging strategy may easily be applied to other diseases where knowledge of the presence and/or the spatial distribution of one or more proteins would be useful for diagnostic and/or prognostic determination of a patient's disease state and/or indication for a particular treatment regimen and may not be limited to breast cancer. This novel Raman-based molecular imaging tool may help, for example, physicians to administer the most effective personalized treatment to improve patient outcomes.

SERS-NPs may be the perfect vehicle to enable highly specific molecular targeting and highly sensitive multiplexed imaging capabilities. SERS-NPs may be engineered to carry a variety of imaging and targeting agents. They possess a large surface area ideal for conjugation of active biomarker-targeting moieties and/or additional imaging agents. Unlike small molecule targeting agents that display a single ligand, the large surface area of the nanoparticle may allow for multiple targeting ligands on their surface, which increases the binding avidity and thus binding affinity of the imaging nano-probe to the target site. Their size may be ideal for interacting with molecular receptors, and compared to their small molecule targeting agents, SERS-NPs may offer higher imaging sensitivity.

The diagnostic method of this disclosure may be non-destructive so clinicians may utilize and interrogate the same tissue sections before and after our imaging is applied. For example, the Raman imaging of this disclosure may offer high specificity and multiplexed imaging useful for identifying molecular expression levels in the tumor post-surgery to determine the most effective targeted therapy for the patient moving forward.

This disclosure relates to a surface enhanced Raman spectroscopy nanoparticle (SERS-NP). The SERS-NP may include a Raman active core and a Raman active layer; or a Raman active core, a Raman active layer, and a labeling agent; or a Raman active core, a Raman active layer, a labeling agent, and a shell. For example, this nanoparticle may include a Raman active core, and a Raman active layer. In another example, this nanoparticle may further include a labeling agent. In another example, this nanoparticle may further include a labeling agent and a shell. In these examples, the Raman active core may have an outer surface. In these examples, the Raman active layer may include a Raman reporter. In these examples, the Raman active core and the Raman reporter enhance Raman scattering and are thereby suitable for surface-enhanced Raman spectroscopy (SERS). In these examples, the Raman active layer may be formed on the outer surface of the Raman active core. In these examples, the labeling agent is attached to the Raman active layer or the outer surface of the shell. In these examples, the Raman active layer may be positioned between the outer surface of the Raman active core and the inner surface of the shell.

In this disclosure, the Raman reporter may be selected from Table 9, Raman reporter IDs 1-60, or a combination thereof. The Raman reporter may also be selected from Table 9, Raman reporter IDs 4-6, 8, 24, 29-31, 34, 39-42, and 46-49, or a combination thereof.

This disclosure also relates to a staining formulation, useful for staining a sample to identify at least one chemical moiety on at least one surface of the sample. The staining formulation may include at least one flavor ("SERS-flavor"). For example, the staining formulation may include at least two SERS-flavors, or at least three SERS-flavors, or at least four SERS-flavors, or at least five SERS-flavors, or at least six SERS-flavors, at least seven SERS-flavors, or at least eight SERS-flavors, or at least nine SERS-flavors, or at least 10 SERS-flavors. For example, the staining formulation may include at least three SERS-flavors. For example, the staining formulation may include at least four SERS-flavors. For example, the staining formulation may include at least five SERS-flavors. Each SERS-flavor may include at least one surface enhanced Raman spectroscopy nanoparticle (SERS-NP). Each SERS-flavor's SERS-NP may include a Raman reporter and a Raman active core. Each SERS-flavor's SERS-NP may include a Raman reporter and/or Raman active core that is different than those of the other SERS-flavors in the staining formulation.

In this disclosure, each SERS-NP, SERS-flavor or staining formulation may have a Raman spectrum. This Raman spectrum may be determined at an excitation wave with any wavelength. For example, this spectrum may be determined at an excitation wave with about 785 nm wavelength. The determination of this Raman spectrum may be experimentally carried out by using a Raman spectrometer, or this Raman spectrum may be calculated by using a model resting on quantum mechanics.

Because each SERS-flavor may have a different spectrum than the other SERS-flavors that may be present in the staining formulation, when a Raman spectrum of the staining formulation is acquired after the sample and/or the staining formulation is interrogated with an excitation wave, the peaks of the Raman spectrum of each SERS-flavor may overlap with each other, which may cause error in identification and/or quantification of the chemical moiety. This error may increase with increasing number of chemical moieties that need to be identified and/or quantified. This error may need to be minimized to increase identification and/or quantification accuracy of the chemical moieties.

This error may be minimized by carefully choosing the SERS-flavors that may be included in the staining formulation. The SERS-flavors may be chosen by using a method to calculate a metric with which the peak overlap may be minimized This metric may be any metric. Using this metric, the staining formulations, which have potentials to minimize peak overlap errors, may be designed by ranking the potential formulations. Any such calculation method is within the scope of this disclosure.

For example, a linear system sensitivity model (LSSM) and/or a spectral dissimilarity objective (SDO) may be used to choose the staining formulations' SERS-flavors such that an error caused by the SERS-flavors' Raman spectra's peak overlap is minimized For example, potential staining formulations may be ranked by using LSSM and a singular value decomposition (SVD), and calculating a condition number, $\kappa_2$; or by using an SDO and an SVD and calculating a determinant or a log(det) for a Raman spectrum of the staining formulation determined at an excitation wave with about 785 nm wavelength In this disclosure, the staining formulation may further include at least one isotype control SERS-flavor. In another example, the isotype control Raman flavor may include at least one SERS-NP functionalized with a nonspecific IgG as a labeling agent to account for any untargeted binding to the sample.

In this disclosure, the sample may express at least one biomarker as a chemical moiety. Each SERS-flavor's SERS-NP may include a labeling agent that can bind to the at least one biomarker, or a chemical moiety that is not a biomarker. In one example, the sample may be a cell belonging to cancerous tissue. The sample may express a biomarker as a chemical moiety. The biomarker may include epidermal growth factor receptor (EGFR), cluster of differentiation-47 (CD47), integrin $\alpha_v\beta_3$, cMET, human epidermal growth factor receptor 2 (HER2), or a combination thereof.

This disclosure also relates to a system useful for identifying and/or quantify at least one chemical moiety on at least one surface of a sample. The system may include a Raman spectroscopy system. The sample may be stained by using any staining formulation of this disclosure. The system may be configured to obtain and analyze Raman scattering of the sample. The system may further be configured to identify and quantify the chemical moiety. The system may further include a staining system configured to stain the sample.

In this disclosure, the Raman reporter may have an anchoring group to bind to the Raman active core. This anchoring group may include thiol, sulfide, disulfide, isothiocyanate, cyanate, nitrogen in aromatic ring, amine, or a combination thereof. In one example, the Raman reporter may bind to the Raman active core by hydrophobic or ionic interactions.

In this disclosure, the Raman active core may include a metal core, a metal oxide, an alloy thereof, or a composite thereof. In one example, the Raman active core may include a metal or a composite core. In another example, the Raman active core may include gold, silver, copper, platinum, palladium, titanium, carbon, aluminum, zinc, chromium, iron, an oxide thereof, an alloy thereof, or a composite thereof. In another example, the Raman active core may include gold, silver, copper, platinum, palladium, copper oxide, titanium oxide, iron oxide, zinc oxide, aluminum oxide, carbon, an alloy thereof, or a composite thereof. In another example, the Raman active core may include gold.

In this disclosure, the Raman active core may have any shape. For example, the Raman active core may include a core with empty inner core, a porous structure, a solid, a plate, a spherical particle, the like, or a combination thereof.

In this disclosure, the labeling agent may include a water soluble homobifunctional, heterobifunctional, or photoreactive crosslinker that may have a chemical group that can react with a functional group of an antibody or another biotargeting species. The labeling agent may further include another chemical group that can react with a functional group on the outer surface of the SERS-NP's shell. In one example, the labeling agent may include PEG. The labeling agent may further include an antibody, peptide, aptamer or any other targeting ligand.

In this disclosure, the shell may include an oxide. Examples of an oxide may include silica, alumina, titania, zirconia, chitosan, modified cellulose, polyvinyl pyrrolidone, or a mixture thereof. In one example, the shell may include silica.

In this disclosure, the sample may include a solid sample, a liquid sample, or any combination thereof. In one example, the sample may include a tissue. In another example, the tissue may include human tissue, animal tissue, plant tissue, a virus, a bacterium, a cell, the like, or a combination thereof.

EXAMPLE 1. Raman Imaging with Surface-Enhanced Raman Spectroscopy Nanoparticles (SERS-NPs).

The Raman molecular imaging technique of this disclosure, which uses SERS-NPs and measures the inelastic scattering of light from a sample, offers unsurpassed multiplexing capabilities. For example, the Raman imaging of this disclosure may reveal biomarkers' localization on the tumor cells providing a map of the tumor's molecular expression with microscopic detail (FIG. 1). With this Raman technique, both autofluorescence and photobleaching, which may be crucial disadvantages of fluorescence imaging techniques, may be prevented.

The optical molecular imaging of this disclosure rests on Raman scattering, which generates distinct spectral fingerprints that may be used to identify specific chemical motifs. When light is scattered from a molecule, most photons are elastically scattered, maintaining their initial optical frequency. However, a small fraction of light is scattered at optical frequencies different from and usually lower (Stokes shifted) than the frequency of the incident photons, a process known as Raman scattering.

Previous Raman spectroscopy approaches for clinical diagnosis have primarily relied on interrogating the intrinsic chemical differences between malignant and normal tissues with devices that may have required surface contact with the tissue of interest. However, the inefficiency associated with intrinsic Raman scattering remains a significant limitation for effective diagnosis. Because these conventional/prior Raman spectroscopy approaches may often lead to poor sensitivity, requiring long exposure times (up to minutes) per spectral acquisition (for a single pixel of spatial sampling), and/or high laser powers that can destroy the sample. In addition, changes in the intrinsic Raman spectra generated by diseased vs. benign tissues may be subtle, with no way to directly correlate the spectral changes with macromolecular features such as protein biomarkers that are the basis for precision medicine. These issues have limited the clinical translation of conventional Raman spectroscopy.

The Raman imaging technique of this disclosure, which uses the composition of SERS-NPs, overcomes these major limitations, thereby providing a rapid examination of, for example, tissue histology specimens, assessment of molecular expressions of the samples, and facilitation of the personalized therapy.

Figure 2:
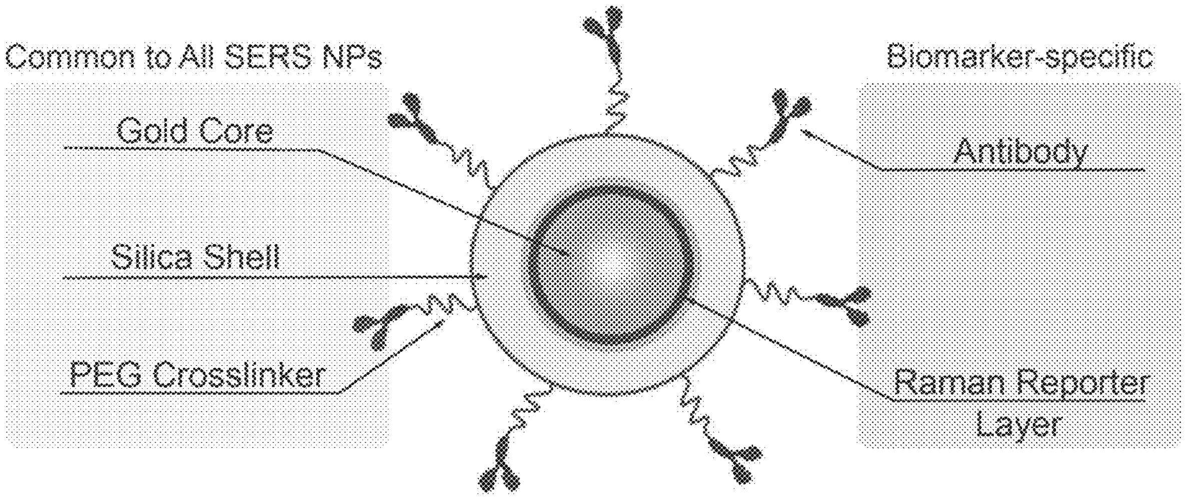
FIG. 2. A SERS-NP may include a gold core, a Raman-active layer, and a silica shell. The Raman active layer may be positioned between the gold core and the silica shell. The silica shell may provide protection for the Raman-active layer. The Raman-active layer may be formed by chemically binding a reporter molecule that may emit a desirable Raman spectral signature from the surface of the gold core. Our SERS-NPs may be synthesized using a single Raman reporter molecule, not by binding a mixture of Raman reporters to a gold nanoparticle's surface. Enhancement of Raman scattering may be achieved by the gold core inside many neighboring nanoparticles interacting with the incident laser to exhibit surface plasmon resonance. The outer surface of the silica shell may be thiolated to enable functionalization with biomarker-targeting antibodies, allowing the particles to preferentially bind to an epitope of a protein of interest.

Rather than interrogating the weak intrinsic Raman signal from the tissue itself, we may probe an enhanced Raman signal from SERS-NPs that may bind tumor biomarkers. These SERS-NPs may exhibit a plasmon resonance effect on the surface of their encapsulated metallic core that dramatically increases the Raman scattered light emitted by small molecules adsorbed onto the metallic core surface, therefore, requiring less laser power, enabling more sensitive detection, and faster imaging on the order of msec per spectral acquisition. These SERS-NPs may include, for example, a Raman active gold core, a unique Raman active layer that may serve as a spectral "barcode," and a glass shell (FIG. 2). The diameter of the gold core, for example, may be about 60 nanometers (nm). The total particle size of the SERS-NP may be about 120 nm in diameter. By coupling these SERS-NPs to various biotargeting agents (e.g., antibodies or ligands), which recognize biomarkers with high specificity, we may sensitively and precisely localize the SERS-NPs and thus multiple important biomarkers, for example, on histology samples, to determine the unique molecular expression profile of the patient's diseased tissue.

Figure 3:
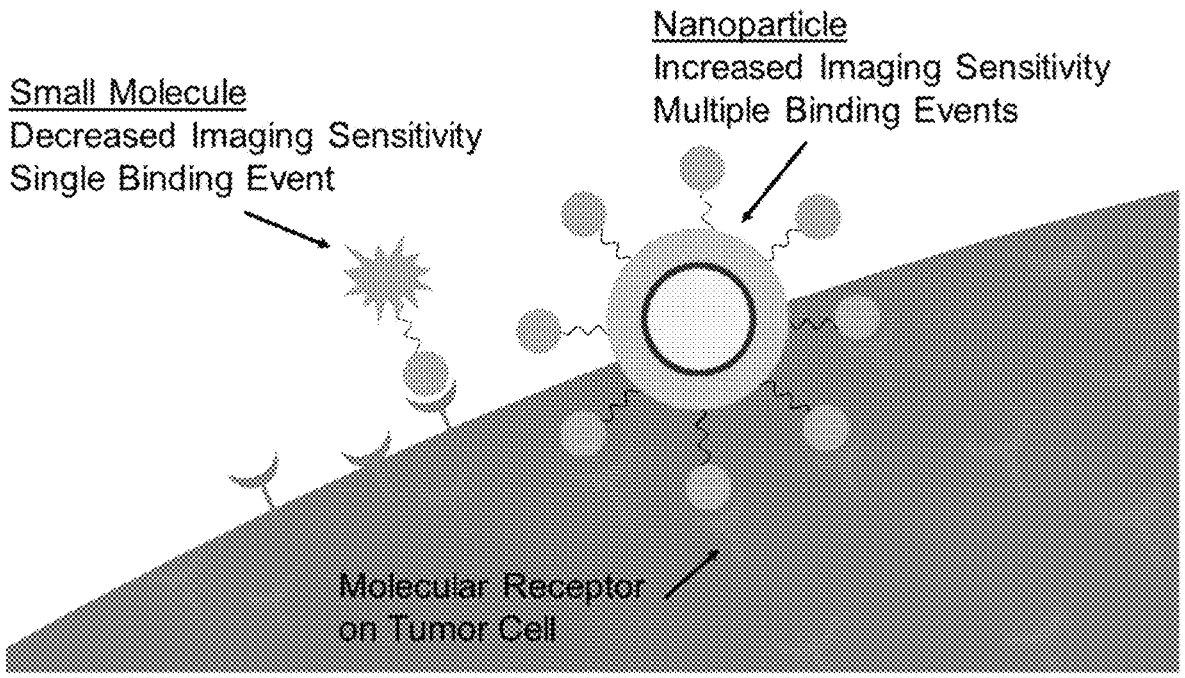
FIG. 3. Depicts advantages of using nanoparticles. Active molecular targeting may be enhanced with nanoparticles due to their multiple targeting ligands and binding events with receptors.

The SERS-NPs may allow the deposition of multiple targeting agents on their large surface, which increases the binding affinity to the sample, unlike small molecule targeting agents that only display a single targeting agent (FIG. 3). Therefore, several low binding agents of the SERS-NPs may work in tandem to create an accumulated strength that results in a high-affinity nanoparticle construct for targeting, for example, over-expressed multiple receptors on tumor cells.

The gold core may serve as a plasmon resonant surface enhancer for our Raman reporters. When close to metallic nanoparticle cores, Raman reporters have been reported to experience a drastic increase in Raman scattering due to a localized electric field enhancement of, for example, up to 3,000 times. As a result, such SERS-NPs may produce, for example, up to 14 orders of magnitude higher signal intensities of Raman scattering, making these SERS-NPs ultrasensitive Raman imaging contrast agents.

Figure 4:
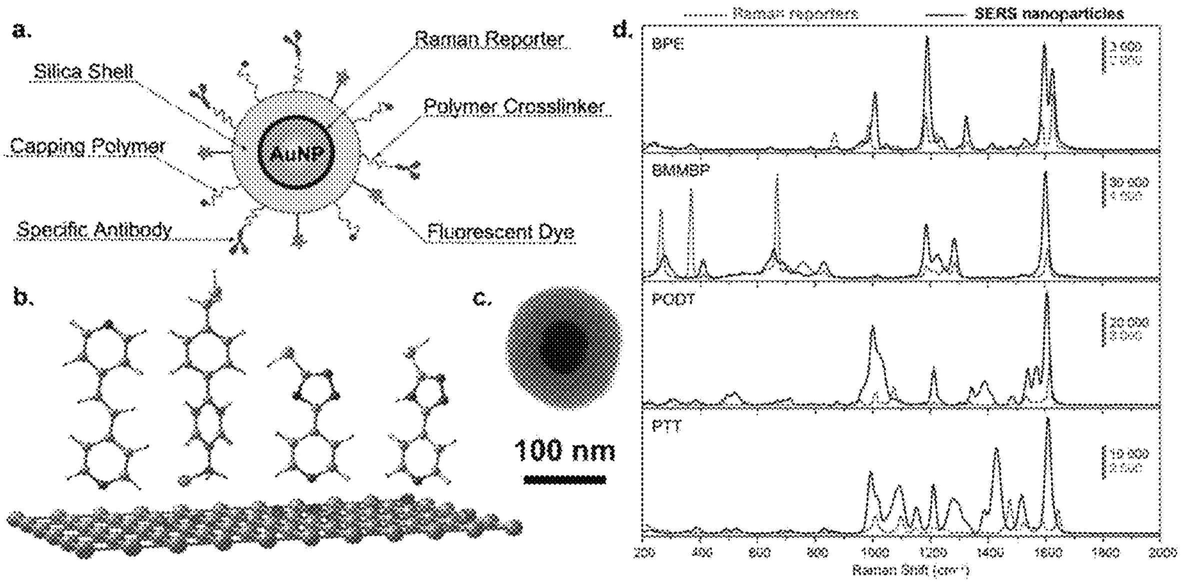
FIG. 4. Depicts (a) Schematic structure of the SERS-NPs — contrast agents for targeting various biomarkers. (b) Structures of the Raman reporters over gold surface: BPE (trans-1,2-bis(4-pyridyl)ethylene), BMMBP (4,4'-bis(mercaptomethyl)biphenyl), PODT (5-(4-pyridyl)-1,3,4-oxadiazole-2-thiol), and PTT (5-(4-pyridyl)-1H-1,2,4-triazole-3-thiol). (c) Typical TEM image of the prepared SERS-NPs. (d) Experimental Raman spectra of individual concentrated solutions (0.5 M) of Raman reporter molecules: BPE, BMMBP, PTT, and PODT (red); and SERS spectra of Au-NPs (0.25 nM) labeled by the same reporters (blue) with excitation using an about 785-nm laser (165 mW, 10%, 1 s).

The Raman-active layer adsorbed onto the metallic surface may provide a unique and bright spectral barcode (FIG. 4), allowing for multiple "flavors" of SERS-NPs to be simultaneously used for a multiplexing approach that may far exceed the capabilities of existing optical techniques (e.g., fluorescence) and may provide faster analysis than conventional/previous contact Raman devices designed for examining intrinsic tissue signatures.

Figure 59:
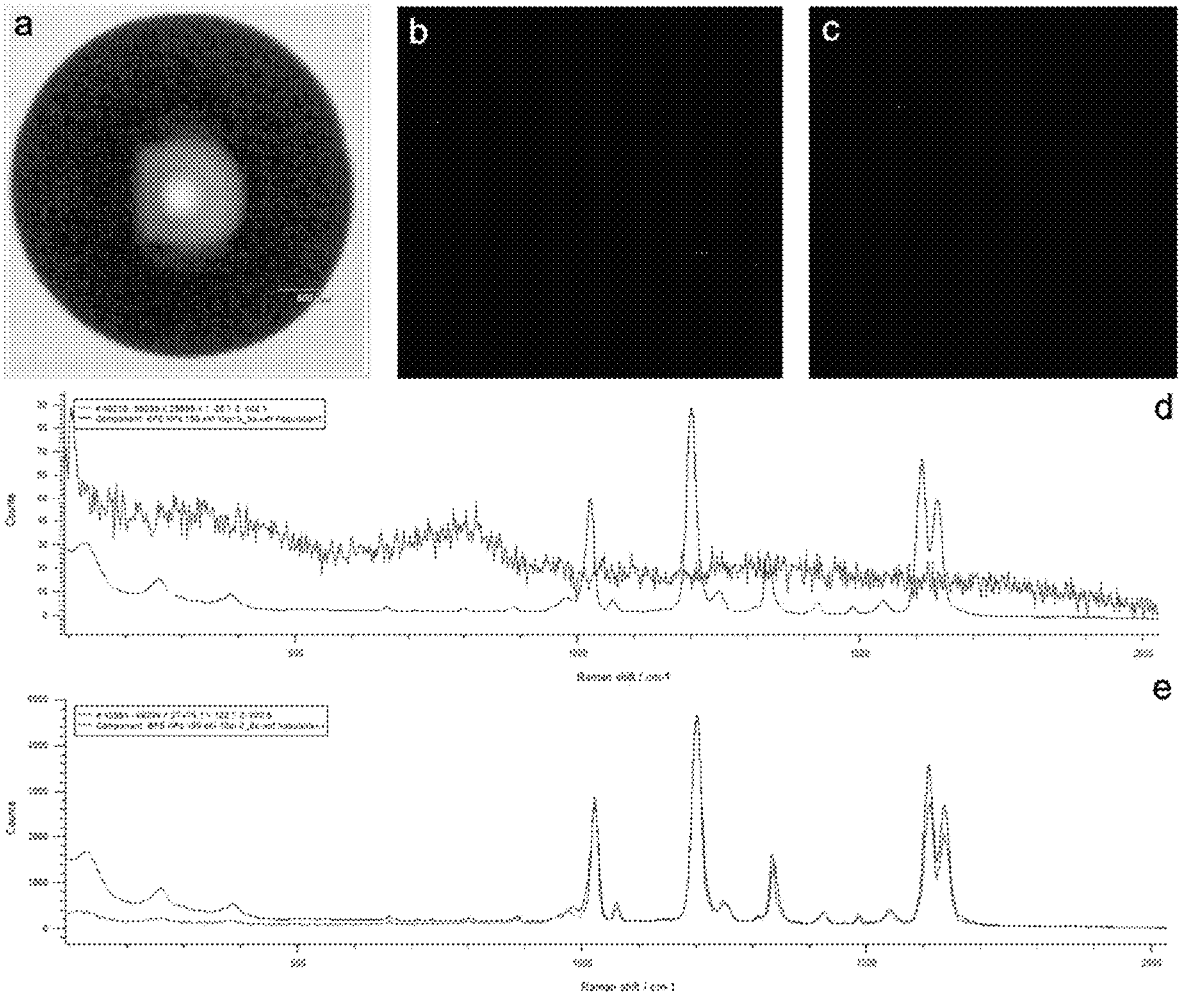
FIG. 59. Sensitivity of SERS-NPs down to single contrast agent demonstrated on BPE-labeled about 60 nm diameter Au-NPs coated with about 30 nm silica shell. a, White light image of an about 1 μL droplet deposited on a stainless steel slide. b, Raman imaging channel for about 15 aM SERS-NPs, ca. 9 SERS-NPs in a droplet. c, Raman imaging channel for about 7.5 aM SERS-NPs, ca. 4-5 SERS-NPs in a droplet. Scanned area: about 2,770 μm×about 2,680 μm≅7.4 $mm^2$; exposure time: about 0.275 s, scanning time: about 33 min, step size: about 10.6 μm×about 10.6 μm, 100% laser power. d, red line—Raman spectrum of background (black pixels in Raman imaging channels, b and c), blue line—SERS spectra of SERS-NP's reference. e, Red line—Raman spectrum of locations where SERS-NPs are present (red pixels in Raman imaging channels, b and c), blue line—SERS spectra of SERS-NP's reference.

Experiments with SERS-NPs of this disclosure have shown that we were able to detect femtomolar (fM) concentrations of SERS-NPs in solution. We also could detect a single SERS-NP on a tissue sample (FIG. 59). The developed Raman spectroscopy technique was related to a topical application of these SERS-NPs nanoparticles onto human tissue for molecular assessment. We evaluated the ability of the proposed Raman imaging technique to multiplex on fresh human tissue samples.

Twenty-six SERS-flavors were intravenously injected into a nude mouse. The 24 h post-injection in vivo and ex vivo images revealed a clear distinction between each of the channels belonging to a different Raman reporter with minimal crosstalk in biological tissue.

Furthermore, equal concentrations of SERS-NP-flavors were mixed to assess co-localized multiplexing on human tissue and their Raman spectra were correctly unmixed in their respective channels. We successfully measured varying concentrations of co-localized SERS-NPs on human tissue, indicating that the Raman technique of this disclosure may be used to quantify binding potential to specific biomolecular targets.

The intrinsic background signal from human tissue itself did not interfere with the ability to demultiplex (i.e., deconvolute) the SERS-NP spectra acquired with our Raman device. These results show great potential for multiplexing, where several SERS-NPs administered simultaneously could detect the expression of multiple biomarkers on a given tissue.

EXAMPLE 2. Breast Cancer Diagnosis

This imaging strategy may be used, for example, in diagnosing breast cancer. Only in the U.S., over 200,000 women are diagnosed with breast cancer each year, with a mortality rate of more than 40,000 patients. The majority undergo surgery along with a combination of therapies. With the advent of several new targeted and immuno-therapies, knowing the molecular expression profile of an individual patient's tumor is more critical than ever to stratify patients and properly ensure an effective treatment response.

Approximately 80% of women are good candidates for targeted breast cancer therapies. Still, failure to fully understand the molecular expression and tumor heterogeneity across the tumor may lead to the administration of ineffective treatments that come with all the harsh side effects and no benefits, increasing patient morbidity and healthcare costs. We lack easy means for providing detailed molecular mapping of the patients' tumors to enable a more personalized therapy optimized for them.

Breast cancer is a complex disease with many morphological and molecular features that present clinically. With the advent of targeted hormone therapies, clinicians have used biomarker expression of estrogen receptor (ER), the progesterone receptor (PR), and even the human epidermal growth factor receptor 2 (HER2) to clinically classify the disease and dictate preferable therapeutic approaches for treatment. The proteomic era has made it possible to identify new biomarkers involved in breast cancer development, survival, invasion, and even predicting treatment response. Together, clinical and molecular data may contribute to more personalized management of breast cancer patients.

An exemplary overview of the clinical strategy of this disclosure is schematically depicted in FIG. 1. Raman imaging technique of this disclosure may be performed on excised tumor tissue that has been prepared for histology to generate a rapid molecular expression profile of the tumor. This Raman imaging technique may be used in conjunction with our targeted-SERS-NPs to identify their localization across the entire histology section rapidly. A ratiometric imaging strategy may quantify biomarker expression by comparing the signal from targeted-SERS-NPs vs. control SERS-NPs.

Our experiments have demonstrated effective molecular targeting and multiplexing with these SERS-NPs in human breast cancer cells lines and on fresh human breast tissue samples. Our Raman imaging approach may measure the expression of a panel of biomarker targets including HER2, EGFR (epidermal growth factor receptor), CD44, CD24, CD47, and ER; one or more of which is over-expressed in >85% of breast cancer patients.

Each SERS-NP-flavor may be conjugated with monoclonal antibodies to target a unique protein biomarker overexpressed on a sample, for example, a breast cancer tissue. Each SERS-NP-flavor within a multiplexed mixture may be identified and quantified through a spectral-demultiplexing software algorithm.

Our team has done extensive work to optimize and validate least-squares-based demultiplexing algorithms with numerous experiments to verify the linearity of SERS-NP-flavor measurements on different tissue types. Recent data obtained by our team shows the ability of multiplexed SERS-NPs to quantify the specific vs. non-specific binding levels of targeted and untargeted (control) SERS-NPs that are topically applied on fresh tissue specimens.

The protocol utilized an about 5 minutes (min) incubation time followed by about 20 seconds (s) rinse and about 100 milliseconds (ms) integration time for imaging at each point. Our experiments also showed that Raman imaging with SERS-NPs did not interfere with subsequent H&E pathology or immunohistochemistry, necessary for clinical translation.

EXAMPLE 3. Personalized Medicine

Personalized medicine is rapidly becoming the preferred strategy for effective cancer therapy. Chemotherapeutic approaches have evolved greatly over the years, from non-specific cytotoxic drugs that may damage both healthy and cancerous cells to more specific approaches that may target unique molecular features of cancer cells. Both targeted therapies and immunotherapies have recently shown improved therapeutic effectiveness with less overall toxicity to the patient. However, not all targeted therapies are best suited for all cancer patients, hence the need for a more personalized therapeutic approach.

To ensure each patient is given the best targeted therapy, it is essential to understand the specific molecular expression profile of that patient's tumor before choosing an effective treatment regimen. The profiling of the patient's tumor may enable a more personalized and effective therapeutic approach and may reduce the overall toxicity and cost associated with cancer care.

EXAMPLE 4. Multiplexing Capabilities and Sensitivity of SERS-NPs

Multiplexing capabilities and sensitivity of SERS-NPs may strongly be dependent on the selected Raman-active reporter. These Raman-active molecules may be responsible for giving each batch of SERS-NPs its unique spectral fingerprint.

In this example, we studied four types of SERS-NPs, which included a gold nanoparticle cores (Au-NPs) labeled with (1) trans-1,2-bis(4-pyridyl)ethylene (BPE), (2) 4,4'-bis (mercaptomethyl)biphenyl (BMMBP), (3) 5-(4-pyridyl)-1, 3,4-oxadiazole-2-thiol (PODT), and (4) 5-(4-pyridyl)-1H-1, 2,4-triazole-3-thiol (PTT).

We demonstrated that we may choose the best predictions by resting on inner products of DFT-calculated Raman spectra and experimental Raman spectra. We also calculated the spectra of these Raman reporters bound to $Au_{20}$ clusters to interrogate how SERS enhancement would affect their spectral fingerprint. We found a correlation between B3LYP-D3-calculated enhancement factors and experimental enhancement factors with which we may predict which Raman reporters offer improved sensitivity.

We observed about 10-fold and about 100-fold increase in sensitivity with PTT and BMMBP, respectively, compared to BPE.

EXAMPLE 5. Raman Reporters

Surface-enhanced Raman spectroscopy (SERS), which may provide unprecedented sensitivity and outstanding multiplexing capability, may be utilized for bioimaging applications, such as biological sensing, molecular imaging, and immunoassay development. Typically, the unique SERS fingerprint originates from a Raman reporter molecule bound to the surface of a metallic nanoparticle core. Subsequently, the SERS-NP may be conjugated to a targeting ligand, such as antibody, peptide, or aptamer, which selectively recognize biomolecules. This recognition enables the detection of various biomarkers via the characteristic Raman fingerprint of the Raman reporter, for example, chemisorbed on the NP surface (FIG. 4*a*).

For the candidate Raman reporters to be suitable for the use in multiplexed, sensitive molecular imaging of biomarkers in vitro, ex vivo, and in vivo, these reporters may need to satisfy several criteria. We may need large Raman scattering cross-sections for high SERS signal levels and improved sensitivity. Higher Raman scattering intensities may result from the presence of polarizable □-electrons, for example, those found in organic structures with conjugated aromatic systems. In addition, a Raman reporter may need to have high local symmetry that reduces the number of Raman bands while increasing their magnitude. Fewer Raman peaks may reduce the likelihood of spectral overlap between the Raman reporters' fingerprints, increasing multiplexing compatibility. Raman reporter molecules may also need to possess functional anchoring groups for efficient binding to the metal nanoparticle core surface. For example, Raman reporters may have thiol or pyridine moieties for chemisorption on gold surfaces. Finally, a Raman reporter may need to have low or no photobleaching risk to ensure the stability of the Raman signal.

Spectral features and enhancement factors (EFs) influence SERS tag quality. Narrow and sharp Raman emission peaks (with a width of ~1-2 nm) located in the fingerprint range, e.g., 500-2000 $cm^{-1}$, may provide, for example, more than 100-plex imaging capability. Qualitative and quantitative aspects, molecular fingerprints, and/or EFs may need to be understood to evaluate the SERS-NP's capabilities. A library of SERS-NP flavors (i.e., SERS-NPs with different Raman reporters) may be built by, for example, integrating density functional theory (DFT) modeling of Raman scattering with experimental guidance and validation.

The most frequently used non-resonant Raman reporter for labeling SERS nanoparticles is trans-1,2-bis(4-pyridyl) ethylene (BPE). BPE binds to the gold nanoparticle core through the nitrogen atom in a pyridine ring. Attempts to understand BPE to gold binding effect on calculated and experimental SERS spectra have so far only been examined with planar gold nanostructured substrates.

In this example, we chose BPE as a model Raman reporter as it is generally known to exhibit acceptable enhancement and spectral features (FIG. 4*b*).

We also examined a molecule with a similar carbon skeleton but with a thiol anchoring group instead of a pyridine—4,4'-bis(mercaptomethyl)biphenyl (BMMBP) that was sigma-bound to the gold nanoparticle for the first time.

Furthermore, we investigated 5-(4-pyridyl)-1,3,4-oxadiazole-2-thiol (PODT) molecule that has been utilized in SERS imaging and possesses thiol and pyridine anchoring groups.

Lastly, we investigated a new Raman reporter, 5-(4-pyridyl)-1H-1,2,4-triazole-3-thiol (PTT), with similar chemical structure and anchoring groups, except for triazole substituted by oxadiazole (FIG. 4*b*).

All four selected tags (i.e., Raman reporters) gave high EFs, unique molecular fingerprints, indicating that we may use these reporters successfully for bioimaging applications (FIG. 4*d*).

In our experiments, the synthesized SERS-NPs included an about 60 nm gold nanoparticle core labeled with one of the Raman reporters, BPE, BMMBP, PODT, or PTT, and an about 40 nm silica shell. The core-shell structure of gold-silica nanoparticles may allow their transfer into different solvents, enhance the plasmon band, and/or afford easy surface functionalization, e.g., with thiol groups for further conjugation. These thiol groups may be exploited to decorate the nanoparticle's shell surface with antibodies for bioimaging applications or with fluorophores or radionuclides for use with multiple modalities (FIG. 4*a, c*). We utilized a NIR laser with about 785 nm wavelength with low fluorescence background, deep tissue penetration, and no significant photodamage.

We performed the frequency analysis, and Raman calculations using GGA-type BP86, BP86VWN, and BPBE; meta-GGA M06-L; and hybrid GGA B3LYP, PBE0, and B3PW91 with D3 dispersion correction and 6-311++G(d,p) and LANL2DZ basis sets within the Q-Chem package.

First, we evaluated the performance of the functionals on standard Raman spectra, with all spectra smoothed using a Lorentzian convolution of about 5 $cm^{-1}$. Further applied theoretical model chemistry was chosen based on a matrix constructed of inner products between calculated Raman spectra with each functional and experimental Raman spectra of respective powder after performing baseline subtraction and normalizing to unit 2-norm (FIG. 5*a*).

Smaller inner product values, or similarity scores, indicate a relatively lower match between the calculated Raman spectrum and experimental Raman spectrum. Larger inner product values indicate that the calculations may more accurately predict experimentally observed spectral features such as peak locations and intensities.

Figure 5:
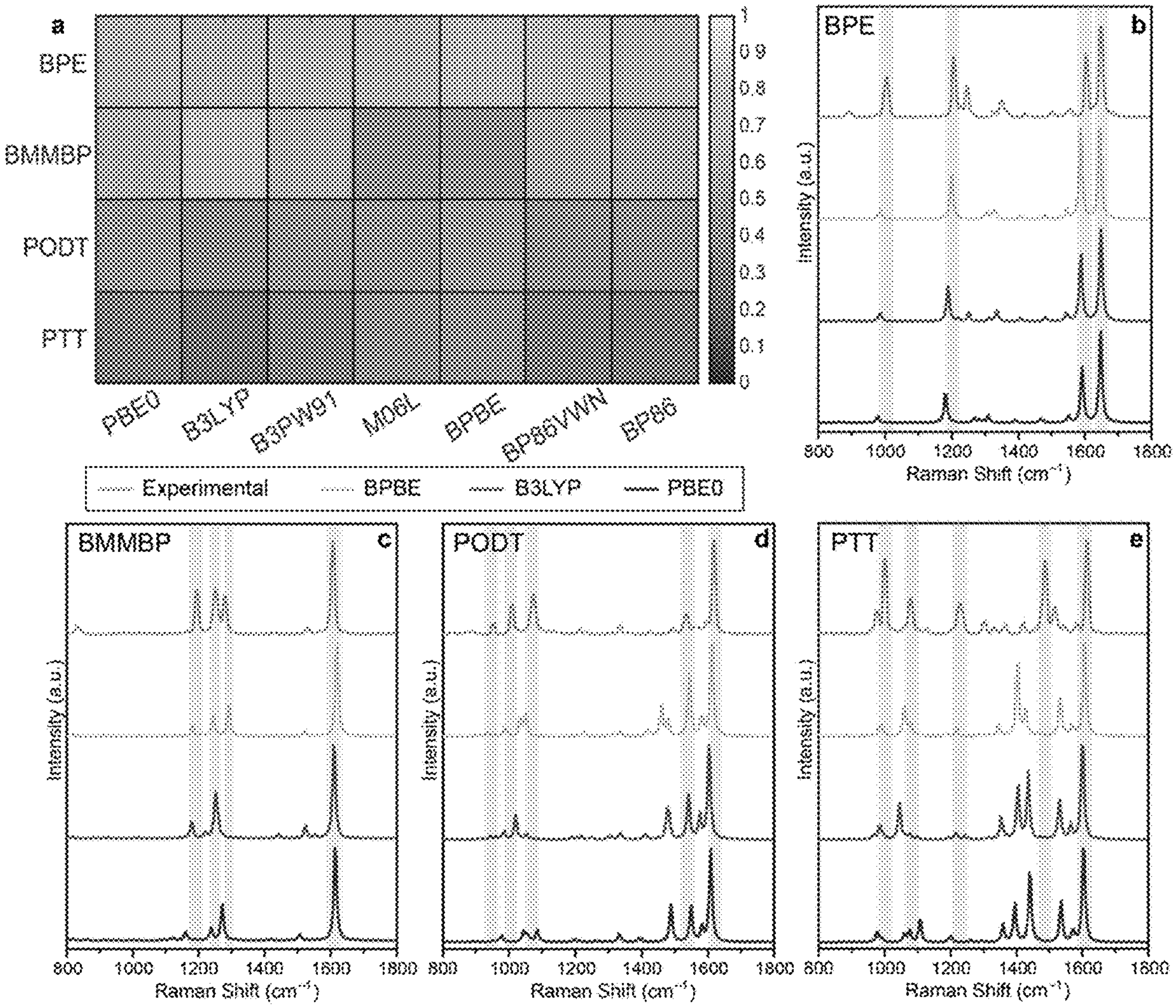
FIG. 5. Depicts correlation matrix built from the spectra calculated with different functionals and respective experimental Raman spectra for each Raman reporter molecule. The color bar indicates the level of fitting signals, where 1 (yellow) means 100% fit and 0 (dark blue) means 0% fit (a). Experimental and calculated gas-phase (BPBE, B3LYP, and PBE0 functionals with 6-311++G(d,p) basis set) Raman spectra for isolated molecules: BPE (b), BMMBP (c), PODT (d), and PTT (e).
Figure 17:
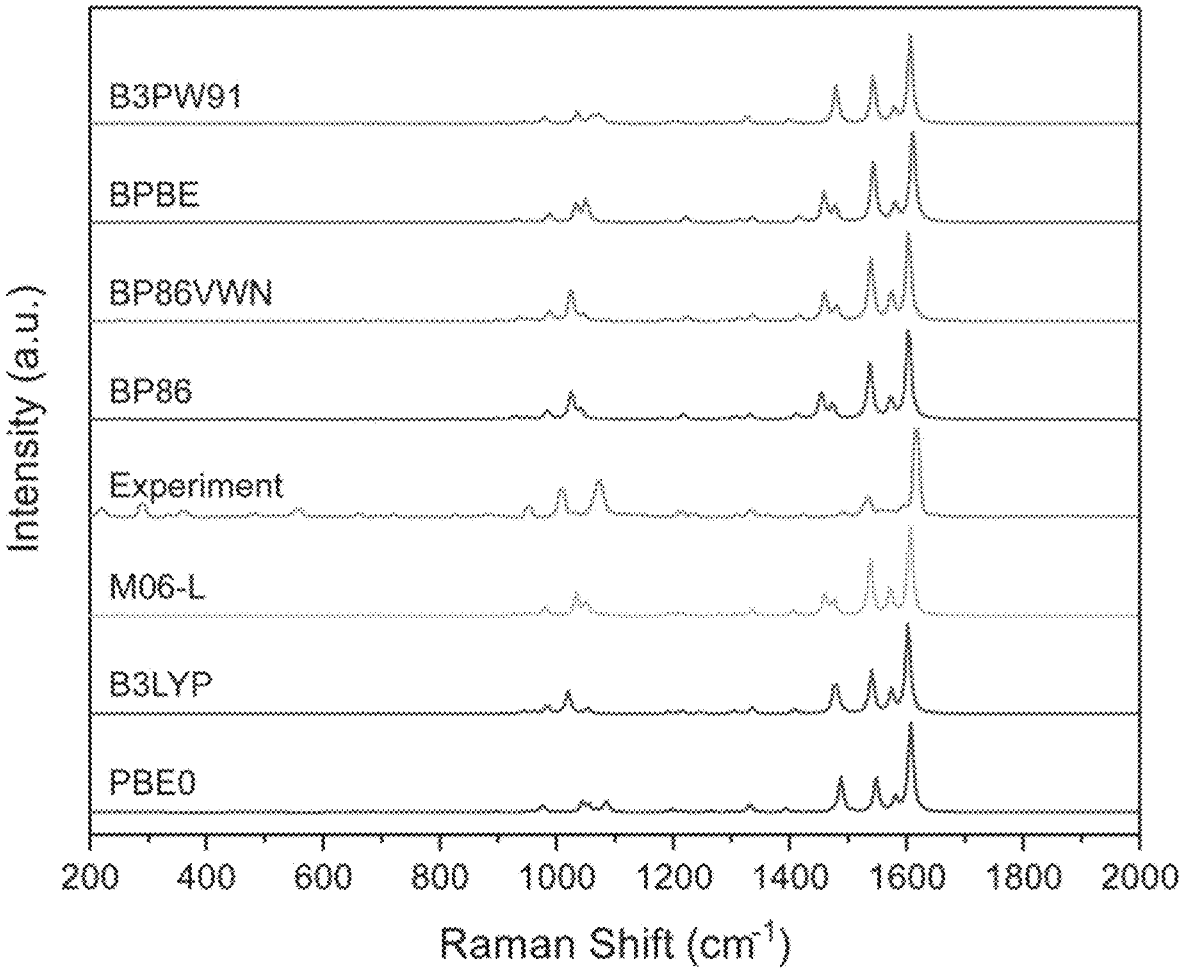
FIG. 17. Normalized calculated gas-phase and measured using 785 nm excitation wavelength (from purified crystalline powder) Raman spectra of 5-(4-pyridyl)-1,3,4-oxadiazole-2-thiol (PODT). Full geometry optimization and frequency calculation for isolated BPE were performed at the density functional theory (DFT) level using various functionals: B3PW91, BPBE, BP86VWN, BP86, M06-L, B3LYP, and PBEO, with 6-311++G(d,p) basis set. All the calculated Raman cross-sections were convoluted by a Lorentzian function with the full width half maximum of 5 $cm^{-1}$ for a better comparison with experimental spectra.
Figure 18:
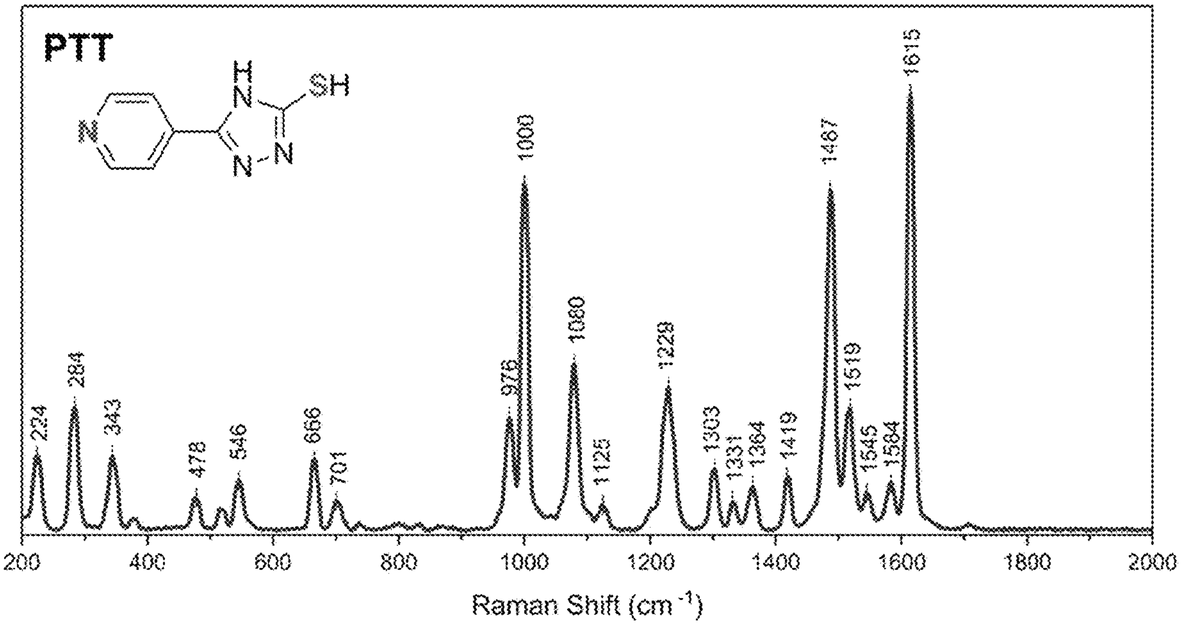
FIG. 18. Raman spectrum of 5-(4-pyridyl)-1H-1,2,4-triazole-3-thiol (PTT) measured from purified crystalline powder using 785 nm excitation wavelength.
Figure 19:
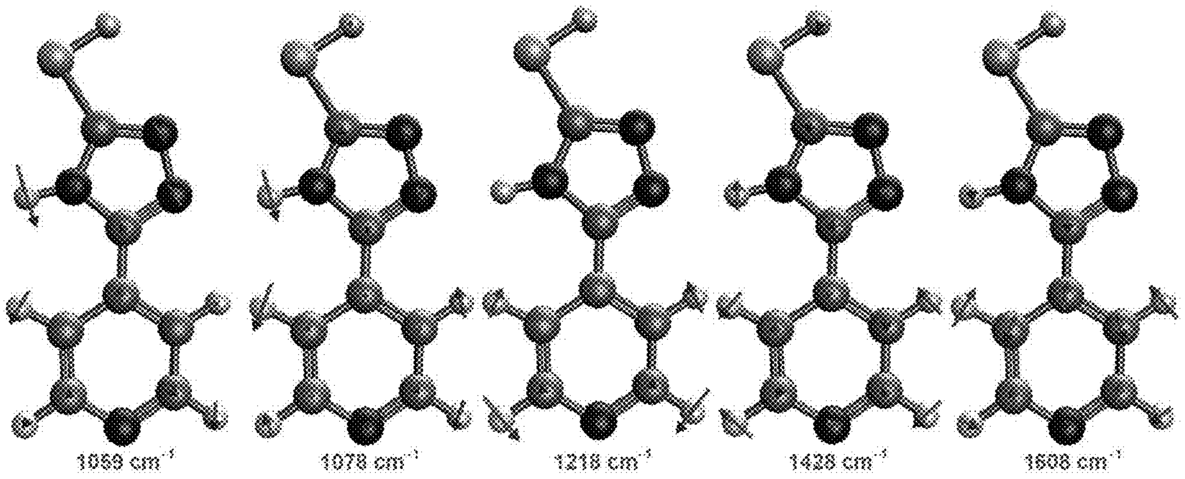
FIG. 19. Vibrational modes of PTT corresponding to the Raman peaks at 1059, 1078, 1218, 1428, and 1608 $cm^{-1}$.
Figure 20:
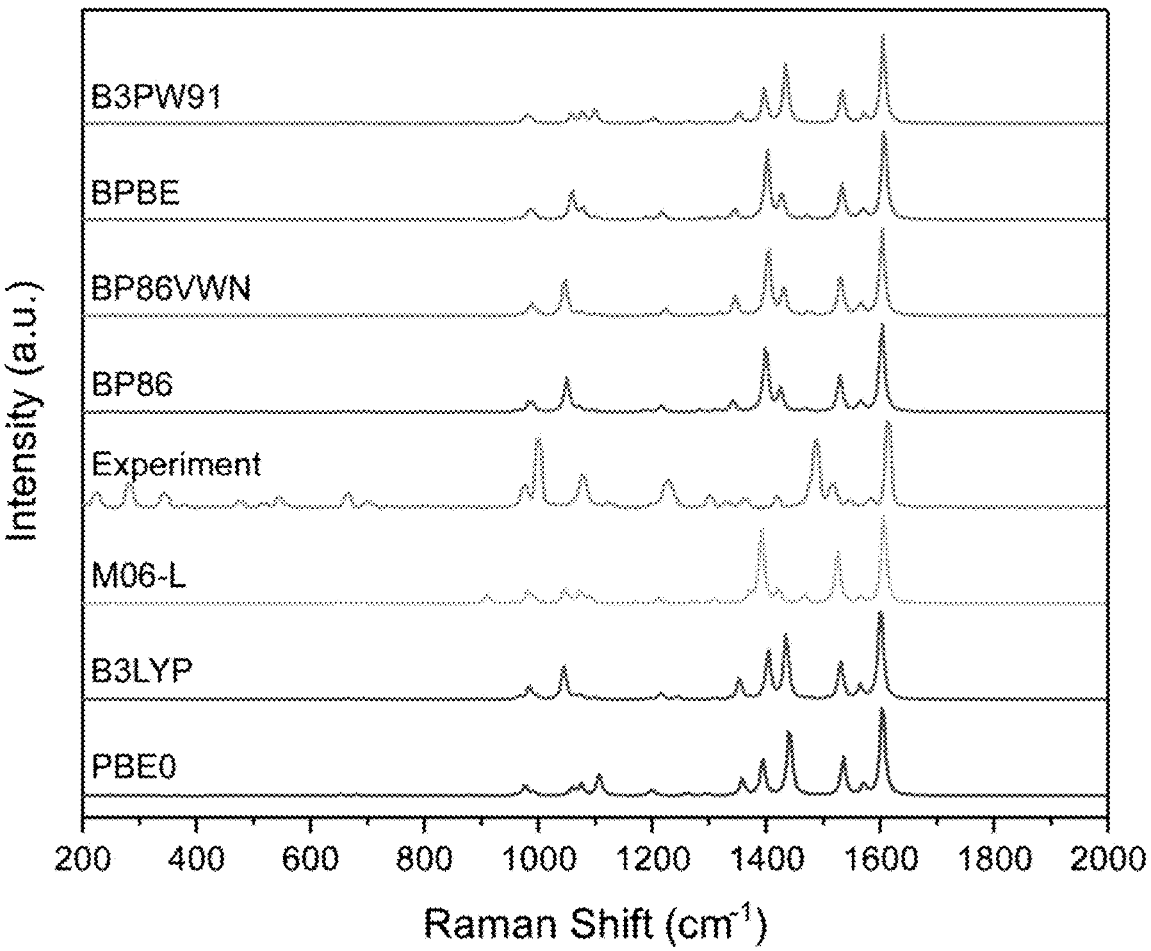
FIG. 20. Normalized calculated gas-phase and measured using 785 nm excitation wavelength (from purified crystalline powder) Raman spectra of 5-(4-pyridyl)-1H-1,2,4-triazole-3-thiol (PTT). Full geometry optimization and frequency calculation for isolated BPE were performed at the density functional theory (DFT) level using various functionals: B3PW91, BPBE, BP86VWN, BP86, M06-L, B3LYP, and PBEO, with 6-311++G(d,p) basis set. All the calculated Raman cross-sections were convoluted by a Lorentzian function with the full width half maximum of 5 $cm^{-1}$ for a better comparison with experimental spectra.

The correlation matrix showed BPBE as the best functional for fitting experimental Raman spectra for BPE, PODT, and PTT (FIG. 5*b-e*). However, the B3LYP-computed spectrum for BMMBP demonstrated 0.80 similarity score (FIG. 17), while BPBE functional gave a more accurate qualitative prediction of frequencies and vibrational modes (FIG. 5*c*).

SERS spectra may look different from standard Raman spectra due to surface selection rules, electric field gradient effects, chemical effects, surface chemistry, etc.

Figure 21:
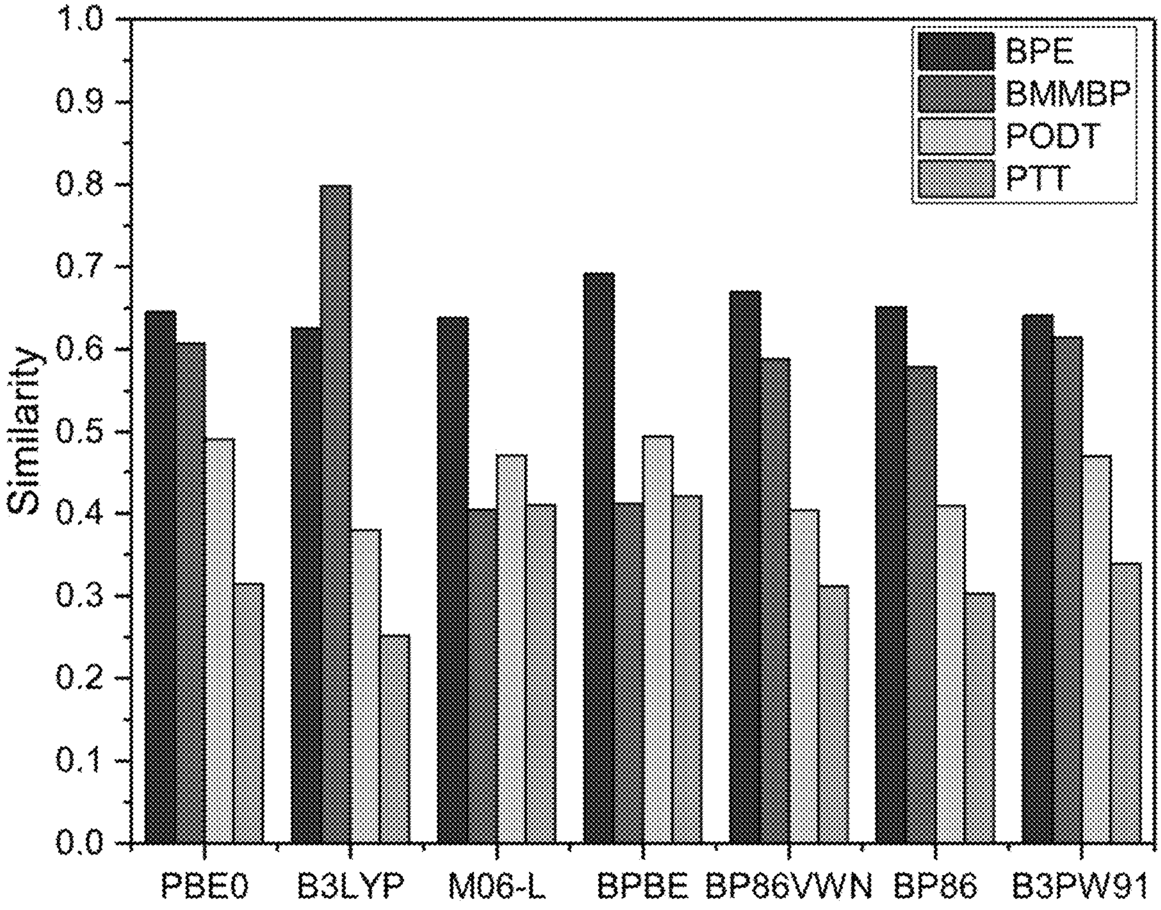
FIG. 21. Similarity of the calculated with different functionals (PBEO, B3LYP, M06-L, BPBE, BP86VWN, BP86, and B3PW91 in 6-311++G(d,p) basis set) Raman spectra with the respective experimental spectra of Raman reporter molecules, where 1 means 100% fit and 0 means 0% fit.

We chose three functionals with 6-311++G(d,p)/LANL2DZ basis set for calculations for the Raman reporters bound to gold: BPBE, the GGA-family functional that fits spectra of individual molecules the best according to the correlation matrix (FIGS. 5*a*, 21), B3LYP, the most used functional for frequency calculations, and PBEO, the hybrid functional that provides the lowest error for electron densities.

Figure 6:
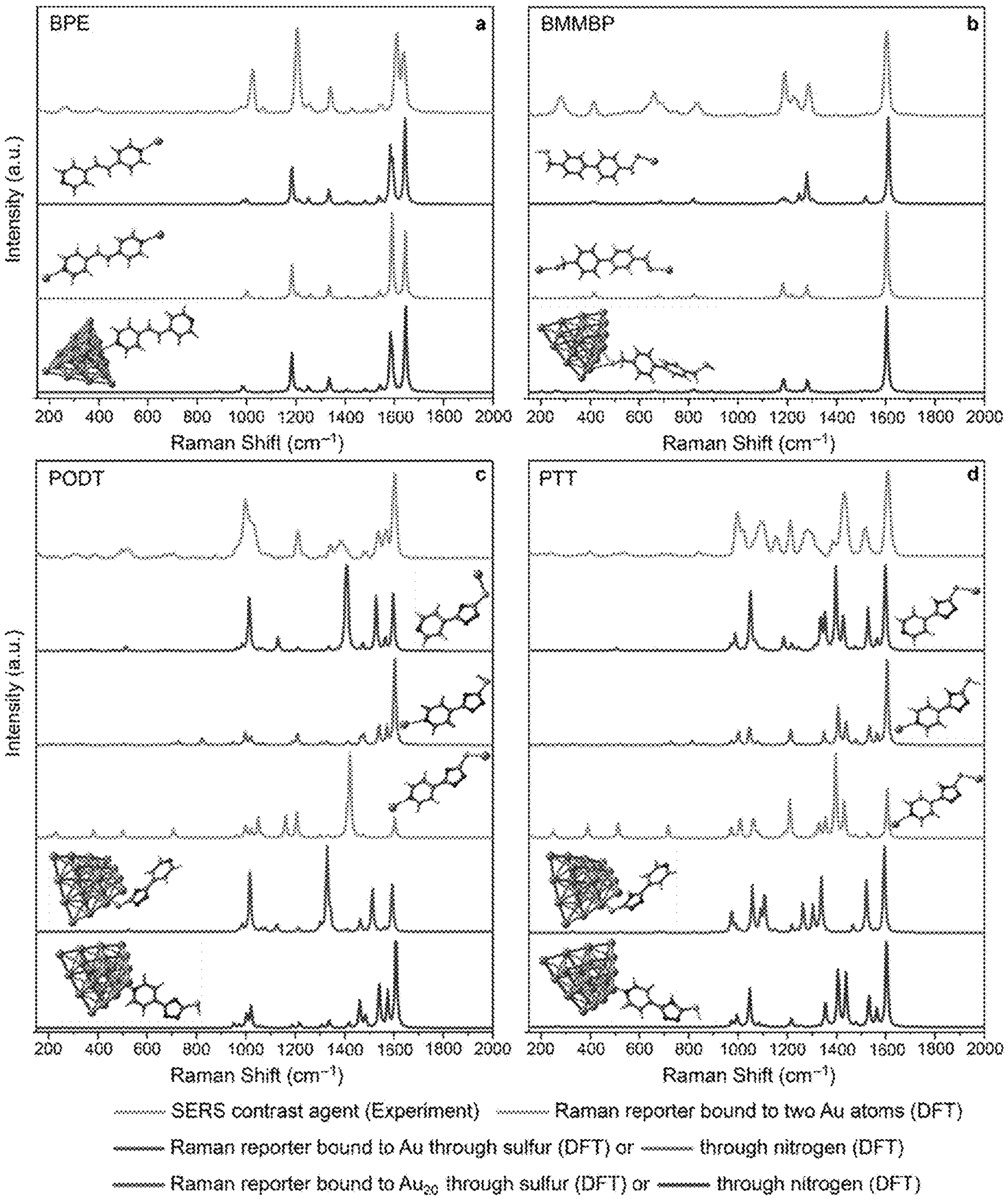
FIG. 6. Depicts experimental and calculated SERS spectra of BPE (a), BMMBP (b), PODT (c), and PTT (d). Experimental SERS spectra were measured for Raman-labeled 60 nm Au-NPs. Full geometry optimization and frequency DFT calculations were performed at B3LYP/6-311++G(d,p)/LANL2DZ level of theory.
Figure 39:
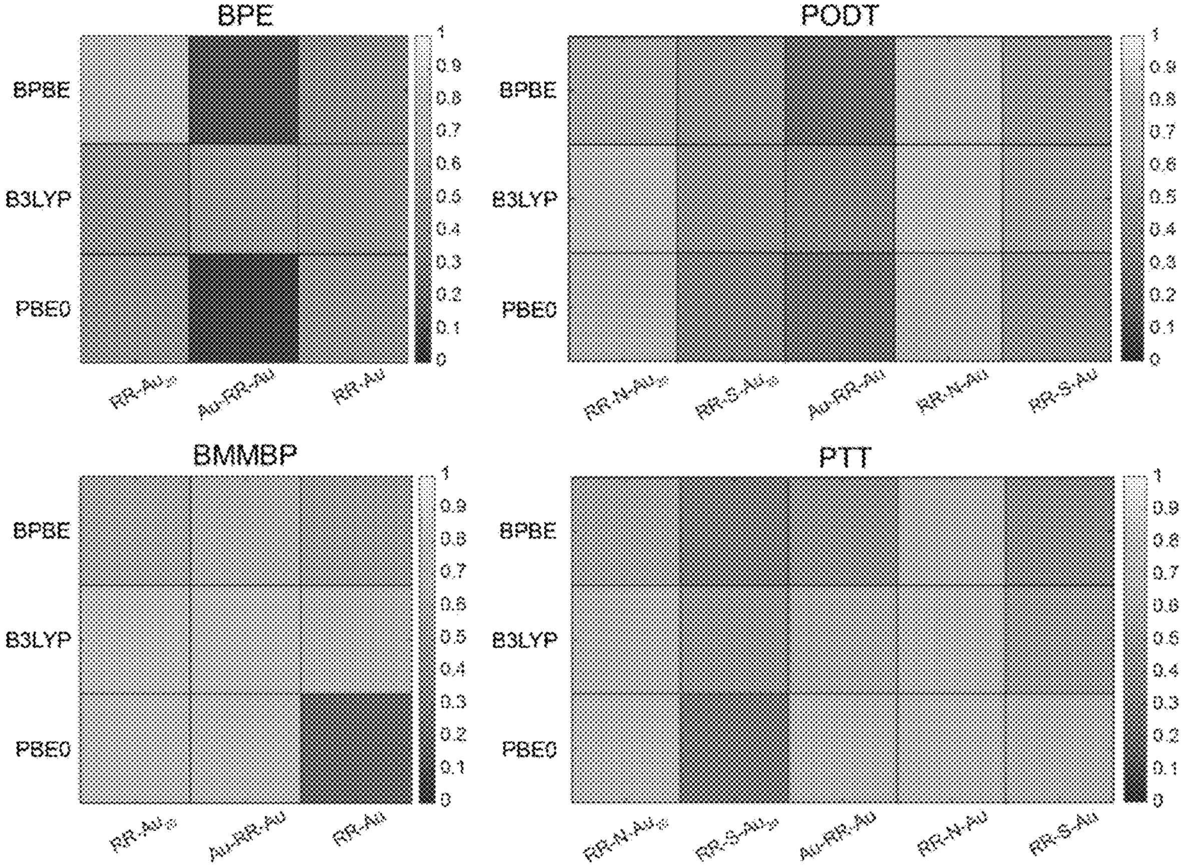
FIG. 39. Correlation matrices built from the calculated with different functionals SERS spectra with the respective Raman reporter (RR) molecules. The color bar indicates the level of fitting signals, where 1 (yellow) means 100% fit and 0 (dark blue) means 0% fit (e).
Figure 40:
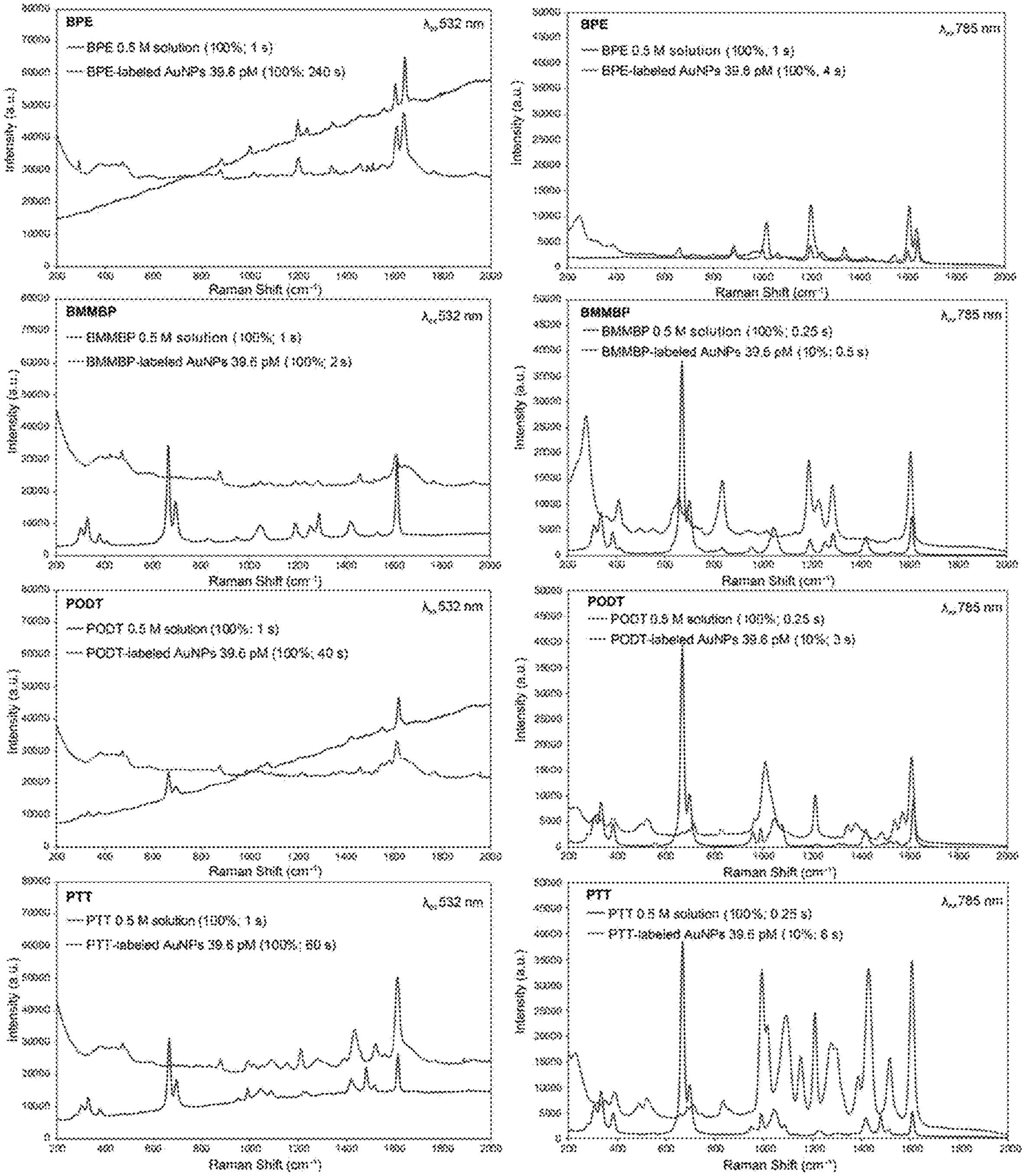
FIG. 40. Unprocessed normal Raman and SERS spectra of 0.5 M solution of Raman reporters and 39.6 pM colloidal solution of 60 nm Au-NPs with excitation wavelength 532 nm (46 mW) and 785 nm (165 mW). Note high fluorescence background on Raman spectra with $\lambda_{ex}$ 532 nm.
Figure 41:
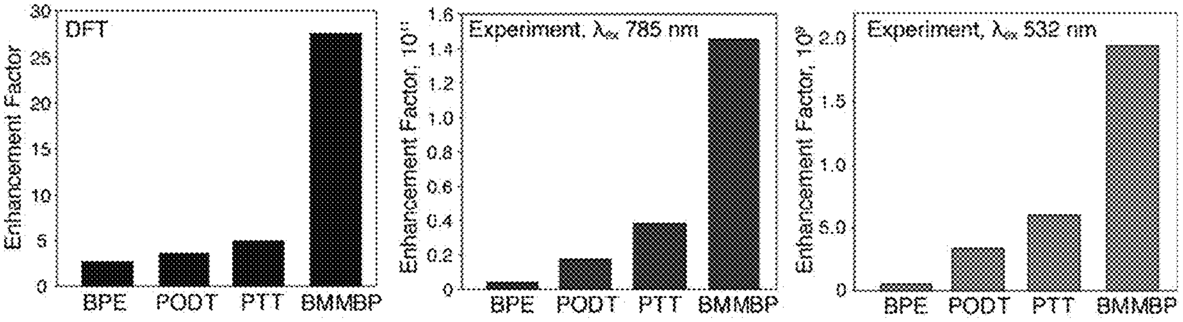
FIG. 41. Calculated and experimental enhancement factors for 60 nm Au-NPs ($EF_{NP}$) labeled with BPE, PODT, PTT or BMMBP.
Figure 42:
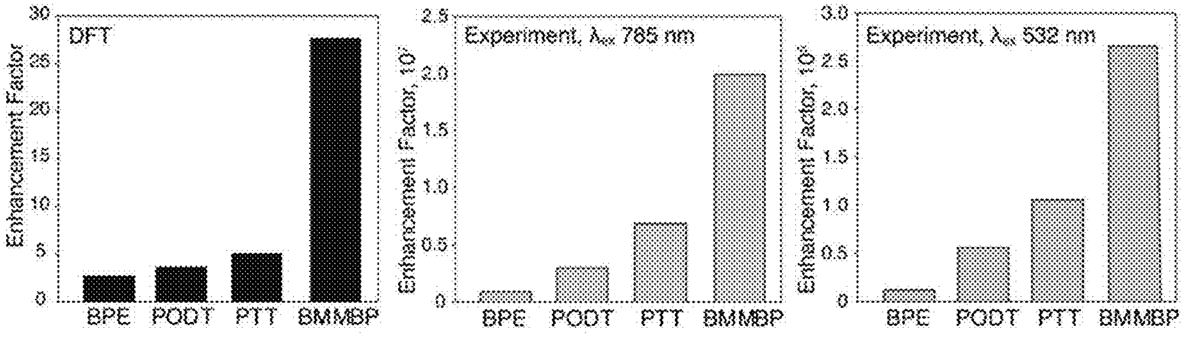
FIG. 42. Calculated and experimental enhancement factors for each Raman reporter ($EF_{RR}$), BPE, BMMBP, PODT or PTT, on the surface of 60 nm Au-NPs.
Figure 43:
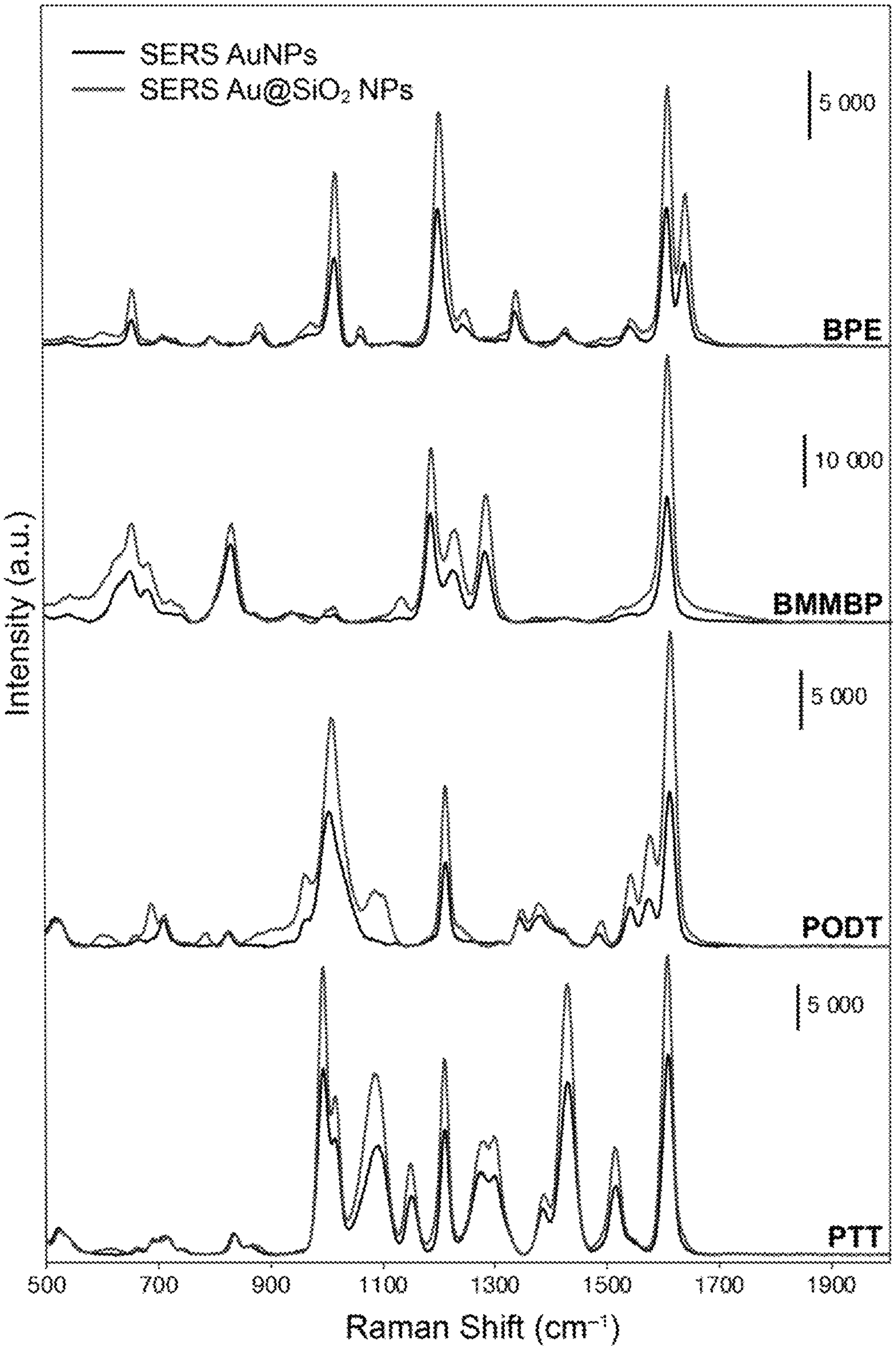
FIG. 43. SERS spectra of uncoated Raman-labeled gold nanoparticles (SERS Au-NPs, 39.6 pM) and silica coated Raman-labeled gold nanoparticles (SERS Au@$SiO_2$ NPs, 39.6 pM) with BPE (100%, 4 s), BMMBP (10%, 0.5 s), PODT (10%, 3 s), or PTT (10%, 6 s) as Raman reporter.

Predicted spectra fit the experimental spectra well (FIG. 5*b-e*). SERS-NP models were simulated as Raman reporter molecules bound to the surface of Au t o clusters (FIG. 6). Correlation matrices were built from those calculated with BPBE, B3LYP, and PBE0 functionals and respective experimental SERS spectra for each nanoparticle flavor (FIG. 39). These matrices demonstrated that B3LYP yielded the most accurate predicted spectrum. Interestingly, the higher similarity scores were obtained for the DFT models of PODT and PTT bound to gold through pyridine rather than the —SH group. Thus we demonstrated that this was a preferable type of interaction.

Understanding and estimating enhancement factors may be necessary for designing SERS-NPs as sensitive, quantitative, and multiplexable contrast agents. We achieved maximum labeling efficiency for each type of non-aggregated Au-NPs by online monitoring of the labeling reaction. Experimental EFs were calculated for each SERS-NP and Raman reporter molecule with nanoparticle concentrations measured by nanoparticle tracking analysis (NTA):

$$EF = \frac{\text{Signal from Tag Solution}}{\text{Signal from Solution of Label Molecule}} \times \frac{\text{Concentration of Label Solution}}{\text{Concentration of Label on Tag}}$$

The most prominent peak of each Raman reporter was observed at ca. 1600 $cm^{-1}$ corresponding to the symmetrical stretching C—C and bending C—H vibrations of pyridine in BPE (about 1610 $cm^{-1}$), PODT (about 1606 $cm^{-1}$), and PTT (about 1611 $cm^{-1}$) , and the symmetrical stretching C—C and bending C—H vibrations of the benzene ring in BMMBP (about 1606 $cm^{-1}$) (see below for detailed assignments). These most abundant signals were chosen for EF evaluation.

Figure 7:
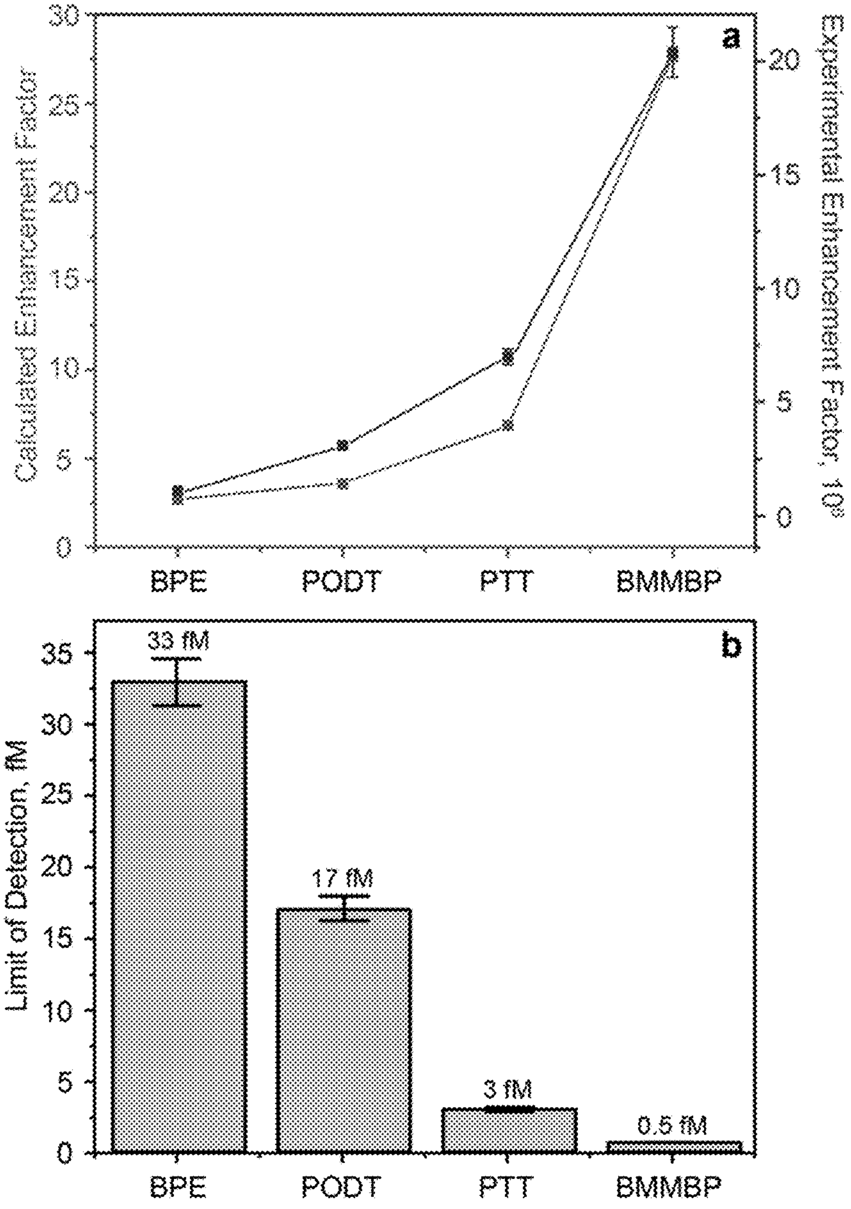
FIG. 7. Correlation between experimental and DFT calculated EFs for bare SERS nanoparticles (a) and limits of detection (LODs) for each silica-coated SERS nanoparticle with excitation using an about 785-nm laser (about 165 mW, 10%, 10 s) (b).

The calculated EFs were assessed as a ratio of the Raman band intensity for the reporter molecule bound to the surface of an $Au_{20}$ cluster to the intensity of the unenhanced reporter molecule, both calculated in the best level of theory: B3LYP/6-311++G(d,p)/LANL2DZ. Gold-enhanced PODT, PTT, and BMMBP outperformed BPE in enhancement factors and sensitivity. The presence of sulfur in Raman reporters may increase nucleophilicity, making the molecules more polarizable. PTT and BMMBP-labeled nanoparticles showed more than one and two orders higher EFs and, thus, the lower limit of detection (LOD) compared to BPE, respectively (FIG. 7).

This means that these SERS-NPs may be as bright as surface-enhanced resonance Raman spectroscopy (SERRS) NPs that have NIR dyes as Raman reporters with absorption peaks that are matched with the excitation light sources (e.g., 785-nm diode lasers), but do not have overcrowded spectral fingerprints with high fluorescence background that could complicate detection in highly multiplexed mixtures.

We compared experimental EFs observed for 60 nm spheric gold core and DFT modeled EFs for the Au t o cluster. It is important to note that these experimentally observed EFs and calculated EFs correlate and change with decreasing LOD of Raman reporters (FIG. 7*a*). The Au20 cluster may not exhibit a plasmon feature. Yet, one may compare a relative contribution of chemical mechanism to the SERS signals enhancement for each Raman reporter. This is the first example of such observation for a series of molecules, which was achieved with the B3LYP-D3 functional.

We have demonstrated an approach to virtually predict the spectral features and potential enhancement factor of Raman reporter molecules for potential multiplexed imaging applications. B3LYP-D3/6-311G++(d,p)/LANL2DZ may preferably be used in fitting experimental data. A multi-marker approach may potentially improve the sensitivity and specificity of detecting certain disease processes Raman spectroscopic imaging may yield rich multiplexed information in a single imaging acquisition, making it an ideal imaging strategy to further develop for multi-marker interrogation. The DFT approach of this disclosure may also be extended to predict the presence and position of peaks in the cell-silent Raman spectral window. For PODT and PTT that have sulfhydryl group and aromatic amine, DFT calculations predicted the Raman reporters preferably to bind to the Au-NPs through the nitrogen atom Enhancement factors and sensitivity of SERS-NPs may be calculated by DFT and prioritized according to the highest sensitivity or due to a similar sensitivity level for multiplexed applications. Finally, we observed that EFs calculated with B3LYP-D3 correlate well with experimental values and match the limits of detection for the corresponding Raman reporters.

EXAMPLE 6. Raman Signatures of Isolated Raman Reporters

Figure 8:
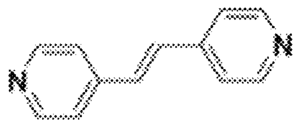
FIG. 8. Raman reporter molecules.
Figure 8:
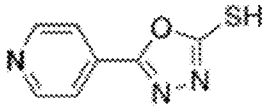
Figure 8:
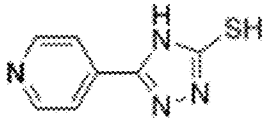
Figure 8:
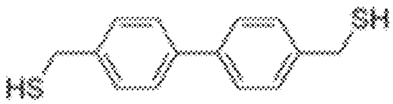
Figure 9:
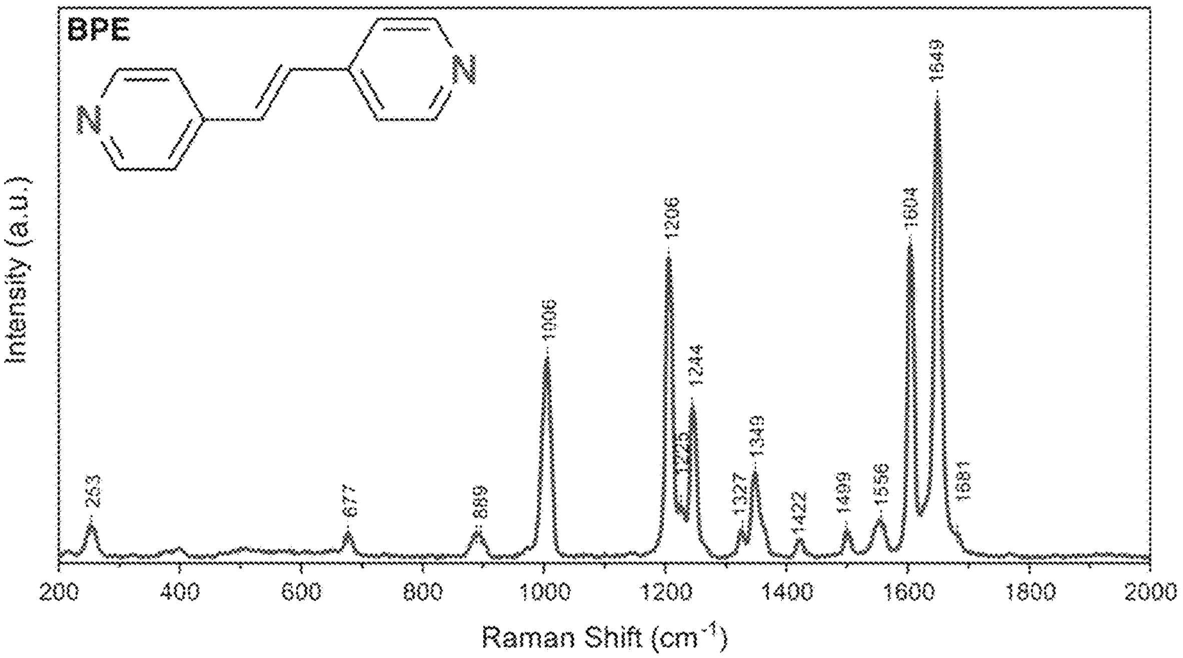
FIG. 9. Raman spectrum of trans-1,2-bis(4-pyridyl)ethylene (BPE) measured from purified crystalline powder using 785 nm excitation wavelength.
Figure 10:
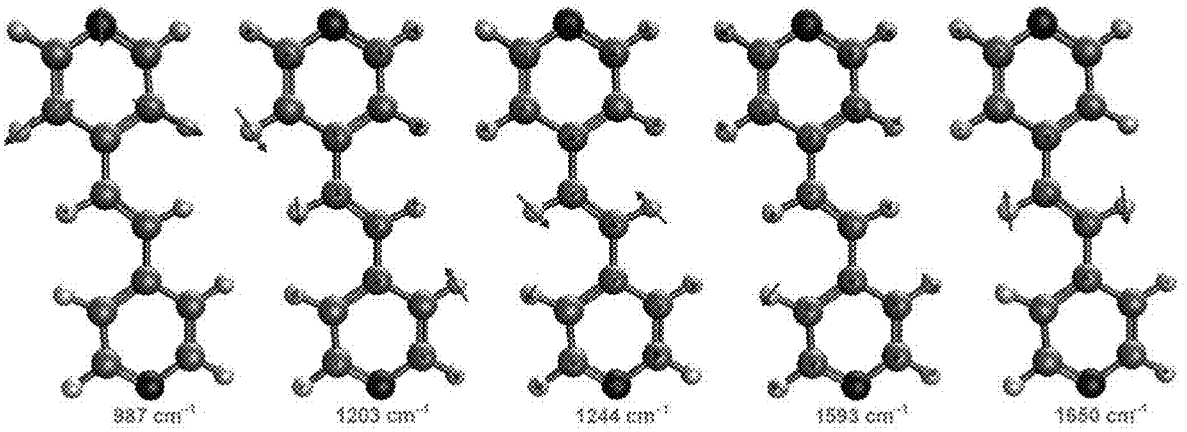
FIG. 10. Vibrational modes of BPE corresponding to the Raman peaks at 987, 1203, 1244, 1593, and 1650 $cm^{-1}$.
Figure 11:
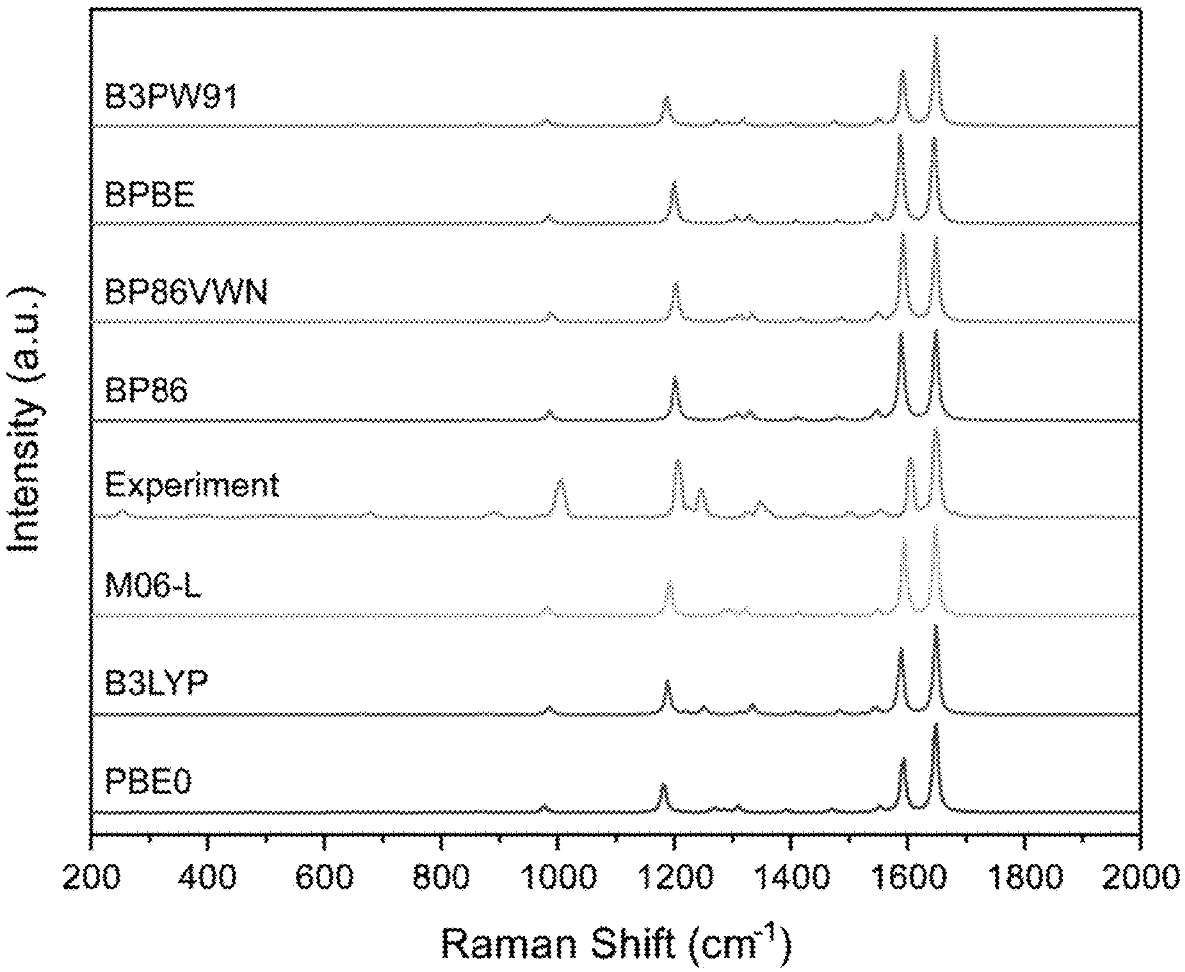
FIG. 11. Normalized calculated gas-phase and measured using 785 nm excitation wavelength (from purified crystalline powder) Raman spectra of trans-1,2-bis(4-pyridyl)ethylene (BPE). Complete geometry optimization and frequency calculation for isolated BPE were performed at the density functional theory (DFT) level using various functionals: B3PW91, BPBE, BP86VWN, BP86, M06-L, B3LYP, and PBEO, with 6-311++G(d,p) basis set. All the calculated Raman cross-sections were convoluted by a Lorentzian function with the full-width-half-maximum of 5 $cm^{-1}$ for a better comparison with experimental spectra.
Figure 12:
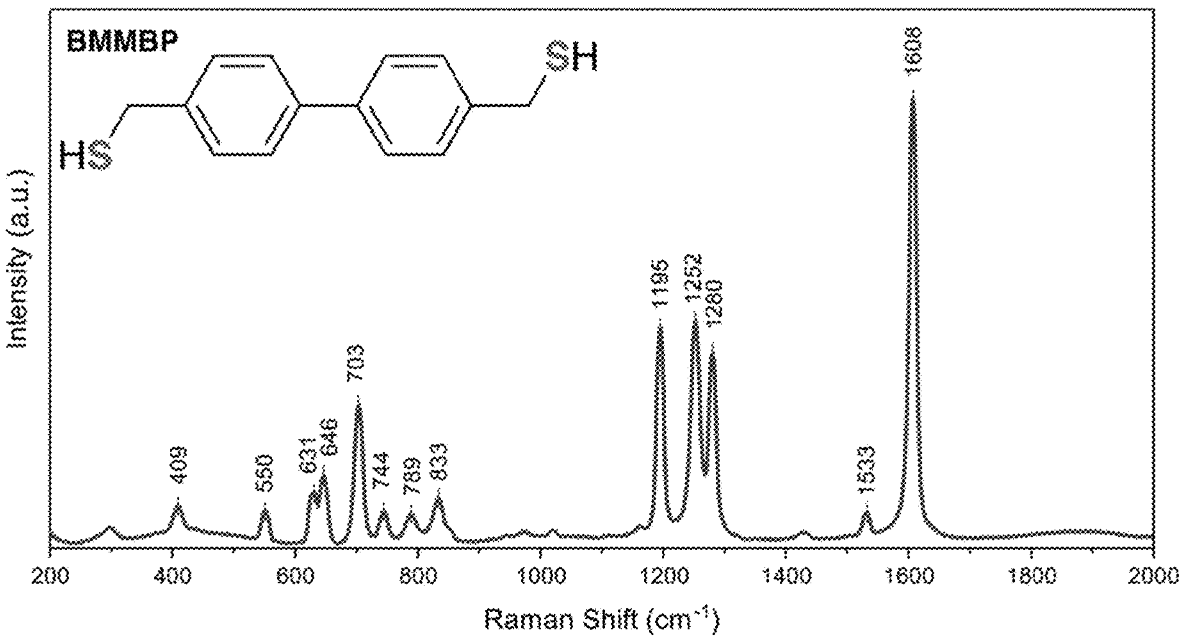
FIG. 12. Raman spectrum of 4,4'-bis(mercaptomethyl) biphenyl (BMMBP) measured from purified crystalline powder using 785 nm excitation wavelength.
Figure 13:
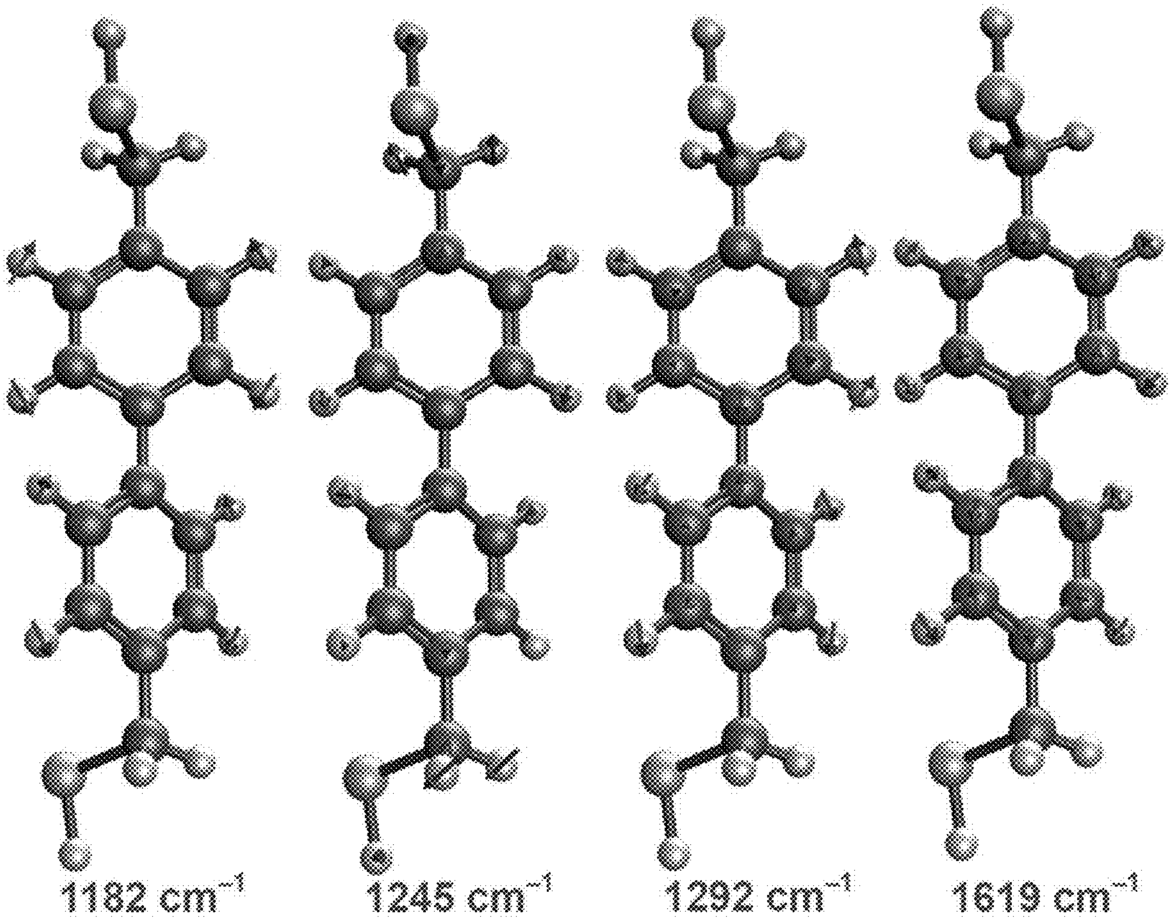
FIG. 13. Vibrational modes of BMMBP corresponding to the Raman peaks at 1182, 1245, 1292, and 1619 $cm^{-1}$.
Figure 14:
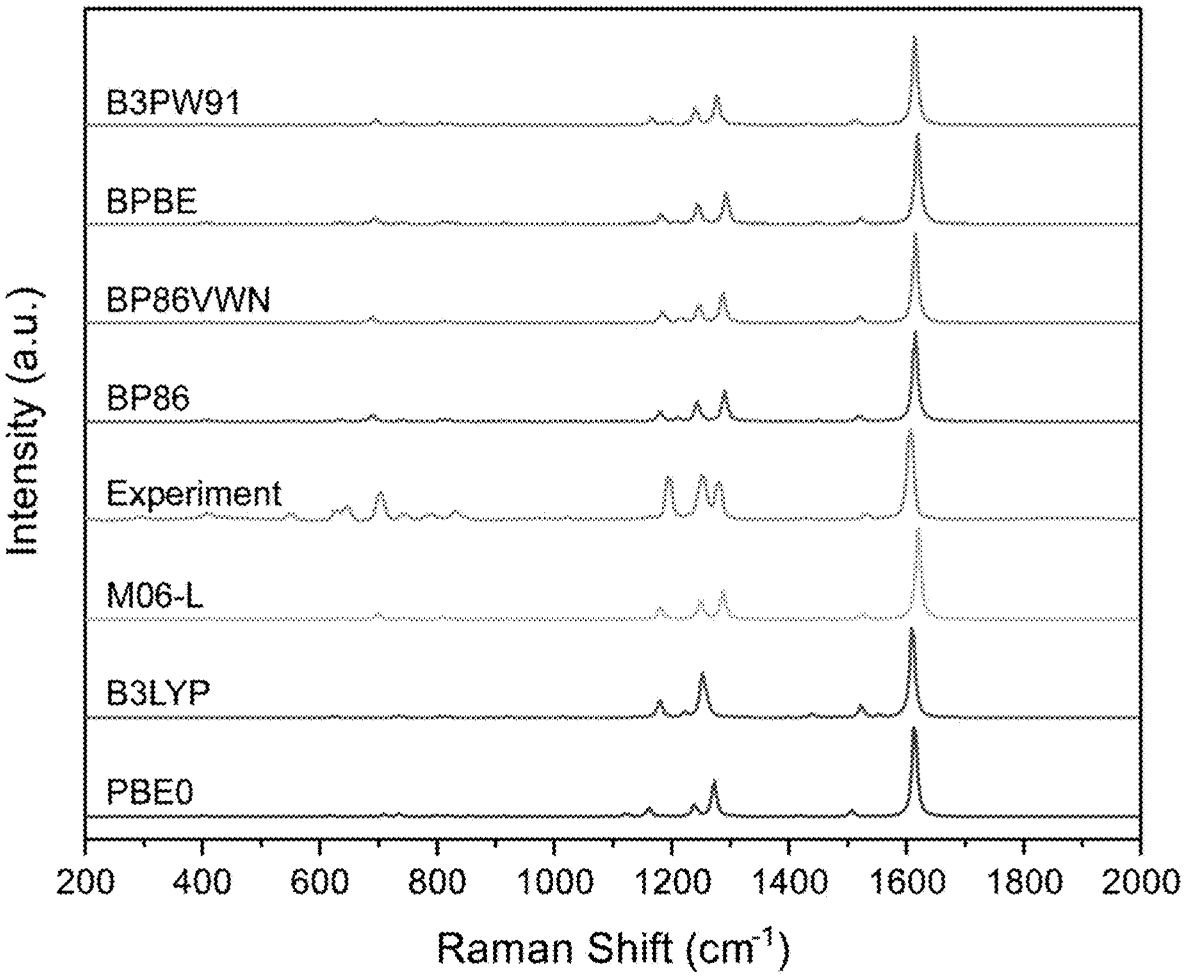
FIG. 14. Normalized calculated gas-phase and measured using 785 nm excitation wavelength (from purified crystalline powder) Raman spectra of 4,4'-bis(mercaptomethyl) biphenyl (BMMBP). Full geometry optimization and frequency calculation for isolated BPE were performed at the density functional theory (DFT) level using various functionals: B3PW91, BPBE, BP86VWN, BP86, M06-L, B3LYP, and PBEO, with 6-311++G(d,p) basis set. All the calculated Raman cross-sections were convoluted by a Lorentzian function with the full width half maximum of 5 $cm^{-1}$ for a better comparison with experimental spectra.
Figure 15:
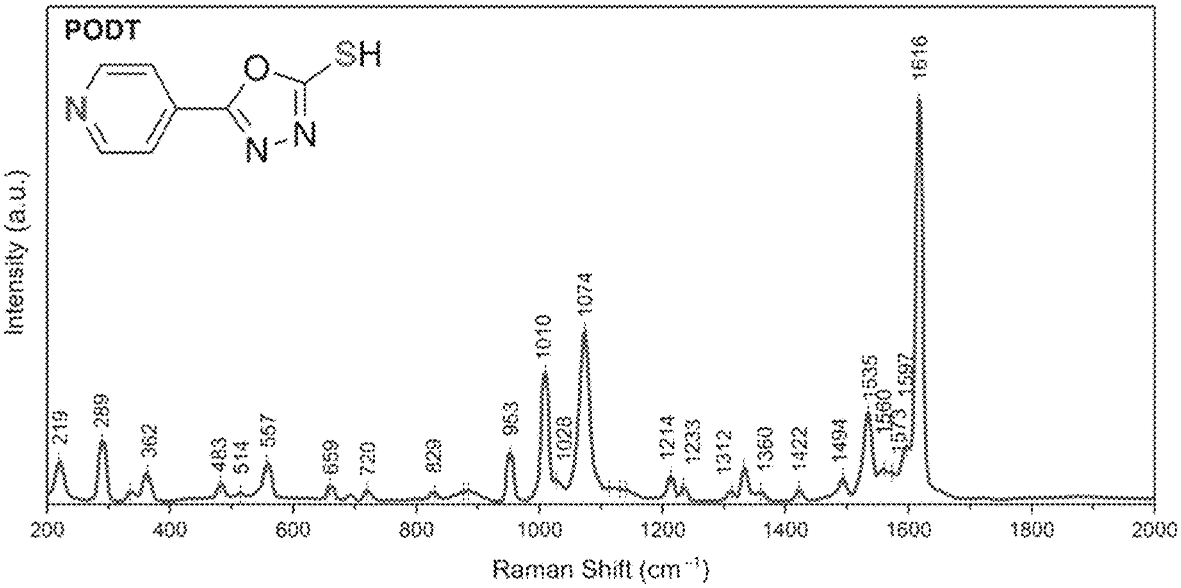
FIG. 15. Raman spectrum of 5-(4-pyridyl)-1,3,4-oxadiazole-2-thiol (PODT) measured from purified crystalline powder using 785 nm excitation wavelength.
Figure 16:
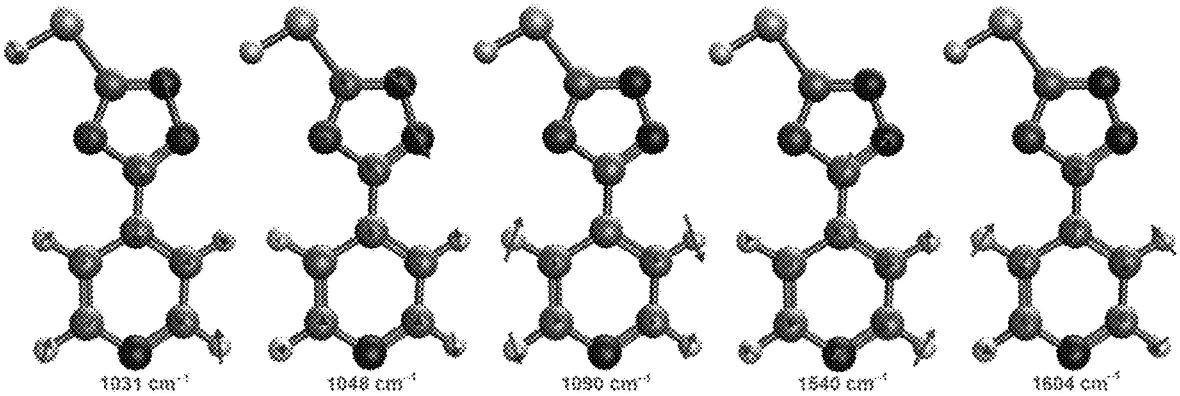
FIG. 16. Vibrational modes of PODT corresponding to the Raman peaks at 1031, 1048, 1090, 1540, and 1604 $cm^{-1}$.

Four Raman reporter molecules investigated in this example is shown in FIG. 8. Calculated and experimental values and spectra of these Raman reporters are shown in FIGS. 9-21, and tabulated in Tables 1-5.

Prior to plotting the computational spectra, the Raman shifts were scaled (Table 5) so that the most intense bands from the experimental spectra overlap with the computed ones.

TABLE 1

Comparison of the experimental and calculated (BPBE/6-311++G(d, p))[a] Raman spectra of BPE ($C_{2h}$ symmetry) in the spectral range 200-2000 $cm^{-1}$.

| Raman Shift, $cm^{-1}$ | | $S_{Raman}$[c], | |
|---|---|---|---|
| Experimental | Calculated[b] | $Å^4$/amu | Assignments[d] |
| 253 | 283 | 2.3 | $\delta(C_{vin}—C_{py})$ |

TABLE 1-continued

Comparison of the experimental and calculated (BPBE/6-311++G(d, p))[a] Raman spectra of BPE ($C_{2h}$ symmetry) in the spectral range 200-2000 $cm^{-1}$.

| Raman Shift, $cm^{-1}$ | | $S_{Raman}$[c], | |
|---|---|---|---|
| Experimental | Calculated[b] | Å$^4$/amu | Assignments[d] |
| 677 (w) | 666 | 0.7 | in-plane ν$_{ring}$ |
| 889 (w) | 877 | 20.9 | δ(C—H)$_{vin}$, δ(C—N—C), ν(C—C)$_{py}$ |
| | 880 | 12.4 | γ(C—H) |
| 1006 (m) | 987 | 166.3 | ring breathing |
| | 988 | 141.2 | ring breathing |
| 1206 (s) | 1203 | 1383.8 | ν(ring-C$_{vin}$), δ(C—H)$_{py}$ |
| 1225 (w) | 1224 | 9.8 | δ(C—H)$_{py}$, ν (C—N) |
| 1244 (m) | 1297 | 55.6 | δ(C—H)$_{vin}$, in-plane ν$_{ring}$ |
| 1327 (w) | 1311 | 241.6 | δ(C—H)$_{vin}$, ν(C—C) |
| 1349 (m) | 1332 | 285.1 | δ(C—H), δ(C$_{vin}$—C) |
| 1422 (w) | 1414 | 101.2 | δ(C—H), δ(C$_{vin}$—C) |
| 1499 (w) | 1483 | 122.8 | δ(C—H)$_{py}$, ν(C—C)$_{py}$ |
| 1556 (m) | 1551 | 311.8 | δ(C—H)$_{py}$, ν(C—N)$_{py}$, ν(C—C) |
| 1604 (vs) | 1593 | 2867.8 | ν(C—C)$_{py}$, δ(C—H)$_{py}$ |
| 1649 (vs) | 1650 | 3014.8 | ν(C═C)$_{vin}$ |

[a]Empirically chosen scaling factor: 1.0068.
[b]w, weak; m, medium; s, strong; vs, very strong.
[c]$S_{Raman}$, Raman scattering activity (Å$^4$/amu).
[d]ν, stretch; δ, in-plane bend; γ, out-of-plane bend; vin, vinyl; py, pyridyl.

TABLE 2

Comparison of the experimental and calculated (BPBE/6-311++G(d, p))[a] Raman spectra of BMMBP ($C_2$ symmetry) in the spectral range 200-2000 $cm^{-1}$.

| Raman Shift, $cm^{-1}$ | | $S_{Raman}$,[c] | |
|---|---|---|---|
| Experimental | Calculated[b] | Å$^4$/amu | Assignments[d] |
| 409 (w) | 407 | 30.7 | out-of-plane skeletal |
| 550 (w) | 549 | 12.2 | out-of-plane skeletal |
| 631 (w) | 631 | 10.5 | δ(C—C—C)$_{bp}$, δ(H—C—H)$_{me}$ |
| | 635 | 19.7 | δ(C—C—C)$_{bp}$, δ(H—S—C) |
| 646 (w) | 644 | 8.7 | δ(S—H), out-of-plane skeletal |
| 703 (m) | 694 | 134.1 | ν(C—S) |
| 744 (w) | 742 | 33.1 | out-of-plane skeletal |
| 789 (w) | 810 | 39.1 | ring deformation |
| 833 (w) | 821 | 29.5 | γ$_s$(C—H)$_{bp}$ |
| 1195 (m) | 1182 | 219.1 | δ(C—H) |
| 1252 (m) | 1245 | 432 | γ$_s$($CH_2$) |
| 1280 (m) | 1292 | 731.6 | inter-ring C—C stretching, δ$_{as}$(C—H)$_{bp}$ |
| 1533 (w) | 1523 | 130.5 | ring stretching, δ$_{as}$(C—H)$_{bp}$ |
| 1608 (vs) | 1619 | 2136.0 | ν(C—C)$_{bp}$, δ(C—H)$_{bp}$ |

[a]Empirically chosen scaling factor: 1.0068.
[b]w, weak; m, medium; s, strong; vs, very strong.
[c]$S_{Raman}$, Raman scattering activity (Å$^4$/amu).
[d]ν, stretch; δ, in-plane bend; γ, out-of-plane bend; s, symmetric; as, asymmetric; bp, biphenyl; me, methylene.

TABLE 3

Comparison of the experimental and calculated (BPBE/6-311++G(d, p))[a] Raman spectra of PODT ($C_s$ symmetry) in the spectral range 200-2000 $cm^{-1}$.

| Raman Shift, $cm^{-1}$ | | $S_{Raman}$,[c] | |
|---|---|---|---|
| Experimental | Calculated[b] | Å$^4$/amu | Assignments[d] |
| 219 (w) | 203 | 1.0 | τ(C—O—C), τ(S—H), τ(N—C)$_{py}$ |
| 289 (m) | 253 | 8.2 | δ(C—S), δ(C$_{ox}$—C$_{py}$) |
| 362 (w) | 314 | 0.9 | δ(S—H), ν(C$_{ox}$—C$_{py}$), δ(C—H) |
| 483 (w) | 459 | 3.5 | δ(C$_{ox}$—C$_{py}$), δ(C—S), |
| 557 (w) | 503 | 2.0 | τ(C—H), τ(S—H), τ(C—C)$_{py}$ |
| 659 (w) | 665 | 6.7 | δ(C—C)$_{py}$, δ(C—N)$_{py}$ |
| 720 (w) | 697 | 5.1 | ν(C$_{ox}$—C$_{py}$), δ(C—N)$_{py}$, δ(C—C)$_{py}$ |
| 829 (w) | 985 | 85.1 | (ring breathing)$_{py}$, ν(C—O)$_{ox}$ |
| 953 (m) | 1031 | 174.5 | ν(N—N)$_{ox}$, ν(C—O)$_{ox}$, δ(S—H), (ring breathing)$_{py}$ |
| 1010 (s) | 1048 | 214.0 | ν(N—N)$_{ox}$, ν(C—O)$_{ox}$, ν(C—S)$_{ox}$, (ring breathing)$_{py}$ |
| 1074 (s) | 1090 | 3.5 | δ(C—H)$_{py}$ |
| 1214 (w) | 1186 | 10.7 | ν$_s$(C—O)$_{ox}$, δ(S—H), δ(C—H)$_{py}$, (ring breathing)$_{py}$ |
| 1233 (w) | 1218 | 51.2 | δ$_s$(C—H)$_{py}$, ν$_s$(C—N)$_{py}$ |
| 1312 (w) | 1291 | 6.4 | δ$_{as}$(C—H)$_{py}$, ν$_{as}$(C—C)$_{py}$, ν$_{as}$(C—N)$_{py}$, ν$_s$(C—O)$_{ox}$ |
| 1327 (w) | 1310 | 30.2 | δ$_{as}$(C—H)$_{py}$, ν$_s$(C—C)$_{py}$, ν$_s$(C—N)$_{py}$, ν$_s$(C—O)$_{ox}$ |
| 1360 (w) | 1332 | 46.8 | δ$_{as}$(C—H)$_{py}$, δ(C$_{ox}$—C$_{py}$) |
| 1422 (w) | 1414 | 60.7 | δ$_s$(C—H)$_{py}$, (ring breathing)$_{ox}$ |
| 1494 (w) | 1475 | 150.4 | δ$_{as}$(C—H)$_{py}$, ν$_s$(C—N)$_{ox}$ |
| 1535 (m) | 1540 | 604.1 | ν$_s$(C—N)$_{ox}$, ν$_{py\ ring}$, ν(C$_{py}$—C$_{ox}$), δ$_{as}$(C—H)$_{py}$ |
| 1597 (sh) | 1577 | 177.8 | ν(C—N)$_{ox}$, ν$_{py\ ring}$, ν(C$_{py}$—C$_{ox}$), δ(C—H)$_{py}$ |
| 1616 (vs) | 1608 | 962.3 | ν$_s$(C—C)$_{py}$, δ$_s$(C—H)$_{py}$ |

[a]Empirically chosen scaling factor: 1.0068.
[b]w, weak; m, medium; s, strong; vs, very strong; sh, shoulder.
[c]$S_{Raman}$, Raman scattering activity (Å$^4$/amu).
[d]ν, stretch; δ, in-plane bend; γ, out-of-plane bend; s, symmetric; as, asymmetric; py, pyridyl; ox, oxadiazole.

TABLE 4

Comparison of the experimental and calculated (BPBE/6-311++G(d, p))[a] Raman spectra of PTT ($C_s$ symmetry) in the spectral range 200-2000 $cm^{-1}$.

| Raman Shift, $cm^{-1}$ | | $S_{Raman}$,[c] | |
|---|---|---|---|
| Experiment | Calculated[b] | Å$^4$/amu | Assignments[d] |
| 224 (m) | 252 | 6.9 | δ(S—C—N)$_{py}$, δ(C—C—C)$_{py}$ |
| 284 (m) | 311 | 1.2 | τ$_{py}$, γ(S—N—N—C), γ(C—N—N—C) |
| 343 (m) | 357 | 0.1 | ν(C$_{py}$—C$_{tr}$), δ$_{py}$, δ(S—C—N), ν(C—C)$_{py}$ |
| 478 (w) | 456 | 4.5 | τ(H—N—N—C), τ$_{py}$ |

TABLE 4-continued

Comparison of the experimental and calculated (BPBE/6-311++G(d, p))[a] Raman spectra of PTT ($C_s$ symmetry) in the spectral range 200-2000 $cm^{-1}$.

| Raman Shift, $cm^{-1}$ | | $S_{Raman}$,[c] | |
|---|---|---|---|
| Experiment | Calculated[b] | $Å^4$/amu | Assignments[d] |
| 520 (w) | 504 | 1.8 | ν(S—C), δ(C—C—C)$_{py}$, δ(C—N—C)$_{py}$ |
| 546 (m) | 514 | 2.2 | τ$_{py}$, τ(H—N—N—C), τ(H—C—C—C) |
| 666 (m) | 664 | 6.4 | δ$_{py}$ |
| 701 (w) | 695 | 6.4 | δ$_{py}$, ν(C$_{py}$—C$_{tr}$) |
| 976 (m) | 984 | 54.0 | δ(N—C—N)$_{tr}$, ν(N—C)$_{tr}$, ν(N—C)$_{py}$ |
| | 991 | 77.0 | δ$_{py}$, δ$_{tr}$ |
| 1000 (s) | 1059 | 249.7 | δ(N—C—N)$_{py}$, δ(C—N—C)$_{py}$, δ(C—C—C)$_{tr}$, ν(N—C)$_{tr}$ |
| 1080 (s) | 1078 | 95.7 | δ(H—C—C), δ(C—C—N) |
| 1125 | 1101 | 23.2 | ν(N—N) |
| 1229 (s) | 1218 | 66.9 | δ(H—C—N)$_{py}$, δ(H—C—C)$_{py}$, ν(N—C)$_{py}$ |
| 1303 | 1315 | 21.0 | ν(N—C)$_{tr}$, δ(N—C—N), δ(H—C—C) |
| 1331 | 1345 | 87.5 | δ(H—C—C), δ(H—C—N), δ(H—N—N), δ(N—C—N) |
| 1364 | 1382 | 3.2 | ν(N—C)$_{tr}$, δ(H—N—N), δ(H—C—N) |
| 1419 | 1402 | 611.7 | δ(H—C—N), ν(N—C)$_{tr}$, ν(C—C) |
| 1487 (s) | 1428 | 221.9 | ν(N—C)$_{tr}$ |
| 1519 (m) | 1471 | 26.4 | δ(H—C—N), δ(H—C—C) |
| 1545 (w) | 1533 | 329.0 | ν(C$_{py}$—C$_{tr}$), ν(N—C)$_{tr}$, ν(C—C)$_{py}$, δ(H—N—N), δ(H—C—N) |
| 1584 (w) | 1570 | 86.6 | ν(N—C)$_{py}$, ν(C—C)$_{py}$, δ(C—C—C)$_{py}$ |
| 1615 (s) | 1608 | 827.6 | ν(C—C)$_{py}$, δ(H—C—C)$_{py}$ |

[a]Empirically chosen scaling factor: 1.0068.
[b]w, weak; m, medium; s, strong; vs, very strong; sh, shoulder.
[c]$S_{Raman}$, Raman scattering activity ($Å^4$/amu).
[d]ν, stretch; δ, in-plane bend; γ, out-of-plane bend; s, symmetric; as, asymmetric; py, pyridyl; tr, triazole.

TABLE 5

Empirically chosen coefficients for different levels of theory with 6-311++G(d, p) basis set.

| Level of theory | Coefficient |
|---|---|
| B3PW91 | 0.9672 |
| BPBE | 1.0068 |
| BP86VWN | 1.0116 |
| BP86 | 1.0096 |
| M06-L | 0.9728 |
| B3LYP | 0.9767 |
| PBE0 | 0.9599 |

EXAMPLE 7. Synthesis of Gold Nanoparticles with Raman Reporters

Figure 22:
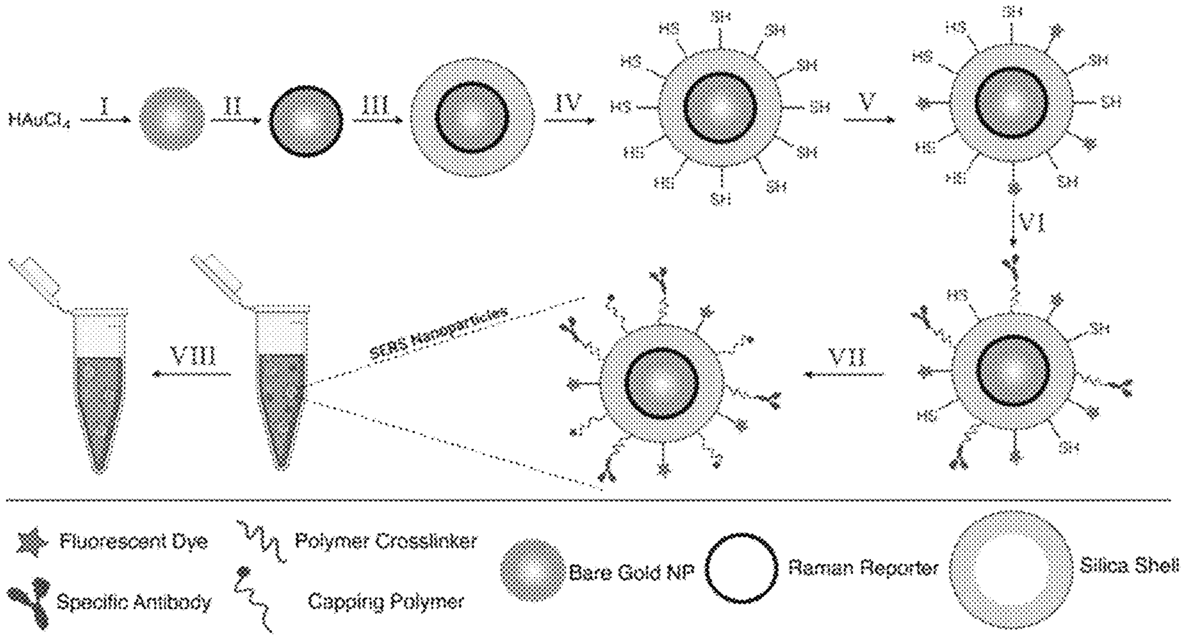
FIG. 22. Scheme of Raman-labeled nanoparticles preparation.
Figure 23:
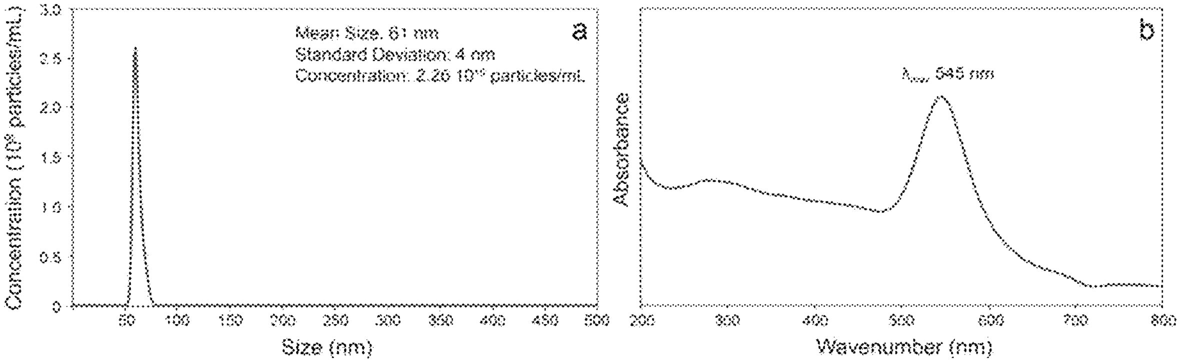
FIG. 23. Size distribution of the prepared bare Au-NPs measured by NTA (a); UV-vis spectrum of the silica coated Raman-labeled Au-NPs (b).
Figure 24:
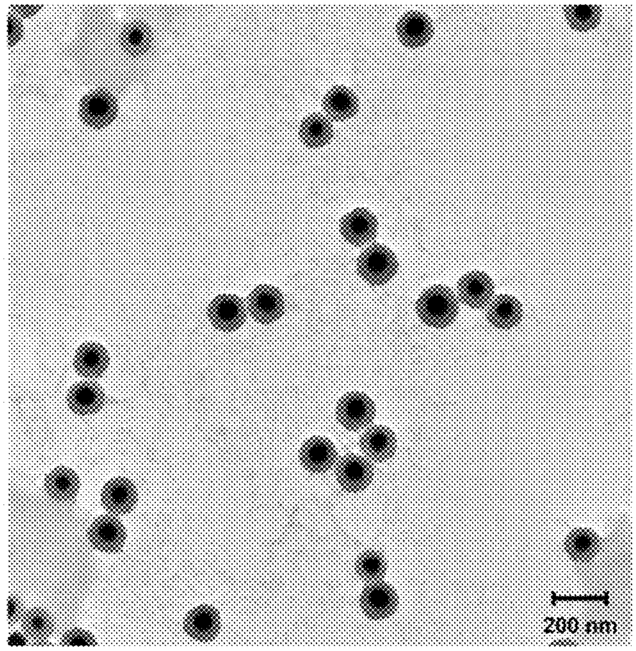
FIG. 24. Typical TEM image of the silica coated Raman-labeled Au-NPs.
Figure 25:
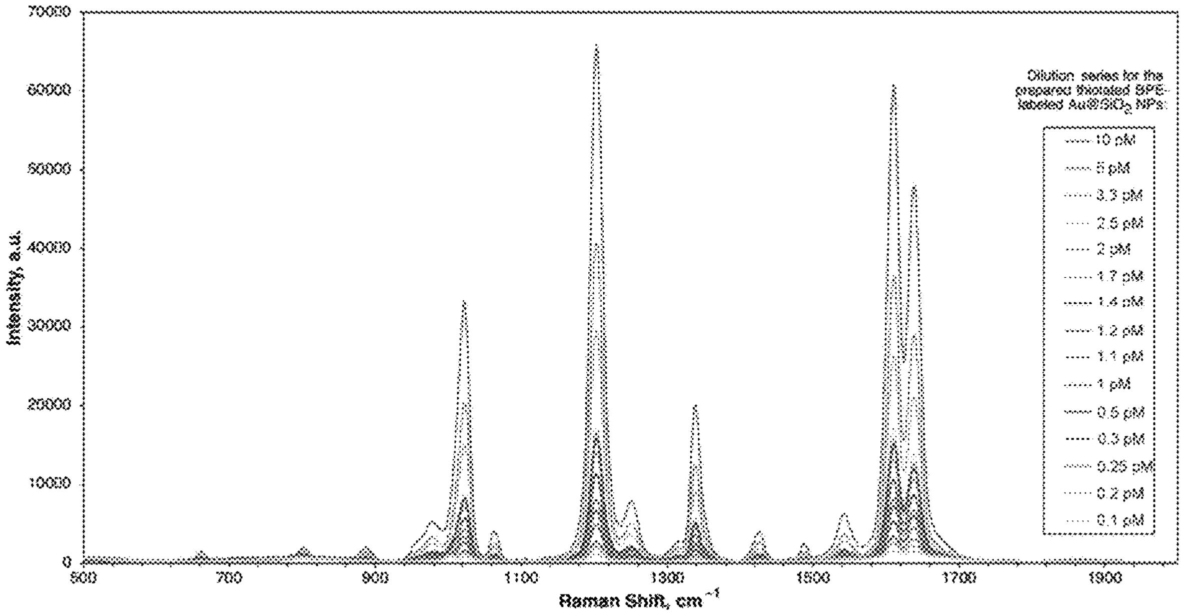
FIG. 25. SERS spectra of BPE-labeled Au-NPs. All SERS spectra were acquired using an about 165 mW and about 785 nm near infrared diode laser using a 50× objective lens and power neutral density filter of 10%. We used 10 s of acquisition time and a silicon wafer for calibration.
Figure 26:
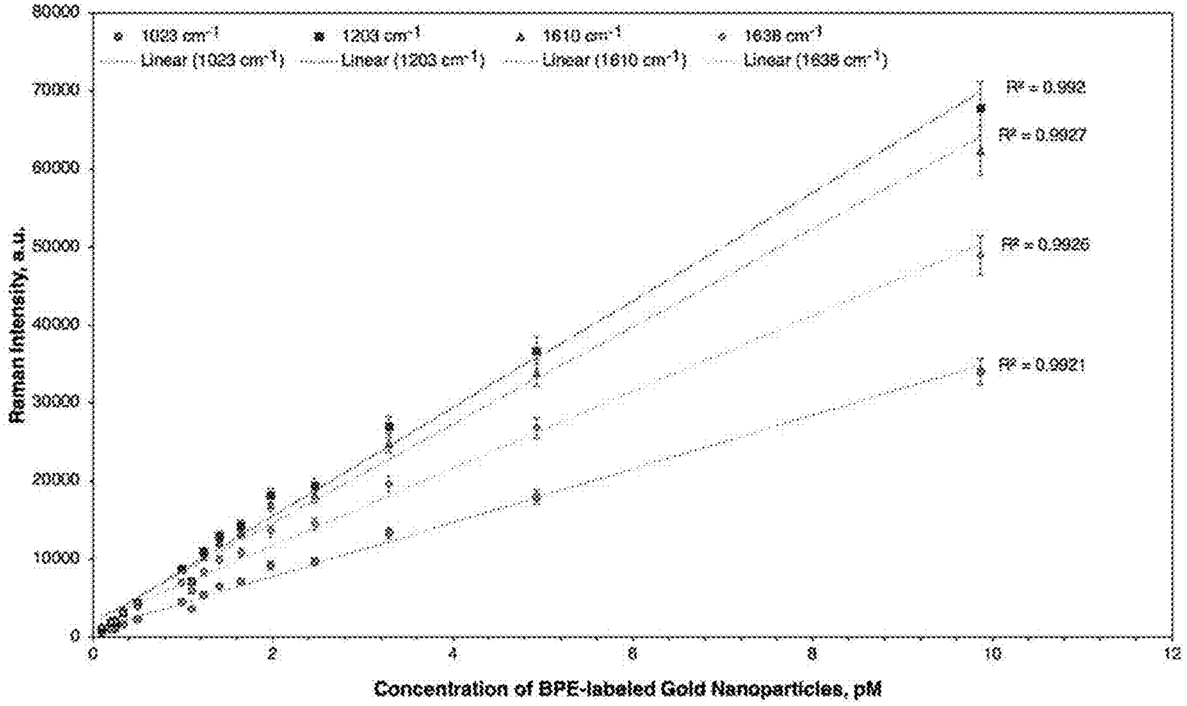
FIG. 26. Calibration curves for BPE-labeled Au-NPs. All SERS spectra were acquired using an about 165 mW and about 785 nm near infrared diode laser using a 50× objective lens and power neutral density filter of 10%. We used 10 s of acquisition time and a silicon wafer for calibration.
Figure 27:
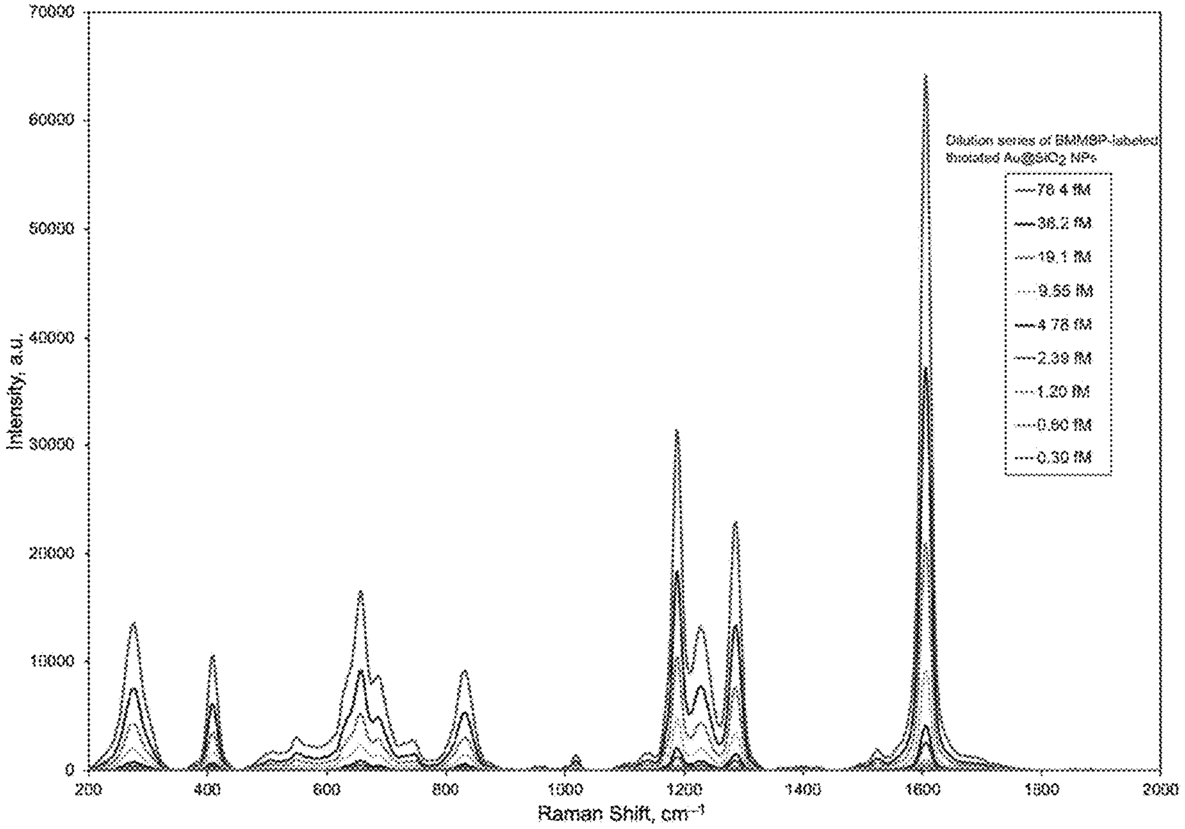
FIG. 27. SERS spectra of BMMBP-labeled Au-NPs. All SERS spectra were acquired using an about 165 mW and about 785 nm near infrared diode laser and using a 50× objective lens and power neutral density filter of 10%. We used 10 s of acquisition time and a silicon wafer for calibration.
Figure 28:
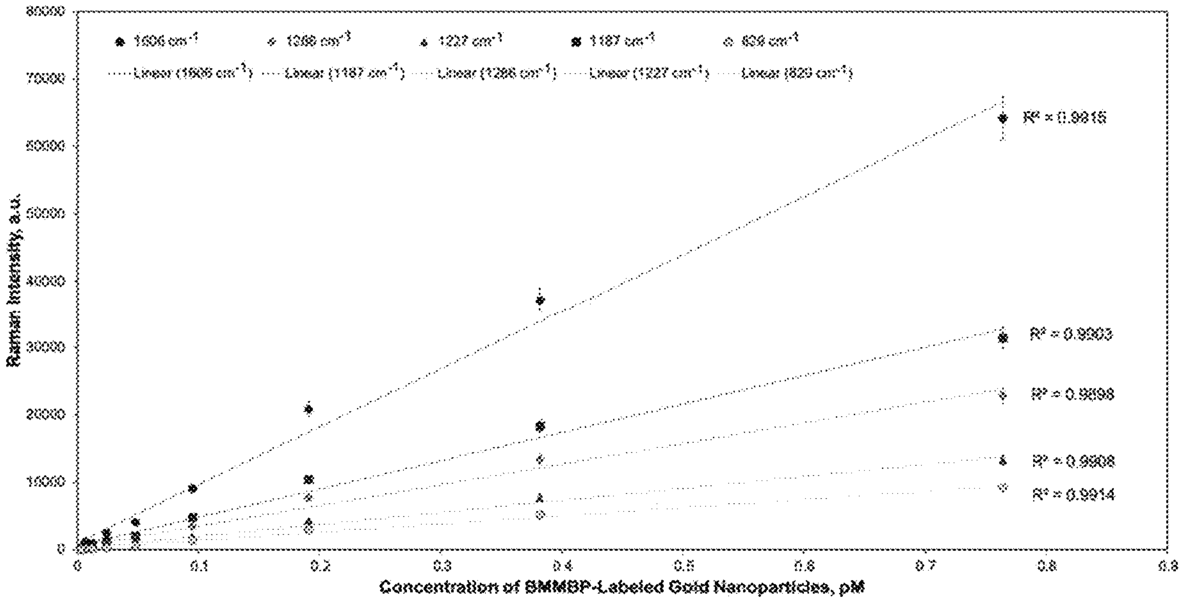
FIG. 28. Calibration curves for BMMBP-labeled Au-NPs. All SERS spectra were acquired using an about 165 mW and about 785 nm near infrared diode laser and using a 50× objective lens and power neutral density filter of 10%. We used 10 s of acquisition time and a silicon wafer for calibration.
Figure 29:
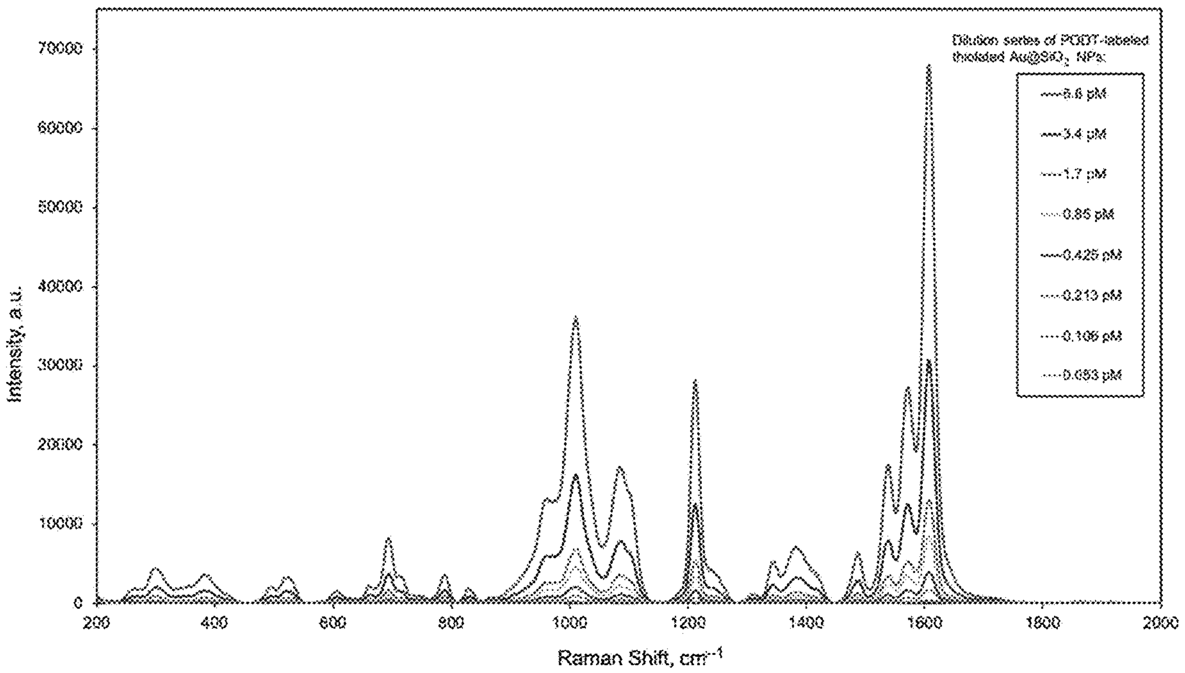
FIG. 29. SERS spectra of PODT-labeled Au-NPs. All SERS spectra were acquired using an about 165 mW and about 785 nm near infrared diode laser and using a 50× objective lens and power neutral density filter of 10%. We used 10 s of acquisition time and a silicon wafer for calibration.
Figure 30:
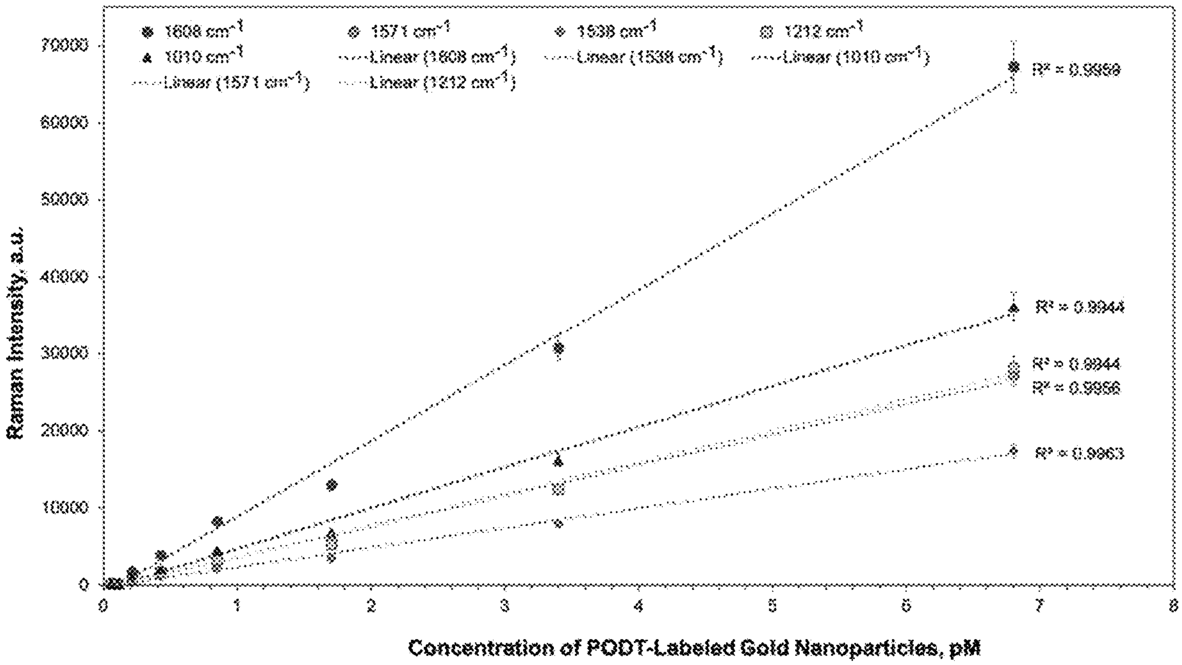
FIG. 30. Calibration curves for PODT-labeled Au-NPs. All SERS spectra were acquired using an about 165 mW and about 785 nm infrared diode laser and using a 50× objective lens and power neutral density filter of 10%. We used 10 s of acquisition time and a silicon wafer for calibration.
Figure 31:
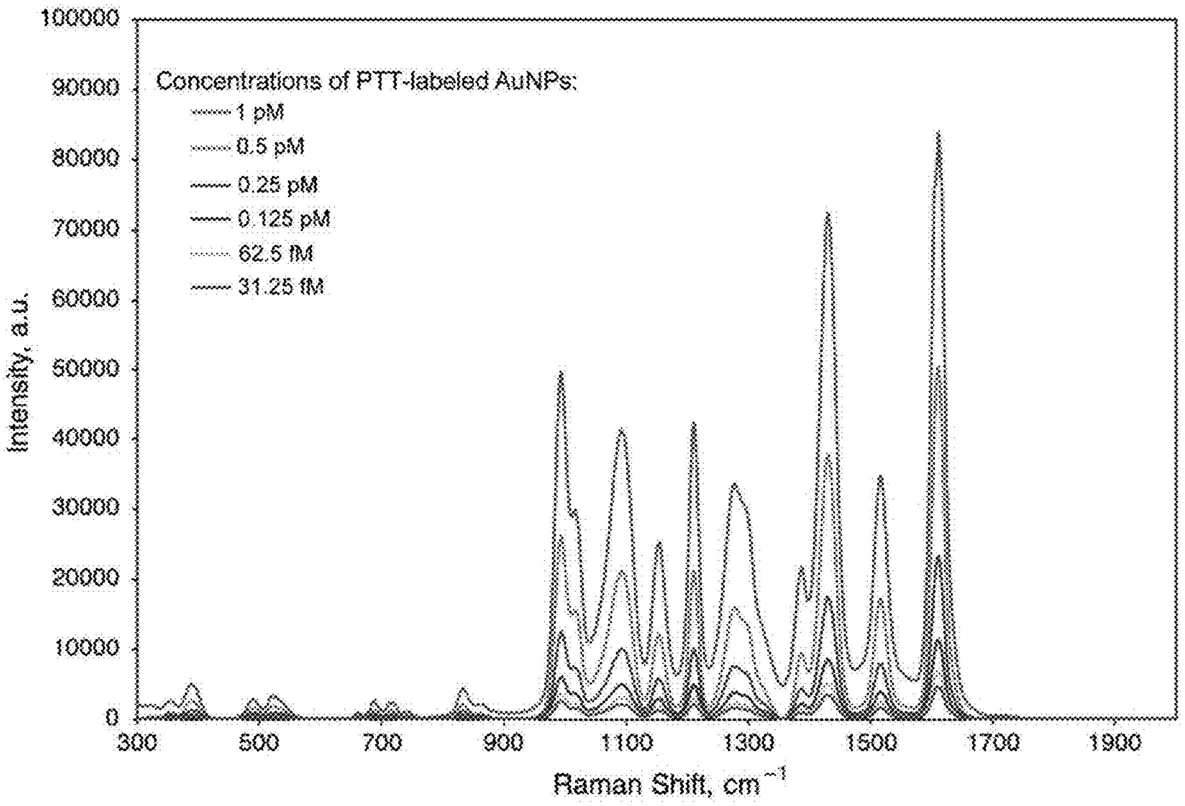
FIG. 31. SERS spectra of PTT-labeled Au-NPs. All SERS spectra were acquired using an about 165 mW and about 785 nm near infrared diode laser using a 50× objective lens and power neutral density filter of 10%. We used 10 s of acquisition time and a silicon wafer for calibration.
Figure 32:
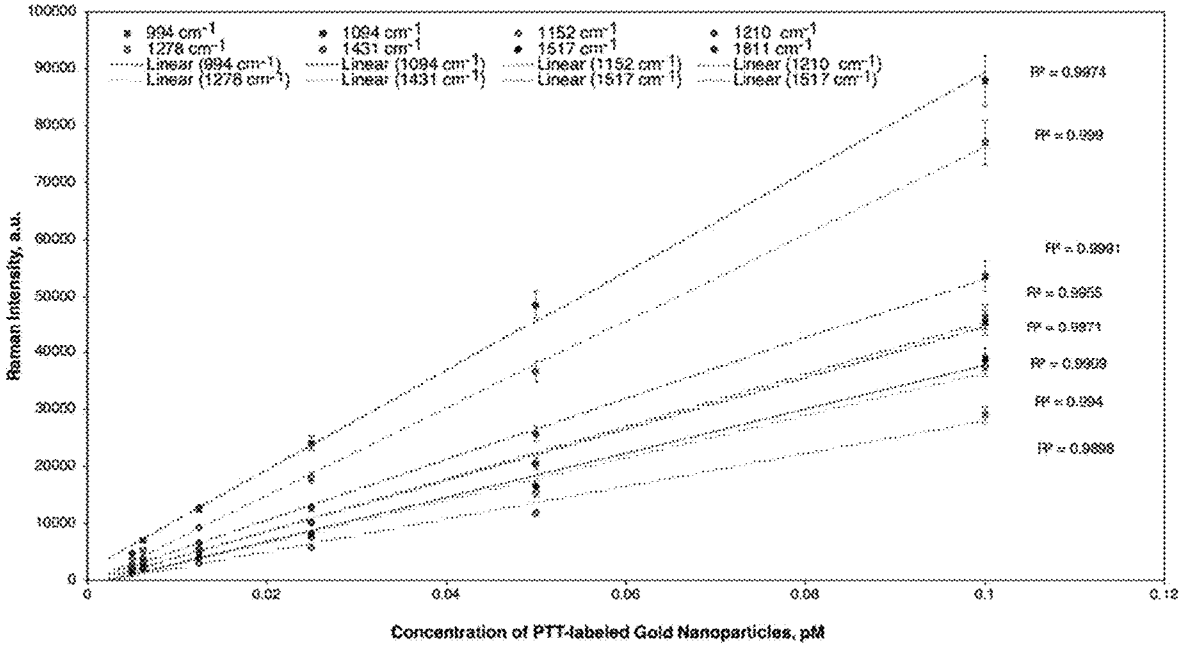
FIG. 32. Calibration curves for BPE-labeled Au-NPs. All SERS spectra were acquired using an about 165 mW and about 785 nm near infrared diode laser using a 50× objective lens and power neutral density filter of 10%. We used 10 s of acquisition time and a silicon wafer for calibration.
Figure 33:
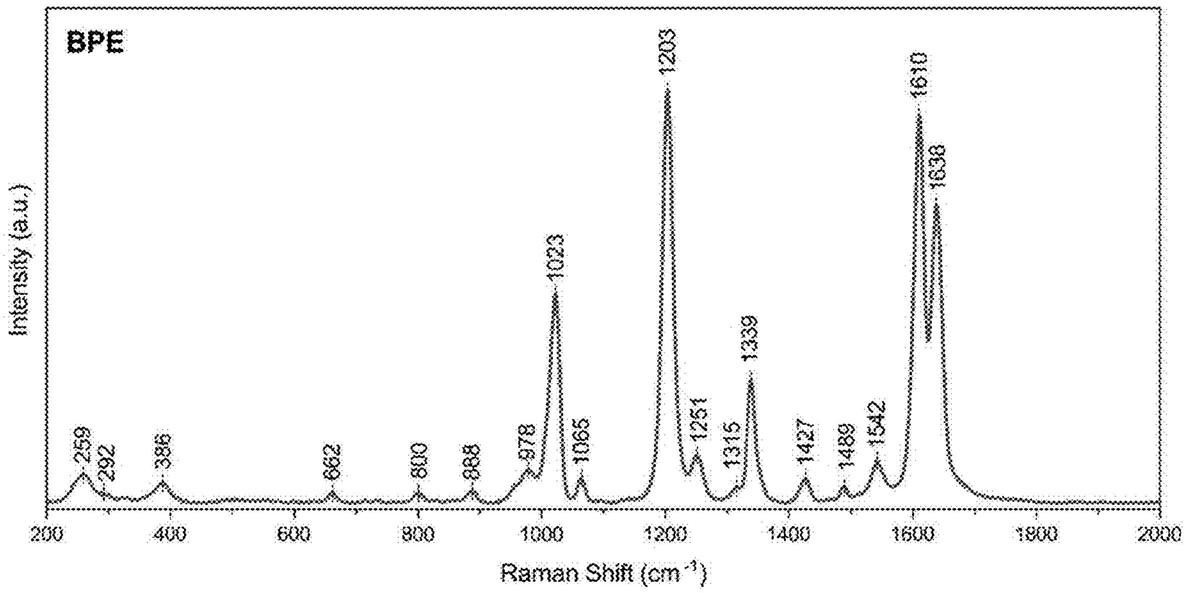
FIG. 33. SERS spectrum of BPE-labeled Au-NPs using 785 nm excitation wavelength.
Figure 34:
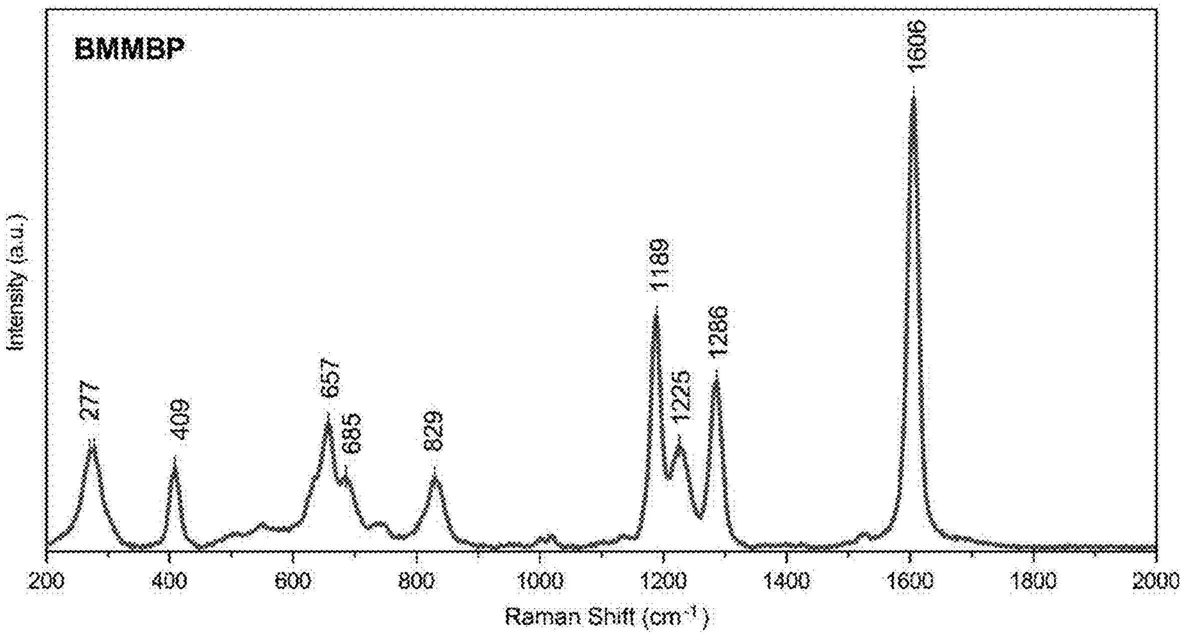
FIG. 34. SERS spectrum of BMMBP-labeled Au-NPs using 785 nm excitation wavelength.
Figure 35:
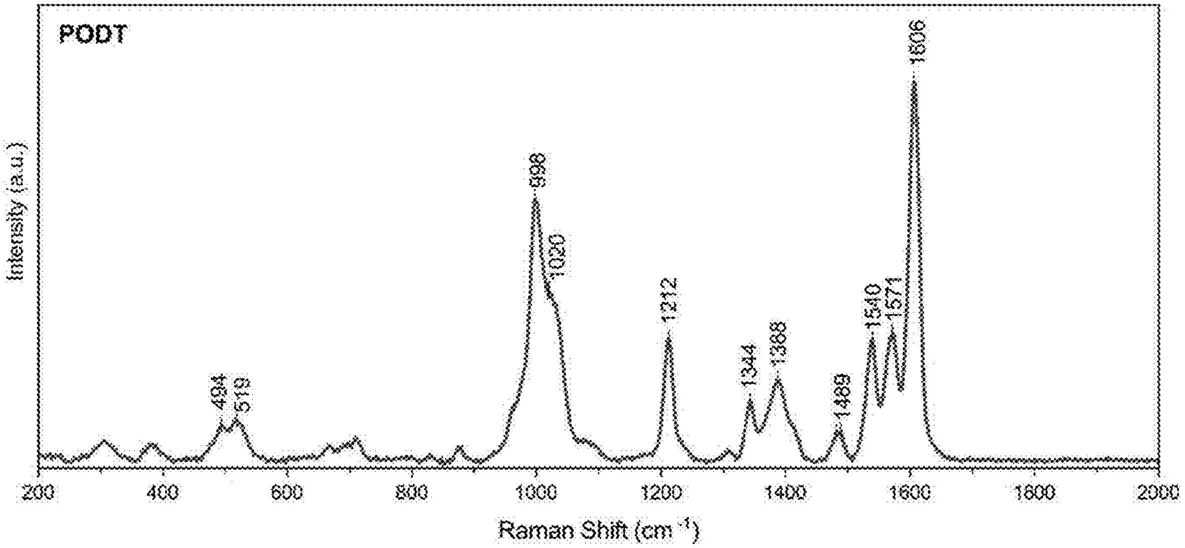
FIG. 35. SERS spectrum of PODT-labeled Au-NPs using 785 nm excitation wavelength.
Figure 36:
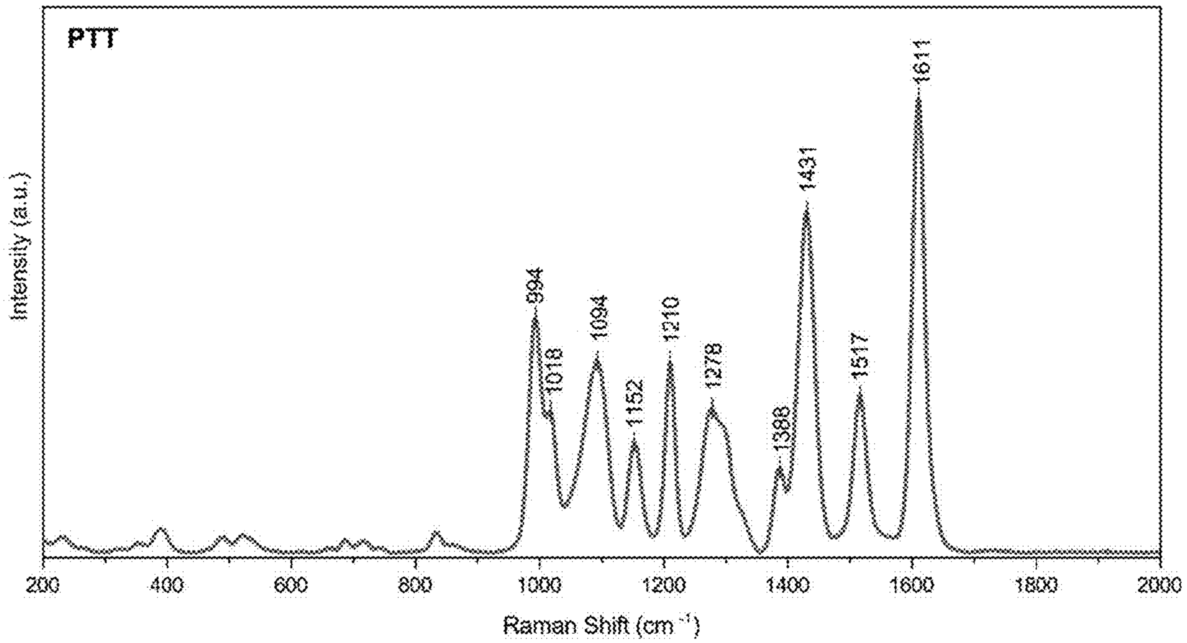
FIG. 36. SERS spectrum of PTT-labeled Au-NPs using 785 nm excitation wavelength.
Figure 37:
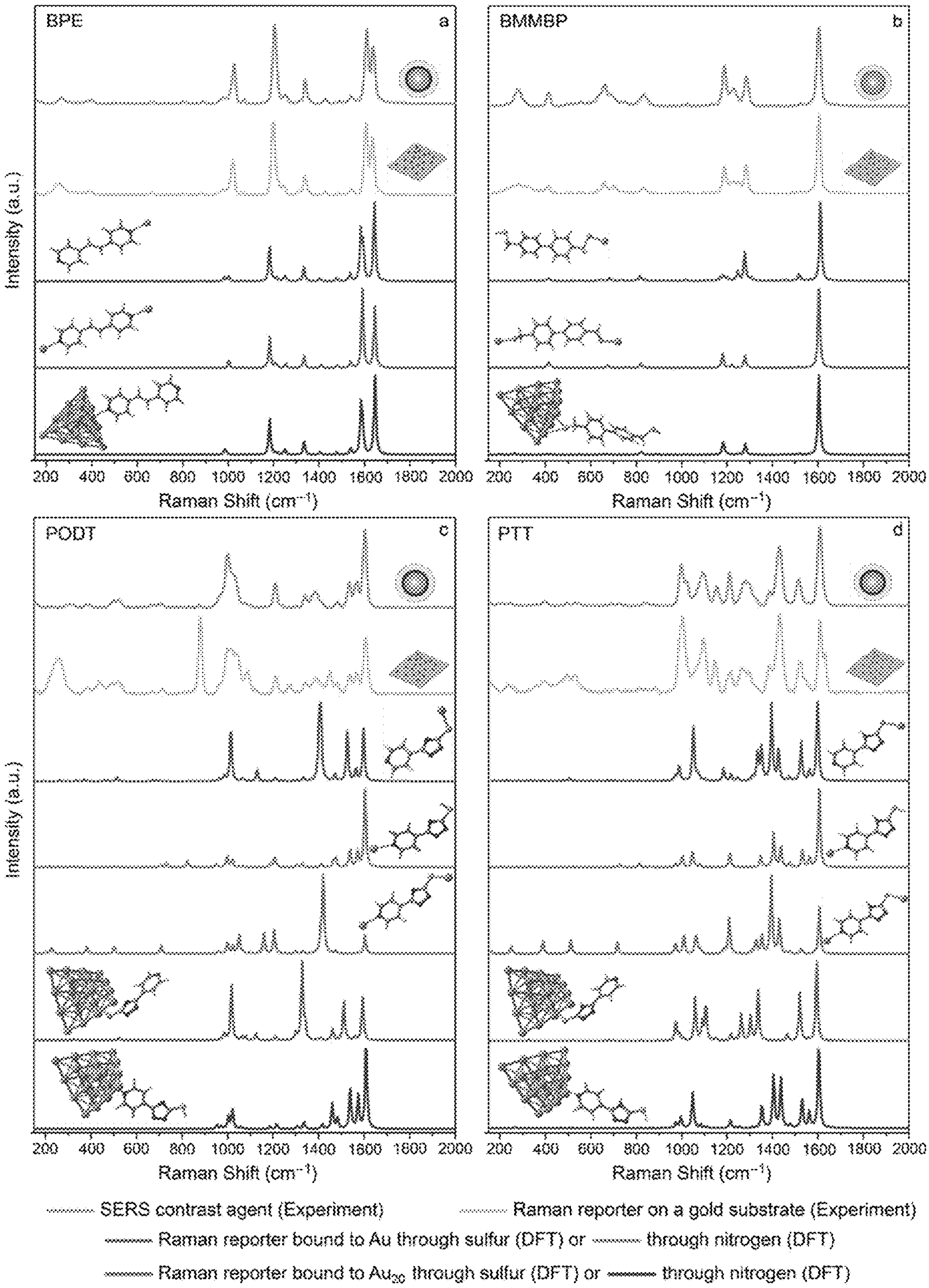
FIG. 37. Experimental and calculated SERS spectra of BPE (a), BMMBP (b), PODT (c), and PTT (d). Experimental SERS spectra were measured for Raman-labeled 60 nm gold contrast agents and Raman molecule with 60 nm Au substrate. Full geometry optimization and frequency calculations were performed at the density functional theory (DFT) level using B3LYP functional with 6-311++G(d,p) basis set. All the calculated Raman cross-sections were convoluted by a Lorentzian function with the full width half maximum of 5 $cm^{-1}$ for a better comparison with experimental spectra.
Figure 38:
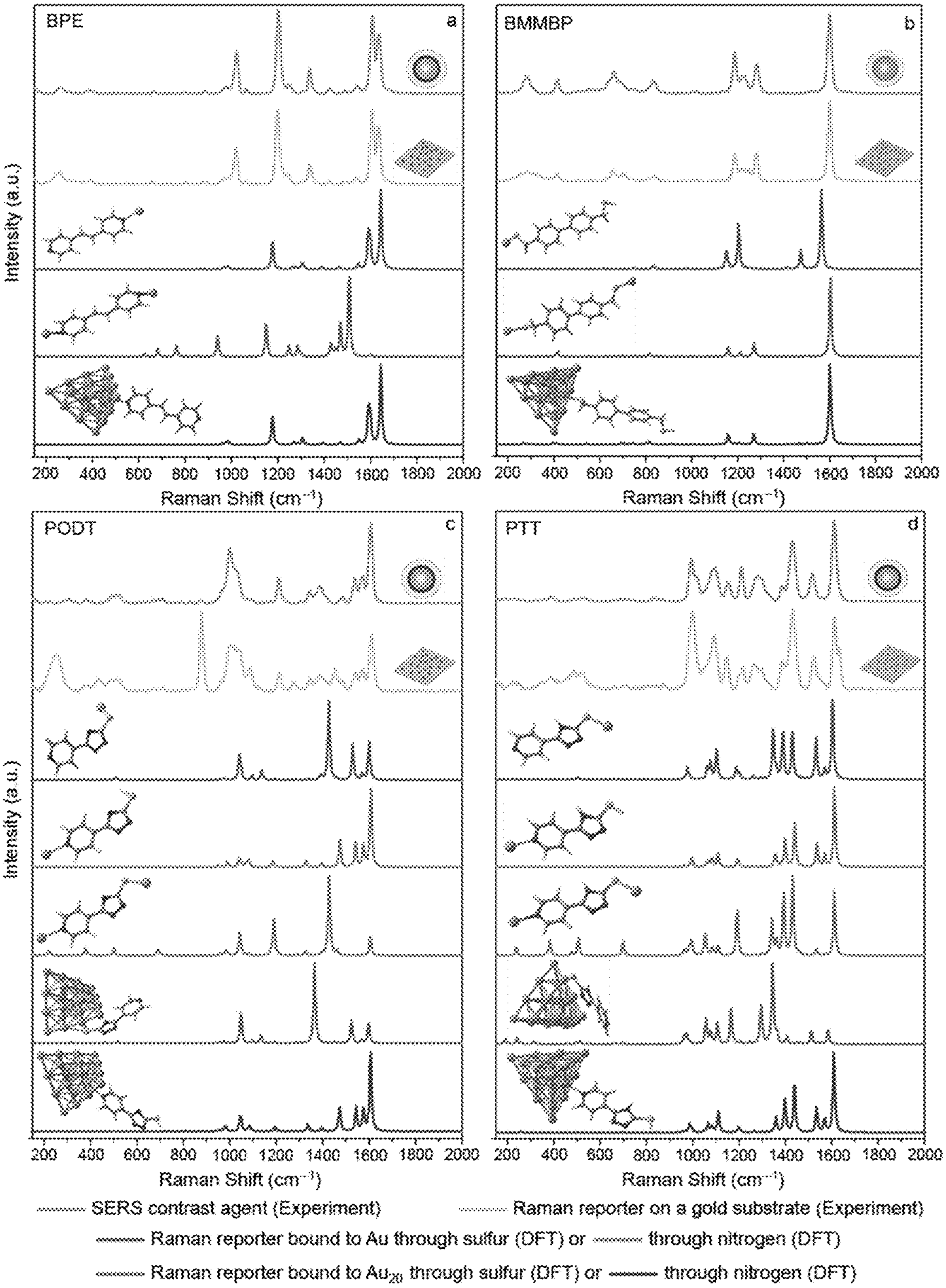
FIG. 38. Experimental and calculated SERS spectra of BPE (a), BMMBP (b), PODT (c), and PTT (d). Experimental SERS spectra were measured for Raman-labeled 60 nm gold contrast agents and Raman molecule with 60 nm Au substrate. Full geometry optimization and frequency calculations were performed at the density functional theory (DFT) level using PBEO functional with 6-311++G(d,p) basis set. All the calculated Raman cross-sections were convoluted by a Lorentzian function with the full width half maximum of 5 $cm^{-1}$ for a better comparison with experimental spectra.

Bare citrate stabilized Au-NPs. We adopted Au-NPs with a diameter of about 60 nm as SERS substrates. A modified method of hydroxylamine seeding of colloidal Au-NPs was used to fabricate spherical gold nanoparticles (FIG. 22, Step I). Prior to synthesis, all the used glassware was cleaned with aqua regia. Deionized water (Milli-Q grade, Millipore) with a resistivity of about 18.2 MΩ·cm was used throughout the experiment. Gold (III) chloride hydrate ($HAuCl_4·xH_2O$, about 99.995%), hydroxylamine hydrochloride ($NH_2OH$□HCl, about 99%), trisodium citrate dihydrate ($C_6H_5Na_3O_7·2H_2O$, about 99.0%), and sodium borohydride ($NaBH_4$, about 99%) were purchased from Sigma-Aldrich, Briefly, about 3 mL of about 30 mg/mL $HAuCl_4$ was added to about 450 mL of cold water (about 4□C) under vigorous stirring. Then, about 0.6 mL of about 0.135 g/mL sodium citrate and about 0.085 g/mL hydroxylamine hydrochloride mixture was added rapidly. After about 10 s, about 0.12 mL of about 0.001% $NaBH_4$ was injected rapidly. The color of the solution changed dramatically from clear to black, then to purple, and finally to red. The colloidal solution was stirred for an additional about 10 min.

The resulting colloidal solution was characterized with a Cary 60 UV-Vis (Agilent Technologies, US) spectrophotometer, and its maximal absorption band was observed at about 535 nm. Size and concentration were verified using dynamic light scattering (DLS) Zeta Sizer Nano ZS (Malvern Panalytical, UK) and nano-tracking analysis (NTA) NanoSight NS300 (Malvern Panalytical, UK). According to DLS and NTA measurements, the size distribution was about 61±4 nm.

Labeling Au-NPs with Raman reporters. The colloid was rendered vitreophilic with the dropwise addition of about 32 μL of about 1 mM 3-aminopropyltrimethoxysilane. After about 15 mM of vigorous stirring, about 0.1 mM solution of Raman reporter molecule: BPE (about $4.7·10^3$ molecules per Au-NP), BMMBP (about $7.3·10^3$ molecules per Au-NP), PODT (about $6.1·10^3$ molecules per Au-NP), or PTT (about $5.7·10^3$ molecules per Au-NP), was added (FIG. 22, Step II). After about 5 mM of stirring, a total of about 400 μL of about 2.16 wt % solution of active silica—sodium silicate in about 3 M NaOH was added. The resulting solution had a pH of about 9.5. The solution was stirred for another about 15 mM and then allowed to stand.

Coating Raman reporter labeled Au-NPs with a silica shell. About 100 mL of ethanol was added to the solution to proceed with silica growth via the Stöber method. Growth of about 40 nm of additional glass shell was accomplished by the dropwise addition of about 500 μL of ammonia and about 40 μL of tetraethyl orthosilicate. The reaction was stirred for about 24 h (FIG. 22, Step III). The surface of spherically shaped nanoparticles was chemically inert.

Next, our SERS-NPs were additionally functionalized with thiol groups in Stöber process with organosilane (3-mercaptopropyl)trimethoxysilane (FIG. 22, Step IV). A fluorophore was covalently conjugated through the thiols for robust validation of presence of SERS-NPs (FIG. 22, Step V). Some of the surface thiol groups were purposefully left free for the further conjugation of the antibodies specifically targeting each of the antigen present on the analyzed tissue sample. Therefore, we added monoclonal antibodies to the final nanoparticles along with the heterobifunctional poly (ethylene glycol) (PEG) crosslinker—SM$(PEG)_{12}$ (FIG. 22, Step VI). Following the primary conjugation reaction, methoxy-terminated passivation ligand MM$(PEG)_{12}$ blocked residual thiols on the nanoparticles (FIG. 22, Step VII).

Results of the characterization of Au-NPs and SERS-NPs are shown in FIGS. 23-32. Experimental and DFT calculated SERS spectra are shown in FIGS. 33-43. The results are tabulated in Tables 6-7.

Each Raman reporter molecule demonstrated 4-6 dominant vibrational modes connected to the chemical structures (Table 6). As BPE, PODT, BMMBP, and PTT interact with the metal, there is a shift in their normal modes.

TABLE 6

Assignments of experimental Raman and SERS spectra for BPE, BMMBP, PODT, and PTT.

| Raman | | SERS | | |
|---|---|---|---|---|
| Raman Shift, $cm^{-1}$ | Normalized Intensity, a.u. | Raman Shift, $cm^{-1}$ | Normalized Intensity, a.u. | Assignments |
| | | BPE - $C_{2h}$ symmetry | | |
| 1006 | 0.436 | 1023 | 0.511 | ring breathing |
| 1206 | 0.655 | 1203 | 1.000 | $\nu(\text{ring-C}_{vin})$, $\delta(\text{C—H})_{py}$ |
| 1244 | 0.330 | 1251 | 0.121 | $\delta(\text{C—H})_{vin}$, in-plane $\nu_{ring}$ |
| 1349 | 0.187 | 1339 | 0.303 | $\delta$(C—H), $\delta(\text{C}_{vin}\text{—C})$ |
| 1604 | 0.684 | 1610 | 0.943 | $\nu(\text{C—C})_{py}$, $\delta(\text{C—H})_{py}$ |
| 1649 | 1.000 | 1638 | 0.724 | $\nu(\text{C=C})_{vin}$ |
| | | BMMBP - $C_2$ symmetry | | |
| 1195 | 0.485 | 1189 | 0.515 | $\delta$(C—H) |
| 1252 | 0.503 | 1225 | 0.226 | $\gamma_s(CH_2)$ |
| 1280 | 0.428 | 1286 | 0.371 | inter-ring C—C stretching, $\delta_{as}(\text{C—H})_{bp}$ |
| 1608 | 1.000 | 1606 | 1.000 | $\nu(\text{C—C})_{bp}$, $\delta(\text{C—H})_{bp}$ |
| | | PODT - $C_s$ symmetry | | |
| 953 | 0.121 | — | — | $\nu(\text{N—N})_{ox}$, $\nu(\text{C—O})_{ox}$, $\delta$(S—H), (ring breathing)$_{py}$ |
| 1010 | 0.318 | 998 | 0.694 | $\nu(\text{N—N})_{ox}$, $\nu(\text{C—O})_{ox}$, $\nu(\text{C—S})_{ox}$, (ring breathing)$_{py}$ |
| 1074 | 0.423 | — | — | $\delta(\text{C-H})_{py}$ |
| 1535 | 0.222 | 1540 | 0.326 | $\nu_s(\text{C—N})_{ox}$, $\nu_{py\ ring}$, $\nu(\text{C}_{py}\text{—C}_{ox})$, $\delta_{as}(\text{C—H})_{py}$ |
| 1560 | 0.082 | 1571 | 0.345 | $\nu(\text{C=N})_{tr}$, $\nu(\text{C—C})_{py}$, $\nu(\text{C—N})_{py}$ |
| 1616 | 1.000 | 1606 | 1.000 | $\nu_s(\text{C—C})_{py}$, $\delta_s(\text{C—H})_{py}$ |
| | | PTT - $C_s$ symmetry | | |
| 1000 | 0.793 | 994 | 0.521 | $\delta(\text{N—C—N})_{py}$, $\delta(\text{C—N—C})_{py}$, $\delta(\text{C—C—C})_{tr}$, $\nu(\text{N—C})_{tr}$ |
| 1080 | 0.381 | 1094 | 0.423 | $\delta$(H—C—C), $\delta$(C—C—N) |
| 1229 | 0.327 | 1210 | 0.421 | $\delta(\text{H—C—N})_{py}$, $\delta(\text{H—C—C})_{py}$, $\nu(\text{N—C})_{py}$ |
| 1487 | 0.779 | 1431 | 0.751 | $\nu(\text{N—C})_{tr}$ |
| 1615 | 1.000 | 1611 | 1.000 | $\nu(\text{C—C})_{py}$, $\delta(\text{H—C—C})_{py}$ |

TABLE 7

LODs and EFs of the prepared SERS-NPs.

| Raman reporter | LOD | Enhancement Factor: Experimental for Raman reporter | Enhancement Factor: Experimental for nanotags | Enhancement Factor: Calculated |
|---|---|---|---|---|
| BPE | 33 fM | 9.20□$10^{5}$ | 4.04□$10^{9}$ | 2.70 |
| PODT | 17 fM | 2.98□$10^{6}$ | 1.90□$10^{10}$ | 3.64 |
| PTT | 3 fM | 6.82□$10^{6}$ | 3.92□$10^{10}$ | 6.81 |
| BMMBP | 0.5 fM | 1.99□$10^{7}$ | 1.48□$10^{11}$ | 27.65 |

The following equations were used in calculations.

$$EF_{NP} = \frac{\text{Signal from Tag Solution}}{\text{Signal from Solution of Label Molecule}} \times \frac{\text{Concentration of Label Solution}}{\text{Concentration of Tag}}$$

-continued $$EF_{RR} = \frac{\text{Signal from } NP \text{ Solution}}{\text{Signal from Solution of Label Molecule}} \times \frac{\text{Concentration of Label Solution}}{\text{Concentration of Label on } NP}$$

EXAMPLE 8. SERS-NP Library

Molecular imaging of biological samples stained with SERS-NPs, which we call SERS-NP contrast agents or SERS-flavors, may leverage the chemical specificity of Raman spectroscopy to transmit the state of biomarker expression in the form of multiplexed Raman spectroscopic optical signals. The enhancement factor of the scattering cross-section achieved by localized surface plasmon resonance (LSPR) of nanoscale gold affords high sensitivity and fast mapping speeds using non-destructive laser intensities. The Raman spectrum of each SERS-flavor serves as an unambiguous barcode for discovering and localizing protein targets.

In this example, we present a library of SERS-flavors to be successfully multiplexed and imaged, comprising 26 members. Each SERS-flavor may be fabricated as a layer of Raman reporter species sandwiched between an about 60 nm gold core and a silica shell, which is further decorated with bio-targeting moieties. Our Raman reporters have been curated with the guiding principle of minimizing spectral complexity to maximize multiplexing opportunities, staving off the overcrowding problem which plagues fluorescence spectroscopy.

We showed in Raman hyperspectral imaging experiments that accurate spectral demultiplexing may be achieved with all 26 flavors mixed in various combinations. A maximally orthogonal subset was chosen for further assessment in a Karnaugh array of all possible multiplexing scenarios and for validation of quantitative demultiplexing. Clustering of the SERS flavors against spectral content highlights the spectral features which distinguish them into distinct "vibronic families" and visually highlight unoccupied spectral bands, which may guide the development of future SERS-NPs to our expanding library.

We then showed an example application of multiplexed SERS imaging by using SERS-NPs to detect cultured cancer cells and ratiometrically demultiplex their labels to estimate differential biomarker expression. And finally, cancerous human tissue sections were stained with the SERS-NPs of this disclosure and imaged to demonstrate their utility for interrogating subcellular biomarker expression in clinical samples.

Figure 44:
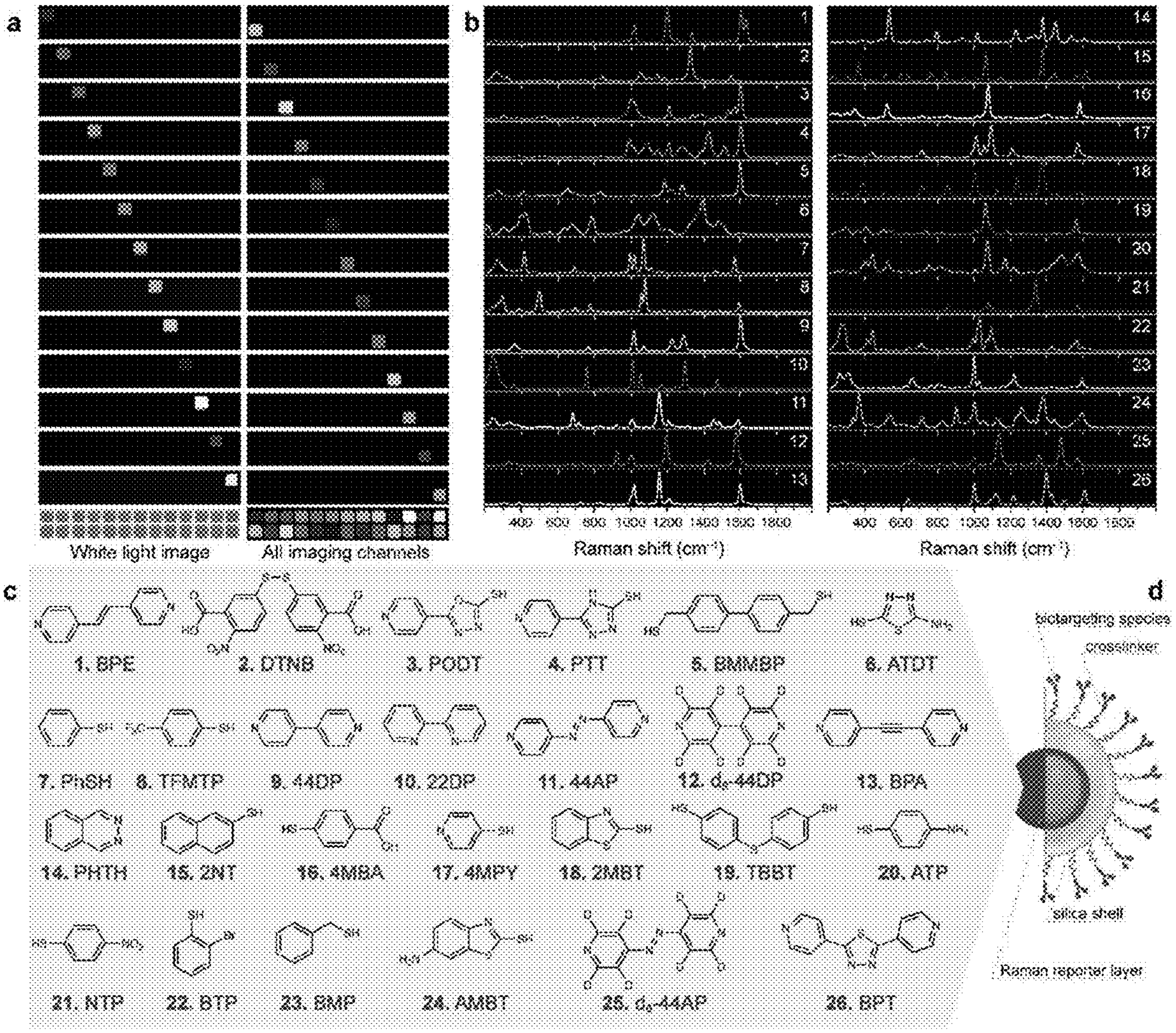
FIG. 44. Multiplexed detection of spatially separated SERS-NPs. a, 26 SERS imaging channels corresponding to the presence of a single SERS-NP's presence and the white light preview of the 26 microplate wells containing spatially separated SERS-NPs. For demonstrating multiplexed analysis, each imaging channel was artificially assigned a different color from the 26-color palette. b, Raman signatures to which the imaging channels in a are correlated. Each SERS-NP's signature is unique enough to be distinguished from each of the other SERS fingerprints in the library. c, Raman reporters making up the Raman-active layer of the SERS-NP which emits the desirable unique signature in b (full names found in Table S2). d, Architecture of SERS-NP consisting of a 60 nm gold core labeled with one of 26 Raman reporters from c and coated with a silica shell. The inert silica shell that caps Raman reporter layer is further thiolated to enable functionalization with biomarker-targeting species, e.g., antibodies or peptides, allowing the particles to preferentially bind to an epitope of a target protein.

We designed SERS-NPs so that their Raman peaks can be mutually separated from each other. FIG. 44*d* shows a schematic of SERS-NPs used for imaging Due to the LSPR effect of Au-NPs, the intensity of Raman signals for adsorbed molecules is enhanced dramatically, allowing them to be detected at extremely low concentrations. Narrow peaks and unique molecular fingerprints may make SERS-NPs one of the best candidates for extracting highplex data from a single biological sample, animal model, or patient.

However, not all molecules inelastically may scatter light with equal efficiency, may have distinct and narrow Raman bands, and may possess functional groups capable of binding to a gold surface.

Figure 49:
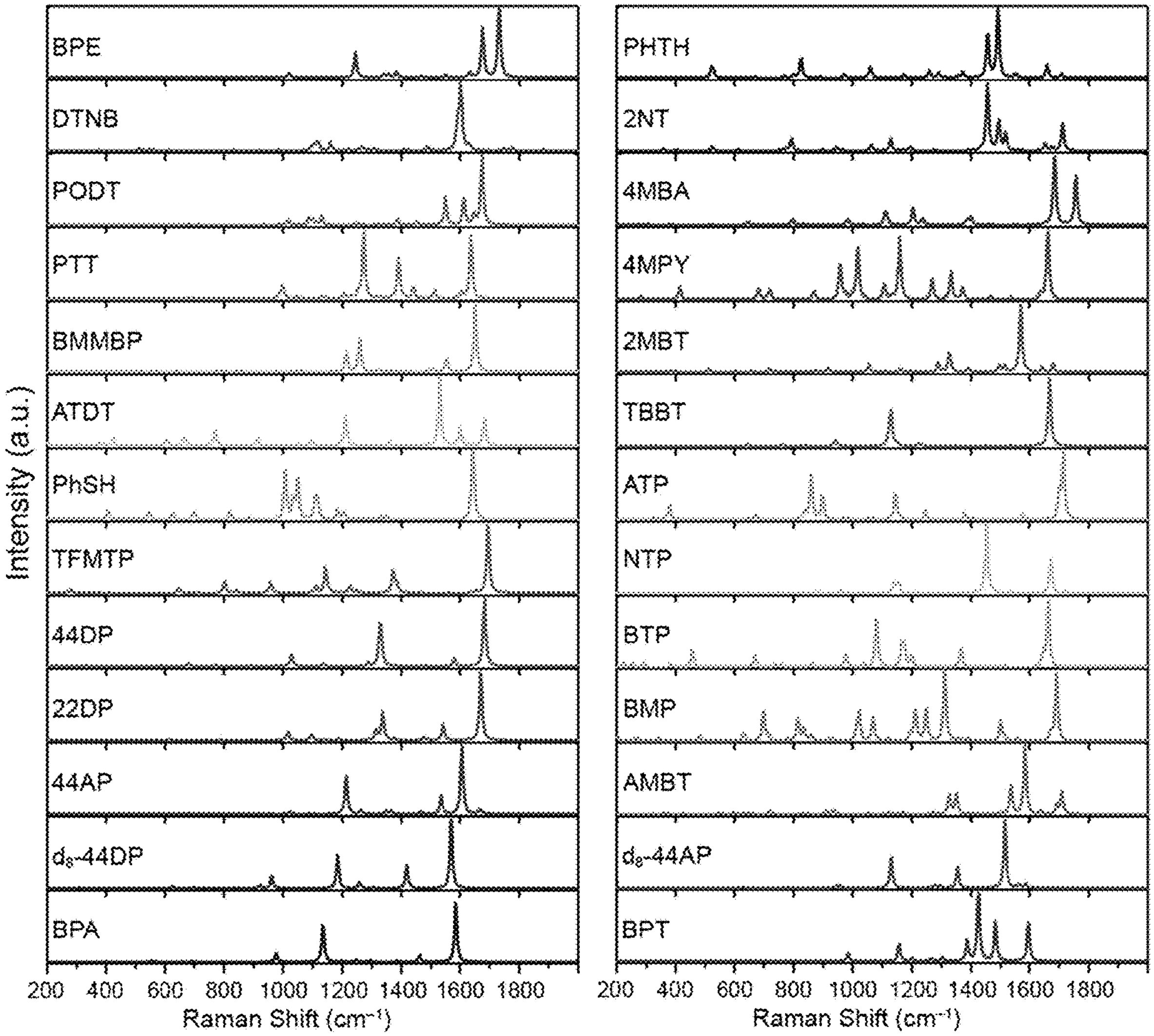
FIG. 49. Normalized calculated gas-phase Raman spectra of Raman reporter molecules that were bound to Au-NP and capped with silica shell. Full geometry optimization and frequency calculation for isolated Raman reporter molecules were performed at the density functional theory (DFT) level using PBE0 functional with D3 dispersion correction and triple-zeta valence (6-311++G(d,p)) basis set. All the calculated Raman cross sections were convolved with a Lorentzian function with the full width half maximum of 5 $cm^{-1}$.

We evaluated various small organic molecules that all have an aromatic it π-system, several symmetry elements, and at least one gold-anchoring functional group, and ab initio calculated their Raman spectra using density functional theory (DFT). Based on the DFT-calculated molecular fingerprints (FIG. 49) and seeking overall dissimilarity and significant Raman scattering enhancement factors (EFs), we selected 26 molecules presented in FIG. 44*c* and Tables 8-9 as Raman reporters for labeling about 60 nm spherical Au-NPs and encapsulated them with an about 30 nm silica shell. High EFs allowed utilization of SERS-NPs as imaging contrast agents with acceptable signal-to-noise ratios and low limits of detection (LODs).

In summary, in this example, we present an expansive library of 26 nanoparticles, each bearing a unique Raman fingerprint, and reveal the unprecedented potential of SERS-NPs to specifically target biomarkers and gain an unparalleled understanding of the spatial relationships between a multitude of cell types using Raman imaging Our ability to demultiplex a mixture of 26 SERS-NPs in a single imaging pixel opens entirely new opportunities to efficiently interrogate heterogeneous molecular expression found within and across patient samples.

We have demonstrated that our SERS-NPs can effectively target specific biomarkers while providing highplexed subcellular image resolution in biological samples. SERS-NPs may serve as guides between the molecular world of biomarkers and the macro-world of tissue architecture, helping to link highplex data to patient outcomes in clinical studies, providing insights to guide therapeutic decisions, and uncovering novel therapeutic targets through the discovery of new biomarkers. With these combined capabilities, we anticipate an exciting path forward for using highplexed SERS-NP imaging to enable the emerging practice of personalized medicine and improve human health.

EXAMPLE 9. Multiplexing of Spatially Separated SERS-NPs

First, we investigated the multiplexing capabilities of the de novo prepared SERS-NPs emulating the most likely scenario in a high-plexed imaging assay where biomarkers are rarely precisely coincident but rather spatially separated. A single region of interest (ROI) encompassing 26 wells, each containing a pure solution of a SERS-NP flavor, was mapped. The Raman spectra (Fig. lb) contained in the map were demultiplexed by direct classical least squares (DCLS) regression into the 26 respective SERS imaging channels, i.e., the channel whose grayscale intensities denote the intensity of the flavor's signal contribution to the pixel's spectrum (FIG. 44*a*). Notably, multiplexed detection of 26 distinct, spatially separated SERS flavors was achieved in one pass of Raman mapping with each flavor's reference spectrum included in the DCLS design matrix, experimentally confirming that, in this multiplexing format, the library's spectra were unique enough to be correctly identified.

EXAMPLE 10. Comprehensive Testing of Mixed SERS-NPs

In principle, computed demultiplexing results may be more accurate when utilizing reference spectra comprising less overlapping SERS signatures. For a given application, only a subset of all the available SERS-NPs may be needed to label targets of interest.

Figure 45:
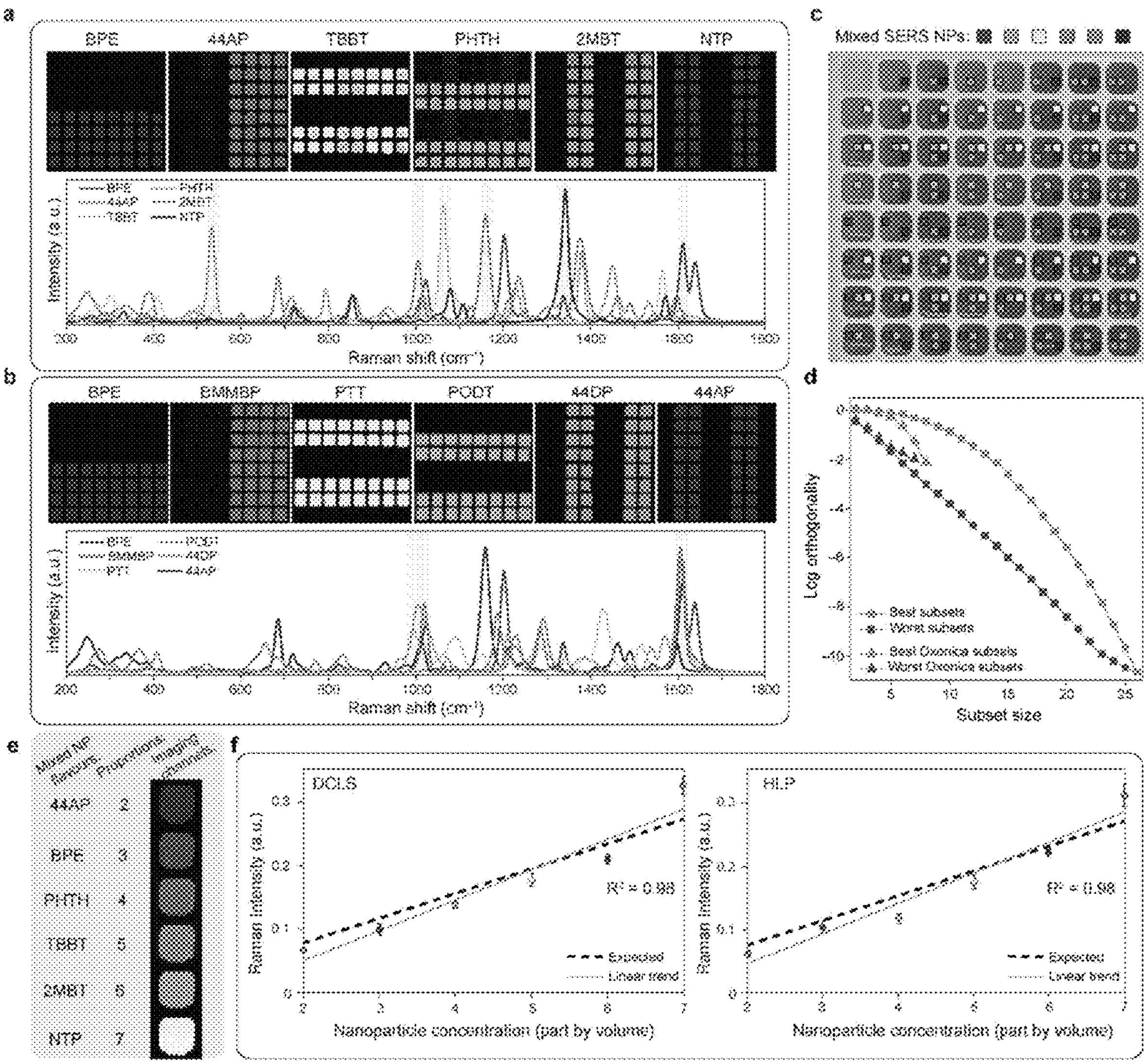
FIG. 45. In-depth qualitative and quantitative test of mixture of SERS flavors. a, b, Raman images of the most and least unique 6-plex subsets mixed in wells with plots of corresponding molecular fingerprints of SERS-NPs. a shows imaging channels for unmixing of the 6 SERS-NPs whose signatures are most unique, and b shows imaging channels for unmixing of the 6 least unique SERS-NPs. c, 6-variable Karnaugh map arrangement of all possible combinations as an ultimate test of multiplexing capabilities of SERS-NPs. d, orthogonality trend for the library of 26 SERS-NPs utilized in this work and 8 SERS-NPs from highest plexity demonstrated by Zavaleta, C. et al.[6] e, preferable 6-plex combination of SERS-NPs mixed in a linearly increasing volume ratio series of 2:3:4:5:6:7, then the mixture mapped in a single microplate well. Spectral demultiplexing of the mixture's map into the respective 6 SERS imaging channels yields weight values indicating how prominent the SERS-NP's reference signature was at each pixel in the map. f, trends of weight values averaged over the scanned ROI are highly linear, matching the linearity of the concentrations in the mixture, validating that the concentrations of these 6 SERS flavors can also be quantified. Quantitative demultiplexing can be achieved using DCLS as well as with alternative, more sophisticated algorithms such as NNLS or HLP.

For any plexity, the spectra that maximize orthogonality according to the determinant may serendipitously minimize occurrences of peaks occupying identical Raman shift bands, especially the most intense peaks, ensuring that the spectral resolving power of one's Raman instrumentation may best be utilized to distinguish their features. The distinguishment of features may require adequate separation and measurement resolution, therefore endeavoring to have Raman reporters' spectral features as non-overlapping as possible preserves the ability to detect spectral features when extensively mixed and diluted. The orthogonality, or pseudo-determinant, metric of a design matrix of N 2-norm normalized Raman spectra is computed by virtue of its singular values, which relate it to the volume of an N-simplex. The log-orthogonality is computed as the sum of the logarithm of singular values to avoid underflow for larger design matrices (FIG. 45*d*). To exhaustively validate the multiplexing capabilities of a SERS subset size that would make for a SERS imaging assay of unprecedented size, we studied two—the least and most similar—subsets of six types of SERS-NPs with the highest and lowest determinant, respectively. The most prominent peaks of a unique subset may occur in separate Raman shift bands such that one can even deconvolve them visually, i.e., based on single peak intensity, while the least unique subset consists of flavors that have prominent peaks overlap primarily at ca. 1000, 1200, and 1600 $cm^{-1}$ (FIG. 45*b*)

Figure 52:
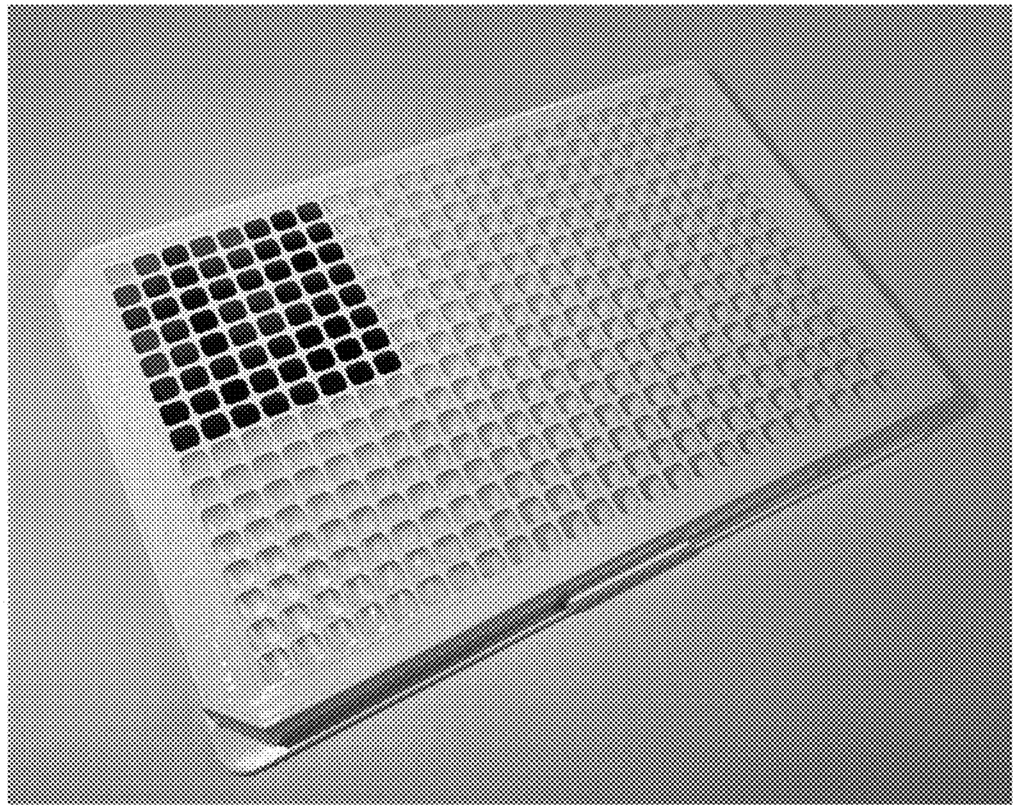
FIG. 52. 384-wellplate used for preparing and Raman imaging of multiplexed mixtures of SERS-NPs with all possible mixtures of six types of SERS-NPs in Karnaugh map fashion.

To reveal whether any combination of these SERS-NPs was susceptible to unacceptable demultiplexing error, or whether any of the Raman signatures were inadequately unique as to allow approximation using linear combinations of other incorrect signatures, each possible combination of the six flavors was mixed and imaged in the wells of a 384-well microplate (FIG. 52).

To validate that unmixing of SERS-NPs can be performed correctly and none of the flavors are mistaken for linear combinations of the others, we imaged 6 SERS-NP flavors mixed in all possible combinations (FIG. 45*a-c*). As this Raman imaging experiment sought to capture all combinations of the presence and absence of each of the six flavors, the Karnaugh array arrangement was chosen due to its popularity in interrogating patterns of Boolean variable states. This mimics all possible combinations of mixing that may be encountered in the mapping of an unknown labeled specimen. FIGS. 45*a,b* show the demultiplexed SERS imaging channels of the Karnaugh map of mixtures and the spectra of the SERS-NPs used. The results indicate that each SERS-NP type appeared in the correct wells and imaging channels.

Another feature for a diagnostic assay platform is performing unmixing while preserving quantitative information. We mixed six SERS-NPs in different proportions (FIGS. 45*e,f*) and observed the expected trend with high linearity shown in FIG. 45*f*. For this quantitation, we employed DCLS and the hybrid least-squares principal component analysis (HLP) demultiplexing algorithm. HLP was shown to be effective at accounting for background spectral contributions from biological tissue and imaging substrates, accounting for natural fluctuations in SERS-NP signals, and remaining robust when handling Raman spectra with a low signal-to-noise ratio (SNR). Having shown that DCLS achieves a trend just as linear as HLP given the same dataset, we infer that DCLS unmixing of these six flavors should be adequate, i.e., their signatures are distinct and stable enough to be reliably approximated using DCLS, barring attempts to detect signatures below the LOD. Thus, the results of the comprehensive analysis of the mixture of six SERS flavors proved that they may be unmixed both qualitatively and quantitatively.

EXAMPLE 11. Multiplexing of Co-localized SERS-NPs

Figure 46:
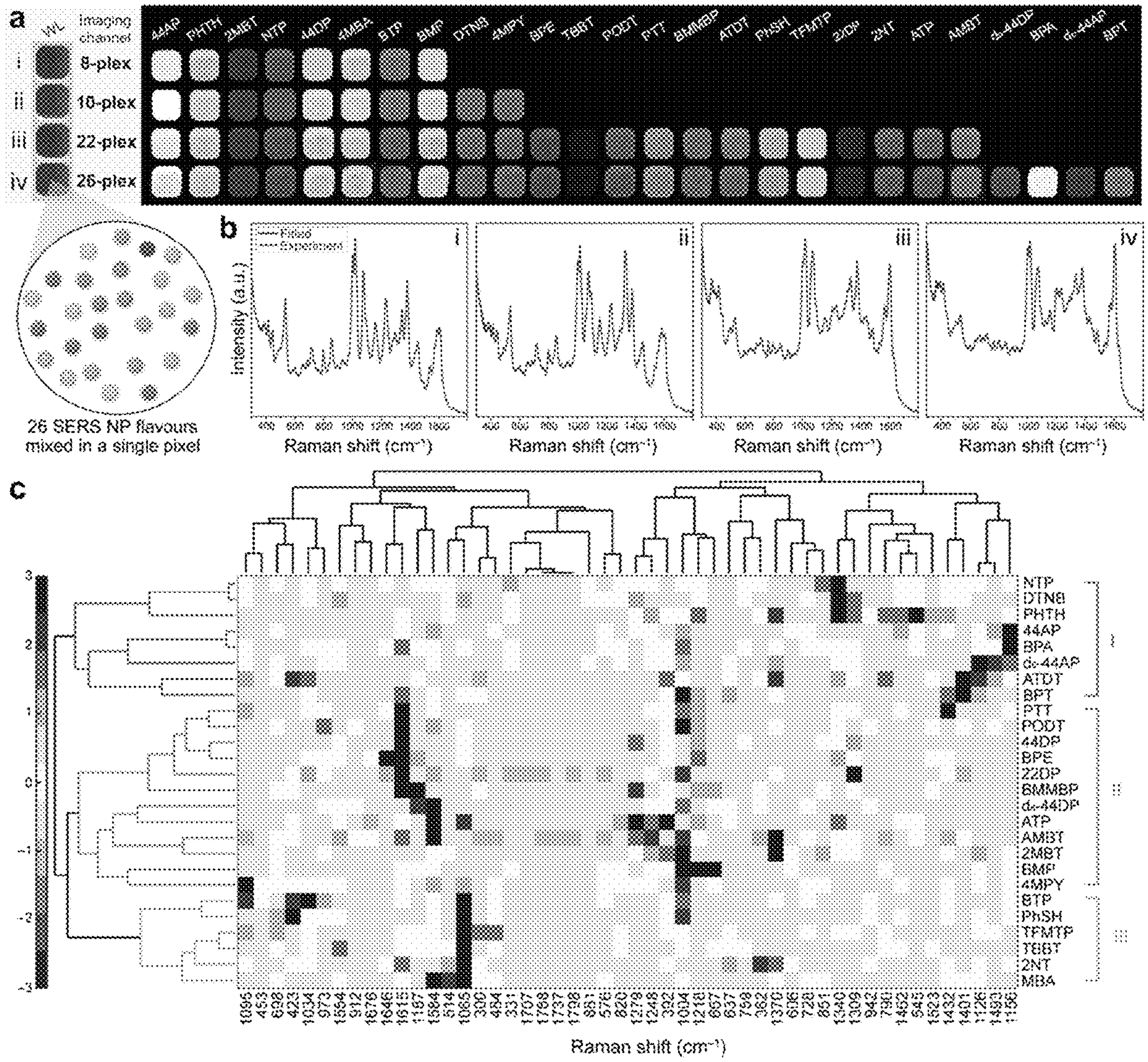
FIG. 46. Increasingly highplex mixtures mapped colocalized in a single well and hierarchical clustering of 26-plex SERS library features. a, white light (WL) image and SERS imaging channels of the demultiplexed Raman image depicting the mixed spectrum's content of the given SERS-NP's signature. For demonstrating multiplexed analysis, each imaging channel was artificially assigned a different color from the 26-color palette (Supplemental, Fig. S9). b, representative spectra from the 8-, 10-, 22-, and 26-plex mixtures along with respective least squares fitted spectra constructed as a best fit linear combination of SERS-NP reference spectra. c, hierarchical clustering dendrogram of the library of 26 SERS-NPs. The clustering was performed on baseline subtracted SERS spectra normalized to unit variance. For this grid, hierarchical clustering has arranged the SERS flavors into three vibronic families labeled I, II, and III. Spectral intensities along the horizontal axis have been arranged to highlight the spectral features which are shared among that vibronic family and indicate how that family differs from the others.

Considering that various biomarkers can be precisely coincident in a single scanning pixel in a real biological sample, we mixed multiple SERS flavors together with increasing plexity. Mixtures of 8, 10, 22, and 26 SERS-NPs were pipetted into four separate wells and imaged in a colocalized fashion, rather than spatially separated as demonstrated above (FIG. 44*a*). Raman imaging of each well (FIG. 46*a*) was followed by demultiplexing of the single well image into the respective 26 SERS imaging channels.

We, for the first time, successfully demonstrated that when colocalized, as many as 26 SERS fingerprints are multiplexed in a single Raman spectrum acquisition (FIG. 46*b*) and can still be reliably demultiplexed. Hierarchical clustering analysis of the library of 26 SERS-NPs identified three distinct "vibronic families" shown in FIG. 46*c*. This clustering analysis was computed by maximizing the adjacent correlations across each z-score normalized spectrum, resulting in the grouping of Raman reporters with similar spectral features, i.e., their Raman peaks or lack thereof.

Figure 53:
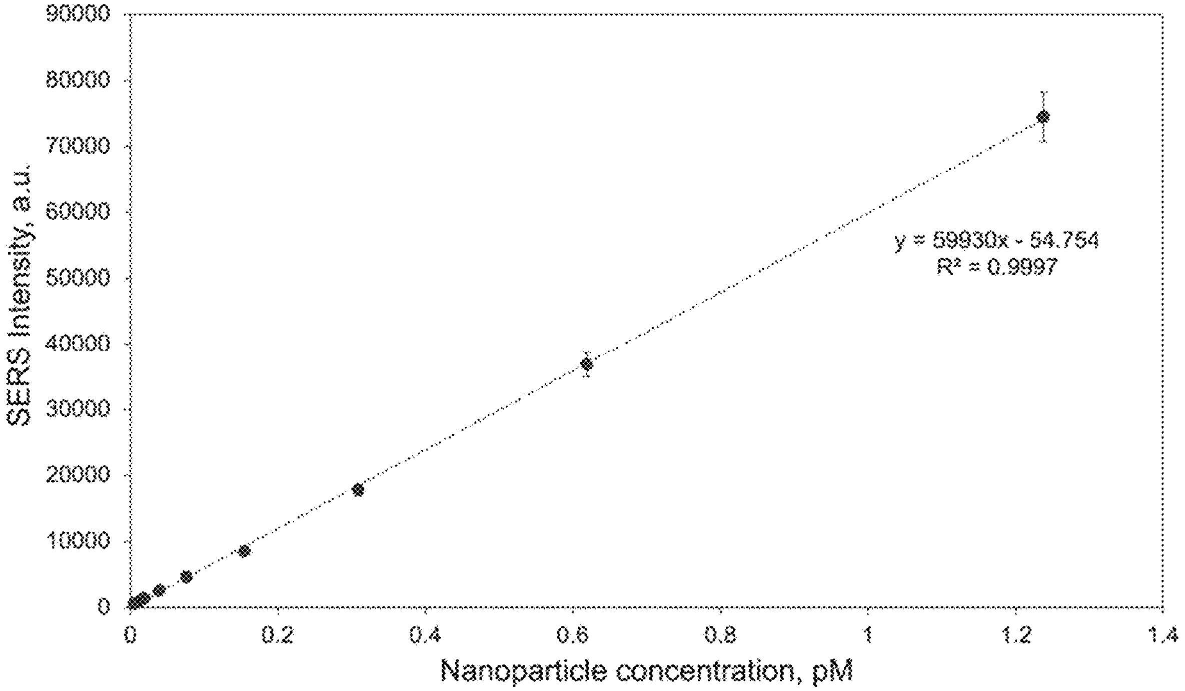
FIG. 53. Calibration curve of SERS intensities for PTT-labeled Au-NPs at about 165 mW laser power ($\lambda_{ex}$ 785 nm) and 2.5 s acquisition time. LOD for PTT-labeled Au-NPs: 0.75 fM.
Figure 54:
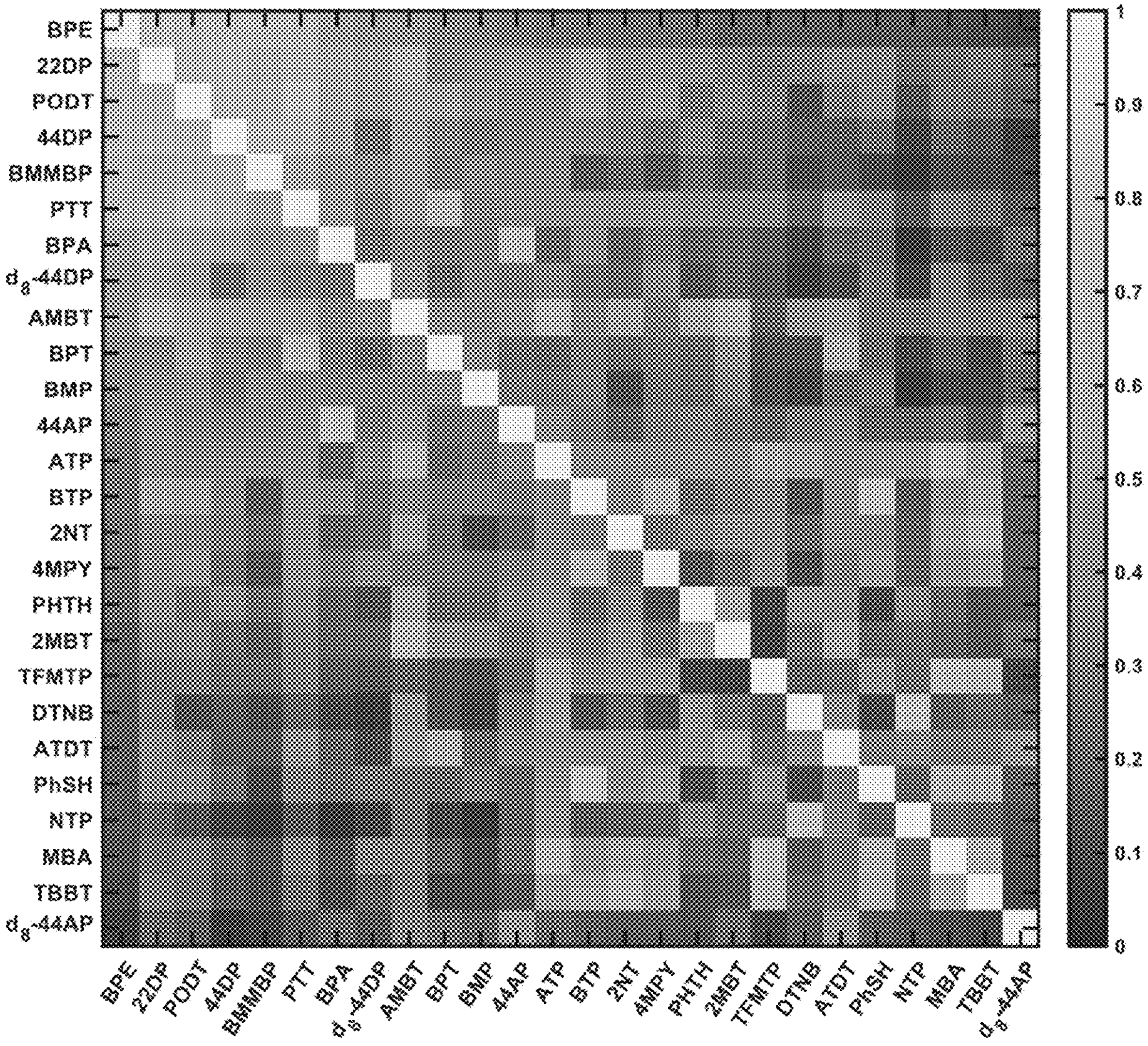
FIG. 54. Gram matrix of 26-plex SERS library. Some combinations of the Raman signatures in a SERS-NP library will inevitably be more similar than others. The same energy shift, or peak, may be achieved by different molecules having like vibrational modes or by exhibiting distinct vibrational modes which happen to cause similar energy shifts. Therefore, it is the total set of energy shifts and their probabilities which make a molecule's Raman spectrum unique. Here, we show the covariance matrix of our whole SERS library constructed as inner products of each pair of Raman signatures after performing baseline subtraction and normalizing to unit 2-norm. Lower inner product values indicate the Raman signatures are more different, and higher inner product values indicate that the Raman signatures are more similar, sharing many of their spectral features such as peak locations and intensities.
Figure 55:
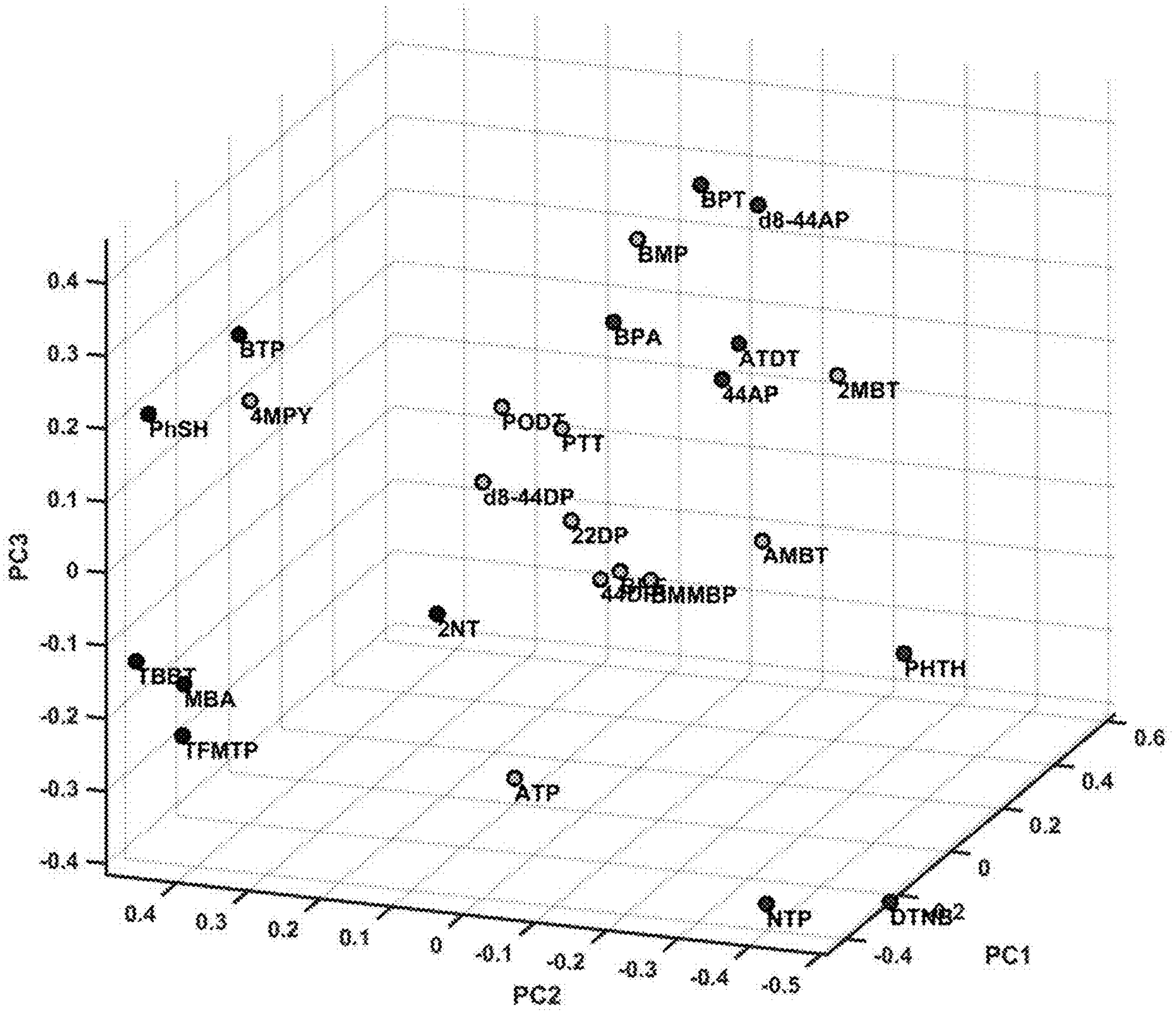
FIG. 55. PCA scores that indicate three vibronic families of the prepared SERS-NPs.
Figure 56:
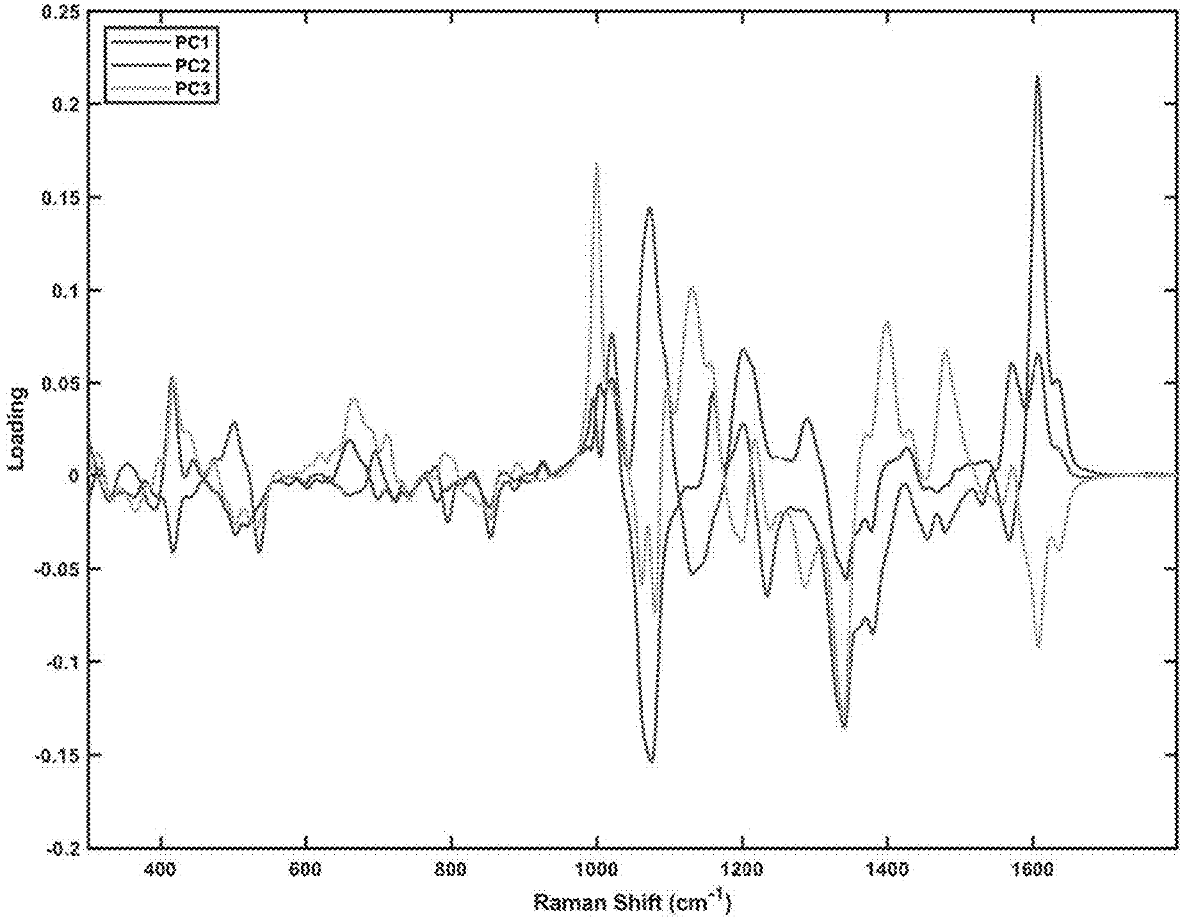
FIG. 56. Loading plots for the prepared SERS-NPs.
Figure 57:
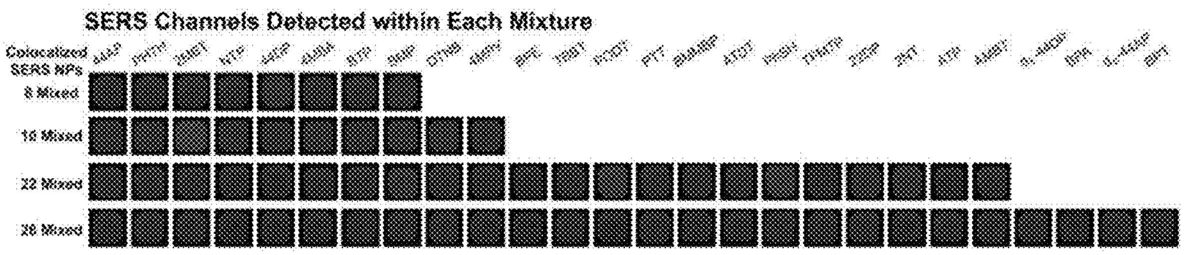
FIG. 57. Increasingly high-plex mixtures mapped co-localized in a single well all shown in red scale.

The Raman reporters, which were grouped by hierarchical clustering, did indeed share structural and/or vibrational mode similarities. The first vibronic family includes SERS-NPs bearing Raman peaks either at ca. 1200 or 1400 $cm^{-1}$ that correspond to C—N stretching or N—N bending and C—H stretching, respectively. The presence of a Raman peak at ca. 1000 $cm^{-1}$ (N—N stretching) in combination with signals at either ca. 1200 $cm^{-1}$ ($C_{ring}$—H bending) or 1600 $cm^{-1}$ (stretching of $(C—C)_{ring}$) typifies the second vibronic family SERS-NPs of the third vibronic family had the most prominent peak at ca. 1000 $cm^{-1}$ (ring breathing). Pairwise similarities of flavors can be visualized as a Gram matrix (FIG. 54). The families identified by hierarchical clustering also correspond to clusters observed in 3-dimensional principal component analysis (PCA) (FIGS. 55-56). This sort of clustering analysis may be an indispensable tool for further expanding our SERS-NP library as it may directly highlight the Raman shifts presently unoccupied by any of the current library's signatures. Notable multiplexing capacity and high sensitivity, with limits of detection in attomolar range (FIG. 53), of SERS-NPs may break new ground in molecular spatial profiling.

EXAMPLE 12. Multiplexed Targeted Detection of Cancer Cells Using SERS-NPs in Conjunction with Raman Imaging Having cultivated the SERS library and validated the capability to quantitatively and accurately multiplex, we sought to deploy them to evaluate their targeting efficiency toward specific biomarkers on well-characterized cell lines.

To demonstrate their potential as highly specific molecular targeting imaging agents, we functionalized our SERS-NPs by chemically conjugating them to moieties that recognize prototypical cancer biomarkers. We investigated their targeting efficiency on cultured cancer cells with well-known biomarker expression profiles.

Nonspecific binding may confound the interpretation of assays and bioimaging datasets. Fortunately, with our SERS-based Raman imaging strategy, we have a unique opportunity to include a competitive isotype NP functionalized with a nonspecific IgG to account for any untargeted binding.

This allows us to generate a map of specific to non-specific binding ratios that may more accurately depict the true molecular expression profile of the cells without the confounding contribution of non-specific binding.

The five cancer cell lines employed in this study were A431, DLD-1, U87-MG, HCC827, and BT474, each of which is known for their overexpression of a respective biomarker: epidermal growth factor receptor (EGFR, also known as ErbB1 or HER1), cluster of differentiation-47 (CD47), integrin αvβ3, cMET, and human epidermal growth factor receptor 2 (HER2). Each cell line was labeled with corresponding targeted SERS-NPs and IgG-conjugated SERS-NPs. Ratiometric Raman images shown in FIG. 47*a* demonstrated excellent spatial co-registration with the cells depicted in the white light images. High specific to non-specific ratios were also observed (FIG. 47*c*) that proved that our newly developed SERS-NPs are capable of specifically targeting cells based on their protein overexpression profile.

Figure 47:
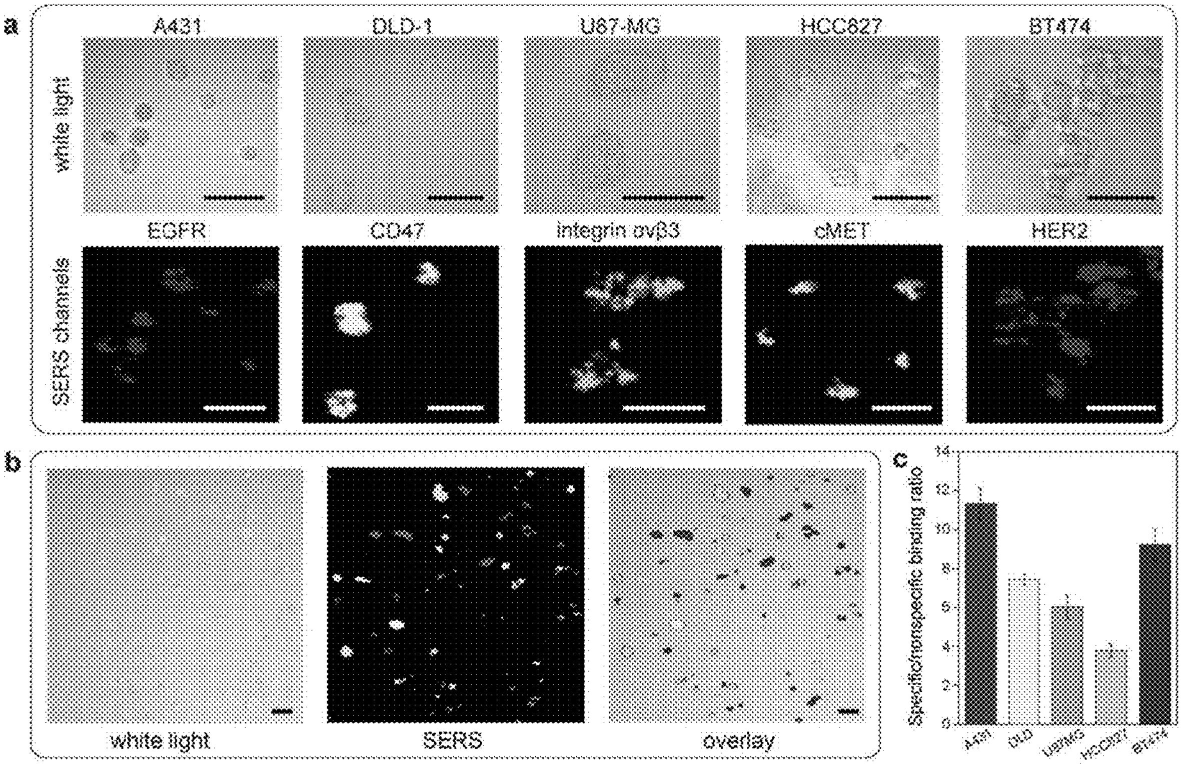
FIG. 47. Binding affinity of targeted NPs to membrane receptors on cultured cells. a, white light and corresponding SERS ratiometric images of A431 cells labeled by EGFR-targeted BPE-flavored NPs (red), DLD-1 cells labeled by CD47-targeted TBBT-flavored NPs (yellow), integrin αvβ3-targeted PHTH-flavored U87-MG cells (green), HCC827 cells labeled by cMET-targeted 2MBT-flavored NPs (blue), and BT474 cells labeled by HER2-targeted NTP-flavored NPs (purple). All cells were incubated with corresponding specific along with non-specific, isotype control, 44AP-flavored NPs conjugated to IgG antibody. b, mixture of all 5 cell lines each labeled by targeted SERS-NPs shown in white light image and imaging channels. Scale bars represent 50 μm. c, quantitative ratiometric analysis of specific aEGFR-, aHER2-, aCD47-, aCMET-, and RGD-analog-conjugated SERS-NPs binding to non-specific binding of isotype IgG-conjugated SERS-NP on the corresponding cancer cell lines. Error bars represent standard error of mean.
Figure 58:
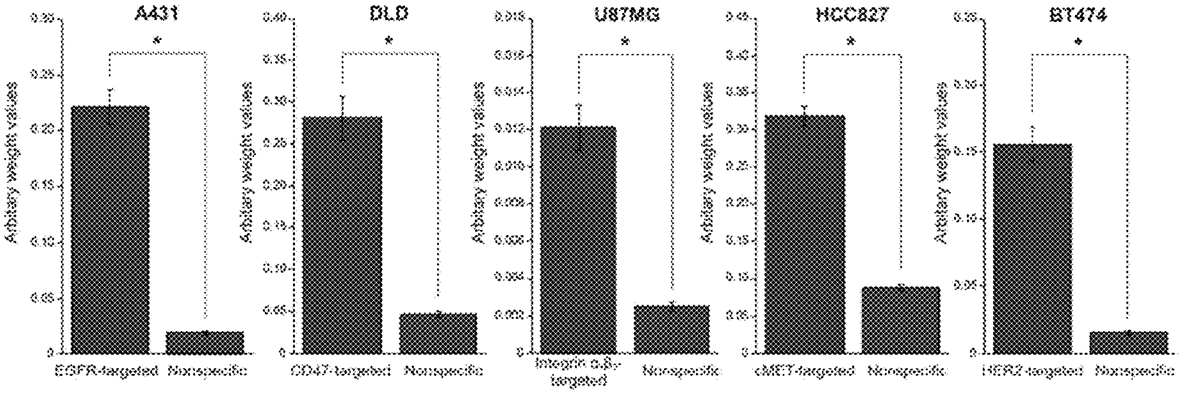
FIG. 58. Specificity of targeted SERS nanoparticles binding to respective cancer cell line estimated by weight values calculated from SERS maps in ImageJ. All types of targeted SERS nanoparticles show significant binding as opposed to non-specific SERS nanoparticles *($p$ <0.05). Error bars represent standard error of mean.

All types of targeted SERS-NPs showed significant binding with respect to non-specific SERS-NPs (FIG. 58). Moreover, we demonstrated on a mixture of cells that our targeted SERS-NPs allow spatial recognition of each cancer cell type after a single imaging acquisition of the mixed cell population (FIG. 47*b*).

EXAMPLE 13. Spatial Molecular Profiling of Human Tissue Using SERS-NPs in Conjunction with Raman Imaging After we demonstrated the ability of our SERS-NPs to specifically target cancer biomarkers, we decided to harness our microscopic Raman imaging capabilities to study the molecular expression profile of a given biomarker in a formalin-fixed paraffin-embedded (FFPE) human tissue section.

Breast cancer is a highly heterogeneous disease. Inter- and intra-tumor heterogeneity, caused by a variety of distinct genetic alterations in mammary epithelial cells, may determine the risk of disease progression and therapeutic resistance in individual patients and manifest the necessity of advancing personalized medicine. FFPE tissue sections are the most frequently analyzed type of samples by pathologists in practice.

Figure 48:
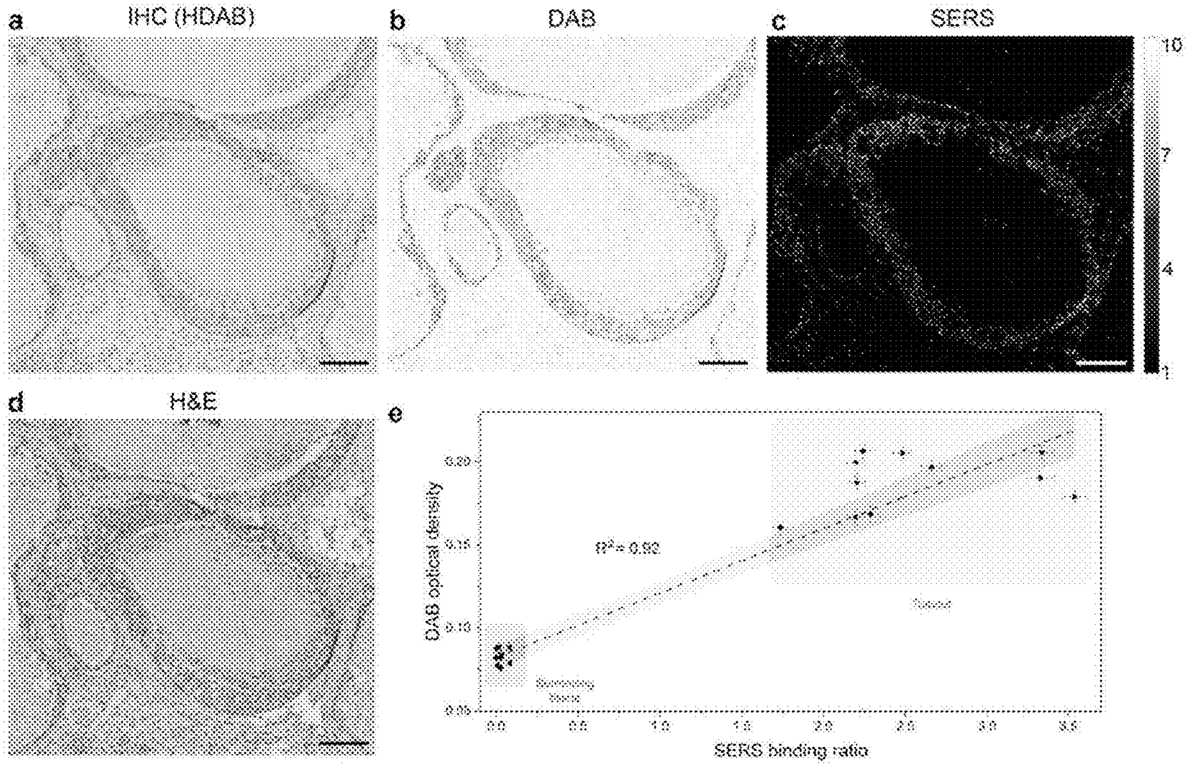
FIG. 48. Spatial molecular profiling of FFPE tissue sections. Optical images of adjacent FFPE human tissue sections of ductal carcinoma in situ: a, IHC-stained for HER2 with hematoxylin counterstain, b, with color-deconvolved DAB precipitate, and d, H&E-stained. c, SERS ratiometric image of FFPE tissue section stained with 2-plex mixture of aHER2-conjugated 22DP-labeled and IgG-conjugated BMMBP-labeled Au@$SiO_2$ nanoparticles representing specific binding to HER2 and non-specific binding to tissue, respectively. Scale bars for optical and SERS images represent 200 μm. e, DAB optical density plotted as a function of SERS binding ratio for the FFPE tissue section. Linear trend with confidence band (95%) was adjusted for the data with $R^2$=0.92.

Therefore, we utilized our SERS nanoparticles for targeting HER2 on an about 4 μm thick section of a human ductal carcinoma in situ (DCIS) tissue specimen. Immunohistochemistry (IHC) staining with 3,3'-diaminobenzidine (DAB), which is considered to be a gold-standard technique in pathology, allowed validation of our SERS ratiometric images (FIGS. 48*a,b*). Our SERS Raman image agreed with the IHC digital image on an adjacent FFPE tissue section. Tumor areas with stronger IHC coloration demonstrated a higher specific to nonspecific binding ratio. The Pearson correlation coefficient between SERS binding ratios and IHC color intensity was determined to be 0.96 (FIGS. 48*e*), indicating a strong correlation between the two techniques.

EXAMPLE 14. SERS-NP Fabrication

Figure 50:
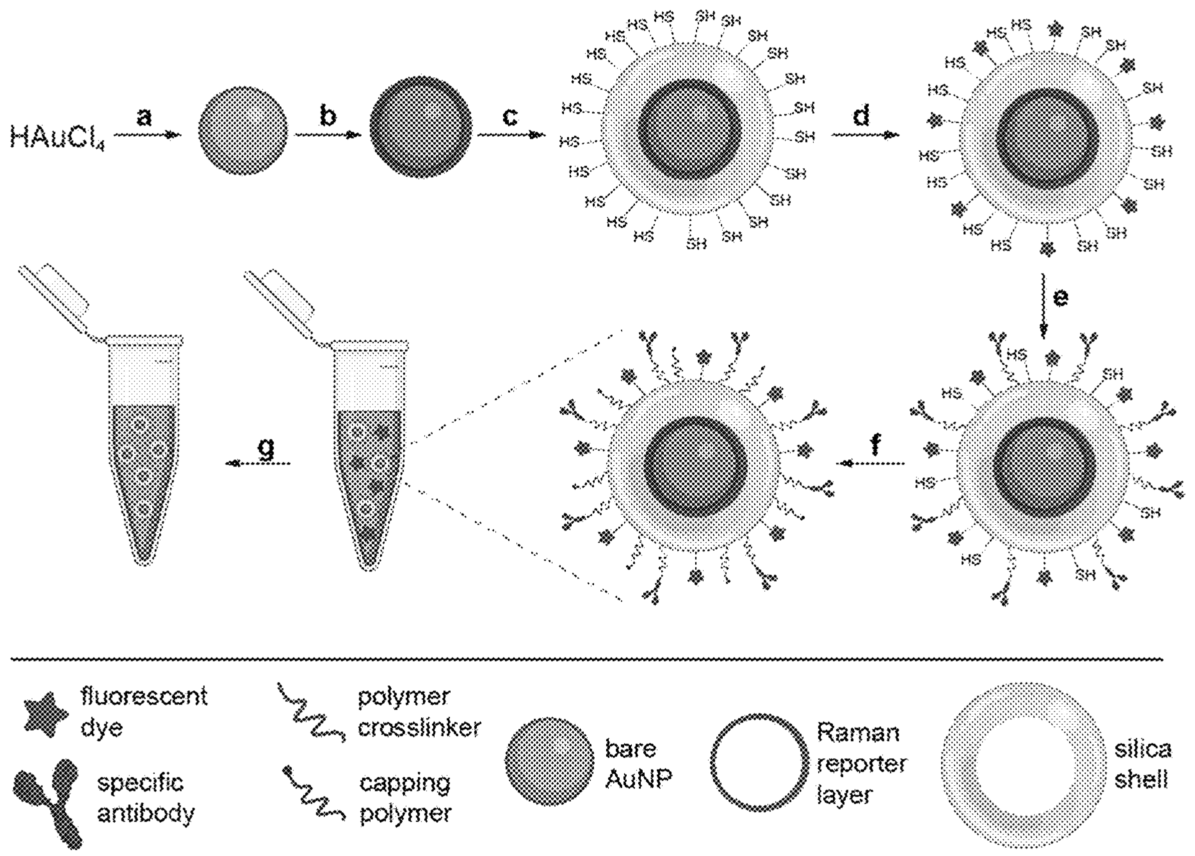
FIG. 50. Scheme of Raman-labeled nanoparticles preparation. a, synthesis of 60 nm spheric Au-NPs. b, labeling of Au-NPs with a Raman reporter. c, silica coating of SERS nanoparticles. d, thiolation of the glass shell. e, labeling SERS nanoparticles with a fluorescent dye. f, bioconjugation with monoclonal antibody. g, capping remaining thiols on the surface of SERS-NPs. h, purification by centrifugation. A SERS-NP is made up of a 60 nm gold core coated with a Raman-active layer which is protected by a silica shell. The Raman-active layer is made by chemically binding a reporter molecule which emits a desirable Raman spectral signature to the surface of the solid gold core. Enhancement of Raman scattering is achieved by the gold core inside many neighboring nanoparticles interacting with the incident laser to exhibit surface plasmon resonance. The silica shell is thiolated to enable functionalization with biomarker-targeting antibodies, allowing the particles to preferentially bind to an epitope of a protein of interest.

A modified method of hydroxylamine seeding of colloidal Au-NPs was used to fabricate spherical gold nanoparticles (FIG. 50). About 3 mL of about 30 mg/mL $HAuCl_4$ was added to about 450 mL of cold water (about 4° C.) under vigorous stirring. Then, about 0.6 mL of about 0.135 g/mL sodium citrate and about 0.085 g/mL hydroxylamine hydrochloride mixture were added rapidly. After about 10 s, about 0.12 mL of about 0.001% $NaBH_4$ was injected rapidly. The color of the solution changed dramatically from clear to black, then to purple, and finally to red. The colloidal solution was stirred for an additional about 10 min. The as-synthesized gold nanoparticles (about 25 mL; about 37.5 pM) were diluted with about 25 mL of water and then were rendered vitreophilic with the dropwise addition of about 40 μL of about 1 mM 3-aminopropyltrimethoxysilane. After about 15 min of vigorous stirring, a solution of one of 26 Raman reporters (Table 9) in ethanol was added. After about 5 min of stirring, a total of about 500 μL of about 2.16 wt % sodium silicate was added. The solution was stirred for another about 15 min and then allowed to stand for about 24 h. About 125 mL of ethanol was added to the solution to proceed with silica growth via the Stöber method. Growth of about 30 nm of additional glass shell was accomplished by the dropwise addition of about 625 μL of ammonia and about 50 μL of tetraethyl orthosilicate. The reaction mixture was stirred at room temperature for about 24 h. Next, the SERS-NPs were additionally functionalized with thiol groups in the second Stoller process with organosilane (3-mercaptopropyl)trimethoxysilane. NPs were purified and concentrated by centrifugation at about 1500 g for about 30 min for 5 times. Some of the surface thiol groups were purposefully left free for the further conjugation of the antibodies specifically targeting each of the antigens present on the analyzed tissue sample. Therefore, we added monoclonal antibodies: a-EGFR, a-HER2, a-CD47, a-cMET, and IgG, and RGD-analog (Table 8) to the final SERS nanoparticles along with the heterobifunctional poly(ethylene glycol) crosslinker—$SM(PEG)_{12}$ (about 300 mAb molar equivalents per NP; about 3 h at room temperature, RT). Following the primary conjugation reaction, methoxy-terminated passivation ligand $MM(PEG)_{12}$ blocked residual thiols on the nanoparticles (about $6 \cdot 10^5$ $MM(PEG)_{12}$ molar equivalents per NP; about 10 h at about 4° C.). Finally, SERS-NPs were purified four times via centrifugation (about 1500 g for about 10 min). The supernatant was removed and replaced with about 1% BSA in MOPS buffer after each round of centrifugation. The conjugated NPs were stored at about 4° C. and protected from light.

EXAMPLE 15. SERS-NP Characterization

Figure 51:
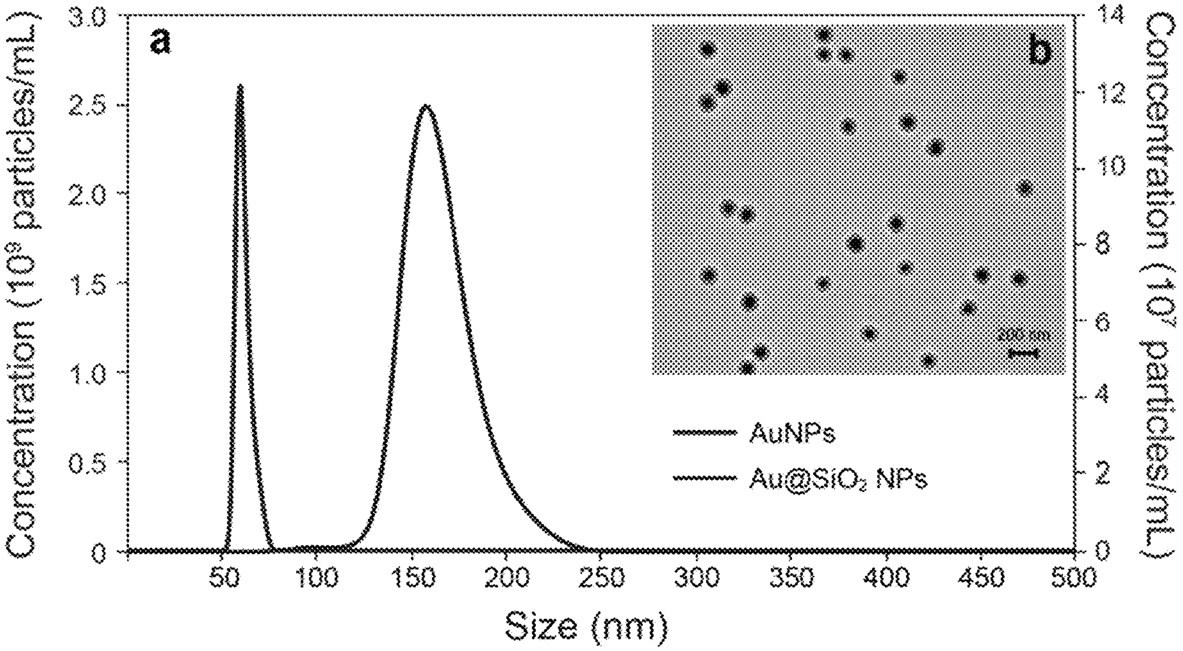
FIG. 51. a, size distribution of the prepared bare Au-NPs (blue) and silica-coated Au-NPs (purple) measured by nanoparticle tracking analysis (NTA). b, typical TEM image of silica-coated Au-NPs.

The bare gold colloidal solution was characterized with a Cary 60 UV-Vis (Agilent Technologies, US) spectrophotometer, and its maximal absorption band was observed at about 535 nm. Size and concentration were verified using dynamic light scattering (DLS) and nanoparticle-tracking analysis (NTA) with Zeta Sizer Nano ZS (Malvern Panalytical, UK) and NanoSight NS300 (Malvern Panalytical, UK), respectively. According to DLS and NTA measurements, the size distribution was 61±4 nm. SERS spectra were obtained to confirm the success of the labeling procedure and SERS activity by using an RA800-series Biological Analyser Raman instrument (Renishaw, UK). All SERS spectra were acquired using an about 165 mW and about 785 nm near-infrared diode laser and using a 50× objective lens and power neutral density filter of about 10%. We used about 10 s of acquisition time and a silicon wafer for calibration. The silica-coated Au-NPs ($Au@SiO_2$) were characterized by transmission electron microscopy (TEM; JEOL 1200ex-II, Japan) with 80 kV, 150,000× magnification) to study the SERS-NP structural morphology (FIG. 51). Size and concentration of $Au@SiO_2$ were determined by UV-vis spectroscopy and NTA. Surface thiol concentration was determined by Ellman's assay. The concentration of the final biomarker-targeted SERS nanoparticles was calculated ($\varepsilon_{520}$ $_{nm}$=3.531x10$^{10}$ $M^{-1}$x$cm^{-1}$) from UV-vis spectra acquired via NanoDrop™ 2000/2000c spectrophotometer (Thermo Fisher Scientific, US).

EXAMPLE 16. Raman Measurements

SERS imaging was performed using RA800-series Biological Analyser Raman instrument (Renishaw, UK) with an about 165 mW and about 785 nm near-infrared diode laser, 50× objective lens, and power neutral density filter of 2.5%. We used about 0.2 s of acquisition time and a silicon wafer for calibration.

EXAMPLE 17. Spectral Unmixing Processing

In preparation for a SERS imaging acquisition, reference spectra were collected of the separate, pure solutions of the SERS flavors being utilized. For cell and tissue labeling, solutions of fully targeting-functionalized SERS-NPs were characterized by nanoparticle-tracking analysis (NanoSight NS300, Malvern Panalytical) to procure stock solutions of known, identical concentrations. Identical laser power and spectral collection times were used to measure the reference spectra and the subsequent imaging. Demultiplexing of Raman mapping results into interpretable images made up of weight values, or abundances, of SERS flavor content was performed using the direct classical least-squares function of Renishaw's Windows-based Raman Environment (WiRE) software suite. For HLP demultiplexing, datasets of reference spectra comprising 100 separate spectral acquisitions of stock solutions were used to capture the statistical nature of SERS flavor emissions, and software authored by Van de Sompel and co-workers was used to attain weight values additionally regularized by PCA information.

EXAMPLE 18. Cell Lines and Cell Culture

The cell lines used for the study were obtained from American Type Culture Collection (ATCC). BT474, a human ductal carcinoma cell line, DLD-1, a human colorectal adenocarcinoma, and HCC827, a human lung adenocarcinoma, were cultured and maintained in RPMI 1640 medium supplemented with about 10% FB Essence (Avantor Seradigm, VWR, US) and about 1% Antibiotic/Antimycotic.

A431, a human epidermoid carcinoma, and U87MG, a human glioblastoma cell lines were cultured and maintained in Dulbecco's modified Eagle's medium (DMEM) supplemented with about 10% FB Essence (Avantor Seradigm, VWR, US) and 1% Antibiotic/Antimycotic. All cell lines were propagated at about 37° C. in an about 5% carbon dioxide atmosphere. The cells were passaged when the culture flask attained 75-90% confluency using TrypLE Express (Gibco, Thermofisher, US) to detach adherent cells.

EXAMPLE 19. Preparation and Staining of Tissue Sections

Formalin-fixed and paraffin-embedded (FFPE) human tissue sections were acquired from Cell Marque, Sigma (237S, DCIS-44A2, ductal carcinoma in situ). Tissue sections were dewaxed in xylene overnight and rehydrated in grades of alcohol (ethanol:deionized water about 100:0, about 90:10, about 80:20, about 70:30, about 50:50, about 0:100; about 5 min each). In an about 95-° C. water bath, heat-induced epitope retrieval was conducted in Tris-EDTA buffer at about pH 9 (target retrieval solution, Dako) for about 20 min. The samples were immediately cooled and then blocked with about 3% BSA and about 5% normal goat serum (NGS) in TBS for about 1 h. Tissue samples were washed twice with TBS and about 0.1% Triton X-100 (TBST), and twice with TBS for about 10 min. Samples were incubated overnight at about 4° C. with 2-plex 50 pM mixture of aHER2- and IgG-conjugated SERS nanoparticles. Tissue samples were washed twice with TBST for about 10 min, twice with TBS for about 10 min, with TBS on a rocker for about 2 h, and dried before SERS measurements.

EXAMPLE 20. Materials

Gold (III) chloride hydrate ($HAuCl_4 \cdot xH_2O$, 99.995%), trisodium citrate dihydrate ($C_6H_5Na_3O_7 \cdot 2H_2O$, 99.0%), (3-aminopropyl)triethoxysilane (APTMS, 98%), 5-amino-1,3,4-triazole-2-thiol (ATDT, 98%), 4,4'-bis(mercaptomethyl)biphenyl (BMMBP, 97%), 4-(trifluoromethyl)thiophenol (TFMTP, 99%), 4,4'-dipyridyl (44DP, 98%), 4,4'-azopyridine (44AP, 99%), phthalazine (PHTH, 98%) 4-mercaptopyridine (4MPY, 96%), 2-mercaptobenzothiazole (2MBT, 97%), 4,4'-thiobisbenzenethiol (TBBT, 98%), 4-aminothiophenol (ATP, 96%), 4-nitrothiophenol (NTP, 99%), 2-bromothiophenol (BTP, 97%), benzyl mercaptan (BMP, 99%), 6-amino-2-mercaptobenzothiazole (AMBT, 97%), sodium silicate aqueous solution (~26.5%), tetraethyl orthosilicate (TEOS, 99%), 3-(N-morpholino)propanesulfonic acid (MOPS, 99.5%), MOPS sodium salt (MOPS, 99.5%), and bovine serum albumin (BSA, cold ethanol fraction, pH 5.2, 96%) were purchased from Sigma-Aldrich. 1,2-Bis(4-pyridyl)ethylene (BPE, 97%) and 5,5'-dithiobis-(2-nitrobenzoic acid) (DTNB, 99%) were purchased from Beantown Chemical; 5-(4-pyridyl)-1,3,4-oxadiazole-2-thiol (PODT, 97%)—from Alfa Aesar; and 5-(4-pyridyl)-1H-1,2,4-triazole-3-thiol (PTT, 98%), thiophenol (PhSH, 99%), 2,2'-dipyridyl (22DP, 99%), 2-naphthalenethiol (2NT, 99%), and 4-mercaptobenzoic acid (4MBA, 90%)—from Acros Organics. DyLight™ 650-maleimide (DL650), succinimide-$PEG_{12}$-maleimide ($SM(PEG)_{12}$), and methyl-$PEG_{12}$-maleimide ($MM(PEG)_{12}$) were acquired from ThermoFisher Scientific. Anhydrous ethanol (99.5%), extra dry anhydrous DMSO (99.7%, <0.005% water), and phosphate-buffered saline (PBS) were ordered from Koptec, Acros Organics, and Corning, respectively. Deionized water (Milli-Q grade, Millipore) with a resistivity of 18.2 MΩ cm was used throughout the experiment. White polystyrene 384-well plates were purchased from Greiner Bio-One.

TABLE 8

Antibody and peptide conjugates used for labeling cancer cells and staining FFPE tissue sections.

| SERS Flavor | Target | Antibody Clone/ Peptide | Company | Catalogue Number |
|---|---|---|---|---|
| BPE | EGFR | E30 | Agilent Dako | M356301-2 |
| NTP | HER2 | 191924 | R&D | MAB1129 |
| 22DP | HER2 | — | Agilent Dako | A0485 |
| TBBT | CD47 | B6H12 | BD Biosciences | 556044 |
| 2MBT | cMET | 95106 | R&D | MAB3582 |
| 44AP | IgG1 | MOPC-21 | Invitrogen | MA1-10407 |
| BMMBP | IgG1 | MOPC-21 | Invitrogen | MA1-10407 |
| PHTH | integrin $\alpha_v\beta_3$ | Cyclo(Arg-Ala-Asp-D-Tyr-Lys) (RGD analog) | Peptides International | PCI-3894-PI |

TABLE 9

Exemplary Raman reporters suitable for the synthesis of the SERS-NPs
Raman reporters

| ID No. | Chemical Name | Acronym | Chemical Structure |
|---|---|---|---|
| 1 | 1,2-Bis(4-pyridyl)ethylene | BPE | 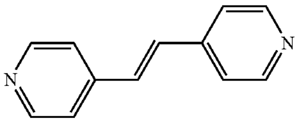 [SMILES: C(=C\c1ccncc1)/c1ccncc1] |
| 2 | 5,5'-Dithiobis-(2-nitrobenzoic acid) | DTNB | 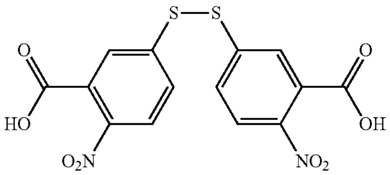 |
| 3 | 5-(4-Pyridyl)-1,3,4-oxadiazole-2-thiol | PODT | 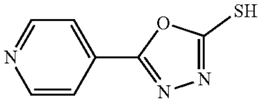 [SMILES: Sc1nnc(-c2ccncc2)o1] |
| 4 | 5-(4-Pyridyl)-1H-1,2,4-triazole-3-thiol | PTT | 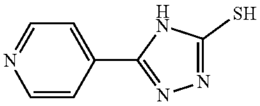 [SMILES: Sc1nnc(-c2ccncc2)[nH]1] |
| 5 | 4,4'-Bis(mercaptomethyl)biphenyl | BMMBP | 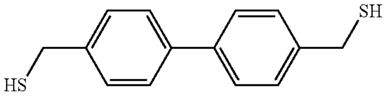 [SMILES: SCc1ccc(-c2ccc(CS)cc2)cc1] |
| 6 | 5-Amino-1,3,4-triazole-2-thiol | ATDT | 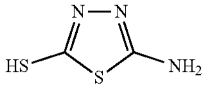 |
| 7 | Thiophenol | PhSH | 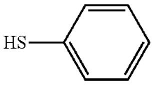 |
| 8 | 4-(Trifluoromethyl)thiophenol | TFMTP | 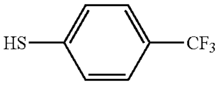 |
| 9 | 4,4'-Dipyridyl | 44DP | 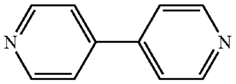 [SMILES: c1cc(-c2ccncc2)ccn1] |
| 10 | $d_8$-4,4'-Dipyridyl | $d_8$-44DP | 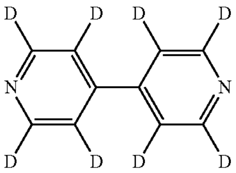 [SMILES: [2H]c1nc([2H])c([2H])c(-c2c([2H])c([2H])nc([2H])c2[2H])c1[2H]] |
| 11 | 2,2'-Dipyridyl | 22DP | 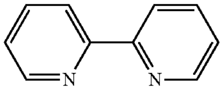 [SMILES: c1ccc(-c2ccccn2)nc1] |
| 12 | 4,4'-Azopyridine | 44AP | 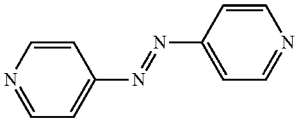 [SMILES: c1cc(/N=N/c2ccncc2)ccn1] |

TABLE 9-continued

Exemplary Raman reporters suitable for the synthesis of the SERS-NPs
Raman reporters

| ID No. | Chemical Name | Acronym | Chemical Structure |
|---|---|---|---|
| 13 | $d_8$-4,4'-Azopyridine | $d_8$-44AP | 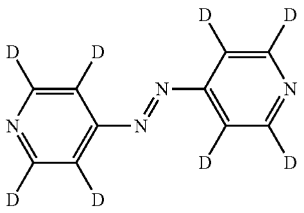 [SMILES: [2H]c1nc([2H])c([2H])c(/N=N/c2c([2H])c([2H])nc([2H])c2[2H])c1[2H]] |
| 14 | Phthalazine | PHTH | 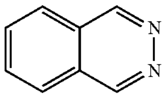 |
| 15 | 2-Naphthalenethiol | 2NT | 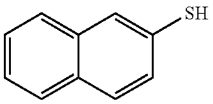 [SMILES: Sc1ccc2ccccc2c1] |
| 16 | 4-Mercaptobenzoic acid | 4MBA | 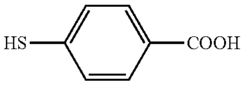 |
| 17 | 4-Mercaptopyridine | 4MPY | 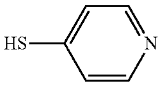 |
| 18 | 2-Mercaptobenzothiazole | 2MBT | 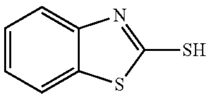 |
| 19 | 4,4'-Thiobisbenzenethiol | TBBT | 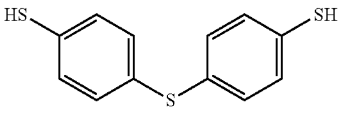 [SMILES: Sc1ccc(Sc2ccc(S)cc2)cc1] |
| 20 | 4-Aminothiophenol | ATP | 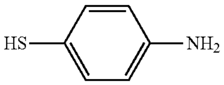 |
| 21 | 4-Nitrothiophenol | NTP | 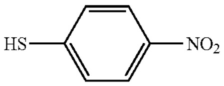 |
| 22 | 2-Bromothiophenol | BTP | 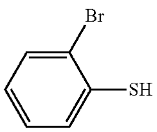 |
| 23 | Benzyl mercaptan | BMP | 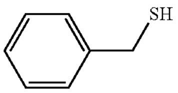 |
| 24 | 6-Amino-2-mercaptobenzothiazole | AMBT | 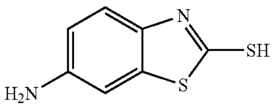 |

TABLE 9-continued

Exemplary Raman reporters suitable for the synthesis of the SERS-NPs
Raman reporters

| ID No. | Chemical Name | Acronym | Chemical Structure |
|---|---|---|---|
| 25 | 1,2-bis(pyridin-4-yl)acetylene | BPA | 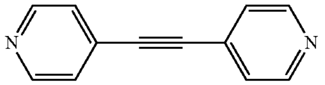 [SMILES: C(#Cc1ccncc1)c1ccncc1] |
| 26 | (Z)-3-(3-fluoropyridin-4-yl)-2-(pyridin-4-yl)acrylonitrile | FPA | 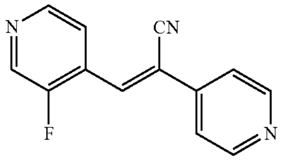 [SMILES: N#C/C(=C\c1ccncc1F)c1ccncc1] |
| 27 | (E)-3-(2-(pyridin-4-yl)vinyl)benzenethiol | PVB | 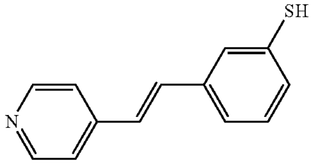 [SMILES: Sc1cccc(/C=C/c2ccncc2)c1] |
| 28 | 2,5-bis(pyridin-4-yl)-1,3,4-thiadiazole | BPT | 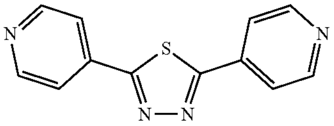 [SMILES: c1cc(-c2nnc(-c3ccncc3)s2)ccn1] |
| 29 | 4-Hydroxyl-2-mercapto-6-propylpyrimidine | HMPP | 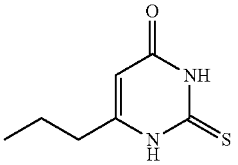 |
| 30 | 1-Phenyl-5-mercaptotetrazole | PMT | 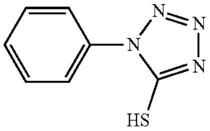 [SMILES: Sc1nnnn1-c1ccccc1] |
| 31 | 4-Amino-5-(2-(pyridine-3-yl)ethyl)-4H-1,2,4-triazole-3-thiol | APETT | 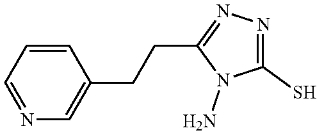 [SMILES: Nn1c(S)nnc1CCc1cccnc1] |
| 32 | 2-Mercapto-4-phenylthiazole | MPT | 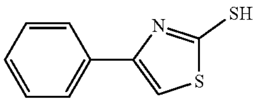 [SMILES: Sc1nc(-c2ccccc2)cs1] |
| 33 | 2-Mercaptobenzoxazole | MBO | 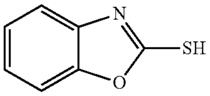 |
| 34 | 4-(1,2,3-Thiadiazol-4-yl)benzylamine | TBA | 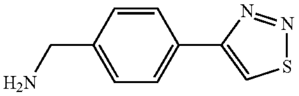 [SMILES: NCc1ccc(-c2csnn2)cc1] |
| 35 | 2-Mercaptobenzimidazole | MBI | 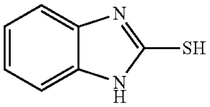 |

TABLE 9-continued

| ID No. | Chemical Name | Acronym | Chemical Structure |
|---|---|---|---|
| | Exemplary Raman reporters suitable for the synthesis of the SERS-NPs Raman reporters | | |
| 36 | 4-Mercaptophenylboronic acid | MPBA | 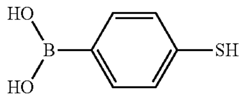 |
| 37 | 4-Phenylpyridine | 4PP | 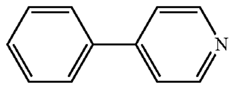 [SMILES: c1ccc(-c2ccncc2)cc1] |
| 38 | 5-Chloro-2-mercaptobenzoxazole | CBOT | 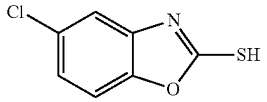 [SMILES: Sc1nc2cc(Cl)ccc2o1] |
| 39 | 1-(3-Ethyny1-4-pyridyl)-2-(4-pyridyl)ethylene | EPPE | 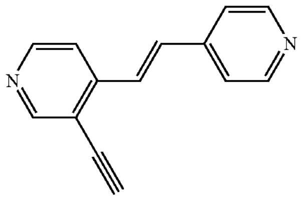 [SMILES: C#Cc1cnccc1/C=C/c1ccncc1] |
| 40 | 4,4' -dipyridyldisulfide | DPDS | 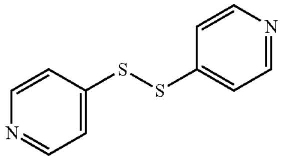 [SMILES: c1cc(SSc2ccncc2)ccn1] |
| 41 | 1,2-bis(4-pyridyl)ethane | BPAN | 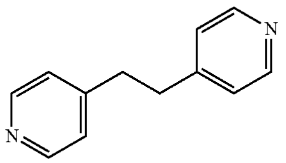 [SMILES: c1cc(CCc2ccncc2)ccn1] |
| 42 | p-Terphenyl-4,4''-dithiol | TDT | 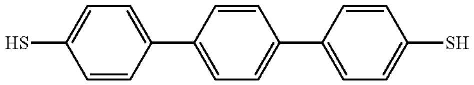 [SMILES: Sc1ccc(-c2ccc(-c3ccc(S)cc3)cc2)cc1] |
| 43 | Biphenyl-4,4'-dithiol | BDT | 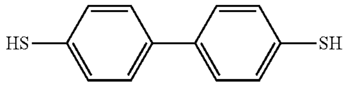 [SMILES: Sc1ccc(-c2ccc(S)cc2)cc1] |
| 44 | 4-(Mercaptomethyl) ethynylbenzene | MMB | 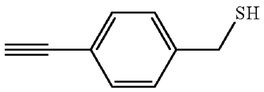 |
| 45 | 5-Phenyl-1H-1,2,4-triazole-3-thiol | PHTT | 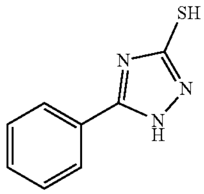 [SMILES: Sc1n[nH]c(-c2ccccc2)n1] |
| 46 | (4-Pyrid-4-ylphenyl)methanol | PPM | 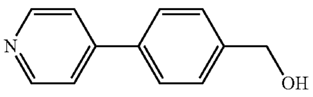 [SMILES: OCc1ccc(-c2ccncc2)cc1] |

TABLE 9-continued

| Exemplary Raman reporters suitable for the synthesis of the SERS-NPs Raman reporters | | | |
|---|---|---|---|
| ID No. | Chemical Name | Acronym | Chemical Structure |
| 47 | 4-(4-Pyridyl)benzoic acid | PBA | 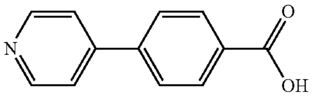 [SMILES: O=C(O)c1ccc(-c2ccncc2)cc1] |
| 48 | 1,2-Bis(4-pyridyl)hydrazine | BPH | 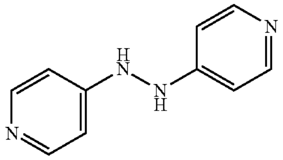 [SMILES: c1cc(NNc2ccncc2)ccn1] |
| 49 | N-(Pyridin-4-methylene)pyridine-4-amine | PMPA | 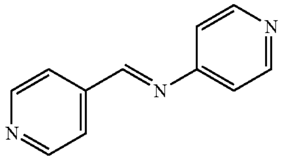 [SMILES: C(=N\c1ccncc1)/c1ccncc1] |
| 50 | 1,5-Dimercaptonaphthalene | DMN | 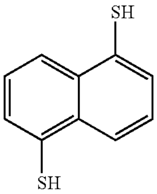 [SMILES: Sc1cccc2c(S)cccc12] |
| 51 | 2-Thiazoline-2-thiol | TAT | 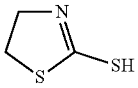 |
| 52 | 4-(1H-pyrazol-4-yl)pyridine | HPP | 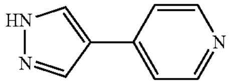 [SMILES: c1cc(-c2cn[nH]c2)ccn1] |
| 53 | 2-Mercapto-5-nitroimidazole | MNBI | 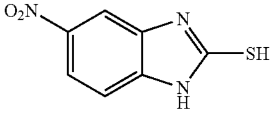 [SMILES: O=[N+]([O-])c1ccc2[nH]c(S)nc2c1] |
| 54 | 4-Mercaptobenzonitrile | 4MBN | 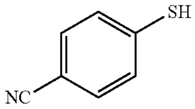 |
| 55 | 4-Chlorophenyl isothiocyanate | CPITC | 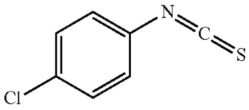 |
| 56 | 4-(Trifluoromethyl)pyrimidine-2-thiol | TFMPIT | 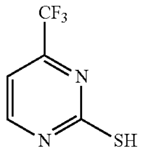 [SMILES: FC(F)(F)c1ccnc(S)n1] |
| 57 | 2-Quinolinethiol | QT | 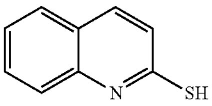 [SMILES: Sc1ccc2ccccc2n1] |

TABLE 9-continued

| Exemplary Raman reporters suitable for the synthesis of the SERS-NPs Raman reporters | | | |
|---|---|---|---|
| ID No. | Chemical Name | Acronym | Chemical Structure |
| 58 | 2-Mercaptopyrimidine | MPI | 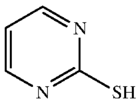 |
| 59 | 5-(Trifluoromethyl)pyridine-2-thiol | TFMPT | 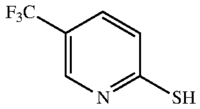 |
| 60 | 5-Fluorobenzoxazole-2-thiol | FBT | 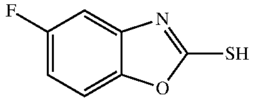 [SMILES: Fc1ccc2oc(S)nc2c1] |

EXAMPLE 21. Staining Formulations Comprising SERS-NPs

This disclosure also relates to a staining formulation useful for staining a sample to identify at least one chemical moiety on at least one surface of the sample.

The sample may be any sample. The sample may include a solid, a liquid, or a combination thereof. The sample may be a medical sample or a non-medical sample. For example, the sample may include a biological sample. For example, the biological sample may include tissue.

The tissue may be any tissue. For example, the tissue may be tissue belonging to a human, an animal, a plant, a virus, a bacterium, a cell, or a combination thereof. For example, the tissue may be breast tissue. The tissue may be diseased or healthy tissue. The tissue may be live tissue or dead tissue.

The chemical moiety may be any chemical moiety. For example, the chemical moiety may include a biomarker. For example, the biomarker may include a protein. For example, the biomarker may include a tissue biomarker. For example, the biomarker may be a tumor biomarker. For example, the biomarker may be a breast tumor biomarker.

This tissue may be stained by using the staining formulation of this disclosure. The staining formulations of this disclosure may include at least one SERS-NPs of this disclosure. The staining formulations of this disclosure may include at least two SERS-NPs of this disclosure. The staining formulations of this disclosure may include at least three SERS-NPs of this disclosure. The staining formulations of this disclosure may include at least one SERS-NPs as an isotype control, which may attach to a chemical moiety that is not targeted for identification.

The staining formulation may include as many SERS-NP flavors required to stain the sample (e.g., cells or tissue) as there are different chemical moieties (e.g., proteins) we need to identify. Each SERS-NP flavor may target only one specific chemical moiety. To achieve such targeting, each SERS-NP flavor may have a different Raman fingerprint than those of the other Raman SERS-NP flavors present within the staining formulation. To have a different Raman fingerprint, each SERS-NP flavor may include at least one SERS-NP that may have a different Raman reporter and/or Raman active core.

The staining formulation may include an additional SERS-NP flavor as an isotype control Raman flavor. The isotype control Raman flavor has a different Raman fingerprint than the Raman SERS-NP flavors present within the staining formulation.

For example, there are 60 Raman reporters in Table 9. Each Raman reporter may be used to prepare a different SERS-NP flavor that has a Raman fingerprint different than the others. The staining formulation may include any Raman reporter of Table 9, Raman report ID no. 1-60, or a combination thereof. One of these SERS-NP may be used to prepare an isotype control Raman flavor. Each SERS-NP flavor may include a different labeling agent to target a specific chemical moiety.

For example, having a library of 60 SERS-NP flavors may mean that we may stain for up to 60 biomarkers. Or, having a library of 60 SERS-NP flavors may mean that we may stain for up to 59 biomarkers, and one of the SERS-NP flavors may be used as the isotype control Raman flavor. As such, we may have unprecedented flexibility to prepare staining formulations that have a smaller combination of SERS-NP flavors (i.e., staining panels) if we target a small number of chemical moieties.

As an example of a 3-plex staining formulation, targeting two biomarkers may require a formulation that includes two SERS-NP flavors and an isotype control SERS-NP flavor, each SERS-NP flavor having a SERS-NP conjugated with a different antibody. With increasing number of available flavors, number of potential 3-plex staining formulations substantially increases. For example, with a library of 26 SERS-NP flavors, we may prepare $$\frac{26!}{(3!)(23!)} = 2600$$

different 3-plex staining formulations.

EXAMPLE 22. Designing Staining Formulations to Reduce Peak Overlap and Minimizing Demultiplexing Error In this example, we used a linear system sensitivity model that may include a subset that may maintain the stability and accuracy of the linear regression routine by minimizing the overlap of spectral features.

We looped over every possible 3-plex linear system design matrix and computed metrics that measure, or rank, how well suited the SERS-NP flavors are for multiplexing based on their Raman fingerprint peak structures alone.

In one example, we used metrics based on the singular value decomposition (SVD), to rank potential staining formulations Minimizing the condition number, $\kappa_2$, of inversion based on the matrix-induced 2-norm or maximizing the determinant have the effect of elucidating which 3-plex (i.e., three SERS-flavors) staining formulation may be best for multiplexing out of all the possible sets we could have chosen.

Figure 60:
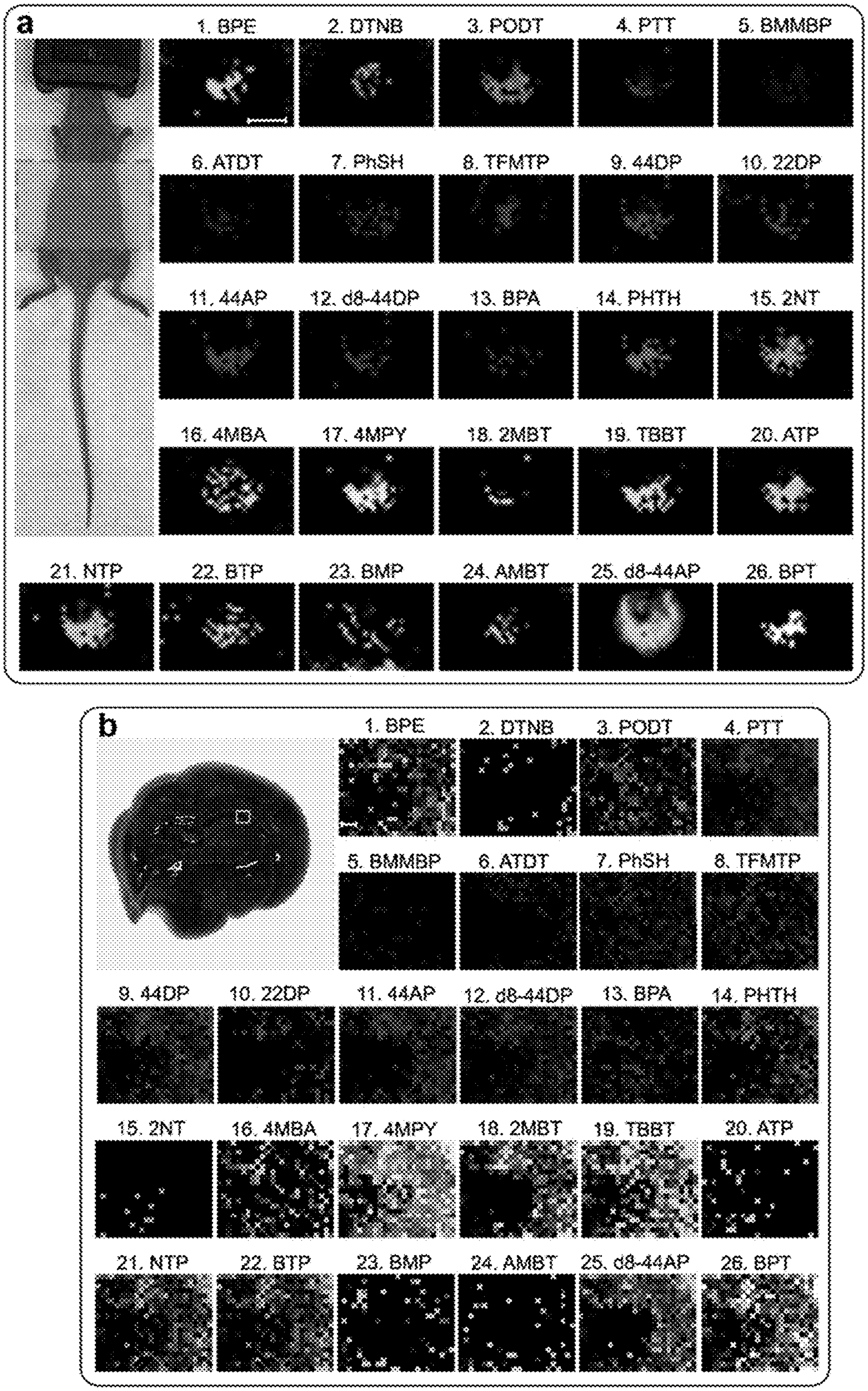
FIG. 60. Evaluation of multiplexing 26 different SERS nanoparticles in vivo (a) and ex vivo (b). Noninvasive in vivo imaging of the area highlighted in red was performed 24 h post intravenous injection of a mixture of the 26 SERS flavors in a living nude mouse (a). Ex vivo imaging of the liver area highlighted in orange was performed 24 h post intravenous injection of a mixture of the 26 SERS flavor (b). The multiplexed images were generated through the non-negative spectral unmixing of Raman spectra in each pixel. Arbitrary colors have been assigned to each unique SERS nanoparticle batch injected. The non-negative least squares (NNLS) spectral unmixing method was able to successfully separate all 26 SERS NPs into their respective imaging channels with minimal crosstalk. Scale bar represents 10 mm.
Figure 61:
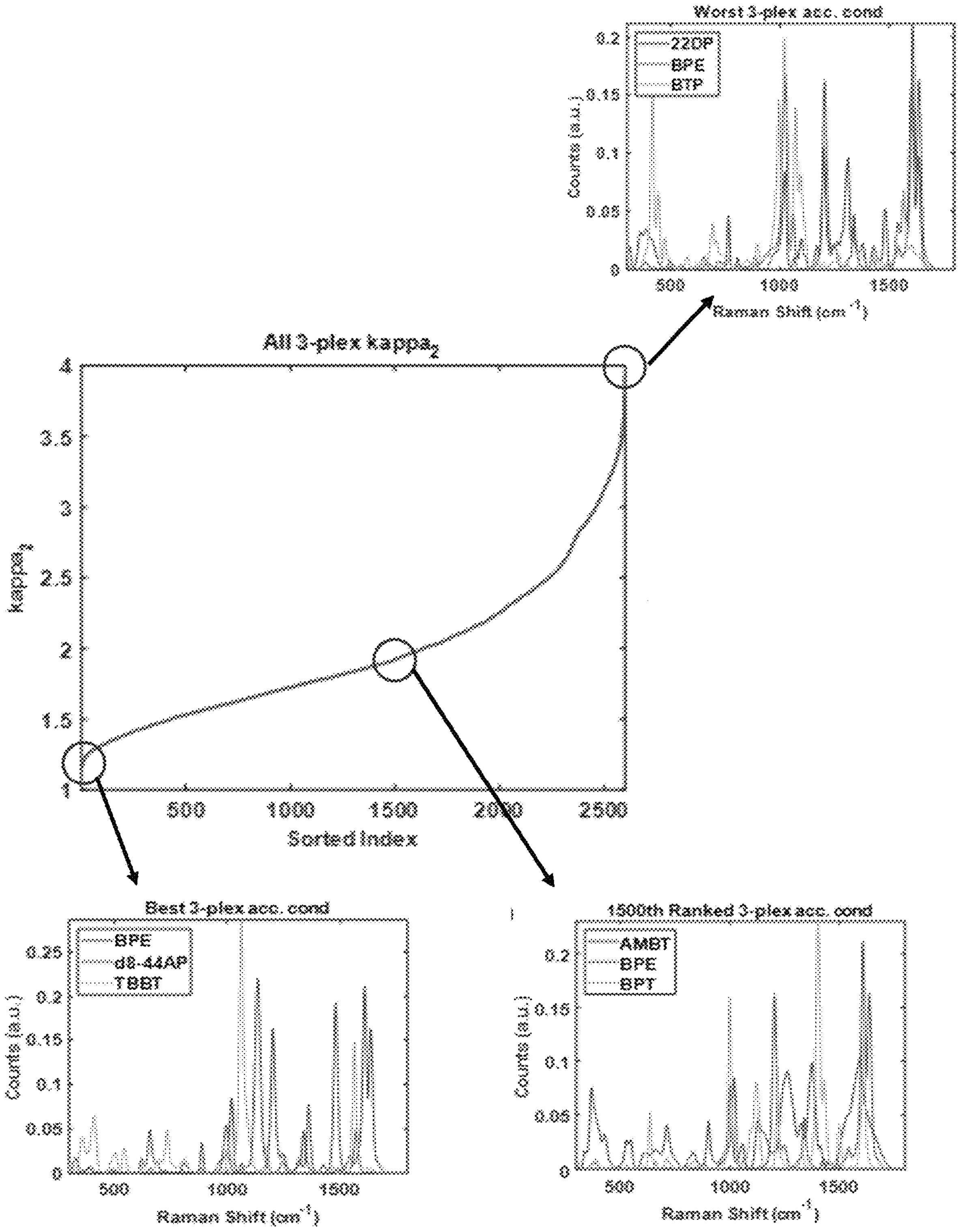
FIG. 61. Exemplary 3-plex staining formulations and their $\kappa_2$ scores. (a) This formulation had a lowest $\kappa_2$ score where peaks of each SERS-NP with a different Raman reporter almost never overlap with the other. (b) This formulation had a mid-$\kappa_2$ score where peaks of SERS-NP with BPE and SERS-NP with BPT overlap significantly, and the other SERS-NP with AMBT has many broad peaks. (c) This formulation had a highest $\kappa_2$ score where prominent peaks of SERS-NPs with different Raman reporters significantly overlap.
Figure 62:
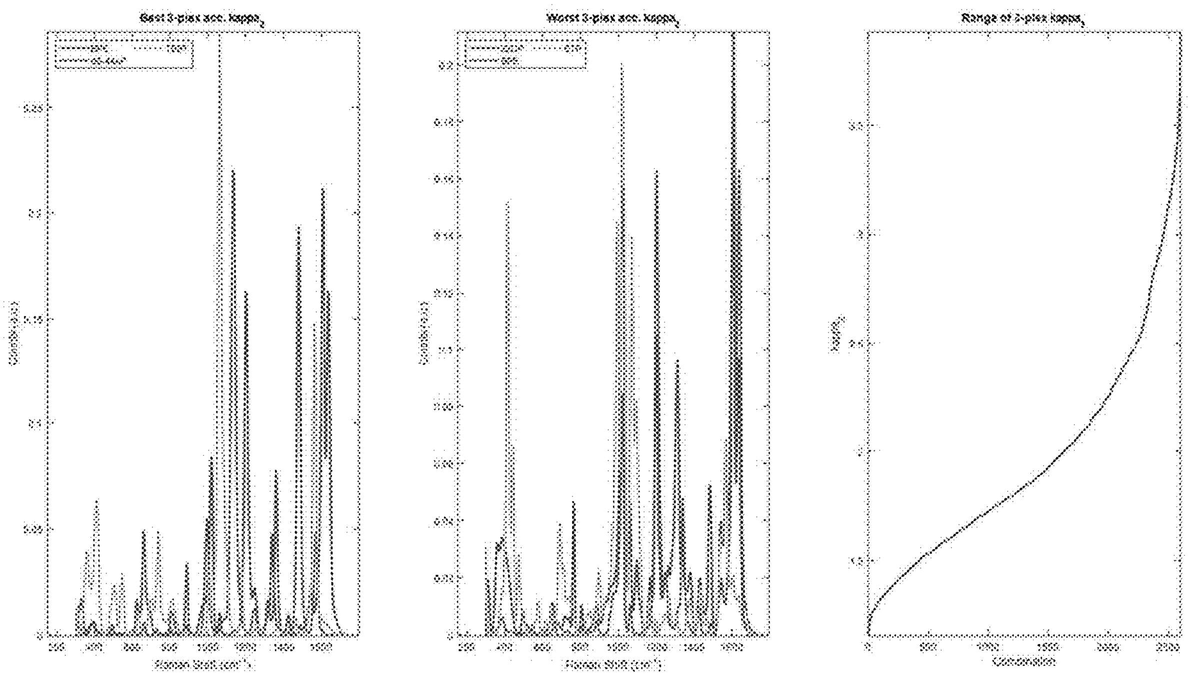
FIG. 62. Exemplary 3-plex staining formulations. (a) The most preferable 3-plex formulation. (b) The least preferable 3-plex formulation. (c) Range of $\kappa_2$ values of 3-plex formulations. The Raman reporters of these formulations were selected from Table 9, Raman reporter ID no. 1-25 and ID no. 28.
Figure 63:
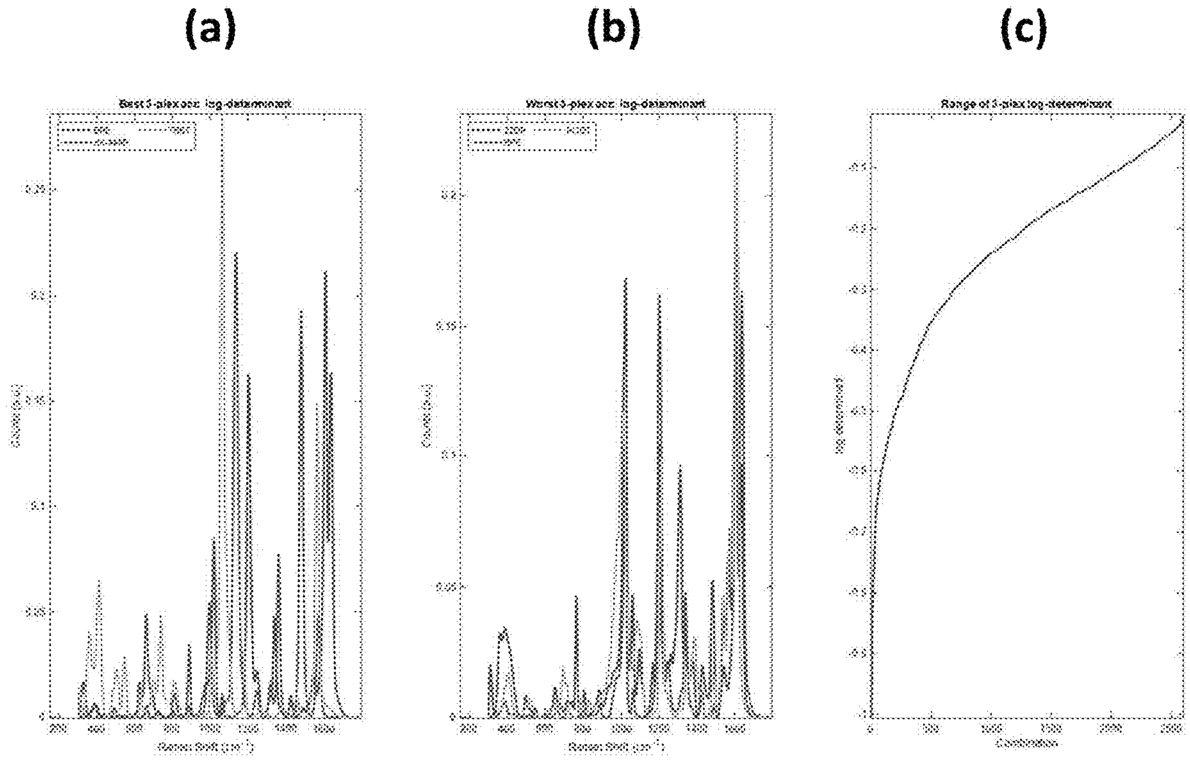
FIG. 63. Exemplary 3-plex staining formulations. (a) The most preferable 3-plex formulation. (b) The least preferable 3-plex formulation. (c) Range of log(det) values of 3-plex formulations. The Raman reporters of these formulations were selected from Table 9, Raman reporter ID no. 1-25 and ID no. 28.
Figure 64:
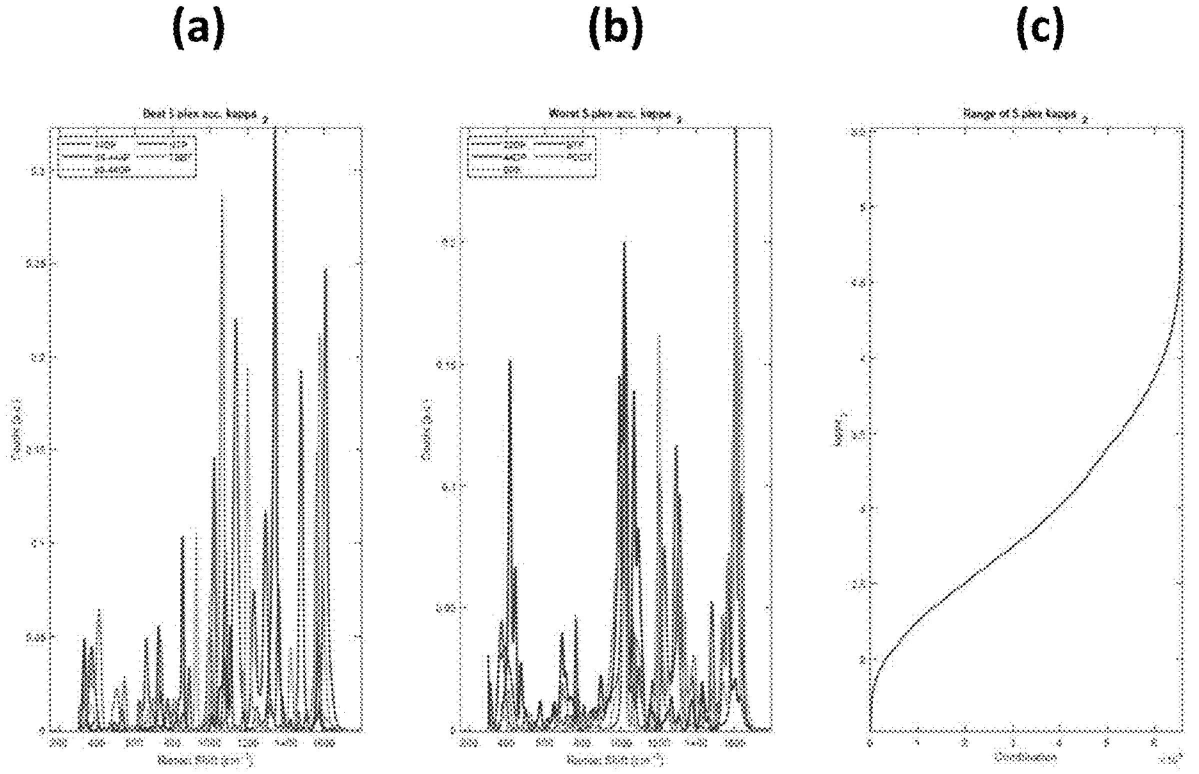
FIG. 64. Exemplary 5-plex staining formulations. (a) The most preferable 5-plex formulation. (b) The least preferable 5-plex formulation. (c) Range of $\kappa_2$ values of 5-plex formulations. The Raman reporters of these formulations were selected from Table 9, Raman reporter ID no. 1-25 and ID no. 28.
Figure 65:
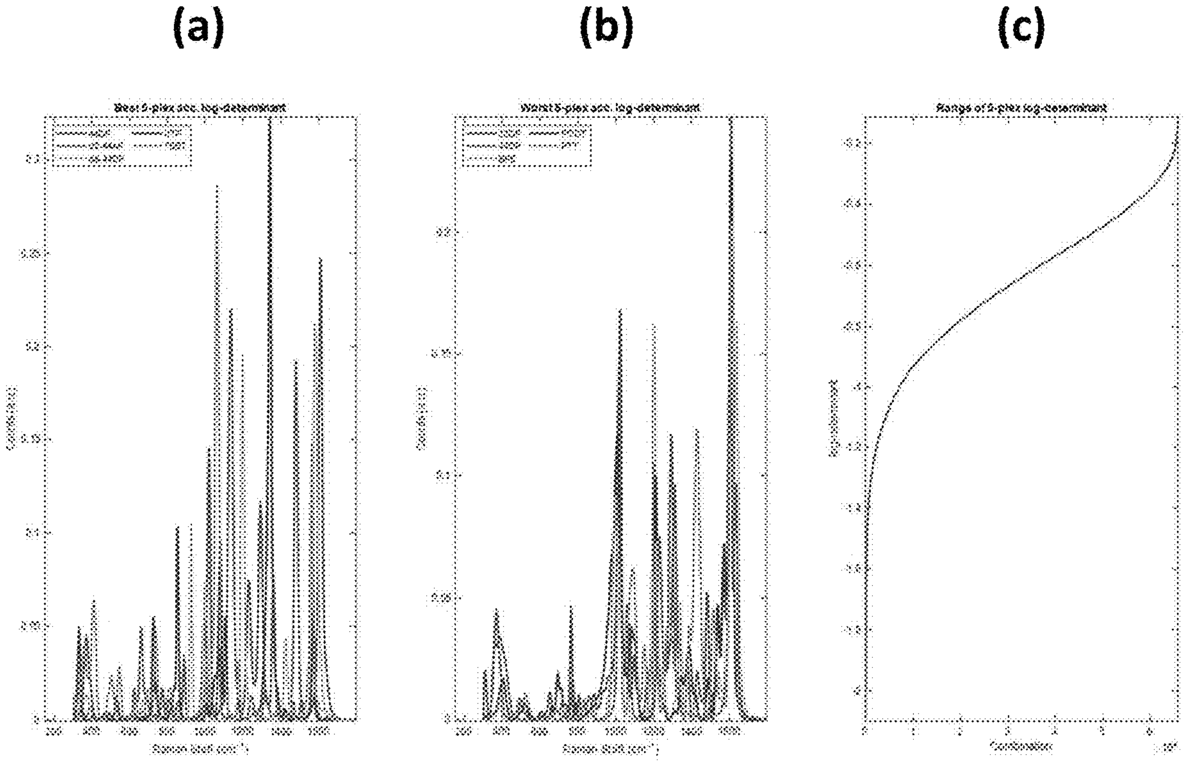
FIG. 65. Exemplary 5-plex staining formulations. (a) The most preferable 5-plex formulation. (b) The least preferable 5-plex formulation. (c) Range of log(det) values of 3-plex formulations. The Raman reporters of these formulations were selected from Table 9, Raman reporter ID no. 1-25 and ID no. 28.
Figure 66:
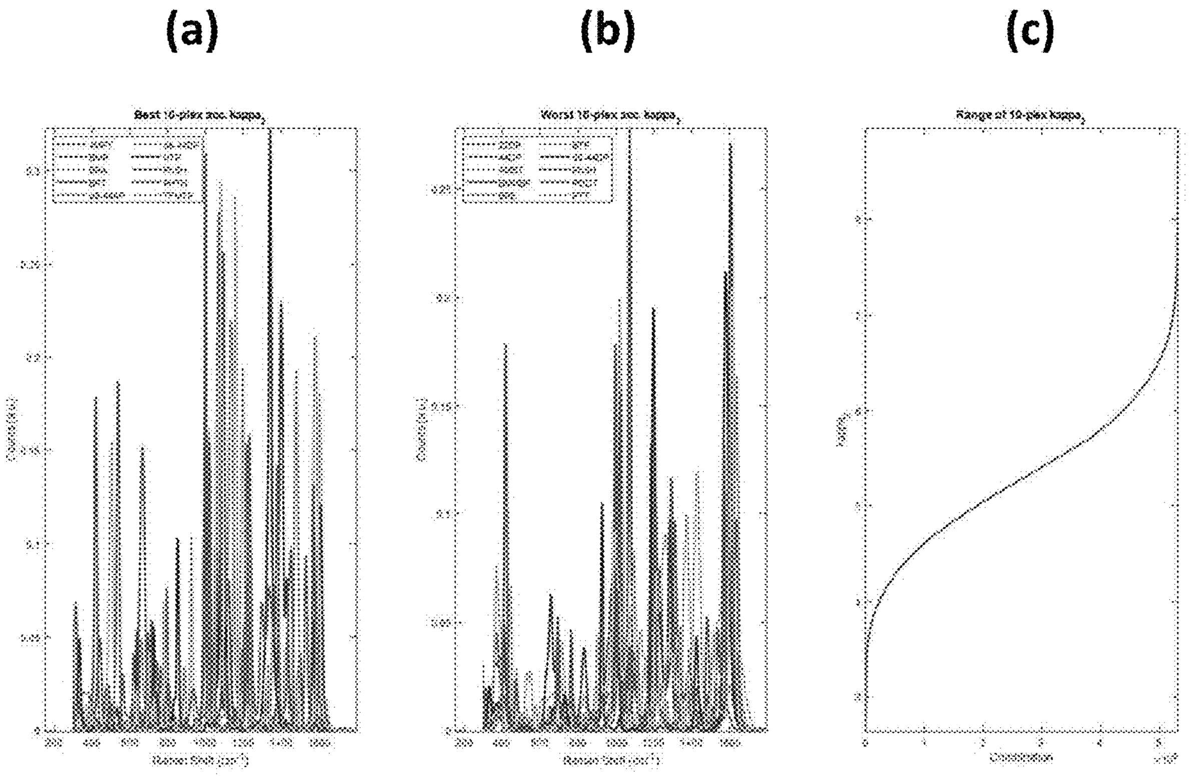
FIG. 66. Exemplary 10-plex staining formulations. (a) The most preferable 10-plex formulation. (b) The least preferable 10-plex formulation. (c) Range of $\kappa_2$ values of 10-plex formulations. The Raman reporters of these formulations were selected from Table 9, Raman reporter ID no. 1-25 and ID no. 28.
Figure 67:
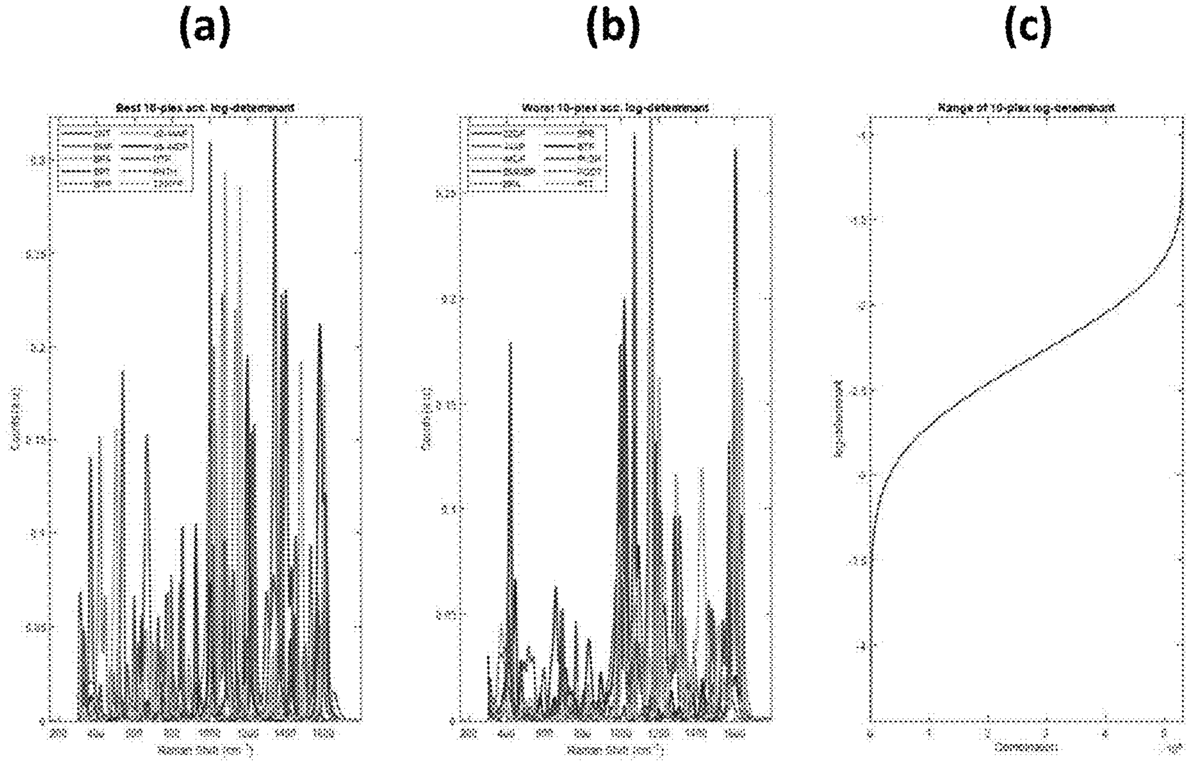
FIG. 67. Exemplary 10-plex staining formulations. (a) The most preferable 10-plex formulation. (b) The least preferable 10-plex formulation. (c) Range of log(det) values of 10-plex formulations. The Raman reporters of these formulations were selected from Table 9, Raman reporter ID no. 1-25 and ID no. 28.
Figure 68:
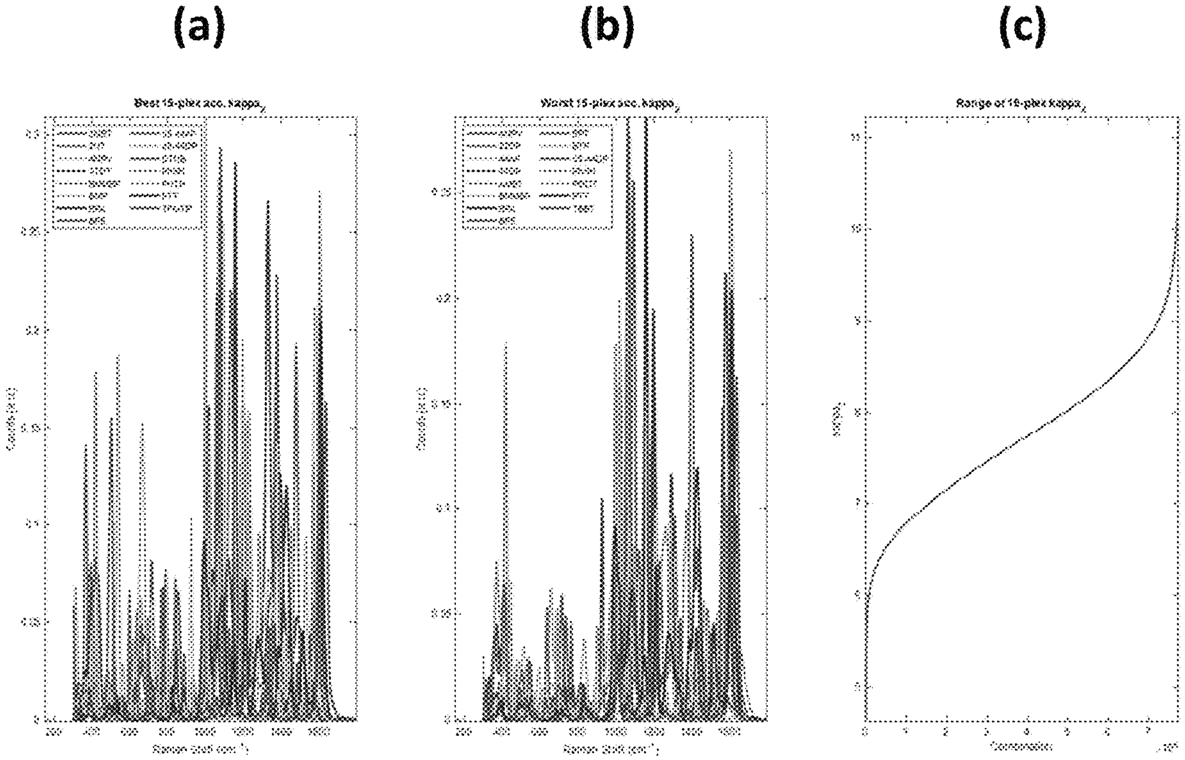
FIG. 68. Exemplary 15-plex staining formulations. (a) The most preferable 15-plex formulation. (b) The least preferable 15-plex formulation. (c) Range of $\kappa_2$ values of 15-plex formulations. The Raman reporters of these formulations were selected from Table 9, Raman reporter ID no. 1-25 and ID no. 28.
Figure 69:
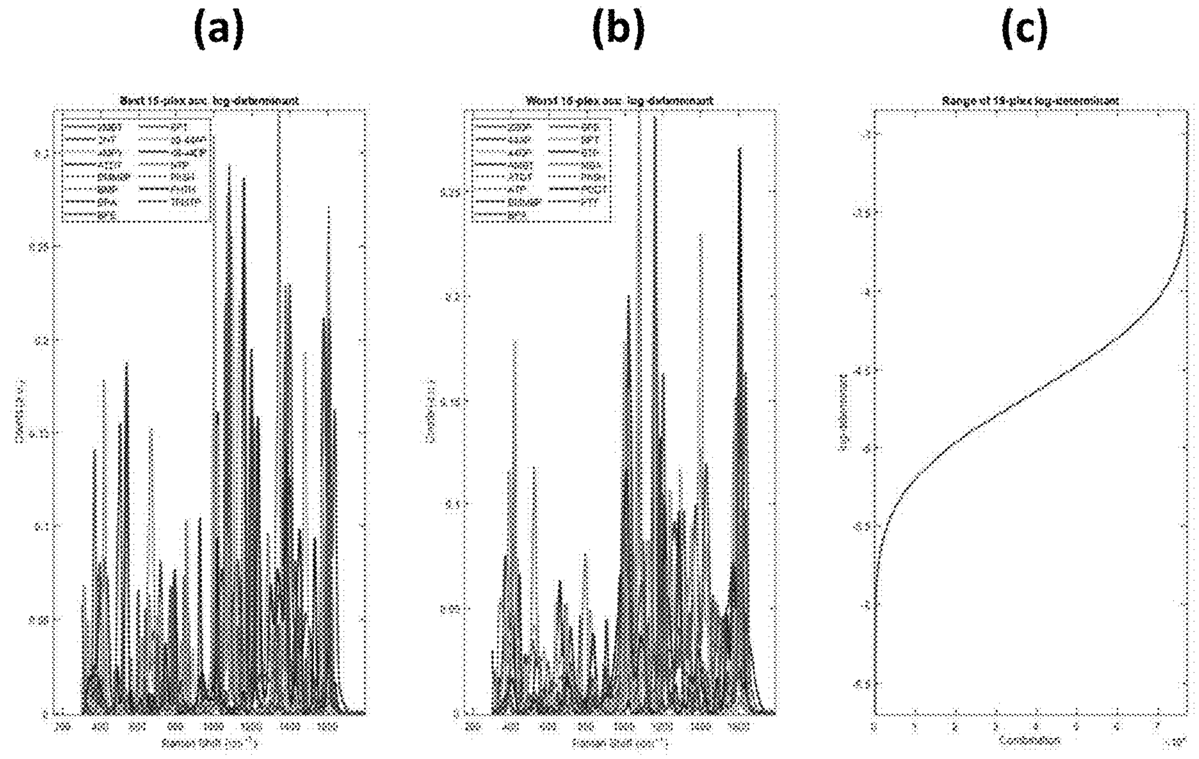
FIG. 69. Exemplary 15-plex staining formulations. (a) The most preferable 15-plex formulation. (b) The least preferable 15-plex formulation. (c) Range of log(det) values of 15-plex formulations. The Raman reporters of these formulations were selected from Table 9, Raman reporter ID no. 1-25 and ID no. 28.
Figure 70:
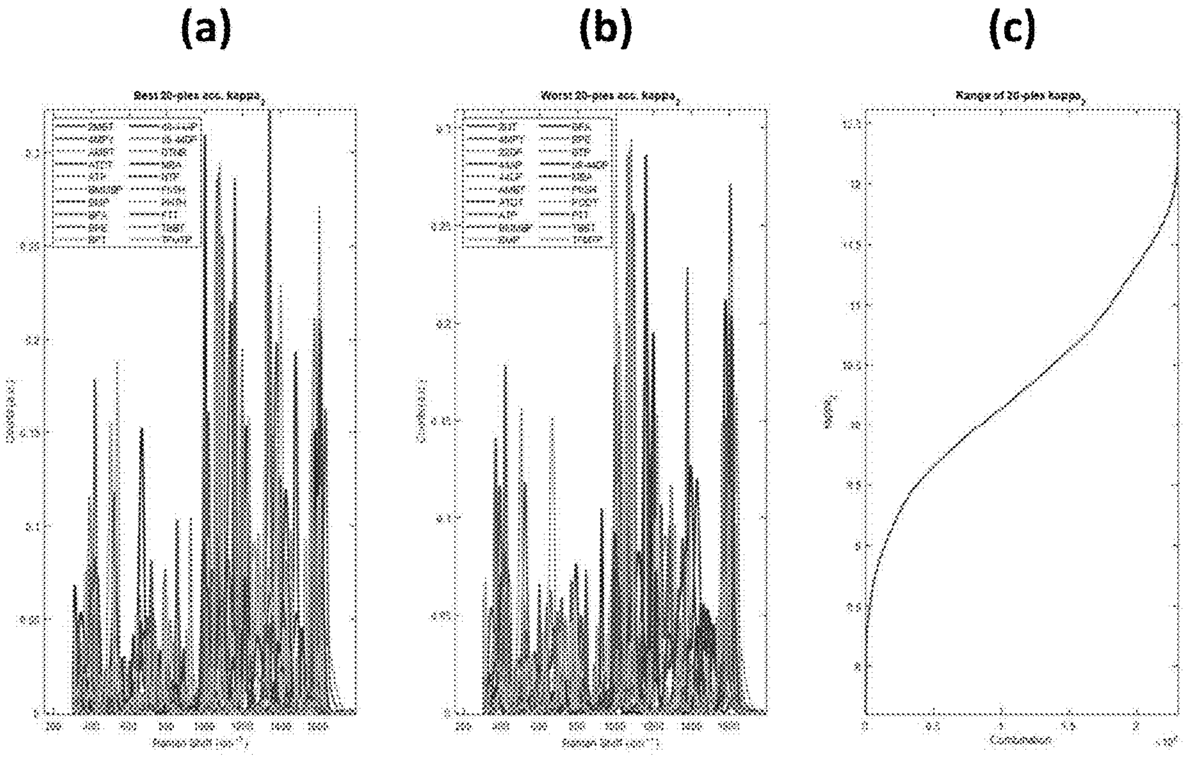
FIG. 70. Exemplary 20-plex staining formulations. (a) The most preferable 20-plex formulation. (b) The least preferable 20-plex formulation. (c) Range of $\kappa_2$ values of 20-plex formulations. The Raman reporters of these formulations were selected from Table 9, Raman reporter ID no. 1-25 and ID no. 28.
Figure 71:
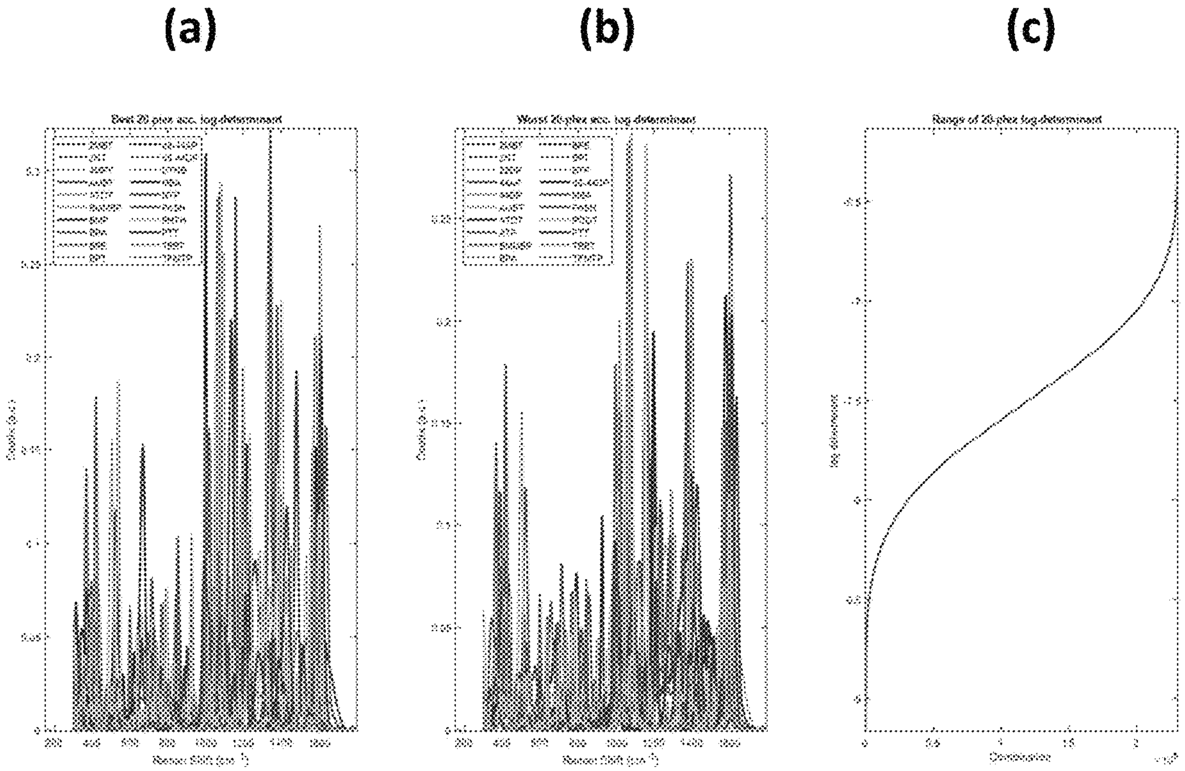
FIG. 71. Exemplary 20-plex staining formulations. (a) The most preferable 20-plex formulation. (b) The least preferable 20-plex formulation. (c) Range of log(det) values of 20-plex formulations. The Raman reporters of these formulations were selected from Table 9, Raman reporter ID no. 1-25 and ID no. 28.
Figure 72:
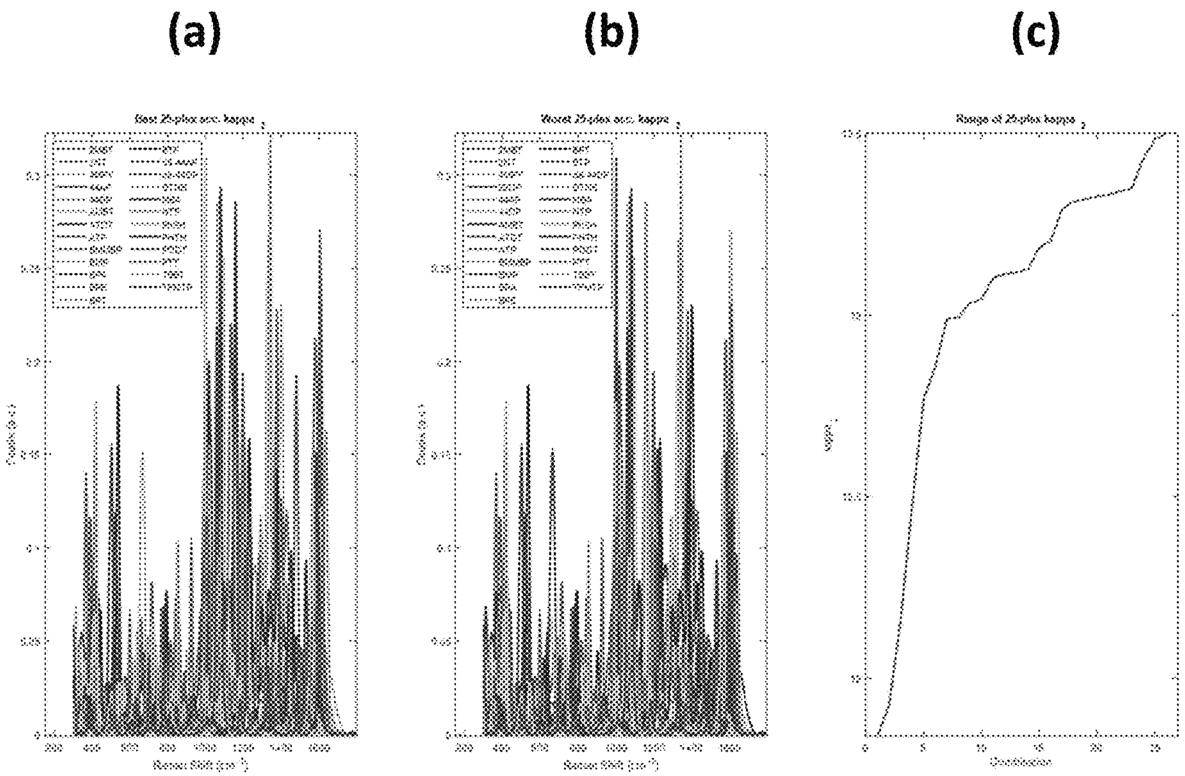
FIG. 72. Exemplary 25-plex staining formulations. (a) The most preferable 25-plex formulation. (b) The least preferable 25-plex formulation. (c) Range of $\kappa_2$ values of 25-plex formulations. The Raman reporters of these formulations were selected from Table 9, Raman reporter ID no. 1-25 and ID no. 28.
Figure 73:
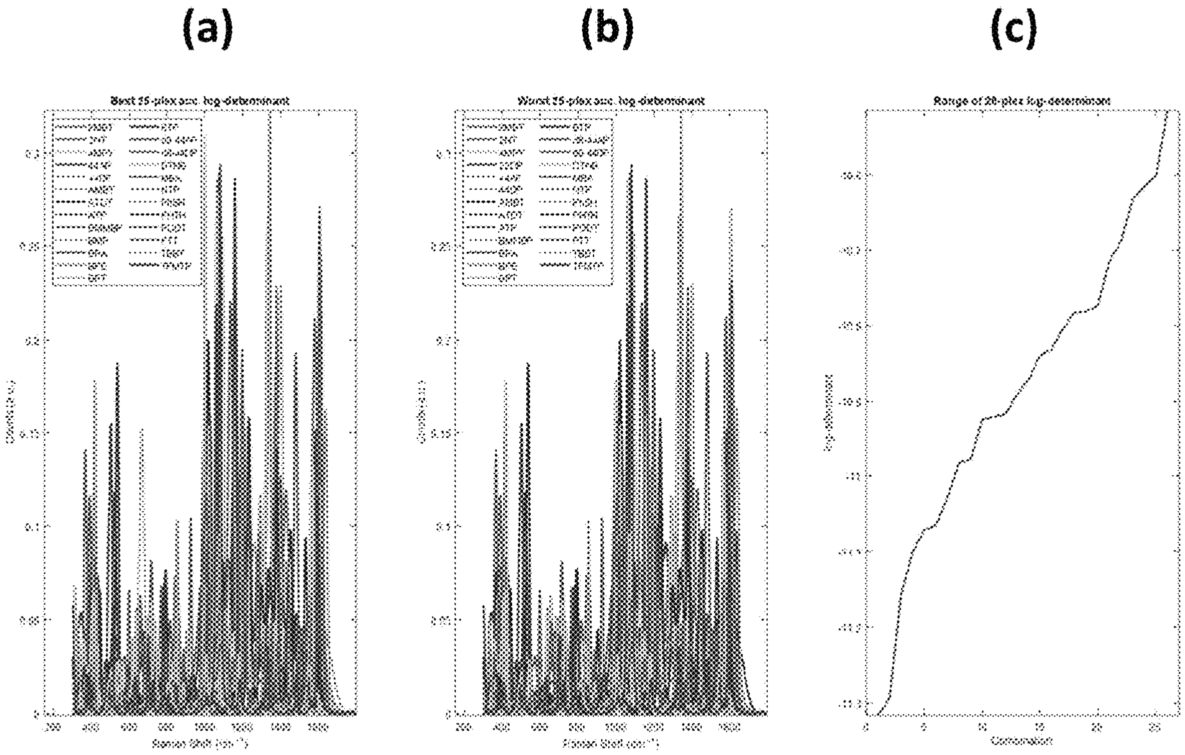
FIG. 73. Exemplary 25-plex staining formulations. (a) The most preferable 25-plex formulation. (b) The least preferable 25-plex formulation. (c) Range of log(det) values of 25-plex formulations. The Raman reporters of these formulations were selected from Table 9, Raman reporter ID no. 1-25 and ID no. 28.

FIG. 60 shows a plot of the sorted $\kappa_2$ scores for all 3-plex sets. The set of references that produced the most preferable $\kappa_2$, the least preferable $\kappa_2$, and a middle-of-the-road $\kappa_2$ are also shown to visually highlight and confirm that the $\kappa_2$ metric is indeed resulting in the desired properties of utilizing spectra which simultaneously are simple and minimize their peak overlap.

This staining formulation design approach may be extended to 26-plex (i.e., 26 SERS-flavor) staining formulations. Table 10 summarizes values for the most preferable $\kappa_2$, the least preferable $\kappa_2$, the most preferable determinant ("det"), the least preferable det, the most preferable log determinant ("log(det)"), and the least preferable log(det), which were calculated by using the design approach disclosed in this example.

TABLE 10

Summary of the most preferable $\kappa_2$ values, the least preferable $\kappa_2$ values, the most preferable determinant ("det") values, the least preferable det values, the most preferable log determinant ("log(det)") values, and the least preferable log(det) values.

| Plexity (i.e., Flavor) | Most Preferable $\kappa_2$ | Least Preferable $\kappa_2$ | Most Preferable det | Least Preferable det | Most Preferable log(det) | Least Preferable log(det) |
|---|---|---|---|---|---|---|
| 2 | 1.044118 | 3.095131 | 0.999069 | 0.5851 | −0.0004 | −0.23277 |
| 3 | 1.154727 | 3.929789 | 0.988021 | 0.365653 | −0.00523 | −0.43693 |
| 4 | 1.28577 | 4.707544 | 0.957572 | 0.21378 | −0.01883 | −0.67003 |
| 5 | 1.522881 | 5.524464 | 0.891822 | 0.122593 | −0.04972 | −0.91153 |
| 6 | 1.678594 | 6.254143 | 0.814294 | 0.074603 | −0.08922 | −1.12724 |
| 7 | 1.912228 | 7.361724 | 0.723286 | 0.048629 | −0.14069 | −1.31311 |
| 8 | 2.139731 | 7.914008 | 0.610528 | 0.028526 | −0.21429 | −1.54475 |
| 9 | 2.339861 | 8.434177 | 0.506609 | 0.019661 | −0.29533 | −1.7064 |
| 10 | 2.636282 | 8.949281 | 0.406945 | 0.011711 | −0.39046 | −1.9314 |
| 11 | 3.039643 | 9.498515 | 0.315812 | 0.007679 | −0.50057 | −2.11471 |
| 12 | 3.365371 | 9.878375 | 0.231729 | 0.004747 | −0.63502 | −2.32356 |
| 13 | 3.776572 | 10.29729 | 0.154757 | 0.002995 | −0.81035 | −2.52366 |
| 14 | 4.052721 | 10.73542 | 0.099692 | 0.001959 | −1.00134 | −2.70792 |
| 15 | 4.628314 | 11.22096 | 0.057762 | 0.001234 | −1.23836 | −2.90867 |
| 16 | 5.252621 | 11.49712 | 0.033223 | 0.000775 | −1.47856 | −3.11098 |
| 17 | 5.781984 | 11.7989 | 0.017991 | 0.000487 | −1.74495 | −3.31241 |
| 18 | 6.263307 | 12.09268 | 0.00944 | 0.000287 | −2.02504 | −3.54209 |
| 19 | 7.003334 | 12.36918 | 0.004612 | 0.000174 | −2.33607 | −3.75913 |
| 20 | 7.600793 | 12.61008 | 0.002169 | 0.000105 | −2.66374 | −3.98002 |
| 21 | 8.36566 | 12.83017 | 0.000974 | 6.39E−05 | −3.01151 | −4.19448 |
| 22 | 8.854846 | 13.03863 | 0.000429 | 4.24E−05 | −3.36766 | −4.37312 |
| 23 | 9.522141 | 13.25838 | 0.000177 | 2.58E−05 | −3.75318 | −4.58829 |
| 24 | 10.67616 | 13.41036 | 7.25E−05 | 1.67E−05 | −4.13991 | −4.77622 |
| 25 | 11.84008 | 13.50138 | 2.71E−05 | 1.22E−05 | −4.56671 | −4.91455 |
| 26 | 13.57569 | 13.57569 | 9.01E−06 | 9.01E−06 | −5.04508 | −5.04508 |

FIGS. 61-72 show plots for the most preferable $\kappa_2$, the least preferable $\kappa_2$, the most preferable log determinant ("log(det)") values, and the least preferable log(det) values together with the Raman spectra of different Raman reporters for various staining formulations.

Figure 74:
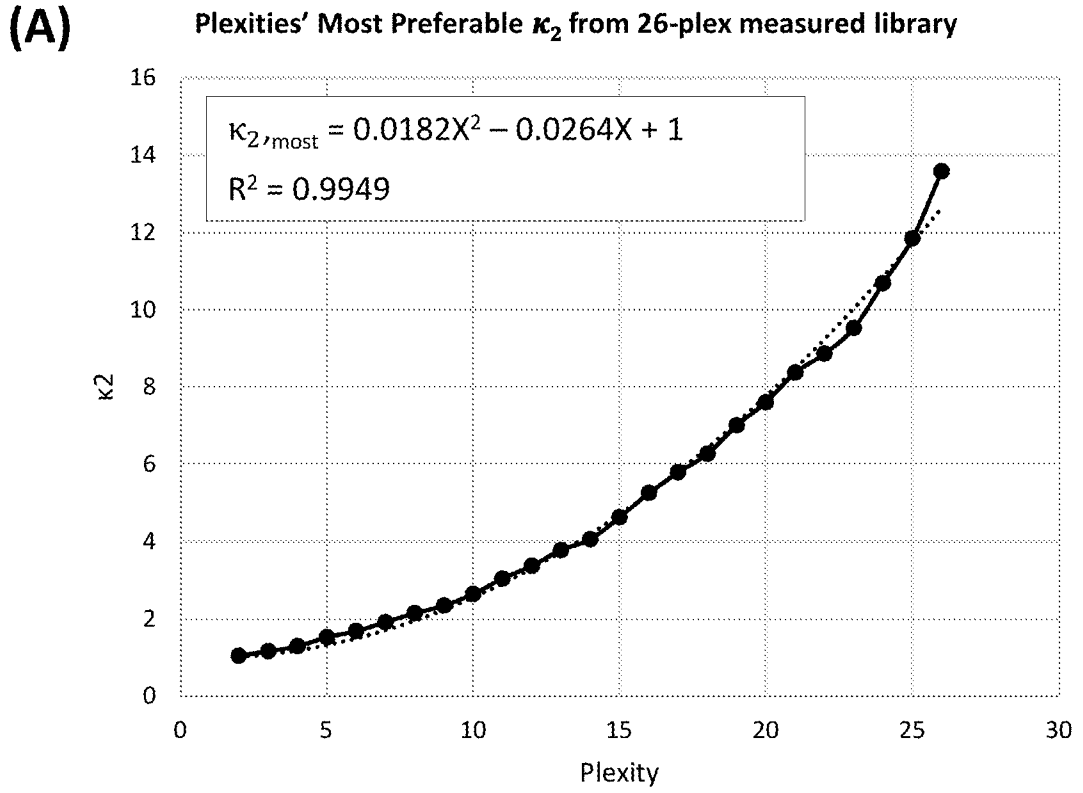
FIG. 74. Exemplary most preferable $\kappa_2$ and least preferable $\kappa_2$ for plexities ranging from 2 to 26 in the context of an available library of 26 SERS-flavors' measured spectra. The Raman reporters of these formulations were selected from Table 9, Raman reporter ID no. 1-25 and ID no. 28.
Figure 74:
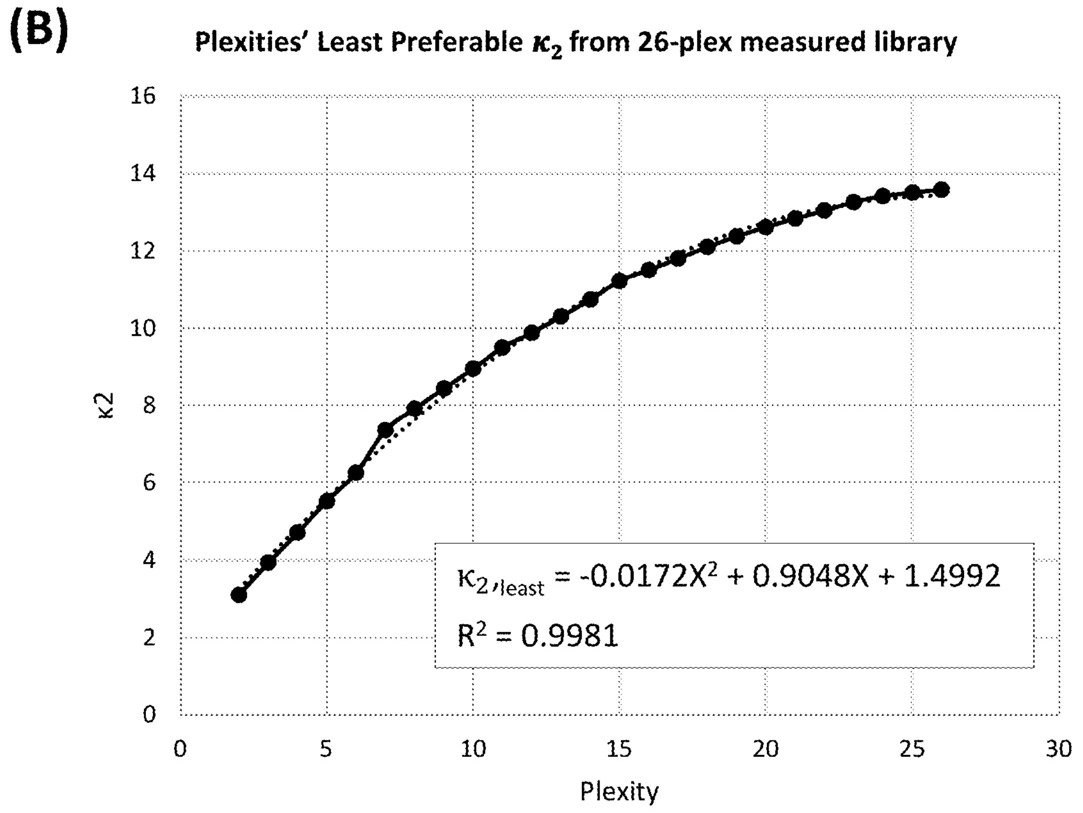

As shown in FIG. 74 (A), the relation between "most preferable $\kappa_2$" and the "plexity" (i.e. number of flavors in the staining formulation) may be approximated by the following equation:

$$\kappa_{2,mos}=0.0182X^2-0.0264X+1$$

Where $\kappa_{2,most}$ is the most preferable $\kappa_2$, and X is the plexity or number of SERS-flavors that may be used to prepare the staining formulation. The coefficient of determination, $R^2$ for this regression equation may be about 0.9949.

As shown in FIG. 74 (B), the relation between "least preferable $\kappa_2$ " and the "plexity" may be approximated by the following equation:

$$\kappa_{2,least}=-0.0172X^2+0.9048X+1.4992$$

Where $\kappa_{2,least}$ is the least preferable $\kappa_2$, and X is the plexity (i.e., number of Raman-flavors). The coefficient of determination, $R^2$ for this regression equation may be about 0.9981.

In one example, to minimize the demultiplexing error, the staining formulation may comprise flavors chosen by using a linear system sensitivity model, wherein a value of $\kappa_2$ may be in a range of a value greater than or equal to (i.e. ≥) $\kappa_{2,most}$ to a value less than or equal to (i.e. ≤) 95% of $\kappa_{2,least}$.

For example, a staining formulation comprising 10 flavors, $\kappa_{2,most}$ may be:

$$\kappa_{2,most}=0.0182\times10^2-0.0264\times10+1=2.556.$$

And, for the same staining formulation design, $\kappa_{2,least}$ may be:

$$\kappa_{2,least}=-0.0172\times10^2+0.9048\times10+1.4992=8.8272.$$

And, 95% of $\kappa_{2,least}$ is 0.95x8.8272=8.38584.

Then, all staining formulations that have a $\kappa_2$ value within a range of greater than or equal to (i.e. ≥) 2.556 and less than or equal to (i.e. ≤) than 8.38584 may be within the scope of this disclosure.

In another example, to minimize the demultiplexing error, the staining formulation may comprise flavors determined by using a linear system sensitivity model, wherein a value of $\kappa_2$ is in a range of a value greater than or equal to (i.e. ≥) $\kappa_{2,most}$ to a value less than or equal to (i.e. ≤) 40% of $\kappa_{2,least}$, or a value less than or equal to (i.e. ≤) 45% of $\kappa_{2,least}$, or a value less than or equal to (i.e. ≤) 50% of $\kappa_{2,least}$, or a value less than or equal to (i.e. ≤) 55% of $\kappa_{2,least}$, or a value less than or equal to (i.e. ≤) 60% of $\kappa_{2,least}$, or a value less than or equal to (i.e. ≤) 65% of $\kappa_{2,least}$, or a value less than or equal to (i.e. ≤) 70% of $\kappa_{2,least}$, or a value less than or equal to (i.e. ≤) 75% of $\kappa_{2,least}$, or a value less than or equal to (i.e. ≤) 80% of $\kappa_{2,least}$, or a value less than or equal to (i.e. ≤) 85% of $\kappa_{2,least}$, or a value less than or equal to (i.e. ≤) 90% of $\kappa_{2,least}$.

In another example, a value of $\kappa_2$ may be a value greater than or equal to 80% of $\kappa_{2,most}$, or a value greater than or equal to 85% of $\kappa_{2,most}$, or a value greater than or equal to 90% of $\kappa_{2,most}$, or a value greater than or equal to 95% of $\kappa_{2,most}$.

Figure 75:
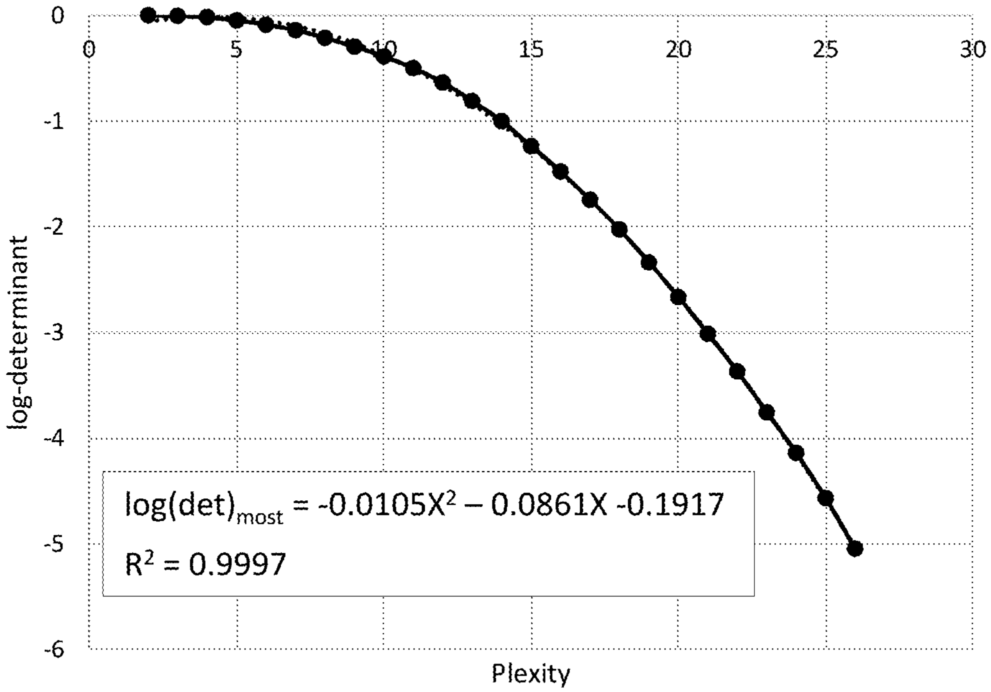
FIG. 75. Exemplary most preferable log(det) and least preferable log(det) for plexities ranging from 2 to 26 in the context of an available library of 26 SERS-flavors' measured spectra. The Raman reporters of these formulations were selected from Table 9, Raman reporter ID no. 1-25 and ID no. 28.
Figure 75:
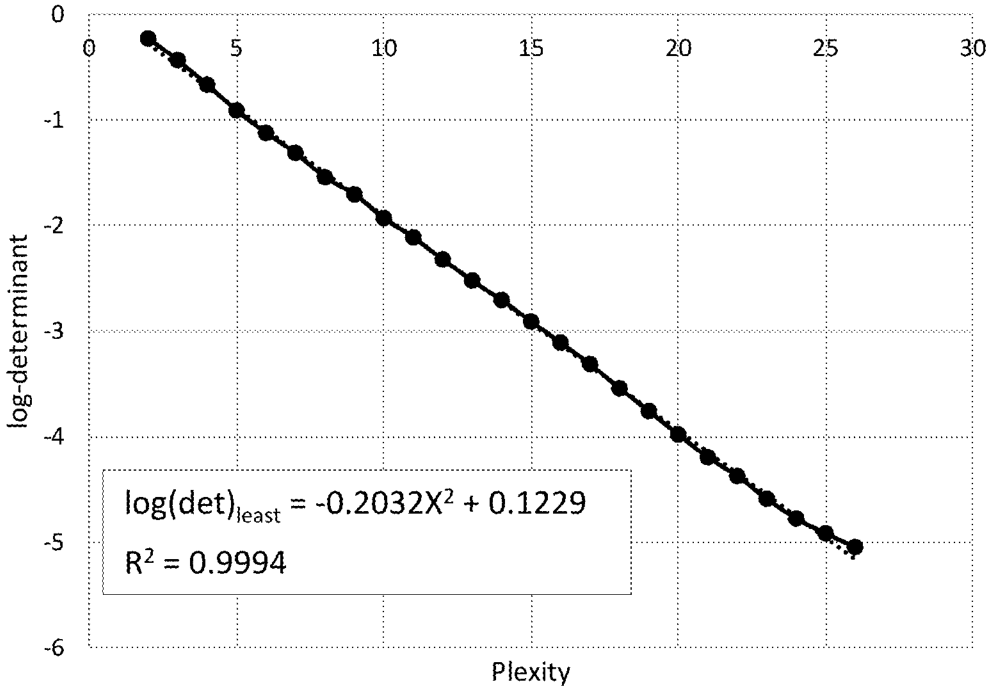

As shown in FIG. 75 (A), the relation between "most preferable log(det)" and the "plexity" (i.e., number of SERS-flavors in the staining formulation) may be approximated by the following equation:

$$\log(\det)_{most} = -0.0105X^2 - 0.0861X - 0.1917$$

Where $\log(\det)_{most}$ is the most preferable log(det), and X is the plexity or number of flavors that may be used to prepare the staining formulation. The coefficient of determination, $R^2$ for this regression equation may be about 0.9997.

As shown in FIG. 75 (B), the relation between "least preferable log(det)" and the "plexity" may be approximated by the following equation:

$$\log(\det)_{least} = -0.2032X^2 + 0.1229$$

Where $\log(\det)_{least}$ is the least preferable log(det), and X is the plexity. The coefficient of determination, $R^2$ for this regression equation may be about 0.9994.

In one example, to minimize the demultiplexing error, the staining formulation may comprise flavors determined by using a spectral dissimilarity objective, wherein a value of log(det) may be in a range of a value less than or equal to (i.e. ≤) $\log(\det)_{most}$ to a value greater than or equal to (i.e. ≥) 95% of $\log(\det)_{least}$.

For example, a staining formulation comprising 10 flavors, $\log(\det)_{most}$ may be:

$$\log(\det)_{most} = -0.0105\text{x}10^2 - 0.0861\text{x}10 - 0.1917 = -2.1027$$

And, $\log(\det)_{least}$ may be:

$$\log(\det)_{least} = -0.2032\text{x}10^2 + 0.1229 = -20.1971.$$

And, 95% of $\log(\det)_{least}$ may be 0.95x−20.1971=−19.187245.

Then, all staining formulations that have a log(det) value within a range of less than or equal to (i.e. ≤) −2.1027 and greater than or equal to (i.e. ≥) −19.187245 may be within the scope of this disclosure.

In another example, to minimize the demultiplexing error, the staining formulation may comprise flavors (i.e. SERS-flavors) determined by using a spectral dissimilarity objective, wherein a value of log(det) is in a range of a value less than or equal to (i.e. ≤) $\log(\det)_{most}$ to a value greater than or equal to (i.e. ≥) 40% of $\log(\det)_{least}$, or a value greater than or equal to (i.e. ≥) 45% of $\log(\det)_{least}$, or a value greater than or equal to (i.e. ≥) 50% of $\log(\det)_{least}$, or a value greater than or equal to (i.e. ≥) 55% of $\log(\det)_{least}$, or a value greater than or equal to (i.e. ≥) 60% of $\log(\det)_{least}$, or a value greater than or equal to (i.e. ≥) 65% of $\log(\det)_{least}$, or a value greater than or equal to (i.e. ≥) 70% of $\log(\det)_{least}$, or a value greater than or equal to (i.e. ≥) 75% of $\log(\det)_{least}$, or a value greater than or equal to (i.e. ≥) 80% of $\log(\det)_{least}$, or a value greater than or equal to (i.e. ≥) 85% of $\log(\det)_{least}$, or a value greater than or equal to (i.e. ≥) 90% of $\log(\det)_{least}$.

In another example, log(det) may be a value equal to or less than 105% of $\log(\det)_{most}$, or a value equal to or less than 110% of $\log(\det)_{most}$, or a value equal to or less than 115% of $\log(\det)_{most}$, or a value equal to or less than 120% of $\log(\det)_{most}$.

We followed this staining formulation design approach because a linear system sensitivity model may indicate that demultiplexing error may need to be reduced to have the abundance intensities in our images be as correct and insensitive to spectral fluctuations and noise as possible.

However, although we may calculate which staining formulation is the most preferable to avoid demultiplexing error should not mean that using anything other than the best staining formulation may result in an unacceptable error. As such, all potential staining formulations that may be designed with this approach are within the scope of this disclosure. Also, all potential staining formulations that may be prepared by using SERS-NPs of this disclosure are within the scope of this disclosure.

EXAMPLE 23. Staining Formulations Comprising SERS-NPs

Figure 76:
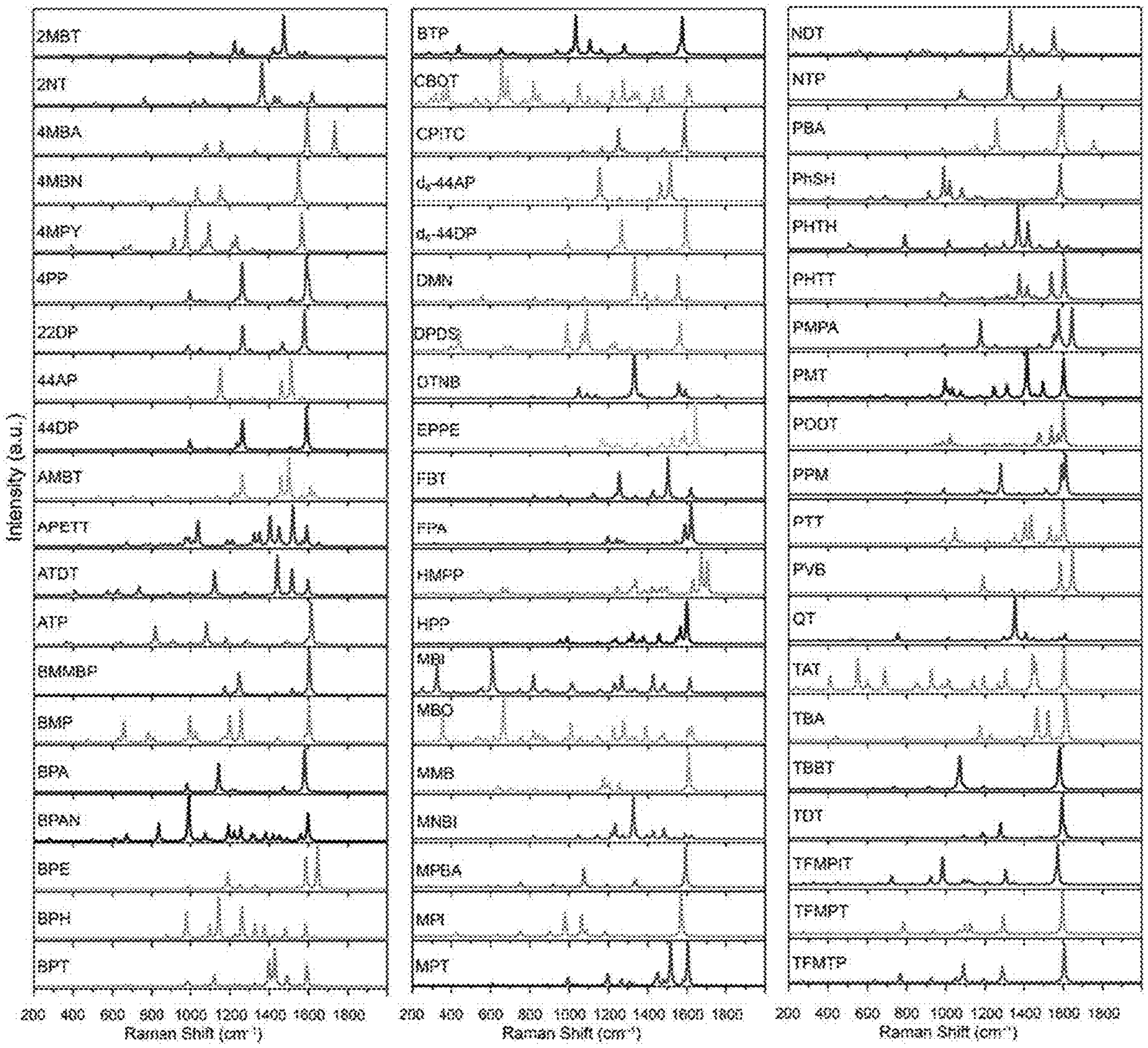
FIG. 76. Exemplary predicted spectra of sixty Raman reporters.

FIG. 76 discloses Raman spectra of sixty different Raman reporters. These spectra were calculated by using the approaches disclosed above. Each Raman reporter may be used in preparation of a different flavor.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range to be broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting.

All references cited herein, including but not limited to published and unpublished applications, patents, and literature references, are incorporated herein by reference for the subject matter referenced, and in their entirety and are hereby made a part of this specification. To the extent publications and patents or patent applications incorporated by reference contradict the disclosure contained in the specification, the specification is intended to supersede and/or take precedence over any such contradictory material.

In this disclosure, the indefinite article "a" and phrases "one or more" and "at least one" are synonymous and mean "at least one".

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

In at least some of the previously described embodiments, one or more elements used in an embodiment can interchangeably be used in another embodiment unless such a replacement is not technically feasible. It will be appreciated by those skilled in the art that various other omissions, additions, and modifications may be made to the methods and structures described herein without departing from the scope of the claimed subject matter. All such modifications and changes are intended to fall within the scope of the disclosed subject matter.

The scope of protection is limited solely by the claims that now follow. That scope is intended and should be interpreted to be as broad as is consistent with the ordinary meaning of the language that is used in the claims when interpreted considering this specification and the prosecution history that follows, except where specific meanings have been set forth, and to encompass all structural and functional equivalents.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A staining formulation, useful for staining a sample to identify at least one chemical moiety on at least one surface of the sample, wherein:

the staining formulation comprises at least two SERS-flavors;

each SERS-flavor comprises at least one surface enhanced Raman spectroscopy nanoparticle (SERS-NP);

each SERS-NP comprises a Raman reporter and a Raman active core;

each SERS-flavor's at least one SERS-NP comprises a Raman reporter and/or Raman active core that is different than those of the other SERS-flavors in the staining formulation;

each SERS-flavor has a Raman spectrum determined at an excitation wave with about 785 nm wavelength;

the staining formulation has a value of a condition number, $\kappa_2$ in a range of a value greater than or equal to $\kappa_{2,most}$ to a value less than or equal to 95% of $\kappa_{2,least}$;

the condition number, $\kappa_2$ is calculated by using a linear system sensitivity model (LSSM) and a singular value decomposition (SVD) for a Raman spectrum of the staining formulation determined at an excitation wave with about 785 nm wavelength;

$\kappa_{2,most}$ is the most preferable $\kappa_2$;

$\kappa_{2,least}$ is the least preferable $\kappa_2$;

$\kappa_{2,most}$ is calculated by using the equation $\kappa_{2,most}=0.0182X^2-0.0264X+1$;

$\kappa_{2,least}$ is calculated by using the equation $\kappa_{2,least}=-0.0172X^2+0.9048X+1.4992$; and X is a number of utilized SERS-flavors.

2. The staining formulation of claim 1, wherein the Raman reporter is a molecule selected by using a simulated Raman and/or SERS spectra calculated with density functional theory (DFT) and/or time dependent density functional theory (TDDFT).

3. The staining formulation of claim 1, wherein the value of $\kappa_2$ is in a range of:

a value greater than or equal to $\kappa_{2,most}$ to a value less than or equal to 40% of $\kappa_{2,least}$; or a value greater than or equal to $\kappa_{2,most}$ to a value less than or equal to 45% of $\kappa_{2,least}$; or a value greater than or equal to $\kappa_{2,most}$ to a value less than or equal to 50% of $\kappa_{2,least}$; or a value greater than or equal to $\kappa_{2,most}$ to a value less than or equal to 55% of $\kappa_{2,least}$; or a value greater than or equal to $\kappa_{2,most}$ to a value less than or equal to 60% of $\kappa_{2,least}$; or a value greater than or equal to $\kappa_{2,most}$ to a value less than or equal to 65% of $\kappa_{2,least}$; or a value greater than or equal to $\kappa_{2,most}$ to a value less than or equal to 70% of $\kappa_{2,least}$; or a value greater than or equal to $\kappa_{2,most}$ to a value less than or equal to 75% of $\kappa_{2,least}$; or a value greater than or equal to $\kappa_{2,most}$ to a value less than or equal to 80% of $\kappa_{2,least}$; or a value greater than or equal to $\kappa_{2,most}$ to a value less than or equal to 85% of $\kappa_{2,least}$; or a value greater than or equal to $\kappa_{2,most}$ to a value less than or equal to 90% of $\kappa_{2,least}$.

4. The staining formulation of claim 1, wherein:

the SERS-NP comprises:

a Raman active core and a Raman active layer; or a Raman active core, a Raman active layer, and a labeling agent; or a Raman active core, a Raman active layer, a labeling agent, and a shell;

the Raman active core has an outer surface;

the shell has an inner surface and an outer surface;

the Raman active layer is positioned between the outer surface of the Raman active core and the inner surface of the shell;

the labeling agent is attached to the Raman active layer or the outer surface of the shell;

the Raman active layer comprises a Raman reporter.

5. The staining formulation of claim 1, wherein the Raman reporter is selected from Table 9, Raman reporter IDs 1-60, or a combination thereof.

6. The staining formulation of claim 1, wherein the Raman reporter is selected from Table 9, Raman reporter IDs 1-26, or a combination thereof.

7. The staining formulation of claim 1, wherein at least one Raman flavor is an isotype control SERS-flavor.

8. The staining formulation of claim 1; wherein the isotype control Raman flavor comprises at least one SERS-NP functionalized with a nonspecific IgG as a labeling agent to account for any untargeted binding to the sample.

9. The staining formulation of claim 1; wherein the sample expresses at least one biomarker as a chemical moiety; and wherein each SERS-flavor's SERS-NP comprises a labeling agent that can bind to the at least one biomarker, or a chemical moiety that is not a biomarker.

10. The staining formulation of claim 1; wherein:

the sample is a cell belonging to cancerous tissue;

the sample expresses a biomarker as a chemical moiety; and the biomarker comprises epidermal growth factor receptor (EGFR), cluster of differentiation-47 (CD47), integrin $\alpha_v\beta_3$, cMET, human epidermal growth factor receptor 2 (HER2), or a combination thereof.

11. The staining formulation of claim 1; wherein the staining formulation comprises at least three SERS-flavors, or at least four SERS-flavors, or at least five SERS-flavors, or at least six SERS-flavors, or at least seven SERS-flavors, or at least eight SERS-flavors, or at least nine SERS-flavors, or at least ten SERS-flavors.

12. The staining formulation of claim 1; wherein the staining formulation comprises at least four SERS-flavors.

13. The staining formulation of claim 1; wherein the staining formulation comprises at least five SERS-flavors.

14. A staining formulation, useful for staining a sample to identify at least one chemical moiety on at least one surface of the sample, wherein:

the staining formulation comprises at least two SERS-flavors;

each SERS-flavor comprises at least one surface enhanced Raman spectroscopy nanoparticle (SERS-NP);

each SERS-NP comprises a Raman reporter and a Raman active core;

each SERS-flavor's at least one SERS-NP comprises a Raman reporter and/or Raman active core that is different than those of the other SERS-flavors in the staining formulation;

each SERS-flavor has a Raman spectrum determined at an excitation wave with about 785 nm wavelength;

the staining formulation has a value of a log(det) in a range of a value less than or equal to $\log(\det)_{most}$ to a value greater than or equal to 95% of $\log(\det)_{least}$;

the log(det) is calculated by using a spectral dissimilarity objective (SDO) and a singular value decomposition (SVD) for a Raman spectrum of the staining formulation determined at an excitation wave with about 785 nm wavelength;

$\log(\det)_{most}$ is most preferable log(det);

$\log(\det)_{least}$ is least preferable log(det);

$\log(\det)_{most}$ is calculated by using the equation, $\log(\det)_{most}=-0.0105X^2-0.0861X-0.1917$;

$\log(\det)_{least}$ is calculated by using the equation $\log(\det)_{least}=-0.2032X^2+0.1229$; and X is number of SERS-flavors.

15. A SERS-flavor comprising a surface enhanced Raman spectroscopy nanoparticle (SERS-NP) wherein:

the SERS-NP comprises:

a Raman active core and a Raman active layer; or a Raman active core, a Raman active layer, and a labeling agent; or a Raman active core, a Raman active layer, a labeling agent, and a shell;

the Raman active core has an outer surface;

the shell has an inner surface and an outer surface;

the Raman active layer is positioned between the outer surface of the Raman active core and the inner surface of the shell;

the labeling agent is attached to the Raman active layer or the outer surface of the shell;

the Raman active layer comprises a Raman reporter;

the Raman active core and the Raman reporter enhance Raman scattering and are thereby suitable for surface-enhanced Raman spectroscopy (SERS); and the Raman reporter is selected from Table 9, Raman reporter IDs 4-6, 8, 24, 29-31, 34, 39-43, and 46-49, or a combination thereof.

16. A system, useful for identifying and/or quantifying at least one chemical moiety on at least one surface of a sample, wherein:

the system comprises a Raman spectroscopy system;

the sample is stained by using the staining formulation of claim 1;

the system is configured to obtain and analyze Raman scattering of the sample; and the system is further configured to identify and/or quantify the chemical moiety.

17. A system, useful identifying at least one chemical moiety on at least one surface of a sample, wherein:

the system comprises a Raman spectroscopy system and a staining system configured to stain the sample;

the sample is stained by using the staining formulation of claim 1;

the system is configured to obtain and analyze Raman scattering of the sample; and the system is further configured to identify the chemical moiety.

18. The staining formulation of claim 1, the Raman reporter is a molecule selected by using a simulated Raman and/or SERS spectra calculated with density functional theory (DFT) and/or time dependent density functional theory (TDDFT).

19. The staining formulation of claim 1, wherein the staining formulation comprises at least three SERS-flavors, or at least four SERS-flavors, or at least five SERS-flavors, or at least six SERS-flavors, or at least seven SERS-flavors, or at least eight SERS-flavors, or at least nine SERS-flavors, or at least ten SERS-flavors.

20. The staining formulation of claim 1, wherein the staining formulation comprises at least four SERS-flavors.

21. The staining formulation of claim 1, wherein the staining formulation comprises at least five SERS-flavors.

22. The staining formulation of claim 1, wherein the value of $\kappa_2$ is in a range of:

a value greater than or equal to $\kappa_{2,most}$ to a value less than or equal to 40% of $\kappa_{2,least}$; or a value greater than or equal to $\kappa_{2,most}$ to a value less than or equal to 45% of $\kappa_{2,least}$; or a value greater than or equal to $\kappa_{2,most}$ to a value less than or equal to 50% of $\kappa_{2,least}$; or a value greater than or equal to $\kappa_{2,most}$ to a value less than or equal to 55% of $\kappa_{2,least}$; or a value greater than or equal to $\kappa_{2,most}$ to a value less than or equal to 60% of $\kappa_{2,least}$; or a value greater than or equal to $\kappa_{2,most}$ to a value less than or equal to 65% of $\kappa_{2,least}$; or a value greater than or equal to $\kappa_{2,most}$ to a value less than or equal to 70% of $\kappa_{2,least}$; or a value greater than or equal to $\kappa_{2,most}$ to a value less than or equal to 75% of $\kappa_{2,least}$; or a value greater than or equal to $\kappa_{2,most}$ to a value less than or equal to 80% of $\kappa_{2,least}$; or a value greater than or equal to $\kappa_{2,most}$ to a value less than or equal to 85% of $\kappa_{2,least}$; or a value greater than or equal to $\kappa_{2,most}$ to a value less than or equal to 90% of $\kappa_{2,least}$.

23. The staining formulation of claim 1, wherein the value of log(det) is in a range of:

a value less than or equal to $\log(\det)_{most}$ to a value greater than or equal to 40% of $\log(\det)_{least}$, or a value less than or equal to $\log(\det)_{most}$ to a value greater than or equal to 45% of $\log(\det)_{least}$; or a value less than or equal to $\log(\det)_{most}$ to a value greater than or equal to 50% of $\log(\det)_{least}$; or a value less than or equal to $\log(\det)_{most}$ to a value greater than or equal to 55% of $\log(\det)_{least}$; or a value less than or equal to $\log(\det)_{most}$ to a value greater than or equal to 60% of $\log(\det)_{least}$; or a value less than or equal to $\log(\det)_{most}$ to a value greater than or equal to 65% of $\log(\det)_{least}$; or a value less than or equal to $\log(\det)_{most}$ to a value greater than or equal to 70% of $\log(\det)_{least}$; or a value less than or equal to $\log(\det)_{most}$ to a value greater than or equal to 75% of $\log(\det)_{least}$; or a value less than or equal to $\log(\det)_{most}$ to a value greater than or equal to 80% of $\log(\det)_{least}$; or a value less than or equal to $\log(\det)_{most}$ to a value greater than or equal to 85% of $\log(\det)_{least}$; or a value less than or equal to $\log(\det)_{most}$ to a value greater than or equal to 90% of $\log(\det)_{least}$.

24. The staining formulation of claim 1, wherein:

the SERS-NP comprises:

a Raman active core and a Raman active layer; or a Raman active core, a Raman active layer, and a labeling agent; or a Raman active core, a Raman active layer, a labeling agent, and a shell;

the Raman active core has an outer surface;

the shell has an inner surface and an outer surface;

the Raman active layer is positioned between the outer surface of the Raman active core and the inner surface of the shell;

the labeling agent is attached to the Raman active layer or the outer surface of the shell;

the Raman active layer comprises a Raman reporter.

25. The SERS-NP, SERS-flavors, or the staining formulation of claim 1, wherein Raman reporter is selected from Table 9, Raman reporter IDs 1-60, or a combination thereof.

26. The SERS-NP, SERS-flavors, or the staining formulation of claim 1, wherein the Raman reporter is selected from Table 9, Raman reporter IDs 1-26, or a combination thereof.

27. The staining formulation of claim 1, wherein at least one Raman flavor is an isotype control SERS-flavor.

28. The staining formulation of claim 1; wherein the isotype control Raman flavor comprises at least one SERS-NP functionalized with a nonspecific IgG as a labeling agent to account for any untargeted binding to the sample.

29. The staining formulation of claim 1; wherein the sample expresses at least one biomarker as a chemical moiety; and wherein each SERS-flavor's SERS-NP comprises a labeling agent that can bind to the at least one biomarker, or a chemical moiety that is not a biomarker.

30. The staining formulation of claim 1; wherein:

the sample is a cell belonging to cancerous tissue;

the sample expresses a biomarker as a chemical moiety; and the biomarker comprises epidermal growth factor receptor (EGFR), cluster of differentiation-47 (CD47), integrin $\alpha_v\beta_3$, cMET, human epidermal growth factor receptor 2 (HER2), or a combination thereof.

31. The SERS-NP of claim 1; wherein the Raman reporter has an anchoring group, which is comprising thiol, sulfide, disulfide, isothiocyanate, cyanate, nitrogen in aromatic ring, amine, or a combination thereof, to bind to the Raman active core, or the Raman reporter binds to the Raman active core by hydrophobic or ionic interactions.

32. The SERS-NP of claim 1; wherein the Raman active core comprises a metal core, a metal oxide, an alloy thereof, or a composite thereof.

33. The SERS-NP of claim 1; wherein the Raman active core comprises a metal or a composite core.

34. The SERS-NP of claim 1; wherein the Raman active core comprises gold, silver, copper, platinum, palladium, titanium, carbon, aluminum, zinc, chromium, iron, an oxide thereof, an alloy thereof, or a composite thereof.

35. The SERS-NP of claim 1; wherein the Raman active core comprises gold, silver, copper, platinum, palladium, copper oxide, titanium oxide, iron oxide, zinc oxide, aluminum oxide, carbon, an alloy thereof, or a composite thereof.

36. The SERS-NP of claim 1; wherein the Raman active core comprises gold.

37. The SERS-NP of claim 1; wherein the labeling agent comprises a water soluble homobifunctional, heterobifunctional, or photoreactive crosslinker that has a chemical group that can react with a functional group of an antibody or another biotargeting species; and wherein the labeling agent further comprises another chemical group that can react with a functional group on the outer surface of the SERS-NP's shell.

38. The SERS-NP of claim 1; wherein the labeling agent comprises PEG.

39. The SERS-NP of claim 1; wherein the labeling agent further comprises an antibody, peptide, aptamer or any other targeting ligand.

40. The SERS-NP of claim 1; wherein the shell comprises an oxide.

41. The SERS-NP of claim 1; wherein the shell comprises silica, alumina, titania, zirconia, chitosan, modified cellulose, polyvinyl pyrrolidone, or a mixture thereof.

42. The SERS-NP of claim 1; wherein the shell comprises silica.

43. The staining formulation of claim 1; wherein the sample comprises a solid sample, a liquid sample, or any combination thereof.

44. The staining formulation of claim 1; wherein the sample comprises a tissue.

45. The staining formulation of claim 1; wherein the sample comprises a tissue; and wherein the tissue comprises human tissue, animal tissue, plant tissue, a virus, a bacterium, a cell, the like, or a combination thereof.

* * * * *